US006221640B1

(12) United States Patent
Tao et al.

(10) Patent No.: US 6,221,640 B1
(45) Date of Patent: Apr. 24, 2001

(54) ENTEROCOCCAL AMINOACYL-TRNA SYNTHETASE PROTEINS, NUCLEIC ACIDS AND STRAINS COMPRISING SAME

(75) Inventors: Jianshi Tao, North Andover; Mandana Sassanfar; Paul L. Gallant, both of Dedham; Xiaoyu Shen, Boston; Anthony S. Avruch, Watertown, all of MA (US); Russell V. Yu, Munster, IN (US); Shamila Nair, Paris (FR)

(73) Assignee: Cubist Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 08/855,910

(22) Filed: May 14, 1997

(Under 37 CFR 1.47)

(51) Int. Cl.[7] .............................. C12N 9/00; C12N 1/20; C12Q 1/68; C07H 21/04
(52) U.S. Cl. .......................... 435/183; 435/6; 435/320.1; 435/252.3; 435/254.11; 435/325; 536/23.2; 536/24.3
(58) Field of Search ................................ 435/183, 320.1, 435/252.3, 254.11, 325, 6; 536/23.2, 23.4

(56) References Cited

U.S. PATENT DOCUMENTS

| 4,713,337 | 12/1987 | Jasin et al. | 435/172.3 |
|---|---|---|---|
| 4,788,148 | 11/1988 | Nilsson et al. | 435/320 |
| 4,952,501 | 8/1990 | Jasin et al. | 435/69.2 |
| 4,963,487 | 10/1990 | Schimmel et al. | 435/172.3 |
| 5,370,995 | 12/1994 | Hennecke et al. | 435/69.1 |
| 5,561,054 | 10/1996 | Kron et al. | 435/69.1 |
| 5,656,470 | 8/1997 | Martinis et al. | 435/183 |
| 5,688,655 | 11/1997 | Housey | 435/7.21 |

FOREIGN PATENT DOCUMENTS

WO 95/09927  4/1995  (WO).

OTHER PUBLICATIONS

Meinnel, T., et al., "Aminoacyl–tRNA Synthetases: Occurrence, Structure, and Function." In *tRNA: Structure, Biosynthesis, and Function*, Söll, D. and RajBhandary, U., eds. (Washington, DC: American Society for Microbiology), pp. 251–300 (1995).

von der Haar, F. et al, "Target Directed Drug Synthesis: The Aminoacyl–tRNA Synthetases as Possible Targets," *Angew. Chem. Int. Ed. Engl.*, 20(3):217–223 (1981).

Walter, R. D. and Kuhlow, F., "Parasite–Specific Interaction of N–[4–(4' Nitroanilino)–Phenyl]–S–(β–Carboxyethyl)–Dithiocarbamic Acid–Ester with Arginyl–tRNA–Synthetase from *Dirofilaria immitis*," *Trop. Med. Parasit.*, 36:230–232 (1985).

Hughes, J., et al., "Inhibition of Isoleucyl–Transfer Ribonucleic Acid Synthetase in *Escherichia coli* by Pseudomonic Acid," *Biochem. J.*, 176:305–318 (1978).

Hughes, J. and Mellows, G., "Interaction of Pseudomonic Acid A with *Escherichia coli* B Isoleucyl–tRNA Synthetase," *Biochem. J.*, 191:209–219 (1980).

Shiba, K. and Shimmel, P., "Functional Assembly of a Randomly Cleaved Protein," *Proc. Natl. Acad. Sci. USA*, 89:1880–1884 (1992).

Shepard, A., et al., "RNA Binding Determinant in Some Class I tRNA Synthetases Identified by Alignment–Guided Mutagenesis," *Proc. Natl. Acad. Sci. USA*, 89:9964–9968 (1992).

Kim, S., et al., "Diversified Sequences of Peptide Epitope for Same–RNA Recognition," *Proc. Natl. Acad. Sci. USA*, 90:10046–10050 (1993).

Edwards, H., et al., "An *E. coli* Aminoacyl–tRNA Synthetase Can Substitute for Yeast Mitochondrial Enzyme Function In Vivo," *Cell*, 51:643–649 (1987).

Edwards, H. and Schimmel, P., "A Bacterial Amber Suppressor in *Saccharomyces cerevisiae* Is Selectively Recognized by a Bacterial Aminoacyl–tRNA Synthetase," *Mol. Cell. Biol.*, 10(4):1633–1641 (1990).

Weygand–Duraševič, I., et al., "Yeast Seryl–tRNA Synthetase Expressed in *Escherichia coli* Recognizes Bacterial Serine–Specific tRNAs in vivo," *Eur. J. Biochem.*, 214:869–877 (1993).

Jones, M. D., et al., "Natural Variation of Tyrosyl–tRNA Synthetase and Comparison with Engineered Mutants," *Biochemistry*, 25:1887–1891 (1986).

Henkin, T. M., et al., "Analysis of the *Bacillus subtilis* tyrS Gene: Conservation of a Regulatory Sequence in Multiple tRNA Synthetase Genes," *J. Bacteriol.*, 174(4):1299–1306 (1992).

(List continued on next page.)

*Primary Examiner*—Lisa J. Hobbs
(74) *Attorney, Agent, or Firm*—Hamilton, Brook, Smith & Reynolds, P.C.

(57) ABSTRACT

Recombinant nucleic acids which encode aminoacyl-tRNA sythetases of enterococcal origin or portions of such enzymes, have been isolated. These nucleic acids can be used to make expression constructs and transformed host cells for the production of enterococcal aminoacyl-tRNA synthetases. They can also be used in the further isolation of nucleic acids related by DNA sequence similarities, which also encode enterococcal aminoacyl-tRNA synthetases, or portions thereof. A further embodiment of the invention is antisense nucleic acid which can hybridize to the nucleic acid which encodes the aminoacyl-tRNA synthetase of enterococci. The invention also relates to tRNA synthetases such as isolated and/or recombinant enterococcal aminoacyl-tRNA synthetases. Antibodies which bind to these enzymes can be made and can be used in the purification and study of the enzymes. Tester strains, which are cells engineered to rely on the function of the tRNA synthetase encoded by an introduced cloned gene, can be used to test the effectiveness of drug candidates in the inhibition of the essential tRNA synthetase enzyme encoded by an introduced cloned gene.

110 Claims, 9 Drawing Sheets

OTHER PUBLICATIONS

Salazar, O., et al., "*Thiobacillus ferrooxidans* Tyrosyl–tRNA Synthetase Functions In Vivo in *Escherichia coli*," *J. Bacteriol.*, 176(14):4409–4415 (1994).

Iaccarino, M. and Berg, P., "Isoleucine Auxotrophy as a Consequence of a Mutationally Altered Isoleucyl–Transfer Ribonucleic Acid Synthetase," *J. Bacteriol.*, 105:527–537 (1970).

Chalker, A.F., et al., "Analysis and Toxic Overexpression in *Escherichia coli* of a Staphylococcal Gene Encoding Isoleucyl–tRNA Synthetase," *Gene*, 141:103–108 (1994).

Jasin, M. and Schmimmel, P., "Deletion of an Essential Gene in *Escherichia coli* by Site–Specific Recombination with Linear DNA Fragments," *J. Bacteriol.*, 159(2):783–786 (1984).

Low, B., et al., "Isolation and Partial Characterization of Temperature–Sensitve *Escherichia coli* Mutants with Altered Leucyl– and Seryl– Transfer Ribonucleic Acid Synthetases," *J. Bacteriol.*, 108(2):742–750 (1971).

Clarke, S. J., et al., "Isolation and Characterization of a Regulatory Mutant of an Aminoacyl–Transfer Ribonucleic Acid Synthetase in *Escherichia coli* K–12," *J. Bacteriol.*, 113(3):1096–1103 (1973).

Schlesinger, S., and Nester, E. W., "Mutants of *Escherichia coli* with an Altered Tyrosyl–Transfer Ribonucleic Acid Synthetase," *J. Bacteriol.*, 100(1):167–175 (1969).

Grandoni, J.A., et al., "Transcriptional Regulation of the ilv–leu Operon of *Bacillus subtilis*," *Journal of Bacteriology*, 174(10):3212–3219 (1992).

Racher, K.I., et al., "Expression and Characterization of a Recombinant Yeast Isoleucyl–tRNA Synthetase," *J. Biol. Chem.*, 266(26):17158–17164 (1991).

Webster, T., et al., "Specific Sequence Homology and Three–Dimensional Structure of an Aminoacyl Transfer RNA Synthetase," *Science*, 226:1315–1317 (1984).

Jenal, U., et al., "Isoleucyl–tRNA Synthetase of *Methanobacterium thermautotrophicum* Marburg," *J. Biol. Chem.*, 266(16):10570–10577 (1991).

Shiba, K., et al., "Human Cytoplasmic Isoleucyl–tRNA Synthetase: Selective Divergence of the Anticodon–Binding Domain and Acquisition of a New Structural Unit," *Proc. Natl. Acad. Sci. USA*, 91:7435–7439 (1994).

Shiba, K., et al., "Isolation of Higher Eukaryote Aminoacyl–tRNA Synthetase Genes by an Alignment–Guided Cross–Species PCR: Application to Human Isoleucine tRNA Synthetase," [From *Programme and Abstracts*, p. F.46], 15th International tRNA Workshop, Société Francaise de Biochimie et Biologie Moléculaire, Cap d'Agde, France, May 30–Jun. 4 (1993), Abstract No. 364.

Printout of a computer record of parts of a poster presented at Cap d'Agde, France, May 30–Jun. 4, 1993, 15th International tRNA Workshop, Société Francaise de Biochimie et Biologie Moléculaire.

Delorme, C., et al., "Histidine Biosynthesis Genes in *Lactococcus lactis* subsp. *lactis*," *Journal of Bacteriology*, 174(20):6571–6579 (1992).

Barker, D. G., et al., "The Tyrosyl–tRNA Synthetase from *Escherichia coli*," *FEBS Letters*, 150(2):419–423 (1982).

Chow, C. M., and RajBhandary, U. L., "*Saccharomyces cerevisiae* Cytoplasmic Tyrosyl–tRNA Synthetase Gene," *The Journal of Biological Chemistry*, 268(17):12855–12863 (1993).

Härtlein, M. and Madern, D., "Molecular Cloning and Nucleotide Sequence of the Gene for *Escherichia coli* Leucyl–tRNA Synthetase," *Nucleic Acids Research*, 15(24):10199–10210 (1987).

Vander Horn, P. B., and Zahler, S. A., "Cloning and Nucleotide Sequence of the Leucyl–tRNA Synthetase Gene of *Bacillus subtilis*," *J. Bacteriol.*, 174(12):3928–3935 (1992).

Bardowski, J., et al., "Tryptophan Biosynthesis Genes in *Lactococcus lactis* subsp. *lactis*," *Journal of Bacteriology*, 174(20):6563–6570 (1992).

Akins, R. A., and Lambowitz, A. M., "A Protein Required for Splicing Group I Introns in Neurospora Mitochondria Is Mitochondrial Tyrosyl–tRNA Synthetase or a Derivative Thereof," *Cell*, 50:331–345 (1987).

Winter, G., et al., "The Amino Acid Sequence of the Tyrosyl– tRNA Synthetase from *Bacillus stearothermophilus*," *Eur. J. Biochem.*, 132:383–387 (1983).

Glaser, P., et al., "A Gene Encoding a Tyrosine tRNA Synthetase is Located Near sacS in *Bacillus subtilis*," *DNA Sequence*, 1:251–261 (1991).

Natori, Y., et al., "Nucleotide Sequences and Genomic Constitution of Five Tryptophan Genes of *Lactobacillus casei*," *J. Biochem.*, 107:248–255 (1990).

Gagnon, Y., et al., "Clustering and Co–transcription of the *Bacillus subtilis* Genes Encoding the Aminoacyl–tRNA Synthetases Specific Glutamate and for Cysteine and the First Enzyme for Cysteine Biosynthesis," *The Journal of Biological Chemistry*, 269(10):7473–7482 (1994).

Härtlein, M., et al., "Cloning and characterization of the gene for *Escherichia coli* seryl–tRNA synthetase", *Nucleic Acids Research*, 15(3): 1005–1017 (1987).

Samuel, Charles E., et al., "Methionine Transfer Ribonucleic Acid From Folate–Sufficient and Folate–Deficient *Streptococcus faecalis* R,"0 *The Journal of Biological Chemistry*, 247(21):6856–6865 (1972).

Samuel, Charles E. and Rabinowitz, Jesse C., "Initiation of Protein Synthesis by Folate–Sufficient and Folate–Deficient *Streptococcus faecalis* R: Partial Purification and Properties of Methionyl–Transfer Ribonucleic Acid Synthetase and Methionyl–Transfer Ribonucleic Acid Formyltransferase," *Journal of Bacteriology*, 118(1):21–31 (1974).

Samuel, Charles E. and Rabinowitz, Jesse C., "Initiation of Protein Synthesis by Folate–Sufficient and Folate–Deficient *Streptococcus Faecalis*R: Biochemical and Biophysical Properties of Methionine Transfer Ribonucleic Acid," *The Journal of Biological Chemistry*, 249 (4) :1198–1206 (1974).

Menguito, Corazon Aure, "Histidyl–tRNA Synthetase From *Streptococcus equisimilis*: Nucleotide and Protein Sequence Analysis, Expression in *Escherichia coli*, Purification and Characterization of the Protein," Thesis, The University of Texas Graduate School of Biomedical Science, 1992.

Samuel, Charles E. and Rabinowitz, Jesse C., "Effect of Formylation of the Chromatographic Behavior of Methionyl Transfer Ribonucleic Acid," *Analytical Biochemistry*, 47:244–252 (1972).

Csank, C., et al., Data Submission, Isoleucyl–tRNA Synthetase, *Tetrahymena thermophila*, Swiss–Prot Accesssion No. P36422 (1994).

Martindale, D.W., et al., Data Submission, Isoleucyl–tRNA Synthetase, Cytoplasmic, *Saccharomyces cerevisiae*, Swiss–Prot Accession No. P09436 (1989).

Nichols, R.C., Data Submission, Isoleucyl–tRNA Synthetase, *Homo sapiens*, GenBank Accession No. U04953 (1994).

Jenal, U., et al., Data Submission, Isoleucyl–tRNA Synthetase, *Methanobacterium thermoautotrophicum*, Swiss–Prot Accession No. P26499 (1992).

Webster, T., et al., Data Submission, Isoleucyl–tRNA Synthetase, *Escherichia coli*, Swiss–Prot Accession No. P00956 (1986).

Chalker, A.F., et al., Data Submission, Isoleucyl–tRNA Synthetase, *Staphylococcus aureus*, Swiss–Prot Accession No. P41972 (1995).

Yanagisawa, T., et al., Data Submission, Isoleucyl–tRNA Synthetase, *Pseudomonas fluorescens*, Swiss–Prot Accession No. P18330 (1990).

Jenal, U., et al., Data Submission, Hypothetical 43.7 kD Protein in IleS 5′ Region, *Methanobacterium thermoautotrophicum*, Swiss–Prot Accession No. P26498 (1992).

Jones, M.D., et al., Data Submission, Tyrosyl–tRNA Synthetase, *Bacillus caldotenax*, Swiss–Prot Accession No. P04077 (1986).

Winter, G., et al., Data Submission, Tyrosyl–tRNA Synthetase, *Bacillus stearothermophilus*, Swiss–Prot Accession No. P00952 (1986).

Barker, D.G., et al., Data Submission, Tyrosyl–tRNA Synthetase, *Escherichia coli*, Swiss–Prot Accession No. P00951 (1986).

Parkhill, J., et al., Data Submission, Tyrosyl–tRNA Synthetase, *Mycobacterium tuberculosis*, EMBL Accession No. Z98268 (1997).

Parkhill, J., et al., Data Submission, TyrS., *Mycobacterium leprae*, EMBL Accession No. Z95117 (1997).

Blattner, F.R., et al., Data Submission, Tyrosyl–tRNA Synthetase, *Escherichia coli*, GenBank Accession No. AE000259 (1997).

Akins, R.A., et al., Data Submission, Tyrosyl–tRNA Synthetase, Mitochondrial Precursor, *Neurospora crassa*, Swiss–Prot Accession No P12063 (1989).

Henkin, T.M., et al., Data Submission, Tyrosyl–tRNA Synthetase, *Bacillus subtilis*, Swiss–Prot Accession No. P22326 (1991).

Härtlein, M., et al., Data Submission, Seryl–tRNA Synthetase, *Escherichia coli*, Swiss–Prot Accession No. P09156 (1989).

Weygand–Duraševič, I., et al., Data Submission, Seryl–tRNA Synthetase, Cytoplasmic, *Saccharomyces cerevisiae*, Swiss–Prot Accession No. P07284 ((1988).

Lunel, C., et al., Data Submission, Seryl–tRNA Synthetase, *Cricetulus griseus*, Swiss–Prot Accession No. P26636 (1992).

Brakhage, A.A., et al., Data Submission, Phenylalanyl–tRNA Synthetase Alpha Chain, *Bacillus subtilis*, Swiss–Prot Accession No P17921 (1990).

Brakhage, A.A., et al., Data Submission, Phenylalanyl–tRNA Synthetase Beta Chain, *Bacillus subtilis*, Swiss–Prot Accession No. P17922 (1990).

Fayat, G., et al., Data Submission, Phenylalanyl–tRNA Synthetase Alpha Chain, *Escherichia coli*, Swiss–Prot Accession No. P0312 (1988).

Mechulam, Y., et al., Data Submission, Phenylalanyl–tRNA Synthetase Beta Chain, *Escherichia coli*, Swiss–Prot Accession No. P07395 (1988).

Fleischmann, R.D., et al., Data Submission, Phenylalanyl–tRNA Synthetase Alpha Chain, *Haemophilus influenzae*, Swiss–Prot Accession No. P43819 (1995).

Fleischmann, R.D., et al., Data Submission, Phenylalanyl–tRNA Synthetase Beta Chain, *Haemophilus influenzae*, Swiss–Prot Accession No. P43820 (1995).

Keller, B., et al., Data Submission, Phenylalanyl–tRNA Synthetase Alpha Chain, *Thermus aquaticus thermophilus*, Swiss Prot Accession No. P27001 (1992).

Keller, B., et al., Data Submission, Phenylalanyl–tRNA Synthetase Beta Chain, *Thermus aquaticus thermophilus*, Swiss–Prot Accession No. P27002 (1992).

Fraser, C.M., et al., Data Submission, Phenylalanyl–tRNA Synthetase Alpha Chain, *Mycoplasma genitalium*, Swiss–Prot Accession No. P47436 (1996).

Fraser, C.M., et al., Data Submission, Phenylalanyl–tRNA Synthetase Beta Chain, *Mycoplasma genitalium*, Swiss–Prot Accession No. P47437 (1996).

Barstow, D.A., et al., Data Submission, Tryptophanyl–tRNA Synthetase, *Bacillus stearothermophilus*, Swiss–Prot Accession No. P00953 (1986).

Chow, K.C., et al., Data Submission, Tryptophanyl–tRNA Synthetase, *Bacillus subtilis*, Swiss–Prot Accession No. P21656 (1991).

Hall, C.V., et al., Data Submission, Tryptophanyl–tRNA Synthetase, *Escherichia coli*, Swiss–Prot Accession No. P00954 (1986).

Moriya, S., et al., Data Submission, 180 Kilobase Region of Replication Origin, *Bacillus subtilis*, pp. 1–85, DDBJ Accession No. D26185 (1993).

Samuel, C.E. and Rabinowitz, J.C., "Methionyl Transfer RNA of Folate Sufficient and Folate Deficient *Streptococcus faecalis* R," *Fed. Proc.* 31(2):449Abs, Abstract No. 1313 (1972).

Chalker, A.F., Data Submission, *S. aureus* Gene for Isoleucyl–tRNA Synthetase, *Staphylococcus aureus*, EMBL Accession No. X74219 (1997).

Henkin, Tina M., "tRNA–Directed Transcription Antitermination," *Molecular Microbiology* 13(3):381–387 (1994).

Barstow, D.A., et al., Data Submission, *B. stearothermophilus* trpS Gene Encoding Tryptophanyl–tRNA Synthetase, *Bacillus stearothermophilus*, GenBank Accession No. M14742 (1990).

Winter, G., et al., Data Submission, *B. stearothermophilus* Tyrosyl–tRNA Synthetase Gene, *Bacillus stearothermophilus*, GenBank Accession No. J01546 (1990).

Borgford, T. J., et al., Data Submission, *B. stearothermophilus* valS Gene Encoding Valyl–tRNA Synthetase, *Bacillus stearothermophilus*, GenBank Accession No. M16318 (1989).

Breton, R., et al., Data Submission, *Bacillus subtilis* Glutamyl–tRNA Transferase (gltx), Serine Acetyltransferase (cysE), and Cysteinyl–tRNA Synthetase (cysS) Genes, *Bacillus subtilis*, GenBank Accession No. L14580 (1994).

Vander Horn, P.B. and Zahler, S.A., Data Submission, *Bacillus subtilis* Leucyl–Transfer RNA Synthase (leuS) Gene, *Bacillus subtilis*, GenBank Accession No. M88581 (1992).

Putzer, H., Data Submission, *B. subtilis* pheS and pheT Genes for Phenylalanyl–tRNA Synthetase Alpha and Beta Subunits, *Bacillus subtilis*, EMBL Accession No. X53057 (1996).

Putzer, H., et al., Data Submission, *B. subtilis* Threonyl–tRNA Synthetase (thrSv) Gene, *Bacillus subtilis*, GenBank Accession No. M36594 (1990).

Putzer, H., et al., Data Submission, *B. subtilis* Threonyl–tRNA Synthetase (thrS2) Gene, *Bacillus subtilis*, GenBank Accession No. M36593 (1990).

Chow, K.–C. and Wong, J.T.–F, Data Submission, *B. subtilis* trpS Gene Encoding Tryptophanyl–tRNA Synthetase, *Bacillus subtilis*, GenBank Accession No. M24068 (1990).

Henkin, T.M., et al., Data Submission, *Bacillus subtilis* Tyrosine–Transfer RNA Synthetase (tyrS) Gene, *Bacillus subtilis*, GenBank Accession No. M77668 (1993).

Danchin, A., Data Submission, *Bacillus subtilus* tyrS1 Gene for Tyronsine tRNA Synthetase, sacX and sacY Genes, and Three ORFs, *Bacillus subtilis*, EMBL Accession No. X52480 (1993).

Taylor, B.V., et al., Data Submission, *Lactobacillus casei* Valyl–tRNA Synthetase Gene, *Lactobacillus casei*, GenBank Accession No. L08854 (1994).

ENTEROCOCCAL AMINOACYL-TRNA SYNTHETASE PROTEINS, NUCLEIC ACIDS AND STRAINS COMPRISING SAME

BACKGROUND

The genus Enterococcus has been established as a separate genus from Streptococcus, based on nucleic acid hybridization studies (Schleifer, K. H. and R. Kilpper-Bälz, *Int. J. Syst. Bacteriol.* 344:31–34 (1984)). The enterococci include the species *E. faecalis, E. faecium, E. avium, E. casseliflavus, E. durans, E. gallinarum, E. malodoratus, E. raffinosus, B. pseudoavium, E. soliltarius, E. mundtii,* and *E. hirae* (Murray, B. E., "Enterococci," pp. 1415–1420 In Gorbach, S. L., et al., eds., *Infectious Diseases,* W. B. Saunders Co., Harcourt Brace Jovanovich, Inc., Philadelphia, 1992).

*Enterococcus faecalis* and *Enterococcus faecium* are the two most clinically important strains of the genus Enterococcus, accounting for over 95% of all enterococcal infections. As part of the normal flora of the human bowel and genital tract, the enterococci had not been thought to cause serious infection. In recent years, however, the enterococci have emerged as clinically important pathogens responsible for 5–15% of bacterial endocarditis, 15% of intra-abdominal pelvic and wound infections, 5–10% of spontaneous peritonitis, 5–10% of nosocomial bacteremia and 15% of nosocomial urinary tract infections (ibid). Enterococcal isolates are increasingly responsible for nosocomial infections and are a common cause of morbidity and mortality. Recently they have been cited as the second most common pathogen isolated from hospitalized patients (Schaberg, D. R. et al., *Am. J. Med.* 91:(suppl. 3B) 72S–75S (1991)).

The increase in enterococcal disease is most likely due to an increase in the use of invasive devices, an increase in the number of seriously ill patients and an increase in the use of antimicrobial agents to which enterococci have developed resistance (Nicoletti, G. and Stefani, *Eur. J. Clin. Microbiol. Infect. Dis.* 14: (suppl. 1) 33S–37S (1995)).

Enterococci are intrinsically resistant to a large number of antimicrobial agents including beta lactams, polymyxins and lincosamides. In addition, many species have developed resistance to a number of other antimicrobial agents including ampicillin, aminoglycosides, chloramphenicol, erythromycin and vancomycin. Many strains of enterococci now exhibit multiple drug resistance. Some nosocomial isolates of enterococci have displayed resistance to essentially every useful antimicrobial agent, exemplifying the increased difficulty in treating and controlling enterococcal infections (Jones, R. N. et al., *Diagn. Microbiol. Infect. Dis.* 21:95–100 (1995); Jones, R. N. et al., *Diagn. Microbiol. Infect. Dis.* 21:85–93 (1995)).

The incidence of resistance to antimicrobial agents among enterococci is continuing to rise at an alarming rate. The ability of this genus to develop and acquire new resistance has lead, in some cases, to ineffective treatments with agents currently available. The development of a new generation or class of antimicrobial agent is clearly needed to solve the growing threat which enterococcal infections present.

The design of effective antibiotics should exploit the biological differences between the pathogen and host. Designing new antibiotics requires the identification of potential targets in enterococci such as *Enterococcus faecalis*. The search for exploitable differences in the enzymatic pathways of *E. faecalis* and humans is hindered by the limited understanding of the biology of enterococci.

SUMMARY OF THE INVENTION

The invention relates to isolated and/or recombinant nucleic acids which encode Enterococcus (or enterococcal) aminoacyl-tRNA synthetases, including those isolated from naturally occurring enterococci. The invention also relates to recombinant nucleic acid constructs and vectors comprising nucleic acid having a sequence which encodes an enterococcal aminoacyl-tRNA synthetase, or portions of such enzyme. These nucleic acids and DNA constructs can be used in host cells to produce recombinant enterococcal aminoacyl-tRNA synthetases.

A further embodiment of the invention is antisense nucleic acid which can hybridize to the nucleic acid which encodes an aminoacyl-tRNA synthetase of enterococci. In cells, antisense nucleic acid can inhibit the function of a nucleic acid which encodes an aminoacyl-tRNA synthetase of enterococci.

The invention also relates to proteins or polypeptides, referred to herein as isolated and/or recombinant enterococcal aminoacyl-tRNA synthetases, and more specifically, phenylalanyl-, tryptophanyl-, isoleucyl-, leucyl-, tyrosyl-, and seryl-tRNA synthetases. These enzymes are useful in the biochemical separation of the amino acid which they specifically recognize and in quantitations of the amino acid and ATP. Antibodies which bind to these enzymes can be made and can be used in the purification and study of the enzymes.

The above recombinant enterococcal aminoacyl-tRNA synthetases can be produced in host cells described herein. Tester strains, which are cells engineered to rely on the function of the tRNA synthetase encoded by an introduced cloned gene, are also an embodiment of the invention. Tester strains can be used to test the effectiveness of drug candidates in the inhibition of the essential tRNA synthetase enzyme encoded by the introduced cloned gene. The isolated and/or recombinant enterococcal phenylalanyl-, tryptophanyl-, isoleucyl-, leucyl-, tyrosyl-, and seryl-tRNA synthetases can be used in methods for detecting and identifying inhibitors of their activities. In these ways, potential inhibitors of the enzyme can be screened for antimicrobial or antibiotic effects, without requiring the culture of pathogenic strains of Enterococcus, such as *Enterococcus faecalis*.

DETAILED DESCRIPTION OF THE INVENTION

Figure 1:
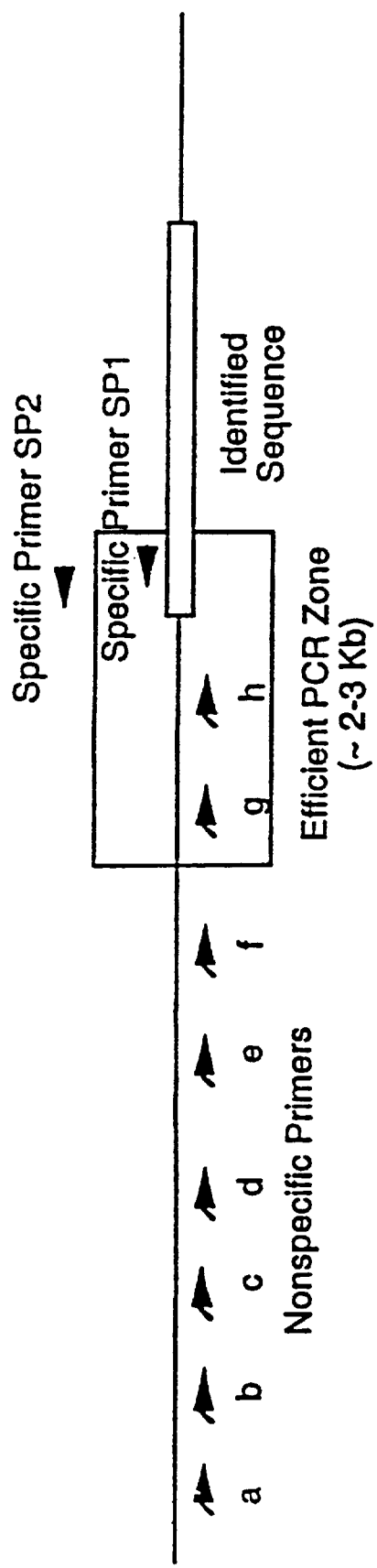
FIG. 1 is an illustration of the strategy for semi-specific PCR (polymerase chain reaction). A series of nonspecific primers (a–h) were each used in separate PCR amplifications to pair with a specific primer SP1. The annealing of the nonspecific primer is possible under certain conditions, since statistically, short stretches of DNA complementary to the 3' ends of those nonspecific primers occur periodically in the bacterial genome. As shown here, nonspecific primers g and h anneal to the template close enough to the site where SP1 anneals (to the complementary template strand) to efficiently produce PCR products from primer pairs SP1/g and SP1/h. A second specific primer, SP2, is located downstream of SP1, and is used for screening the desired semi-specific PCR products by DNA sequencing.

The aminoacyl-tRNA synthetases are enzymes with the common general function of catalyzing the following reaction:

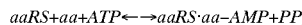

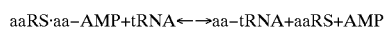

(aaRS=aminoacyl-tRNA synthetase; aa=amino acid; ATP=adenosine 5'-triphosphate; AMP=adenosine 5'-monophosphate; $PP_i$=inorganic pyrophosphate) The second (aminoacylation) step is often referred to as "charging" the tRNA.

Generally, with the exception of some Gram-positive bacteria studied, in which one aminoacyl-tRNA synthetase can charge both $tRNA^{Glu}$ and $tRNA^{Gln}$, there are 20 aminoacyl-tRNA synthetases, each specific for a different amino acid, in each bacterial organism. Eucaryotic organisms also typically encode 20 cytoplasmic aaRSs, one specific for each amino acid. In addition, eucaryotic organisms generally encode a separate set of mitochondrial aaRSs. In the yeast *Saccharomyces cerevisiae*, the cytoplasmic and mitochondrial enzymes are encoded by separate nuclear genes. However, several exceptions have been found in which one gene encodes both cytoplasmic and mitochondrial enzyme, for example, the histidyl- and valyl-tRNA synthetases (Natsoulis, G., et al. *Cell* 46:235–243 (1986); Chatton, B. et al., *J. Biol. Chem.* 263:52–57 (1988)). Generally, each aminoacyl-tRNA synthetase recognizes and reacts with a specific amino acid and with one or more tRNAs that recognize the codons specific for that amino acid (cognate tRNAs). The specificity of the aaRS for the amino acid is determined by protein-amino acid interactions, and the specificity of the aaRS for the tRNA is determined by protein-RNA interactions, using different sites on the aaRS and tRNA molecules.

The tRNA synthetases can be subdivided into two groups of enzymes, class I and class II, based on short regions of sequence homology as well as distinct active site core tertiary structures (Eriani, G., et al., *Nature* 347:203–206 (1990); Moras, D., *Trends Biochem. Sci.* 17:159–164 (1992)). The twenty tRNA synthetases of *E. coli* have been divided into two classes of ten enzymes each (see, e.g., Burbaum, J. J. and P. Schimmel, *J. Biol. Chem.* 266(26):16965–16968 (1991)). The isoleucyl-, leucyl-, tryptophanyl- and tyrosyl-tRNA synthetases are class I enzymes; the phenylalanyl- and seryl-tRNA synthetases are class II enzymes.

Nucleic Acids, Constructs and Vectors

The present invention relates to isolated and/or recombinant (including, e.g., essentially pure) nucleic acids having sequences which encode an Enterococcus (or enterococcal) aminoacyl-tRNA synthetase, or a portion of an Enterococcus aminoacyl-tRNA synthetase. In one embodiment, the nucleic acid or portion thereof encodes a protein or polypeptide having at least one function characteristic of an Enterococcus aminoacyl-tRNA synthetase specific for a selected amino acid, such as a catalytic activity (e.g., catalysis of aminoacyl-adenylate formation, formation of $PP_i$, catalysis of aminoacylation of a tRNA), and/or binding function (e.g., tRNA-, amino acid- or ATP-binding) and/or antigenic function (e.g., binding of antibodies that also bind to a naturally occurring enterococcal aaRS), and/or oligomerization function. Oligomerization activity is the ability of a protein subunit or protein fragment to bind together with one or more other protein subunits or protein fragments, thus altering the quaternary structure of the resulting complex. For example, "adhesive" fragments with oligomerization activity can bind to another fragment with no catalytic activity of its own to restore or partially restore catalytic activity (Jasin, M., et al., U.S. Pat. No. 4,952,501). The present invention also relates more specifically to isolated and/or recombinant nucleic acids or a portion thereof having sequences which encode an aminoacyl-tRNA synthetase of *Enterococcus faecalis* origin, or a portion thereof.

The invention further relates to isolated and/or recombinant nucleic acids that are characterized by (1) their ability to hybridize to a nucleic acid encoding an Enterococcus aminoacyl-tRNA synthetase specific for a selected amino acid, such as a nucleic acid having a sequence shown in SEQ ID NO:1, SEQ ID NO:3, SEQ ID NO:5, SEQ ID NO:7, SEQ ID NO:10 or SEQ ID NO:12, or to portions of any of the foregoing (e.g., a portion comprising the open reading frame(s)), or by (2) their ability to encode a polypeptide having the amino acid sequence of an Enterococcus aminoacyl-tRNA synthetase or a subunit thereof, such as a polypeptide having the amino acid sequence shown in the open reading frames in SEQ ID NO:2, SEQ ID NO:4, SEQ ID NO:6, SEQ ID NO:8, (α subunit), SEQ ID NO:9, (β subunit), SEQ ID NO:11 or SEQ ID NO:13, portions thereof, or functional equivalents thereof (e.g., a polypeptide which aminoacylates isoaccepting tRNAs (such as tRNA$^{Phe}$, tRNA$^{Leu}$, tRNA$^{Tyr}$, tRNA$^{Ile}$, tRNA$^{Ser}$, or tRNA$^{Trp}$ of *E. faecalis*, with the appropriate amino acid), or by (3) both characteristics (1) and (2).

The ability to hybridize to a nucleic acid encoding an enterococcal aminoacyl-tRNA synthetase as described above includes hybridization to the strand shown in any of SEQ ID NO:1, SEQ ID NO:3, SEQ ID NO:5, SEQ ID NO:7, SEQ ID NO:10, SEQ ID NO:12, or to the strand which is complementary to the one shown. A nucleic acid which hybridizes to a nucleic acid encoding an enterococcal aaRS, such as DNA having the sequences shown in SEQ ID NO:1, SEQ ID NO:3, SEQ ID NO:5, SEQ ID NO:7, SEQ ID NO:10, or SEQ ID NO:12, can be double- or single-stranded.

Recombinantly produced enterococcal aminoacyl-tRNA synthetases, whether having an amino acid sequence of an enterococcal aminoacyl-tRNA synthetase which can be isolated from naturally-occurring enterococci, or whether having the amino acid sequence of a polypeptide which is a functional equivalent of an enterococcal aminoacyl-tRNA synthetase, can be encoded by nucleic acids which hybridize to a nucleic acid shown in SEQ ID NO:1, SEQ ID NO:3, SEQ ID NO:5, SEQ ID NO:7, SEQ ID NO:10 or SEQ ID NO:12, as in characteristic (1) above.

In one embodiment, the percent nucleotide sequence identity between the nucleic acids having the nucleotide sequences in the coding regions of SEQ ID NO:1, SEQ ID NO:3, SEQ ID NO:5, SEQ ID NO:7, SEQ ID NO:10 and SEQ ID NO:12, and nucleic acids encoding the respective functional equivalents of the polypeptides encoded by these nucleic acids (IleRS, LeuRS, TrpRS, PheRS, TyrRS and SerRS, respectively) is at least about 70%. In a preferred embodiment, the percent nucleotide sequence identity between the nucleic acids having the nucleic acid sequences shown in SEQ ID NO:1, SEQ ID NO:3, SEQ ID NO:5, SEQ ID NO:7, SEQ ID NO:10 and SEQ ID NO:12, and nucleic acids encoding the respective functional equivalents of the polypeptides encoded by these nucleic acids is at least about 80%, and still more preferably, at least about 90%.

Isolated and/or recombinant nucleic acids meeting these criteria comprise nucleic acids having sequences identical to sequences of naturally occurring enterococcal aaRS genes, including polymorphic or allelic variants, and portions thereof, or variants of the naturally occurring genes. Such variants include mutants differing by the addition, deletion or substitution of one or more residues, modified nucleic acids in which one or more residues are modified (e.g., DNA or RNA analogs), and mutants comprising one or more modified residues. Preferred embodiments of isolated and/or recombinant nucleic acids are those encoding seryl-, isoleucyl-, leucyl-, tryptophanyl-, tyrosyl-, or phenylalanyl-tRNA synthetase of those species of genus Enterococcus which can be found to cause infections in humans or in animals, including, but not limited to *E. faecalis, B. faecium, E. avium, E. casseliflavus, E. durans, E. gallinarum, E. malodoratus, E. raffinosus, E. pseudoavium, E. solitarius, E. mundtii*, and *E. hirae*.

Such nucleic acids, including DNA or RNA, can be detected and/or isolated by hybridization (e.g., under high stringency conditions or moderate stringency conditions). "Stringency conditions" for hybridization is a term of art which refers to the conditions of temperature and buffer concentration which permit hybridization of a particular nucleic acid to a second nucleic acid in which the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" and "moderate stringency conditions" for nucleic acid hybridizations are explained on pages 2.10.1–2.10.16 (see particularly 2.10.8–11) and pages 6.3.1–6 in *Current Protocols in Molecular Biology* (Ausubel, F. M. et al., eds., Vol. 1, containing supplements up through Supplement 29, 1995), the teachings of which are hereby incorporated herein by reference. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

By varying hybridization conditions from a level of stringency at which no hybridization occurs to a level at which hybridization is first observed, conditions which will allow a given sequence to hybridize with the most similar sequences in the sample can be determined. Exemplary conditions are described in Krause, M. H. and S. A. Aaronson, *Methods in Enzymology*, 200:546–556 (1991). Also, see especially page 2.10.11 in *Current Protocols in Molecular Biology* (supra), which describes how to determine washing conditions. Washing is the step in which conditions are usually set so as to determine a minimum level of complementarity of the hybrids and to eliminate non-hybridizing radioactive probe as well as background and non-specific weak interactions. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$ of ~17° C. Using these guidelines, the washing temperature can be determined empirically for high, moderate or low stringency, depending on the level of mismatch sought.

Isolated and/or recombinant nucleic acids that are characterized by their ability to hybridize to a nucleic acid encoding an Enterococcus aminoacyl-tRNA synthetase (for example, those nucleic acids having the sequences shown in SEQ ID NO:1, SEQ ID NO:3, SEQ ID NO:5, SEQ ID NO:7, SEQ ID NO:10 or SEQ ID NO:12, or to a portion of such nucleic acids (e.g., under high or moderate stringency conditions), may further encode a protein or polypeptide having at least one function characteristic of an Enterococcus aminoacyl-tRNA synthetase specific for a selected amino acid, such as a catalytic activity (e.g., formation of $PP_i$, aminoacyl-adenylate formation, aminoacylation of a tRNA with amino acid), a binding function (e.g., tRNA-, amino acid-, or ATP-binding), an antigenic function (e.g., binding of antibodies that also bind to a naturally occurring enterococcal aaRS), and/or an oligomerization function. The catalytic or binding function of a protein or polypeptide encoded by hybridizing nucleic acid can be detected by enzymatic assays for activity or binding (e.g., assays which monitor formation of aminoacyl-adenylate or $PP_i$, aminoacylation of tRNA). Functions characteristic of the aminoacyl-tRNA synthetase encoded by the isolated nucleic acids can also be assessed by in vivo complementation activity or other suitable methods. Enzymatic assays, complementation tests, or other suitable methods can be used in procedures for the identification and/or isolation of a nucleic acid which encodes a polypeptide such as a polypeptide having the amino acid sequence shown in SEQ ID NO:2, SEQ ID NO:4, SEQ ID NO:6, SEQ ID NO:11 or SEQ ID NO:13, or a nucleic acid which encodes polypeptides such as those having the amino acid sequences shown in SEQ ID NO:8, or SEQ ID NO:9, or functional equivalents of these polypeptides which possess one or more of the described activities or functions. The antigenic properties of proteins or polypeptides encoded by hybridizing nucleic acids can be determined by immunological methods employing antibodies that bind to an Enterococcus aminoacyl-tRNA synthetase, such as by immunoblot, immunoprecipitation or radioimmunoassay.

Nucleic acids of the present invention can be used in the production of proteins or polypeptides. For example, nucleic acids comprising all or part of a coding sequence for an Enterococcus isoleucyl-tRNA synthetase, or nucleic acids which hybridize to DNA having the sequence shown in SEQ ID NO:1, can be incorporated into various constructs and into vectors created for further manipulation of sequences or for production of the encoded polypeptide in suitable host cells. The same applies for nucleic acids comprising all or part of a coding sequence for an Enterococcus leucyl-tRNA synthetase, or nucleic acids which hybridize to DNA having the sequence shown in SEQ ID NO:3; nucleic acids comprising all or part of a coding sequence for an Enterococcus tryptophanyl-tRNA synthetase, or nucleic acids which hybridize to DNA having the sequence shown in SEQ ID NO:5; nucleic acids comprising all or part of a coding sequence for an Enterococcus phenylalanyl-tRNA synthetase, or nucleic acids which hybridize to DNA having the sequence shown in SEQ ID NO:7; nucleic acids comprising all or part of a coding sequence for an Enterococcus tyrosyl-tRNA synthetase, or nucleic acids which hybridize to DNA having the sequence shown in SEQ ID NO:10; nucleic acids comprising all or part of a coding sequence for an Enterococcus seryl-tRNA synthetase, or nucleic acids which hybridize to DNA having the sequence shown in SEQ ID NO:2.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as PCR and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

Portions of the isolated nucleic acids which code for polypeptides having a certain function can be identified and isolated by, for example, the method of Jasin, M., et al., U.S. Pat. No. 4,952,501. The aminoacyl-tRNA synthetases are known to have different quaternary structures, including both monomeric and multimeric structures (e.g., homodimers, tetramers and heteromultimeric $\alpha_2\beta_2$ forms). Thus, as used herein, a nucleic acid which encodes a portion of an Enterococcus aminoacyl-tRNA synthetase can also encode one of two or more distinct subunits of said tRNA synthetase. In a preferred embodiment, nucleic acids of the present invention are at least about 8, 12, 18, 25, 40, or 50 nucleotides in length. More preferably, the nucleic acids also hybridize specifically to one or more open reading frames among the DNAs having a sequence shown in SEQ ID NO:1, SEQ ID NO:3, SEQ ID NO:5, SEQ ID NO:7, SEQ ID NO:10 or SEQ ID NO:12. That is, specific hybridization occurs between a nucleic acid of the present invention and the double-stranded form of a DNA shown in the foregoing figures, or the complement of a single-stranded DNA having a sequence shown in the foregoing figures.

A further embodiment of the invention is antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell, antisense nucleic acid can inhibit the expression of the gene encoded by the sense strand. Antisense nucleic acids can be produced by standard techniques.

In a particular embodiment, the antisense nucleic acid is wholly or partially complementary to and can hybridize with a target nucleic acid, wherein the target nucleic acid can hybridize to a nucleic acid having the sequence of the complement of the strand shown in SEQ ID NO:1, SEQ ID NO:3, SEQ ID NO:5, SEQ ID NO:7, SEQ ID NO:10 or SEQ ID NO:12. For example, antisense nucleic acid can be complementary to a target nucleic acid having the sequence shown as the coding regions in SEQ ID NO:1, SEQ ID NO:3, SEQ ID NO:5, SEQ ID NO:7, FIG. SEQ ID NO:10 or SEQ ID NO:12 or to a portion of any of the foregoing sufficient to allow hybridization. In another embodiment, the antisense nucleic acid is wholly or partially complementary to and can hybridize with a target nucleic acid which encodes an Enterococcus aminoacyl-tRNA synthetase.

An enterococcal aaRS gene or portion thereof is producible by methods described herein or other suitable methods. For example, primers (e.g., a pair of primers or nested primers) can be designed which comprise a sequence which is complementary or substantially complementary to a portion of the gene encoding an enterococcal aaRS. Primers can contain portions which are complementary to other sequences as appropriate, such as restriction recognition sequences, template sequences (e.g., vector sequences flanking the inserts in a gene library) or other sequences. For instance, pairs of primers complementary to the 5' and 3' ends of the coding sequence and/or flanking regions shown in SEQ ID NO:1, SEQ ID NO:3, SEQ ID NO:5, SEQ ID NO:7, SEQ ID NO:10 or SEQ ID NO:12 can be designed. Such primers can be used in a polymerase chain reaction with a suitable nucleic acid template (e.g., a construct described herein, genomic DNA, a library or another suitable nucleic acid) to obtain an enterococcal aaRS gene or portion thereof.

The *E. faecalis* aminoacyl-tRNA synthetase genes isolated as described in the Examples are representative of a broader class of enterococcal aminoacyl-tRNA synthetase genes derived from various species of the genus Enterococcus. These additional genes can also be used to express enterococcal aminoacyl-tRNAs synthetases, with utilities corresponding to those described herein, and can be used in the production of host cells and tester strains comprising recombinant enterococcal aminoacyl-tRNA synthetase genes using methods described herein. The approaches described herein, including, but not limited to, the approaches to isolate and manipulate an aminoacyl-tRNA synthetase gene of *E. faecalis*, to construct vectors and host strains, and to produce and use the proteins, to produce antibodies, etc., can be applied to other members of the genus Enterococcus, including, but not limited to, species which can cause infections in humans and in animals, such as *E. faecalis, E. faecium, E. avium, E. casseliflavus, E. durans, E. gallinarum, E. malodoratus, E. raffinosus, E. pseudoavium, E. solitarius, E. mundtii,* and *E. hirae*. For example, the *E. faecalis* aminoacyl-tRNA synthetase genes described in the Examples, or sufficient portions thereof, whether isolated and/or recombinant or synthetic, including fragments produced by PCR, can be used to detect and/or recover genes related by sequence similarity from other enterococcal species (e.g., as probes for hybridization or primers for PCR, or in other suitable techniques), from genomic DNA, from an ordered cosmid library or from other suitable sources (e.g., libraries constructed in bacteriophages and plasmids), according to suitable methods.

For example, the identification of additional enterococcal aaRS genes can be accomplished by an extension of the methods used to clone *E. faecalis* aaRSs as described in Examples 2–4. Pairs of degenerate oligonucleotides that were successfully used in a PCR amplification to identify the *E. faecalis* aaRS genes can be used in PCRs using the reaction conditions described below or other suitable conditions. Since these primer pairs, which were created based upon DNA sequence information of non-enterococcal species, were able to amplify an *E. faecalis* PCR product, it is expected that they can be used to amplify a PCR product using template nucleic acid from other species of enterococci, as the genes for each specific aaRS are expected to be closely related in DNA sequence to each other within Enterococcus. The sequence information generated for *E. faecalis* aaRS genes can also be used to design more accurately biased degenerate primers, which can be used alone or in combination with other primers for amplifying aaRS genes of other enterococcal species. The following exemplary PCR reaction conditions can be used: 10 mM Tris-HCl (pH 8.3), 50 mM KCl, 2.5 mM $MgCl_2$, 200 $\mu$M each dinucleotide triphosphate (dNTP), 10–30 ng of genomic DNA of the enterococcal species, 100 pmole of each of the primers, and 2.5 units of Taq polymerase (Boehringer Mannheim). Cycling conditions can be, for example, 30 cycles of denaturing at 95° C. for 30 seconds, annealing at 50° C. for 30 seconds, and elongation at 72° C. for 2 minutes. If it is found that lower stringency is needed, lower annealing temperatures can be used, such as 40–45° C. If extraneous PCR fragments are produced under these conditions, higher stringency conditions can be used (for example, by raising the annealing temperature to about 55° C. or higher as needed) to eliminate any artifactual PCR products.

Once a fragment of the enterococcal aaRS gene is generated by PCR, it can be sequenced, and the sequence of the product can be compared to other DNA sequences, for example, by using the BLAST Network Service at the National Center for Biotechnology Information. The boundaries of the open reading frame can then be identified using semi-specific PCR or other suitable methods such as library screening. Once the 5' initiator methionine codon and the 3' stop codon have been identified, a PCR product encoding the full-length gene can be generated using genomic DNA as a template, with primers complementary to the extreme 5' and 3' ends of the gene or to their flanking sequences. The full-length genes can then be cloned into expression vectors for the production of functional proteins.

*E. faecalis* aaRS genes or portions thereof can be used as probes to identify DNA fragments encoding the corresponding aaRS gene from other species of enterococci by specific hybridization (e.g., by Southern blot). It is predicted that the genes encoding aaRSs from other enterococcal species have a high degree of similarity to the corresponding *E. faecalis* aaRS gene. To identify DNA fragments encoding the aaRS genes from other enterococcus species using *E. faecalis* aaRS genes or gene fragments as probes, a systematic, stepwise series of washes of the Southern blot filter can be done in order of increasing stringency conditions, from low to high, as described below.

A filter can be prepared bound with fragmented DNA from the enterococcal species of interest as well as with DNA from *E. faecalis* (as a positive control) and DNA from a suitable non-Enterococcus species such as *B. subtilis* (as a negative control). The filter can be probed with the radioactively labelled full-length or partial *E. faecalis* aaRS gene under medium stringency conditions, such as 37° C. for 16 hr in 50% formamide, 5×SSC, 1×Denhardt's solution, 0.1% sodium dodecyl sulfate (SDS), and 100 $\mu$g/ml sheared salmon sperm DNA. The probed blot can then be washed with wash buffers of increasing stringency, with monitoring for decreasing background while maintaining a positive signal (presence of a band at the expected molecular weight). An example of the progression of wash buffers is: 2×SSC/0.1% SDS at 37° C. (low stringency wash), then 1×SSC/0.1% SDS at 37° C. (or 42° C.), then finally 0.2× SSC/0.1% SDS at 42° C. (moderate stringency wash). Each wash can be followed by monitoring the signal to noise ratio, e.g., with a Geiger counter. When the background counts become sufficiently low (e.g., detection of a positive signal for the positive control and no signal for the negative control), washing can be terminated and the blot exposed to X-ray film. Using these conditions, it is expected that the *E. faecalis* aaRS genes or gene fragments, when used as probes, can hybridize to the corresponding aaRS genes from other organisms within the genus Enterococcus, using 0.2× SSC/0.1% SDS wash buffer at a temperature of 60° C.–65° C.

Proteins

The invention also relates to proteins or polypeptides encoded by nucleic acids of the present invention. The proteins and polypeptides of the present invention can be isolated and/or recombinant. Proteins or polypeptides referred to herein as "isolated" are proteins or polypeptides purified to a state beyond that in which they exist in cells and include proteins or polypeptides obtained by methods described herein, similar methods or other suitable methods, and also include essentially pure proteins or polypeptides, proteins or polypeptides produced by chemical synthesis or by combinations of biological and chemical methods, and recombinant proteins or polypeptides which are isolated. In one embodiment, proteins or polypeptides are isolated to a state at least about 75% pure; more preferably at least about 80% pure, and still more preferably at least about 85% pure, as determined by Coomassie blue staining of proteins on SDS-polyacrylamide gels. Proteins or polypeptides referred to herein as "recombinant" are proteins or polypeptides produced by the expression of recombinant nucleic acids.

In a preferred embodiment, an isolated protein comprising an enterococcal aaRS or functional portion thereof has at least one function characteristic of an Enterococcus aminoacyl-tRNA synthetase, for example, catalytic activity (e.g., catalysis of aminoacyl-adenylate formation, catalysis of $PP_i$ formation, catalysis of aminoacylation of a tRNA with amino acid), binding function (e.g., tRNA-, amino acid-, or ATP-binding), antigenic function (e.g., binding of antibodies that also bind to a naturally-occurring enterococcal aminoacyl-tRNA synthetase), and/or oligomerization activity. As such, these proteins are referred to as aminoacyl-tRNA synthetases of Enterococcus or enterococcal origin, or Enterococcus or enterococcal aminoacyl-tRNA synthetases, and include, for example, naturally occurring Enterococcus aminoacyl-tRNA synthetases (including polymorphic or allelic variants), variants (e.g., mutants) of those proteins and/or portions thereof. Such variants include mutants differing by the addition, deletion or substitution of one or more amino acid residues, or modified polypeptides in which one or more residues are modified, and mutants comprising one or more modified residues. Note that "amino acid" (e.g., isoleucine, leucine, tryptophan, phenylalanine, tyrosine and serine) as used herein is understood to encompass the different charged forms of the amino acid, including the salt forms found at neutral pH.

In a preferred embodiment, an isolated and/or recombinant enterococcal aminoacyl-tRNA synthetase or functional portion thereof is active, i.e., has a catalytic activity such as formation of aminoacyl-adenylate or $PP_i$ or catalysis of aminoacylation of an isoaccepting tRNA. In a particularly preferred embodiment, like naturally occurring Enterococcus aminoacyl-tRNA synthetases, isolated and/or recombinant Enterococcus aminoacyl-tRNA synthetases of the present invention aminoacylate the isoaccepting cognate tRNAs of the Enterococcus organism with the amino acid in a two-step reaction. For example, in the case of *E. faecalis*, an isolated, recombinant seryl-tRNA synthetase is able to aminoacylate each of the isoaccepting species of cognate $tRNA^{Ser}$ of *E. faecalis* with serine. In the first step, the seryl-tRNA synthetase catalyzes the covalent linkage of serine to ATP to form an aminoacyl-adenylate complex (seryl-adenylate) with the release of pyrophosphate, and, in a second step, catalyzes the covalent linkage of serine to a specific tRNA recognized by the enzyme, releasing AMP.

The isolated proteins of the invention include enterococcal aminoacyl-tRNA synthetases other than *E. faecalis* methionyl-tRNA synthetase and *E. faecalis* histidyl-tRNA synthetase, and more preferably, enterococcal aminoacyl-tRNA synthetases other than entercoccal methionyl-tRNA synthetases and enterococcal histidyl-tRNA synthetases. In a more preferred embodiment, the invention relates to enterococcal Ile-, Tyr-, Leu-, Trp-, Phe- and Ser-tRNA synthetases, and more preferably, to *E. faecalis* Ile-, Tyr-, Leu-, Trp-, Phe- and Ser-tRNA synthetases, or functional equivalents thereof. In one embodiment, the extent of amino acid sequence similarity between a polypeptide having one of the amino acid sequences shown in SEQ ID NO:2, SEQ ID NO:4, SEQ ID NO:6, SEQ ID NO:11 or SEQ ID NO:13, or shown as the translation of the first coding region in SEQ ID NO:8 or the translation of the second coding region in SEQ ID NO:9, and the respective functional equivalents of these polypeptides is at least about 80%. In a preferred embodiment, the degree of amino acid sequence similarity between an enterococcal IleRS, LeuRS, TrpRS, PheRS, TyrRS or SerRS, and the respective functional equivalents thereof is at least about 85%, and still more preferably, at least about 90%.

The invention further relates to fusion proteins, comprising an Enterococcus aminoacyl-tRNA synthetase or functional portion thereof (as described above) as a first moiety, linked to second moiety not occurring in the enterococcal enzyme as found in nature. Thus, the second moiety can be an amino acid or polypeptide. The first moiety can be in an N-terminal location, C-terminal location or internal to the fusion protein. In one embodiment, the fusion protein comprises an *E. faecalis* aminoacyl-tRNA synthetase as the first moiety, and a second moiety comprising a linker sequence and an affinity ligand.

Fusion proteins can be produced by a variety of methods. For example, a fusion protein can be produced by the insertion of an aaRS gene or portion thereof into a suitable expression vector, such as Bluescript SK +/− (Stratagene), pGEX-4T-2 (Pharmacia), pET-15b, pET-20b(+) or pET-24 (+) (Novagen). The resulting construct can be introduced into a suitable host cell for expression. Upon expression, fusion protein can be purified from a cell lysate by means of a suitable affinity matrix (see e.g., *Current Protocols in Molecular Biology* (Ausubel, F. M. et al., eds., Vol. 2, pp. 16.4.1–16.7.8, containing supplements up through Supplement 28, 1994).

The invention also relates to isolated and/or recombinant portions of an aminoacyl-tRNA synthetase of Enterococcus origin. A portion of an aminoacyl-tRNA synthetase of the group above can refer to one of two or more distinct subunits of said tRNA synthetase, for example. Portions of the enzyme can be made which have full or partial function on their own, or which when mixed together (though fully, partially, or nonfunctional alone), spontaneously assemble with one or more other polypeptides to reconstitute a functional protein having at least one function characteristic of an aminoacyl-tRNA synthetase. (See, e.g., Shiba, K. and Schimmel, P., *J. Biol. Chem.* 267:22703–22706 (1992) for an example of three inactive peptides from *E. coli* IleRS spontaneously assembling in vivo to reconstitute active enzyme; see also, Burbaum, J. and Schimmel, P., *Biochemistry* 30(2): 319–324 (1991), describing non-overlapping segments of *E. coli* MetRS that can fold together to reconstitute an active enzyme capable of recognizing and charging tRNA in vitro and in vivo; see also Jasin, M. et al. (U.S. Pat. No. 4,952,501) describing deletion studies of *E. coli* alanyl-tRNA synthetase which showed that large portions of the protein were unnecessary for specific aminoacylation activity.) Based on this type of analysis, functional portions of an Enterococcus aaRS can be made which have at least one function characteristic of an Enterococcus aminoacyl-tRNA synthetase, such as a catalytic function, binding function, antigenic function and/or oligomerization function. Studies on the structure and function of the aaRSs of other organisms provide the basis for dividing the Enterococcus aaRS enzymes into functional domains (Schimmel, P., *Current Biology* 1:811–816 (1991)).

The sequences and structures of the catalytic domains of tRNA synthetases which have been purified and studied led to the identification of two distinct classes designated class I and class II (Schimmel, P., *Ann. Rev. Biochem.* 56:125–158 (1987); Webster, T. A., et al., *Science* 226:1315–1317 (1984); Eriani, G. et al., *Nature* 347:203–206 (1990) and Cusack, S., et al., *Nature* 347:249–255 (1990)).

Class I enzymes, in general, have a well-conserved N-terminal nucleotide binding fold responsible for amino acid binding, aminoacyl-adenylate formation, and tRNA acceptor helix docking. The N-terminal Rossman nucleotide binding fold is comprised of alternating β-strands and α-helices. The HIGH tetrapeptide located in the first half of the Rossman fold and the KMSKS pentapeptide located in the second half of the Rossman fold are motifs conserved among the class I synthetases. The C-terminal domain contains residues needed for interactions with the parts of the tRNA distal to the amino acid attachment site (Shepard, A., et al., *Proc. Natl. Acad. Sci. U.S.A.* 89:9964–9968 (1992); Hou, Y. -M.,et al., *Proc. Natl. Acad. Sci. U.S.A.* 88:976–980 (1991)).

Within the class I and class II enzymes, subgroups can be identified. For example, five enzymes—cysteinyl-, isoleucyl-, leucyl-, methionyl-, and valyl-tRNA synthetases—have been grouped together because they are more closely related in sequence and arrangement of their domains to each other than to the other five members of class I (Hou, Y. -M., et al., *Proc. Natl. Acad. Sci. U.S.A.* 88:976–980 (1991); Eriani, G., et al., *Nucleic Acids Res.* 19:265–269 (1991)). In *E. coli*, these five enzymes of class I vary in size from 461 to 951 amino acids and are active as monomers. The size variation is in large part explained by the variability in the lengths of the two insertions designated connective polypeptide 1 (CP1), which is inserted between the second α-helix and third β-strand of the nucleotide binding fold, and CP2, which is placed between the third α-helix and fourth β-strand (Starzyk, R. M., et al., *Science* 237:1614–1618 (1987)). In all of these enzymes, CP1 is the larger of the two insertions and varies in *E. coli* from 61 in cysteinyl-tRNA synthetase to 300 amino acids in isoleucyl-tRNA synthetase (Hou, Y. -M., et al., *Proc. Natl. Acad. Sci. USA* 88:976–980 (1991)). While a portion of CP1 may be deleted from isoleucyl-tRNA synthetase without loss of aminoacylation function (Starzyk, R. M., et al., *Science* 237:1614–1618 (1987)), this insertion is known to facilitate acceptor helix interactions in the related glutaminyl-tRNA synthetase whose three dimensional structure in complex with tRNA$^{Gln}$ has been determined by X-ray crystallography (Rould, M. A. et al., *Science* 246:1135–1142 (1989)).

In some tRNA synthetases, the C-terminal domain interacts directly with the anticodon (Rould, M. A. et al., *Science* 246:1135–1142 (1989), while in other enzymes there is no contact made between the C-terminal domain and the anticodon (Biou, V., et al., *Science* 263:1404–1410 (1994)). To a first approximation, the two domains in class I tRNA synthetases interact with the two distinct domains of the L-shaped tRNA structure. Thus, the recognition elements of the tRNA synthetase and of the tRNA which are needed for the operational RNA code are segregated into discrete protein and RNA domains.

The primary sequence of the class II enzymes can be characterized by three motifs. These motifs are designated in the order they occur in the sequence as motif 1, motif 2, and motif 3. Although the motifs have a conserved core, they vary in length and are marked by as little as a single invariant amino acid residue.

The motif sequences are defined as follows:
Motif 1: gΦxxΦxPΦΦ
Motif 2: (F/Y/H)Rx(E/D)(4–12x)(R/H)xxxFxxx(D/E)
Motif 3: λxΦgΦgΦeRΦΦΦΦΦ

The abbreviations are: x, variant; Φ, hydrophobic; and λ, small amino acids. Lower case letters indicate that the amino acid is partially conserved. None of these motifs have been found in the class I family. With the exception of *E. coli* Gly- and Phe-tRNA synthetases which only contain a discernible motif 3, class II enzymes characterized to date incorporate all three motifs (Ribas de Pouplana, L. et al., *Protein Science* 2:2259–2262 (1993)).

The second class of tRNA synthetases was firmly defined when the crystal structure of the *E. coli* Ser-tRNA synthetase active site was shown to have no relationship to the Rossmann fold of class I enzymes (Cusack, S. C., et al., *Nature* 347:249–255 (1990)). X-ray diffraction investigations with an ATP-bound Ser-tRNA synthetase co-crystal from *T. thermophilus* revealed the details of a novel ATP binding site (Cusack, S., et al., In *The Translational Apparatus*, K. H. Nierhaus et al., eds., Plenum Press, New York, pp. 1–9, 1993; Belrhali, H., et al., *Science* 263:1432–1436 (1994); Biou, V., et al., *Science* 263:1404–1410 (1994)).

Motif 3 is comprised of a β-strand followed by an α helix and is characterized by a GLER sequence. This motif has been universally detected in all of the class II enzymes studied. The crystal structures of yeast Ser- and Asp- (Ruff, M. S. et al., *Science* 252:1682–1689 (1991)) tRNA synthetases suggest a role for motif 3 in amino acid and ATP binding. Mutations in this region have resulted in a reduction in binding and/or a high $K_m$ for amino acid or ATP binding (Eriani, G., et al., *Nature* 347:203–206 (1993); Anselme, J. and Hartlein, M., *FEBS Lett.* 280:163–166 (1991); Kast, P. and Hennecke, H., *J. Mol. Biol.*, 222:99–124 (1991); Kast, P. et al., *FEBS Lett.* 293:160–163 (1991); Lanker, S., et al., *Cell* 70:647–657 (1992)).

Yeast Asp-tRNA synthetase was the first class II enzyme to be co-crystallized with its cognate tRNA (Ruff, M., et al., *Science* 252:1682–1689 (1991)). The yeast Asp-tRNA synthetase contains a nucleotide binding structure similar to that found in Ser-tRNA synthetase. The combination of these two class II crystal structures provides a model for the active sites of all of the class II tRNA synthetases.

Because motif 1 is at the dimer interface in the crystal structures of yeast Asp-tRNA synthetase (Ruff, M. S., et al., *Science* 252:1682–1689 (1991) and *E. coli* Ser-tRNA synthetase (Cusack, S., et al., *Nature* 347:249–255 (1990); Cusack, S., et al., In *The Translational Apparatus*, K. H. Nierhaus et al., eds., Plenum Press, New York, pp. 1–9, 1993; Price, S., et al., FEBS Lett. 324:167–170 (1993)) and *T. thermophilus* Ser-tRNA synthetase (Cusack, S., et al., In *The Translational Apparatus*, K. H. Nierhaus et al., eds., Plenum Press, New York, pp. 1–9, 1993; Belrhali, H., et al., *Science* 263:1432–1436 (1994); Biou, V., et al., *Science* 263:1404–1410 (1994)), motif 1 was thought to be important for dimerization. This motif was identified in the N-terminal region of *E. coli* Ala-tRNA synthetase (Ribas de Pouplana, et al., *Protein Science* 2:2259–2262 (1993)), but a series of deletion mutations had also previously demonstrated that a region at the C-terminus of the protein is needed for oligomerization (Jasin, M., et al., *Nature* 306:441–447 (1983); Jasin, et al., *Cell* 36:1089–1095 (1984)). Thus, motif 1 is not sufficient for oligomerization of this enzyme.

An idiographic representation of the predicted eight-stranded β-structure with three α-helices of the *E. coli* Ala-tRNA synthetase has been constructed (Ribas de Pouplana, L., et al., *Protein Science* 2:2259–2262 (1993)); Shi, J. -P., et al., *Biochemistry* 33:5312–5318 (1994)). Collectively, over 40 mutations in motif 2 and the region between motif 2 and 3 were individually constructed and tested (Davis, M. W., et al., *Biochemistry* 33:9904–9911 (1994); Shi, J. -P., et al., *Biochemistry* 33:5312–5318 (1994)). These mutations were mostly at conserved residues with chemical functional groups. Although motif 2 is of a different size and has only two identical amino acid residues with its counterpart in yeast Asp- and *T. thermophilus* Ser-tRNA synthetases, the mutational analysis of this motif can be explained in terms of those structures, and shows the importance of predicted motif 2 for adenylate synthesis (Ribas de Pouplana, L., et al., *Protein Science* 2:2259–2262 (1993)). A study of the products of random mutagenesis of this region also demonstrated the importance of motif 2 for adenylate transfer (Lu, Y. and Hill, K. A. W., *J. Biol. Chem.* 269:12137–12141 (1994)). Mutagenesis of specific residues in motif 2 of *E. coli* Ala-tRNA synthetase and mutagenesis of their predicted counterparts in motif 2 of yeast Asp-tRNA synthetase yielded similar results with regard to loss of function (Cavarelli, J., et al., *EMBO L.* 13:327–337 (1994); Davis, M. W., et al., *Biochemistry* 33:9904–9911 (1994)). Evidence was obtained for sequence context determining how the energy of adenylate binding is partitioned between ground and transition states in the two enzymes. In addition, a conserved aspartate residue among Ala-tRNA synthetases at the beginning of motif 3 was shown to be important for the adenylate synthesis and particularly for the adenylate transfer reaction (Davis, M. W., et al., *Biochemistry* 33:9904–9911 (1994)). The functional significance of motif 3 for adenylate synthesis has been demonstrated by mutagenesis in the yeast Asp-tRNA synthetase system (Cavarelli, J., et al., *EMBO J.* 13:327–337 (1994)).

Consideration of this information, along with the remaining teachings of the specification, allows the construction of enterococcal tRNA synthetase derivatives which possess at least one function characteristic of an Enterococcus aminoacyl-tRNA synthetase.

Method of Producing Recombinant aaRSs

Another aspect of the invention relates to a method of producing an enterococcal aminoacyl-tRNA synthetase, variant or portions thereof, and to expression systems and host cells containing a vector appropriate for expression of an enterococcal aminoacyl-tRNA synthetase.

Cells that express a recombinant enterococcal aminoacyl-tRNA synthetase, variant or portions thereof can be made and maintained in culture, under conditions suitable for expression, to produce protein for isolation. These cells can be procaryotic or eucaryotic. Examples of procaryotic cells that can be used for expression include *Escherichia coli, Bacillus subtilis* and other bacteria. Examples of eucaryotic cells that can be used for expression include yeasts such as *Saccharomyces cerevisiae, Schizosaccharomyces pombe, Pichia pastoris* and other lower eucaryotic cells, and cells of higher eucaryotes such as those from insects and mammals. (See, e.g., Ausubel, F. M. et al., eds. *Current Protocols in Molecular Biology*, Greene Publishing Associates and John Wiley & Sons Inc., (1993)).

In one embodiment, host cells that produce a recombinant aaRS protein, variant, or portions thereof can be made as follows. A gene encoding an aaRS, variant or portions thereof can be inserted into a nucleic acid vector, e.g., a DNA vector, such as a plasmid, virus or other suitable replicon, which can be present in a single copy or multiple copies, or the gene can be integrated in a host cell chromosome. A suitable replicon or integrated gene can contain all or part of the coding sequence for an aminoacyl-tRNA synthetase or variant, operably linked to one or more expression control regions whereby the coding sequence is under the control of transcription signals and linked to appropriate translation signals to permit translation. The vector can be introduced into cells by a method appropriate to the type of host cells (e.g., transformation, electroporation, infection). For expression from the aaRS gene, the host cells can be maintained under appropriate conditions (e.g., in the presence of inducer, normal growth conditions, etc.). Proteins or polypeptides thus produced can be recovered (e.g., from the cells, the periplasmic space, culture medium) using suitable techniques.

For example, active Enterococcus aminoacyl-tRNA synthetase can be produced by integrating a gene encoding an *E. faecalis* aaRS into the genome of a virus that enters the host cells. By infection of the host cells, the components of a system which permits the transcription and translation of the Enterococcus aaRS gene are present in the host cells. Alternatively, an RNA polymerase gene, inducer, or other component required to complete such a gene expression system can be introduced into the host cells already containing the Enterococcus aaRS gene, for example, by means of a virus that enters the host cells and contains the required component. The aaRS gene can be under the control of an inducible or constitutive promoter. The promoter can be one that is recognized by the host cell RNA polymerase. The promoter can, alternatively, be one that is recognized by a viral RNA polymerase and is transcribed following infection of the host cells with a virus.

Antibodies

The invention further relates to antibodies that bind to an isolated and/or recombinant enterococcal aminoacyl-tRNA synthetase, including portions of antibodies, which can specifically recognize and bind to one or more tRNA synthetases. The antibodies and portions thereof of the invention include those which bind to one or more enterococcal aminoacyl-tRNA synthetases other than *E. faecalis* histidyl-tRNA synthetase, and preferably, include those which bind to one or more enterococcal aminoacyl-tRNA synthetases other than enterococcal histidyl-tRNA synthetases. In a preferred embodiment, the antibodies specifically bind to a naturally occurring enterococcal aaRS. The antibodies can be used in methods to detect and/or purify a protein of the present invention or a portion thereof by various methods of immunoaffinity chromatography, or to selectively inactivate an active site, or to study other aspects of the structure of these enzymes, for example.

The antibodies of the present invention can be polyclonal or monoclonal. The term antibody is intended to encompass both polyclonal and monoclonal antibodies. Antibodies of the present invention can be raised against an appropriate immunogen, including proteins or polypeptides of the present invention, such as an isolated and/or recombinant Enterococcus aminoacyl-tRNA synthetase or portions thereof, or synthetic molecules, such as synthetic peptides (e.g., conjugated to a suitable carrier). The immunogen can be a protein having at least one function of an Enterococcus aminoacyl-tRNA synthetase, as described herein.

The term antibody is also intended to encompass single chain antibodies, chimeric, humanized or primatized (CDR-grafted) antibodies and the like, as well as chimeric or CDR-grafted single chain antibodies, comprising portions from more than one species. For example, the chimeric antibodies can comprise portions of proteins derived from two different species, joined together chemically by conventional techniques or prepared as a single contiguous protein using genetic engineering techniques (e.g., DNA encoding the protein portions of the chimeric antibody can be expressed to produce a contiguous protein chain. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 BE; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., U.S. Pat. No. 5,585,089; and Queen et al., European Patent No. EP 0 451 216 B1. See also, Newman, R. et al., BioTechnology, 10:1455–1460 (1992), regarding primatized antibody, and Ladner et al., U.S. Pat. No. 4,946, 778 and Bird, R. E. et al., Science, 242:423–426 (1988)) regarding single chain antibodies.)

Whole antibodies and biologically functional fragments thereof are also encompassed by the term antibody. Biologically functional antibody fragments which can be used include those fragments sufficient for binding of the antibody fragment to an Enterococcus aaRS to occur, such as Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons have been introduced upstream of the natural stop site. For example, a chimeric gene encoding a F(ab')$_2$ heavy chain portion can be designed to include DNA sequences encoding the CH$_1$ domain and hinge region of the heavy chain.

Preparation of immunizing antigen, and polyclonal and monoclonal antibody production can be performed using any suitable technique. A variety of methods have been described (see e.g., Kohler et al., Nature, 256: 495–497 (1975) and Eur. J. Immunol. 6: 511–519 (1976); Milstein et al., Nature 266: 550–552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cells, preferably those obtained from the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies (including human antibodies) of the requisite specificity can used, including, for example, methods which select recombinant antibody from a library (e.g., Hoogenboom et al., WO 93/06213; Hoogenboom et al., U.S. Pat. No. 5,565, 332; WO 94/13804, published Jun. 23, 1994; and Dower, W. J. et al., U.S. Pat. No. 5,427,908), or which rely upon immunization of transgenic animals (e.g., mice) capable of producing a full repertoire of human antibodies (see e.g., Jakobovits et al., Proc. Natl. Acad. Sci. USA, 90: 2551–2555 (1993); Jakobovits et al., Nature, 362:255–258 (1993); Lonberg et al., U.S. Pat. No. 5,569,825; Lonberg et al., U.S. Pat. No. 5,545,806; Surani et al., U.S. Pat. No. 5,545,807; and Kucherlapati, R. et al., European Patent No. EP 0 463 151 B1).

Assays for Inhibitors and Tester Strains

The enzymatic assays, binding assays, and construction of tester strains described below, which rely upon the nucleic acids and proteins of the present invention, can be used, alone or in combination with each other or other suitable methods, to identify inhibitors of one or more enterococcal aminoacyl-tRNA synthetases.

Enzyme Assay

Upon the isolation of an aaRS gene from an organism of genus Enterococcus, the gene can be incorporated into an expression system for production of the aaRS, or an aaRS fusion protein, followed by isolation and testing of the enzyme in vitro. The isolated or purified Enterococcus aaRSs can also be used in further structural studies that allow for the design of antibiotics which specifically target one or more aaRSs of Enterococcus, while not affecting or minimally affecting host or mammalian (e.g., human) aaRSs. Because the amino acid sequences of the tRNA synthetases have diverged throughout evolution, significant differences exist between the structure of the enzymes from mammals (e.g., human, bovine) and mammalian pathogens. The design or selection of inhibitors can exploit the structural differences between the pathogen aaRS and the corresponding host (e.g., a mammalian host, such a human) aaRS, to yield specific inhibitors of the pathogen aaRS, which can have antimicrobial activity.

Furthermore, isolated, and/or recombinant, active Enterococcus aaRSs can be used in an in vitro method of screening for inhibitors of aminoacyl-tRNA synthetase activity in which the inhibitory effect of a compound is assessed by monitoring aaRS activity according to standard techniques or other suitable methods. A composition comprising one or more test compounds, (e.g., a mixture of test compounds) can be used in an initial screening, and compounds can be tested in further assays. For example, inhibitors of the activity of isolated, recombinant E. faecalis SerRS, TyrRS, IleRS, LeuRS, TrpRS or PheRS can be identified by the method.

Thus, the invention relates to a method of identifying an inhibitor of an enterococcal aminoacyl-tRNA synthetase comprising contacting an isolated and/or recombinant protein or polypeptide of the present invention (e.g., a protein comprising an enterococcal aminoacyl-tRNA synthetase or functional portion thereof), with a composition comprising one or more candidate inhibitors under conditions suitable for aminoacyl-tRNA synthetase activity, and monitoring activity. A decrease in activity relative to a suitable control (e.g., activity in the absence of the composition comprising inhibitor) is indicative that the composition contains one or more inhibitors of aminoacyl-tRNA synthetase activity.

In one embodiment, the isolated aaRS enzyme is maintained under conditions suitable for aminoacyl-adenylate formation, the enzyme is contacted with a compound to be tested, and formation of the aminoacyl-adenylate or PP$_i$ is monitored. In another embodiment, formation of the aminoacylated tRNA is monitored in an aminoacylation assay. For example, the extent of aminoacylation of tRNA with amino acid catalyzed by an aaRS (e.g., a GST fusion protein or a His-tag fusion protein) can be measured by monitoring the incorporation of [$^3$H]amino acid into trichloroacetic acid-precipitable [$^3$H]aminoacyl-tRNA in the presence of a candidate inhibitor, as compared with activity in the absence of the candidate inhibitor. A reduction in the activity measured in the presence of compound, as compared with the activity in the absence of compound, is indicative of inhibition of aminoacyl-tRNA synthetase activity by the compound. An ICr$_{50}$ value (the concentration of inhibitor causing 50% inhibition of enzyme activity) can be determined for a known amount of aaRS. Inhibitors identified by enzymatic assay can be further assessed for antimicrobial activity using tester strains as described herein, or using other suitable assays.

In a further embodiment, aaRS-dependent production of $PP_i$, which can occur in the presence of amino acid, ATP and isoaccepting tRNA, can be monitored in a suitable assay. For example, TrpRS-dependent production of $PP_i$, in the presence of ATP and isoaccepting tRNA, can be monitored in the presence of inorganic pyrophosphatase, to generate two moles of phosphate ($P_i$) per mole of tryptophanyl-AMP formed. Phosphate production can be monitored in a coupled assay, for example by coupling to phosphorolysis of the chromogenic nucleoside 2-amino 6-mercapto 7-methylpurine ribonucleoside (AMMPR) catalyzed by excess purine nucleoside phosphorylase to yield ribose 1-phosphate and 2-amino 6-mercapto 7-methylpurine (AMMP). The absorbance at 360 nm of AMMP can be followed continuously by spectrophotometer (Lloyd, A. J. et al., *Nucl. Acids Res.* 23:2886–2892 (1995)). It will be appreciated that other coupled assays can be used to monitor aaRS-dependent production of $PP_i$ in which the step following the conversion of $PP_i$ to phosphate requires phosphate and produces a product which can be quantitated.

An $IC_{50}$ value (the concentration of inhibitor causing 50% inhibition of enzyme activity) for a known amount of active aaRS can be determined, based on an assay of aminoacylation or $PP_i$ or aminoacyl-adenylate formation, or other assay of an aminoacyl-tRNA synthetase activity.

Binding Assay

An isolated, recombinant enterococcal aaRS or a portion thereof, or suitable fusion proteins can be used in a method to select and identify compounds which bind specifically to the aaRS, such as *E. faecalis* isoleucyl-, phenylalanyl-, tyrosyl-, leucyl-, seryl- or tryptophanyl-tRNA synthetase, and which are potential inhibitors of aaRS activity. Compounds selected by the method can be further assessed for their inhibitory effect on aaRS activity and for antimicrobial activity.

In one embodiment, isolated or purified enterococcal aaRS can be immobilized on a suitable affinity matrix by standard techniques, such as chemical cross-linking, or via an antibody raised against the isolated or purified aaRS and bound to a solid support. The matrix can be packed in a column or other suitable container and is contacted with one or more compounds (e.g., a mixture) to be tested under conditions suitable for binding of the compound to the aaRS. For example, a solution containing compounds is made to flow through the matrix. The matrix can be washed with a suitable wash buffer to remove unbound compounds and non-specifically bound compounds. Compounds which remain bound can be released by a suitable elution buffer. For example, a change in the ionic strength or pH of the elution buffer can lead to a release of compounds. Alternatively, the elution buffer can comprise a release component or components designed to disrupt binding of compounds (e.g., one or more substrates or substrate analogs which can disrupt binding of compound to the aaRS, such as ATP, a tRNA, the amino acid specific for the aaRS, or other suitable molecules which competitively inhibit binding).

Fusion proteins comprising all of, or a portion of, the aaRS linked to a second moiety not occurring in the Enterococcus aaRS as found in nature (see above), can be prepared for use in another embodiment of the method. Suitable fusion proteins for this purpose include those in which the second moiety comprises an affinity ligand (e.g., an enzyme, antigen, epitope). The fusion proteins can be produced by the insertion of an aaRS gene or portion thereof into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one aspect of this embodiment, the fusion protein can be immobilized on a suitable affinity matrix under conditions sufficient to bind the affinity ligand portion of the fusion protein to the matrix, and is contacted with one or more compounds (e.g., a mixture) to be tested, under conditions suitable for binding of compounds to the aaRS portion of the bound fusion protein. Next, the affinity matrix with bound fusion protein can be washed with a suitable wash buffer to remove unbound compounds and non-specifically bound compounds. Compounds which remain bound can be released by contacting the affinity matrix with fusion protein bound thereto with a suitable elution buffer (a compound elution buffer). Wash buffer can be formulated to permit binding of the fusion protein to the affinity matrix, without significantly disrupting binding of specifically bound compounds. In this aspect, compound elution buffer can be formulated to permit retention of the fusion protein by the affinity matrix, but can be formulated to interfere with binding of the test compound(s) to the aaRS portion of the fusion protein. For example, a change in the ionic strength or pH of the elution buffer can lead to release of compounds, or the elution buffer can comprise a release component or components designed to disrupt binding of compounds to the aaRS portion of the fusion protein (e.g., one or more substrates or substrate analogs which can disrupt binding of compounds to the aaRS portion of the fusion protein, such as tryptophan, ATP, or $tRNA^{Trp}$ for TrpRS, or other suitable molecules which competitively inhibit binding).

Immobilization can be performed prior to, simultaneous with, or after contacting the fusion protein with compound, as appropriate. Various permutations of the method are possible, depending upon factors such as the compounds tested, the affinity matrix-ligand pair selected, and elution buffer formulation. For example, after the wash step, fusion protein with compound bound thereto can be eluted from the affinity matrix with a suitable elution buffer (a matrix elution buffer, such as glutathione for a GST fusion). Where the fusion protein comprises a cleavable linker, such as a thrombin cleavage site, cleavage from the affinity ligand can release a portion of the fusion with compound bound thereto. Bound compound can then be released from the fusion protein or its cleavage product by an appropriate method, such as extraction.

To enrich for specific binding to the aaRS portion of the fusion protein, compounds can be pre-treated, for example with affinity matrix alone, with affinity ligand or a portion thereof (e.g., the portion present in the fusion protein), either alone or bound to matrix, under conditions suitable for binding of compound to the aaRS portion of the bound fusion protein.

One or more compounds can be tested simultaneously according to the method. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rebek et al., Process for Creating Molecular Diversity, U.S. Ser. No. 08/180,215, filed Jan. 12, 1994, relating to compounds without tags; see also, Rutter, W. J. et al. U.S. Pat. No. 5,010,175; Huebner, V. D. et al., U.S. Pat. No. 5,182,366; and Geysen, H. M., U.S. Pat. No. 4,833,092). Where compounds selected from a combinatorial library by the present method carry unique tags, identification of individual compounds by chromatographic methods is possible. Where compounds do not carry tags, chromatographic separation, followed by mass spectrophotometry to ascertain structure, can be used to identify individual compounds selected by the method, for example.

Random sequence RNA and DNA libraries (see Ellington, A. D. et al., *Nature* 346:818–822 (1990); Bock, L. C. et al., *Nature* 355:584–566 (1992); and Szostak, J. W., *Trends in Biochem. Sci.* 17:89–93 (March, 1992)) can also be screened according to the present method to select RNA or DNA molecules which bind to an Enterococcus aaRS. Such molecules can be further assessed for antimicrobial effect upon introduction into a cell (e.g., by expression in the case of an RNA molecule selected by the method).

Tester Strains

Nucleic acids of the present invention can also be used in constructing tester strains for in vivo assays of the effect on the activity of the Enterococcus enzyme of a substance which is added to tester strain cells. A tester strain comprises a host cell having a defect in a gene encoding an endogenous aaRS, and a heterologous aaRS gene which complements the defect in the host cell gene. Thus, complementation of a particular defective host cell aaRS gene by a heterologous aaRS gene is a threshold requirement for a tester strain. Because the aaRS genes are essential, the heterologous gene can be introduced into the host cell simultaneously with inactivation of the host cell gene to preserve viability (except where there is an additional duplicated or cryptic host cell gene; see below). Alternatively, the heterologous gene can be introduced into the host cell before inactivation or loss of the host cell gene. In this case, to test for complementation, the host cell is then subjected to some change in conditions (e.g., a change in temperature, growth medium, selection conditions) which causes inactivation or loss of either the host aaRS gene or gene product, or both.

If the heterologous gene complements the inactivated host cell gene, such a cell can be used to determine whether a substance that is introduced into the cells for testing, can interact specifically with the heterologous tRNA synthetase (or a component in the pathway of the expression of the heterologous tRNA synthetase gene) to cause loss of function of the tested heterologous tRNA synthetase in those host cells. Thus, such cells are "tester strains". Successful cross-species complementation has been described already, for example, for yeast seryl-tRNA synthetase and for yeast isoleucyl-tRNA synthetase in *E. coli* (Weygand-Durasevic, I., et al., *Eur. J. Biochem* 214:869–877 (1993); Racher, K. I., et al., *J. Biol. Chem.* 266:17158–17164 (1991)).

In tester cells to be used in an assay for substances that can inhibit the function of a specific aaRS, the gene for the aminoacyl-tRNA synthetase can, for example, physically replace the host cell aaRS gene or can be present in addition to a host aaRS gene that does not produce a functional product, and the heterologous gene whose gene product is to be tested complements the host gene. A substance to be tested is administered to the tester cells, and the viability or growth of such cells can be compared with that of cells of a suitable control.

As a tester strain comprises a host cell comprising a heterologous aaRS gene (i.e., one from a heterologous species), a suitable host cell is heterologous with respect to the species from which the gene to be tested is isolated. For instance, suitable host cells to test *Enterococcus faecalis* genes can be host cells of a species other than *E. faecalis*. Examples of species which are suitable for use as hosts for the construction of tester strains are *E. coli*, *S. cerevisiae*, and *B. subtilis*. These species are especially amenable to genetic manipulation because of their history of extensive study.

Suitable host cells having a genotype useful for the construction of a tester strain can be constructed or selected using known methods. For example, both in *E. coli* and in *S. cerevisiae*, a first plasmid which contains a functional copy of a host chromosomal aaRS gene (which is to be inactivated later), and some selectable marker gene, can be constructed and introduced into cells. Then, an inactivating mutation can be caused in the chromosomal copy of the aaRS gene.

This can be accomplished, for instance, by causing or selecting for a double crossover event which creates a deletion and insertion. This can be done by introducing into the cells double-stranded DNA having regions of homology to the DNA flanking the target aaRS gene, and having between these regions a gene encoding a selectable marker, either on a suitable vector or as a DNA fragment, as appropriate (Jasin et al., U.S. Pat. No. 4,713,337; Schimmel, P., U.S. Pat. No. 4,963,487; Toth, M. J. and Schimmel, P., *J. Biol. Chem.* 261:6643–6646 (1986); Rothstein, R., *Methods in Enzymology* 194:281–301 (1991)). Such an approach simultaneously inserts a selectable marker and results in a deletion of the endogenous gene between the flanking sequences provided. Where needed to maintain viability, a compatible maintenance plasmid is provided encoding an endogenous or complementing aaRS.

A test plasmid which is compatible with the maintenance plasmid, and which contains the aaRS gene to be tested for complementation, can be introduced into the host cells. If the first plasmid has been constructed to have a mechanism to allow for inhibition of its replication (for example, a temperature sensitive replicon) or to have a mechanism by which cells containing the first plasmid can be selected against (by, for example, the use of 5-fluoroorotic acid to select against *S. cerevisiae* cells which have a first plasmid containing the URA3 gene), cells which survive by virtue of having a complementing aaRS gene on the second plasmid can be selected (Sikorsky, R. S. and Boeke, J. D., *Methods in Enzymology* 194:302–318 (1991)).

Causing or selecting for a double crossover event which creates a deletion and insertion can be used in itself as a one-step method of constructing a tester strain in which a native aaRS gene is replaced by the corresponding foreign gene whose gene product is to be tested. Endogenous recombination mechanisms have been used to advantage previously in *E. coli*, *B. subtilis*, and *S. cerevisiae*, among other organisms. This method depends on the ability of the heterologous gene to be tested to complement the native corresponding aaRS gene. This can be done by introducing into the cells double-stranded DNA having regions of homology to the DNA flanking the target native aaRS gene, and having between these regions a gene encoding a selectable marker as well as the heterologous aaRS gene intended to replace the native aaRS gene. The survival of cells expressing the selectable marker is indicative of expression of the introduced heterologous aaRS gene and complementation of the defect in the endogenous synthetase.

For example, a tester strain useful for testing the effect of a compound on the function of an aaRS expressed by an inserted enterococcal gene, can be constructed in a one-step method in a suitable host cell. Optional positive and negative controls for this cross-species transformation can be used to show that the resulting strain depends on the aaRS gene from *E. faecalis* for growth and that this recombination event is not lethal. For example, *B. subtilis* cells made competent for transformation (Dubnau, D. and Davidoff-Abelson, R., *J. Mol. Biol.* 56:206–221 (1971)) can be transformed with a suitable construct, such as a linearized plasmid containing an insert. Generally, the construct includes a selectable marker gene for antibiotic resistance, or other suitable selectable marker. In one embodiment, a linearized plasmid which contains the enterococcal aaRS gene and an antibiotic resistance gene, situated between sequences homologous to the flanking sequences of the endogenous aaRS gene of the host cells, is used to transform the host cell. For a positive control, the linearized plasmid can be constructed in a similar fashion, except that the native *B. subtilis* aaRS gene replaces the enterococcal gene, such that a normal *B. subtilis* aaRS gene is located adjacent to the antibiotic resistance marker in the insert. As a negative control, the insert can be designed to contain only the flanking sequences and the antibiotic resistance marker, for example. Antibiotic resistant transformants are not expected upon transformation with the negative control construct, as homologous recombination with the construct results in deletion of the endogenous aaRS gene. Successful construction of a tester strain can also be confirmed by Southern analysis.

In cases of gene duplication (e.g., LysU and LysS in *E. coli*; Kawakami, K., et al., *Mol. Gen. Genet.* 219:333–340 (1989); Leveque, F., et al., *Nucleic Acids Res.* 18:305–312 (1990); Clark, R. L. and Neidhardt, F. C., *J. Bacteriol.* 172:3237–3243 (1990)), or the presence of a cryptic gene (e.g., tyrZ in *B. subtilis*, Glaser, P., et al., *DNA Sequ. and Mapping* 1:251–61 (1990); Henkin, T. M., et al., *J. Bacteriol.* 174:1299–1306 (1992)), a suitable tester strain can be constructed by simultaneous inactivation of both of the host genes, or by sequential inactivation. For instance, inactivation of one host gene by a suitable method, such as by insertion of a selectable marker, can be followed by a one-step gene replacement of the remaining host gene with a heterologous enterococcal aaRS gene and a second selectable marker.

The yeast *S. cerevisiae* offers additional possibilities for genetic manipulations to create tester strains, relative to bacteria. Yeast integrating plasmids, which lack a yeast origin of replication, can be used for making alterations in the host chromosome (Sikorski, R. S. and Hieter, P., *Genetics*, 122:19–27 (1989); Gietz, R. D. and Sugino, A., *Gene*, 74:527–534 (1988)). In another embodiment, one-step gene disruptions can be performed in diploid cells using a DNA fragment comprising a copy of an aaRS gene (optionally containing a deletion of the aaRS gene) having an insertion of a selectable marker in the deleted gene. A suitable fragment can be introduced into a diploid cell to disrupt a chromosomal copy of the yeast gene. Successful integration of the disrupted aaRS gene can be confirmed by Southern blotting and by tetrad analysis of the sporulated diploid cells. The diploid cells heterozygous for the disrupted aaRS gene provide a diploid host strain which can be transformed with a plasmid containing the heterologous aaRS gene. These cells can be sporulated and the haploid spores analyzed for rescue of the defective chromosomal aaRS by the heterologous aaRS gene.

Alternatively, those diploid cells that are found to contain one copy of the disrupted chromosomal aaRS gene, as well as one functional copy, can be transformed with a maintenance plasmid which contains a gene which complements the disruption, such as the corresponding wild type yeast aaRS gene, and which provides for a mechanism to select against survival of the cells containing this plasmid. These cells can then be made to sporulate to obtain a haploid null strain containing the disrupted chromosomal aaRS gene and the wild type gene on the maintenance plasmid. This haploid host strain can then be transformed with a test plasmid which expresses a heterologous aaRS gene, and the maintenance plasmid can be selected against by growing this strain under appropriate conditions.

Construction of a tester strain may start with the isolation of a mutant host strain which produces, e.g., an inactive aminoacyl-tRNA synthetase, an aminoacyl-tRNA synthetase which is conditionally inactivatible, or no aminoacyl-tRNA synthetase at all. The procedures used to isolate and/or construct these *E. coli* and *S. cerevisiae* strains, or similar procedures, can be used or adapted to make additional mutant strains of *E. coli*, *S. cerevisiae* or other host organisms.

A number of *E. coli* and *S. cerevisiae* strains have been described that can be used for constructing tester strains. Some of these strains are described below for illustrative purposes. The procedures used to isolate and/or construct these *E. coli* and *S. cerevisiae* strains, or similar procedures, can be used or adapted to make additional mutant strains in *E. coli*, *S. cerevisiae* or other host organisms. Construction of a tester strain may start with the isolation of a mutant host strain which produces, e.g., an inactive tRNA synthetase specific for a particular amino acid, a tRNA synthetase which is conditionally inactivatible, or which carries a chromosomal deletion of a tRNA synthetase.

*E. coli* strains having a defect, such as a null mutation, in an aminoacyl-tRNA synthetase gene can be constructed using a cloned *E. coli* aaRS gene. Each aminoacyl-tRNA synthetase gene of *E. coli* has been cloned (see Meinnel, T. et al., 1995, "Aminoacyl-tRNA synthetases: Occurrence, structure and function", In: tRNA: *Structure, Biosynthesis and Function*, Söll, D. and U. RajBhandary, Eds., (American Society for Microbiology: Washington, D.C.), Chapter 14, pp. 251–292, the teachings of which are incorporated herein by reference). For example, the *E. coli* tyrosyl-tRNA synthetase gene (Barker, D. G., *Eur. J. Biochem.*, 125:357–360 (1982); Barker, D. G. et al., *FEBS Letters*, 150:419–423 (1982)), isoleucyl-tRNA synthetase gene (Webster, T. et al., *Science* 226:1315–1317 (1984); see also, EMBL/GenBank Accession No. D10483), and seryl-tRNA synthetase gene have been cloned and sequenced (Hartlein, M. et al., *Nucl. Acids Res.*, 15(3):1005–1017 (1987)). The cloned genes can also be incorporated into a suitable construct for use as a maintenance plasmid.

A number of *E. coli* strains have been characterized in which an aaRS gene has been inactivated by some method, in whole or in part, yielding an observable phenotypic defect which can be detectably complemented. For example, null strains in which the gene encoding IleRS has been inactivated (IQ843, IQ844, see Shiba, K. and Schimmel, P., *J. Biol. Chem.* 267:22703–22706 (1992)), and a mutant strain (MI1, see Starzyk, et al., *Science* 237:1614–1618 (1987) and Iaccarino and Berg, *J. Bacteriol.* 105:527–537 (1970)) having an isoleucine auxotrophy due to an elevated $K_m$ for isoleucine of the enzyme encoded by the chromosomal ileS allele, have been described.

As a further illustration, null strains in which the gene encoding MetRS has been inactivated, and a mutant strain of

*E. coli* in which the gene encoding MetRS has been conditionally inactivated, have been described (see Kim, et al., *Proc. Natl. Acad. Sci. USA* 90:10046–10050 (1993), describing a metG null strain of *E. coli* carrying a maintenance plasmid, MN9261/pRMS61S); and Barker, D. G. et al. *Eur. J. Biochem.* 127:449–457 (1982) and Starzyk, R. M. et al., *Biochemistry*, 28:8479–8484 (1989), regarding a mutant strain having a methionine auxotrophy because the $k_m$ for methionine of the enzyme encoded by the chromosomal metG allele is elevated).

*E. coli* strain IQ843/pRMS711 and its derivative IQ844/pRMS711 contain a chromosomal deletion of the ileS gene (ΔileS203::kan), and are propagated by expression of wild type IleRS at 30° C. from a temperature-sensitive maintenance plasmid designated pRMS711, which encodes the wild type ileS gene and a gene which confers chloramphenicol resistance. pRMS711 cannot replicate at 42° C., thus, at the non-permissive temperature, the maintenance plasmid is lost. Following the introduction of a test construct into these strains, the growth of chloramphenicol sensitive colonies at a non-permissive temperature (e.g., 42° C.) is indicative of complementation of the chromosomal ileS deletion by the introduced construct (Shiba, K. and P. Schimmel, *Proc. Natl. Acad. Sci. USA*, 89:1880–1884 (1992); Shiba, K. and P. Schimmel, *Proc. Natl. Acad. Sci. USA*, 89:9964–9968 (1992); Shiba, K. and P. Schimmel, *J. Biol. Chem.*, 267:22703–22706 (1992)).

Temperature sensitive alleles are examples of genes encoding conditionally inactivatable tRNA synthetases. For example, temperature-sensitive alleles of the genes encoding cytoplasmic IleRS (ils1-1) and MetRS (mes1-1) have been described in *S. cerevisiae* (Hartwell, L. H., and McLaughlin, C. S., *J. Bacteriol.* 96:1664–1671 (1968); McLaughlin, C. S., and Hartwell, L. H. *Genetics* 61:557–566 (1969)), and are available from the Yeast Genetic Stock Center (University of California-Berkeley; catalog nos. 341 and 19:3:4, respectively). Temperature sensitive strains of *E. coli* having a defect in the tyrS gene encoding TyrRS (see, e.g., Bedouellle, H. and G. Winter, *Nature* 320:371–373 (1986)); and temperature-sensitive serS strains of *E. coli* have also been described (Low, B., et al., *J. Bacteriol.* 108:742–750 (1971); Clarke, S. J. et al., *J. Bacteriol.* 113:1096–1103 (1973); Hartlein, M. et al., *Nucl. Acids Res.* 15:1005–1017 (1987)).

The *S. cerevisiae* genome has been fully sequenced and all of the aminoacyl-tRNA synthetases have been identified. For example, the ILS1 gene encoding cytoplasmic isoleucyl-tRNA synthetase (Englisch, U., et al., *Biol. Chem. Hoppe-Seyler* 368:971–979 (1987)), and the KRS1 gene encoding cytoplasmic lysyl-tRNA synthetase (Mirande, M. et al., *Biochemie* 68:1001–1007 (1986); Mirande, M. and Waller, J. -P., *J. Biol. Chem.* 263:18443–18451 (1988)) of *S. cerevisiae* have been cloned and sequenced. The KRS1 gene was shown to be essential by the construction of a disrupted allele of KRS1 (Martinez, R. et al., *Mol. Gen. Genet.* 227:149–154 (1991)). The yeast VAS1 gene encodes both mitochondrial and cytoplasmic ValRSs (Chatton, B. et al.,*J. Biol. Chem.*, 263(1):52–57 (1988)). Leucyl- and seryl-tRNA synthetase genes from yeast cytoplasm, among others, have also been cloned and sequenced and can be used in the construction of tester strains (see e.g., Weygand-Durasevic, I. et al.,*Nucl. Acids Res.*, 15(5):1887–1904 (1987) regarding *S. cerevisiae* serS; see also Meinnel, T. et al., 1995, "Aminoacyl-tRNA synthetases: Occurrence, structure and function", In: tRNA: *Structure, Biosynthesis and Function*, Söll, D. and U. RajBhandary, Eds., (American Society for Microbiology: Washington, D.C.), Chapter 14, pp. 251–292 and references cited therein).

The gene encoding the *S. cerevisiae* cytoplasmic tyrosyl-tRNA synthetase has been isolated by Chow and RajBhandary (*J. Biol. Chem.* 268:12855–12863, 1993). An *S. cerevisiae* strain has been constructed which carries a disruption of MSY1, the gene encoding mitochondrial tyrosyl-tRNA synthetase. Plasmids carrying MSY1 which rescue this defect, also have been constructed (Hill, J. and A. Tzagoloff, Columbia University; see Edwards, H. and P. Schimmel, *Cell* 51:643–649 (1987)).

For construction of a tester strain in *S. cerevisiae*, a plasmid such as the one reported by P. Walter et al. (*Proc. Natl. Acad. Sci. USA* 80:2437–2441, 1983), which contains the wild type cytoplasmic methionyl-tRNA synthetase gene of *S. cerevisiae*, MES1, can be used to construct mes1 strains, and for the construction of maintenance plasmids to create cytoplasmic tester strains for a MetRS (see also Fasiolo, F. et al., *J. Biol. Chem.* 260:15571–15576 (1985)).

Mitochondrial mutant strains can also be used for the construction of tester strains comprising an enterococcal aminoacyl-tRNA synthetase. Strains having a defect in a mitochondrial aminoacyl-tRNA synthetase can be constructed using a cloned mitochondrial aaRS gene, and used to make tester strains.

For example, an msm1-1 strain or disruption strain QBY43 (aW303ΔMSM1) (MATa ade2-1 his3-11, 15 leu2-3, 112 ura3-1 trp1-1 msm1::HIS3; see Tzagoloff, A., et al.,*Eur. J. Biochem.* 179:365–371 (1989)), can be used for the construction of tester strains comprising an enterococcal methionyl-tRNA synthetase. Strains having a defect in another mitochondrial aminoacyl-tRNA synthetase can be constructed using a cloned mitochondrial aaRS gene, and used to make tester strains (see Meinnel, T. et al., 1995, "Aminoacyl-tRNA synthetases: Occurrence, structure and function", In: tRNA: *Structure, Biosynthesis and Function*, Söll, D. and U. RajBhandary, Eds., (American Society for Microbiology: Washington, D.C.), Chapter 14, pp. 251–292 and ATCC Catalog of Recombinant DNA Materials, American Type Culture Collection, Rockville, Md., regarding mitochondrial aaRS genes. The sequence and disruption of the *S. cerevisiae* mitochondrial leucyl-tRNA synthetase gene (MSL1) has been reported (Tzagoloff, A. et al., *J. Biol Chem.*, 263:850–856 (1988)). An *S. cerevisiae* strain has been constructed which carries a disruption of MSY1, the gene encoding mitochondrial tyrosyl-tRNA synthetase. Plasmids carrying MSY1 which rescue this defect, also have been constructed (Hill, J. and A. Tzagoloff, Columbia University; see Edwards, H. and P. Schimmel, *Cell* 51:643–649 (1987)).

In *S. cerevisiae*, to construct a maintenance plasmid or a test plasmid carrying a heterologous aaRS gene, a suitable vector, such as a yeast centromere plasmid (CEN; single-copy) or 2 μ vector (high copy) can be used. A heterologous aaRS gene to be tested can also be incorporated into the chromosome, using an integrating plasmid, for example. Examples of convenient yeast vectors for cloning include vectors such as those in the pRS series (integrating, CEN, or 2 μ plasmids differing in the selectable marker (HIS3, TRP1, LEU2, URA3); see Christianson, T. W., et al., *Gene*, 110:119–122 (1992) regarding 2 μ vectors; see Sikorski, R. S. and Hieter, P., *Genetics*, 122:19–27 (1989) regarding integrating and CEN plasmids which are available from Stratagene, La Jolla)) and shuttle vectors (integrating, CEN or 2 μ vectors) which contain the multiple cloning site of pUC19 (Gietz, R. D. and Sugino, A., *Gene*, 74:527–534 (1988)). Examples of expression vectors include pEG (Mitchell, D. A. et al., *Yeast*, 9:715–723 (1993)) and pDAD1 and pDAD2, which contain a GAL1 promoter (Davis, L. I. and Fink, G. R., *Cell* 61:965–978 (1990)).

A variety of promoters are suitable for expression. Available yeast vectors offer a choice of promoters. In one embodiment, the inducible GAL1 promoter is used. In another embodiment, the constitutive ADH1 promoter (alcohol dehydrogenase; Bennetzen, J. L. and Hall, B. D.,*J. Biol. Chem.* 257:3026–3031 (1982)) can be used to express an inserted gene on glucose-containing media.

For illustration, a yeast tester strain can be constructed as follows. A *Saccharomyces cerevisiae* strain with convenient markers, such as FY83 (MATa/MATα lys2–128δ/lys2–128δ leu2Δ1/leu2Δ1 ura3–52/ura3–52 trp1Δ63/trp1Δ63) can be used as a host cell. A nucleic acid encoding a yeast cytoplasmic aaRS can be used to create a null allele of the yeast cytoplasmic aaRS gene. For example, a deletion/insertion allele can be constructed by excising the aaRS open reading frame, including the promoter region and 3' flanking region or portions thereof from a cloned gene, and replacing the excised sequence with a selectable marker (e.g., TRP1). This aaRS::TRP1 fragment can be used to transform the diploid strain FY83, and Trp$^+$ transformants can be selected (Rothstein, J., *Methods in Enzymol.* 101:202–211 (1983)). Standard genetic procedures can be employed to identify the appropriate integrant created by this one-step gene disruption (a diploid having the genotype MATa/MATα lys2–128δ/lys2–128δ leu2Δ1/leu2Δ1 ura3–52/ura3–52 trp1Δ63/trp1, Δ63 aaRS::TRP1/AARS); Rose, M. D., et al., *Methods in Yeast Genetics,* 1990, Cold Spring Harbor Press, Cold Spring Harbor, N.Y.).

To construct a maintenance plasmid, a fragment containing the aaRS coding region, its promoter and some of the 3' untranslated region (e.g., a region approximately equivalent to that deleted in the construction of the null allele above) can be excised and introduced into a vector such as YCplac33, a CEN plasmid containing a URA3 selectable marker (Gietz, R. D. and Sugino, A., *Gene* 74:527–534 (1988)). The resulting plasmid can be used to transform the aaRS::TRP1/AARS diploid described above, and Ura$^+$ transformants which contain the maintenance plasmid can be selected. The resulting diploid can be sporulated and a haploid Trp$^+$Ura$^+$ spore (an aaRS null strain), corresponding to an aaRS::TRP1 strain dependent upon the URA3 AARS maintenance plasmid can be isolated.

To construct a test plasmid (a plasmid bearing a heterologous tRNA synthetase gene to be tested for its ability to complement the defect in the endogenous yeast gene), a heterologous aaRS gene to be tested can be inserted into a suitable multicopy vector for expression, for example, by insertion of a nucleic acid fragment containing an enterococcal aaRS gene. Alternatively, to test whether a relatively reduced level of expression of the heterologous tRNA synthetase gene permits complementation, a fragment containing an enterococcal aaRS gene can be inserted into a CEN plasmid for expression. Preferably, the heterologous gene is inserted into the vector so that its ATG start codon is the first ATG within 50 to 100 bp of the transcription start site of the ADH promoter of the vector.

Plasmids bearing a LEU2 selectable marker can be used to transform a null strain, such as the Trp+Ura+Leu– strain described, and Leu+ transformants containing the test plasmid can be selected. Leu+Ura+Trp+ transformants (containing an aaRS::TRP1 allele, a URA3 maintenance plasmid, and the LEU2 test plasmid) can be tested for growth on media containing 5-fluoroorotic acid (5-FOA). 5-FOA is toxic to URA3 cells, and causes loss of the URA3 maintenance plasmid (Boeke, J. et al., *Mol. Gen. Genet.,* 197:345–346 (1984)). Accordingly, growth of cells on media containing 5-FOA is indicative of complementation of the lethal deletion in the aaRS gene on the chromosome (aaRS::TRP1) by the heterologous aaRS gene on the test plasmid. Cells that are unable to grow on 5-FOA are dependent upon the maintenance plasmid for viability, and therefore, are indicative of insufficient activity to complement the lethal deletion in the aaRS gene. Where complementation is observed, the strain can be used to test for inhibitors of the product of the heterologous gene encoded by the test plasmid.

In another embodiment, a eucaryotic host cell is used to construct a mitochondrial tester strain. For example, in yeast, each of the mitochondrial tRNA synthetases is essential for growth on non-fermentable carbon sources (e.g., glycerol). Thus, complementation tests can be conducted in mitochondrial tester strains. As the genes encoding mitochondrial aminoacyl-tRNA synthetases are typically nuclear-encoded, the procedures described above can be modified to construct mitochondrial tester strains having a defect in a mitochondrial aminoacyl-tRNA synthetase. Modification is necessitated by the fact that yeast strains with a defect in mitochondrial protein synthesis, such as a defective aminoacyl-tRNA synthetase, lose their mitochondrial DNA, rapidly becoming rho–. As a result, these strains are unable to grow on non-fermentable carbon sources even if a complementing gene is introduced into the strain. Therefore, in a haploid strain having a defect in a yeast mitochondrial aminoacyl-tRNA synthetase gene (e.g., a gene disruption with a cosegregating selectable marker constructed as indicated above), the haploid strain can be crossed with a rho$^+$ strain having a wild-type mitochondrial aminoacyl-tRNA synthetase gene to restore the mitochondrial DNA. The resulting rho$^+$ diploid can then be transformed with a plasmid which encodes the wild-type yeast mitochondrial aminoacyl-tRNA synthetase (i.e., a maintenance plasmid) and a second selectable marker. Following sporulation, progeny spores which carry the defective mitochondrial aaRS gene, identified by the presence of the cosegregating selectable marker, and the maintenance plasmid, identified by the presence of the second selectable marker, and which are rho$^+$, can be isolated (e.g., by tetrad analysis). Strains constructed in this manner are suitable for complementation assays using genes encoding proteins comprising an enterococcal aminoacyl-tRNA synthetase or functional portion thereof.

For instance, a plasmid encoding an enterococcal aminoacyl-tRNA synthetase gene can be introduced into such a strain on a second plasmid having a third selectable marker. As indicated above, the maintenance plasmid can be selected against (e.g., where the selectable marker is URA3, selection on 5-fluoroorotic acid leads to loss of the maintenance plasmid), and complementation by the enterococcal gene can be monitored on a non-fermentable carbon source.

In another embodiment, a mitochondrial aminoacyl-tRNA synthetase gene disruption with a cosegregating selectable marker can be constructed in a diploid rho$^+$ strain (see e.g., Edwards, H. and P. Schimmel, *Cell* 51:643–649 (1987)). A plasmid encoding an enterococcal aminoacyl-tRNA synthetase gene is introduced on a plasmid having a second selectable marker. Sporulation of a resulting diploid yields two progeny spores carrying the yeast mitochondrial aminoacyl-tRNA synthetase gene disruption, identified by the presence of a cosegregating selectable marker, and two progeny spores carrying the corresponding wild-type gene. The presence of the plasmid can be monitored by the presence of the second selectable marker. Complementation by the enterococcal gene on the introduced plasmid is indicated by growth on non-fermentable carbon sources of spores carrying the disrupted aminoacyl-tRNA synthetase gene.

In the case of a mitochondrial tester strain, the Enterococcus aminoacyl-tRNA synthetase can be imported into mitochondria to achieve complementation of the mitochondrial defect. When it is necessary to achieve import or desirable to improve the efficiency of import of the aminoacyl-tRNA synthetase in the host cell, a gene fusion can be constructed using a sequence encoding a mitochondrial targeting sequence which functions in the host cell. For example, a mitochondrial targeting sequence can be introduced at the amino-terminal end of the Enterococcus aminoacyl-tRNA synthetase. In one embodiment in yeast, the Enterococcus aaRS gene or a sufficient portion thereof is introduced into a vector in which it is placed under the control of the minimal alcohol dehydrogenase promoter and is fused to the yeast cytochrome oxidase IV targeting signal derived from plasmid pMC4 (Bibus et al., *J. Biol. Chem.*, 263:13097 (1988)). Expression of the construct yields a fusion protein with an N-terminally located cytochrome oxidase IV targeting signal joined to the Enterococcus aaRS protein.

If the construction methods described here are not successful initially, one or more natural or synthetic enterococcal or other (e.g., procaryotic, such as a bacterial, or eucaryotic, such as a mammalian or fungal) tRNA gene(s) can be introduced into the host cell to provide one or more suitable tRNA substrates for the enterococcal aaRS. The tRNA genes of a number of species have been cloned and sequenced (Steinberg, S., et al. "Compilation of tRNA sequences and sequences of tRNA genes," *Nucleic Acids Res.* 21:3011–3015 (1993)). A method for constructing a strain of *Streptomyces lividans* in which an essential tRNA gene has been inactivated in the chromosome, and the gene is instead maintained on a plasmid, has been described (Cohen, S. N., WO 94/08033 (1994)).

Use of Tester Strains

To assess the inhibitory effect of a substance on a tester strain, the cells are maintained under conditions suitable for complementation of the host cell defect, under which complementation of the host cell defect is dependent upon the test gene (i.e., assay conditions). A substance to be tested is administered to the tester cells, and the viability or growth of the tester cells can be compared with that of cells of one or more suitable controls. A variety of control experiments can be designed to assess the inhibitory effect of a substance and/or the specificity of inhibition. The following examples are provided for purposes of illustration.

A preliminary test for inhibitory effect may be conducted where desired. For example, a substance to be tested can be administered to tester cells maintained under assay conditions, and the viability or growth of the tester cells in the presence of the substance can be compared with that of tester cells maintained under the same conditions in the absence of the substance. If it is determined that the substance inhibits growth of the tester cells, a further assessment of the specificity of inhibition by the substance can be conducted as described below.

Alternatively, the inhibitory effect of a substance on tester cell growth and the specificity of inhibition can be determined without conducting the preliminary test for inhibitory activity. The following examples, in which the various cell types are in each case exposed to drug, are provided for purposes of illustration only.

To determine the specificity of inhibition, the viability or growth of the tester cells can be compared with that of cells of one or more suitable control strains maintained under the same conditions. In particular, tester strains and control strains are maintained under assay conditions, and exposed to the substance to be tested.

Strains which are similar to the tester strain, but lack the heterologous aminoacyl-tRNA synthetase gene present in the tester strain (i.e., the "test gene"), can serve as control strains. These control strains comprise a "control gene" which is an aminoacyl-tRNA synthetase gene other than the heterologous aaRS gene present in the tester strain (i.e., an aaRS gene from a different species, such as a procaryotic or eucaryotic species). The control gene can be a cytoplasmic or mitochondrial aaRS gene, and it encodes an aaRS specific for the same amino acid as the aaRS encoded by the test gene. Viability or growth of the control strain is dependent upon the control gene under the conditions of the assay.

In one embodiment, a cell which is a cell of the same species as the host cell used to construct the tester strain and which further comprises a control aaRS gene, is selected as a control. For example, the control gene can be a wild-type aaRS gene from the control strain species which encodes an aaRS specific for the same amino acid as the aaRS encoded by the test gene. Such a cell can be used when, for example, the substance or compound to be tested does not significantly affect growth of the control strain under the assay conditions. For example, where an *E. coli* host is used to construct a tester strain having an *E. faecalis* aaRS gene, an *E. coli* strain having a wild-type *E. coli* control gene can be used as a control strain. As another example, if a yeast host cell having a defect in a mitochondrial aaRS gene is used to construct the tester strain, a yeast strain comprising the wild type mitochondrial gene can be used as a control strain.

In another embodiment, the control strain can be a strain, which is constructed in a manner which generally parallels that of the tester strain comprising the test gene, such that complementation of the host cell defect, which is also present in the control strain, is dependent upon the control gene under the assay conditions. In this embodiment, the control strain preferably comprises a host cell of the same species as the host cell used to construct the tester strain, and is closely related in genotype to the tester strain. These preferred control strains comprise a "control gene", which, as indicated above, is an aaRS gene other than the test gene (i.e., an aaRS gene from a different species, such as a heterologous procaryotic or eucaryotic species). Furthermore, the control gene, which can be cytoplasmic or mitochondrial, encodes an aaRS specific for the same amino acid as the test gene. Preferably, the control gene is selected from a species which is a host for the pathogen from which the test gene is derived, permitting the identification of specific inhibitors which selectively inhibit the pathogen aaRS (e.g., human control gene for *E. faecalis* test gene). Alternatively, because the eucaryotic aminoacyl-tRNA synthetases are generally more closely related to each other than to procaryotic aminoacyl-tRNA synthetases, a control gene from another eucaryote (e.g., a different mammalian species) can be used in lieu of one selected from the host species (e.g., a rat or mouse control gene for an *E. faecalis* test gene).

For example, a strain isogenic with a tester strain, except for the substitution of a human control gene, can serve as a control strain. Such a control strain can be constructed using the same methods and the same host cell used to construct the tester strain, with the exception that a human control gene is introduced into the host cell in lieu of the heterologous Enterococcus aaRS gene present in the tester.

Under the conditions of this assay, growth or viability of the control strain is dependent upon the control aaRS gene, which complements the host cell aaRS defect in the control strain. Specific inhibition by a substance can be determined by comparing the viability or growth of the tester strain and control strain in the presence of the substance.

In some cases, further controls may be desired to assess specific inhibition. For this purpose, one or more additional "comparison control" strains are used for purposes of comparison. These additional controls can be used to assess the relative effects of a substance upon growth of the tester and control strains in the presence of the substance.

Strains useful for this purpose include, for example, strains of the same species as the host cell used to construct the tester strain, which contain a wild type version of the aaRS gene which is inactivated in the tester strain. In one embodiment, where an *E. coli* host is used to construct a tester strain comprising an *E. faecalis* test gene, an *E. coli* strain comprising a wild-type *E. coli* aaRS gene can be used as a comparison control strain. In another embodiment, "parental-type" cells (e.g., parent host cells or a similar strain) are used as comparison controls. For example, the parent host cells of the tester strain can serve as a comparison control strain for the tester strain. Where the tester strain and the control strain have the same parent, a single strain can be used as the comparison control strain for both tester and control strains.

For example, a parent host cell from which the tester and control strains were both constructed (e.g., by inactivation and replacement of the wild type host aaRS gene) can be used as a comparison control strain. This comparison control strain contains a wild type version of the aaRS gene which is inactivated in the tester and control strains, and the viability or growth of this comparison control strain is dependent upon the wild type aaRS under the conditions of the assay. Specific inhibition of the heterologous Enterococcus aaRS encoded by the test gene (or a step in the expression of the Enterococcus gene) is indicated if, after administering the substance to the tester strain, growth of the tester strain is reduced as compared with an appropriate comparison control strain, and growth of the control strain is not reduced, or is relatively less reduced, as compared with its appropriate comparison control strain.

Testing for Antibiotic Resistance to tRNA Synthetase Inhibitors

Mutation of a drug target can reduce the effectiveness of antimicrobial or antibiotic agents, and can confer drug resistance. Thus, mutation of a target aminoacyl-tRNA synthetase, such as an *E. faecalis* LeuRS, TyrRS, IleRS, SerRS, TrpRS or PheRS, could reduce the effectiveness of an inhibitor of aaRS activity. To test for mutations that confer resistance to an inhibitor (e.g., an inhibitor of aaRS activity, including such an inhibitor having antimicrobial activity) a variety of approaches can be used. Mutant Enterococcus aaRS genes can be obtained, for example, by isolation of a mutant gene, or by preparing an individual mutant gene or an expression library of mutant Enterococcus aaRS genes, such as a library of mutants of an Enterococcus aaRS gene. The mutant gene or gene library can be introduced into suitable host cells for screening for resistance to a compound.

An isolated tRNA synthetase gene, such as an *E. faecalis* aaRS gene, can be mutagenized by any suitable method including, but not limited to, cassette mutagenesis, PCR mutagenesis (e.g., the fidelity of PCR replication can be reduced to induce mutation by varying $Mg^{2+}$ concentration, increasing the number of amplification cycles, altering temperatures for annealing and elongation, to yield random mutants), or chemical mutagenesis (e.g., nitrosoguanidine, ethylmethane sulfonate (EMS), hydroxylamine) of the entire gene or a portion thereof. The mutagenesis products can be used to construct an expression library of mutant genes (e.g., by inserting the gene into an expression vector, or replacing a portion of an expression vector comprising the wild-type gene with mutant fragments) which is introduced into a host cell.

In one embodiment, if the inhibitor is known to inhibit the host cell (e.g., *E. coli, S. cerevisiae, Bacillus subtilis*) aminoacyl-tRNA synthetase specific for the same amino acid, the mutant genes can be introduced into the wild-type host and the resulting cells can be exposed to drug to assess resistance.

In another embodiment, the procedures described above relating to tester strains are used in the method to identify mutants resistant to inhibitor. Introduction of the heterologous mutant aaRS gene(s) (i.e., mutant test gene(s)) into a host cell is carried out as described above for the production of tester strains. As an illustration, a mutant aaRS gene (e.g., MetRS) library can be introduced into a host cell having a defect in the endogenous gene encoding MetRS. The metG null strain of *E. coli* designated MN9261/pRMS615 is an example of the type of strain that can be constructed and used as a host for the introduction of mutant Enterococcus aaRS gene(s) (in that case, MetRS genes; see Kim et al., *Proc. Natl. Acad. Sci. USA* 90:10046–10050 (1993), describing a strain which carries a null allele of metG, and a temperature sensitive maintenance plasmid, carrying a wild type metG allele (encoding *E. coli* MetRS) and having a temperature sensitive replicon which causes loss of the maintenance plasmid at the non-permissive temperature).

Active, drug-resistant mutants are then identified by a selection process in which cells containing mutant genes encoding active aaRS are identified, and the effect of an inhibitor upon aaRS activity is assessed. Cells are maintained under conditions suitable for expression of the mutated gene, and cells containing an active mutant aaRS (e.g., an active recombinant *E. faecalis* aaRS) are identified by complementation of the host cell defect. Where complementation occurs, each resulting transformant is, in essence, a tester strain comprising a mutant test gene. Cells containing active mutant aaRS as determined by complementation of the host cell defect are then exposed to inhibitor, and the effect of inhibitor on cell growth or viability is assessed to determine whether the active mutant aaRS further confers resistance to inhibitor.

In the case of the metG null strain, complementation by the Enterococcus gene is indicated by growth at the non-permissive temperature at which the maintenance plasmid is lost. Cells which survive loss of the maintenance plasmid due to the presence of the complementing mutant gene are then challenged with inhibitor to assess resistance.

Resistance can be assessed by comparison to a suitable control by methods analogous to those described above for determining inhibition and/or the specificity of inhibition of a substance in tester cells. For example, the relative effects of an inhibitor upon a tester strain comprising the mutant test gene and upon a tester strain differing only in that it contains the test gene lacking the mutation, can be assessed by comparing the viability or growth of cells which are dependent upon either the test gene or mutant test gene for growth under conditions suitable for complementation of the host cell defect. For instance, the effect of inhibitor on the protein encoded by the test gene lacking the mutation can be determined by comparing the growth of cells containing the test gene in the presence of drug to the growth of such cells in the absence of drug, and the effect of inhibitor on the protein encoded by a mutant test gene can be determined by comparing growth of cells containing the mutant test gene in the presence of drug to the growth of such cells in the absence of drug. A decrease in the inhibitory effect on growth of cells carrying the mutant test gene as compared to the inhibitory effect against cells carrying the test gene lacking the mutation is indicative of resistance.

Cells containing a complementing mutant test gene which further confers resistance to an inhibitor can be used to identify derivatives of the inhibitor with improved antimicrobial effect, which circumvent resistance. Such cells can also be used to identify additional inhibitors having inhibitory activity against the active mutant aaRS encoded by the mutant test gene.

In another embodiment, a naturally occurring mutant Enterococcus aaRS gene which confers resistance to an inhibitor upon an Enterococcus cell, can be isolated from the Enterococcus organism using nucleic acids of the present invention as probes. The cloned gene can then be introduced into a host cell as described for the production of tester strains. Tester cells comprising the mutant test gene which confers resistance, and which complements the host defect, can be used as described herein to identify additional inhibitors having reduced susceptibility to the resistance mutation or derivatives of the inhibitor with improved inhibitory activity.

Vectors carrying mutant genes which confer resistance to inhibitor can be recovered and the insert analyzed to locate and identify the mutation by standard techniques, such as DNA sequence analysis, to yield additional information regarding the nature of mutations capable of conferring resistance to selected inhibitors. Mutant proteins can also be expressed and purified for further characterization by in vitro kinetic and binding assays.

Applications in Biochemistry

The Enterococcus aminoacyl-tRNA synthetase or stable subdomains of the protein can be used in a method to separate the amino acid that the enzyme specifically recognizes from a mixture of the amino acid and other compounds such as other amino acids, or to specifically isolate the L-amino acid from the D-amino acid. The tRNA synthetase can be chemically attached to a solid support material in a column or other suitable container. Alternatively, a fusion protein such as a GST-tRNA synthetase fusion or a His-tag-tRNA synthetase fusion can permit attachment to a suitable solid support which binds the GST portion or His-tag portion of the fusion protein, respectively. For example, a mixture of phenylalanine and other compounds can be loaded onto a column under conditions in which phenylalanine binds to phenylalanyl-tRNA synthetase, while other compounds present in the mixture flow through the column. In a later step, phenylalanine can be released from phenylalanyl-tRNA synthetase by changing the conditions in the column, such as washing with a solution of high ionic strength to elute L-phenylalanine, for example.

In a similar manner, the aminoacyl-tRNA synthetase can be used in a method to isolate tRNA that is specifically recognized by the tRNA synthetase.

Enterococcus aminoacyl-tRNA synthetases can be used in the quantitative determination of an amino acid by conversion to the corresponding aminoacyl hydroxamate. An appropriate assay is illustrated by the following series of reactions using phenylalanine as an example.

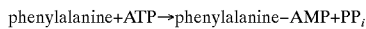

(in the presence of excess pyrophosphatase and ATP at pH 7.5, where pyrophosphatase catalyzes the conversion of the product inorganic pyrophosphate ($PP_i$) to inorganic orthophosphate ($P_i$); ATP is adenosine triphosphate; AMP is adenosine monophosphate)

phenylalanine–AMP+$NH_2OH$→phenylalanine–NHOH+ AMP (at pH 7.5)

phenylalanine–NHOH+$FeCl_3$→colored complex (at acidic pH)

The resulting colored complex can be quantitated by spectrophotometric measurements of absorbance at 540 nm, and compared with a standard curve made using known concentrations of phenylalanine. This assay is based on the reactions described by Stulberg and Novelli, *Methods in Enzymology* 5:703–707 (1962).

The Enterococcus aminoacyl-tRNA synthetases can also be used for the quantitative determination of ATP. In the presence of excess amino acid such as phenylalanine, and in the presence of pyrophosphatase to convert the product $PP_i$ to $P_i$, the ATP is quantitatively converted to AMP and inorganic pyrophosphate by the phenylalanyl-tRNA synthetase. For example,

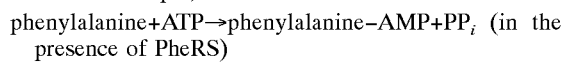

phenylalanine+ATP→phenylalanine–AMP+$PP_i$ (in the presence of PheRS)

$PP_i$+$H_2O$→2$P_i$ (in the presence of pyrophosphatase)

$P_i$ can be quantitated by reaction with molybdate, measuring the absorbance at 580 nm and comparing to a standard curve made using known quantities of orthophosphate.

The present invention is more specifically illustrated in the following examples, which are not intended to be limiting in any way.

EXEMPLIFICATION

Example 1

Preparation of *E. faecalis* Genomic DNA

Two hundred milliliters of an *E. faecalis* (American Type Culture Collection, ATCC Accession No. 33011) cell culture was grown to a cell density of $OD_{600}$=1.7 in BHI medium (VWR). The bacterial cells were harvested by centrifugation at 5,000 g for 10 minutes at 4° C. and then resuspended in 10 ml of cell resuspension buffer (50 mM Tris-HCl, pH 8.0/50 mM ethylenediaminetetraacetic acid (EDTA)/50 mM glucose/15 mg/ml lysozyme). After incubation at 37° C. for 2 hours, the cells were lysed by addition of 25 ml cell lysis buffer (50 mM Tris-HCl, pH 8.0/50 mM EDTA/1% SDS/50 µg/ml proteinase K/20 µg/ml RNaseA), followed by incubation at 55° C. for 7 hours. The cell lysate was then extracted twice with 35 ml of $H_2O$-saturated phenol (USB), twice with 30 ml of $H_2O$-saturated phenol/chloroform (USB), and once with 25 ml $H_2O$-saturated chloroform. Genomic DNA was precipitated by addition of 2 ml of 3 M Na-acetate (pH 5.2) and 40 ml of 100% ethanol. The precipitated DNA fibers were washed with 10 ml each of 100% ethanol and 70% ethanol. The air-dried DNA was then dissolved in 5 ml TE (10 mM Tris-HCl, pH 7.5/1 mM EDTA). Two mg of genomic DNA were isolated, based on UV-spectroscopy analysis and agarose gel electrophoresis.

EXAMPLE 2

Amplification and Characterization of DNA Fragments of Aminoacyl-tRNA Synthetase Genes from *E. faecalis* Genomic DNA Fragments of *E. faecalis* aminoacyl-tRNA synthetase genes were generated by PCR with the primers listed in Table 1. The PCR primers were designed by aligning either coding sequences for corresponding aaRSs from different species, or conserved regulatory DNA sequences (T-Box) upstream of some of the synthetase genes, using the PILEUP program (default parameters) (Needleman and Wunsch, *J. Mol. Biol.* 48:443–453 (1990)), available from the Genetics Computer Group, University of Wisconsin, Madison, Wis.).

For the KIYO-16 (SEQ ID NO:14), KIYO-17 (SEQ ID NO:15), KIYO-18 (SEQ ID NO:16), KIYO-19 (SEQ ID NO:17), and KIYO-20 (SEQ ID NO:18) primers, the amino acid sequences of the following isoleucyl-tRNA synthetases were used in an amino acid sequence alignment using the PILEUP program (Genetics Computer Group (GCG), University of Wisconsin, Madison, Wis.): *Tetrahymena thermophila* cytoplasmic (Swiss Protein Databank Accession No. P36422), *Saccharomyces cerevisiae* cytoplasmic (Swiss-Prot Accession No. P09436), *M. thermoautotrophicum* (Swiss-Prot Accession No. P26499), and *Escherichia coli* (Swiss-Prot Accession No. P00956).

For msi-1 (SEQ ID NO:19) and msi-4 (SEQ ID NO:20), the amino acid sequences of the following IleRSs were used in an amino acid sequence alignment with the Clustal program, using the PAM250 residue weight table (see, for Clustal method, Higgins, D. G. and Sharp, P. M., *Gene* 73:237–244 (1988)): *E. coli* (Swiss Protein Databank Accession No. P00956), *S. aureus* (Swiss-Prot Accession No. P41972), *Pseudomonas fluorescens* (Swiss-Prot Accession No. P18330), *Methanobacterium thermoautotrophicum* (Swiss-Prot Accession No. P26498), *Helicobacter pylori* (See FIGS. 1A–1C (SEQ ID NO:1 and SEQ ID NO:2) of U.S. patent application No. 08/451,715. FIGS. 1A–1C, SEQ ID NO:1 and SEQ ID NO:2 of U.S. patent application No. 08/451,715 are hereby incorporated herein by reference.), and human mitochondrial (Shiba, K. et al., *Proc. Natl. Acad. Sci. USA* 91:7435–7439 (1994)).

For the PILEUP alignment resulting in the choice of sequences for the KIYO-154 (SEQ ID NO:21) and KIYO-156 (SEQ ID NO:22) primers, translated ORF's of the following TyrRS genes were used: *Bacillus caldotenax* (Swiss Protein Databank Accession No. P04077), *B. stearothermophilus* (Swiss-Prot Accession No. P00952), *E. coli* (Swiss-Prot Accession No. P00951), *Neurospora crassa* mitochondrial (Swiss-Prot Accession No. P12063), and *B. subtilis* (Swiss-Prot Accession No. P22326).

For the KIYO-144 primer (SEQ ID NO:23), the alignment by the PILEUP program included the translated ORF's of the following SerRS genes: *E. coli* (Swiss Protein Databank Accession No. P09156), *S. cerevisiae* (cytoplasmic) (Swiss-Prot Accession No. P07284), and *C. griseus* (Chinese hamster) (Swiss-Prot Accession No. P26636).

For the Phe-F1 (SEQ ID NO:25), Phe-F2 (SEQ ID NO:27), Phe-R1 (SEQ ID NO:26), and Phe-R4 (SEQ ID NO:28) primers, the Lasergene System (Biocomputing Software for the Macintosh, from DNASTAR, Inc., Madison, Wis.) Clustal method with the PAM250 residue table was used to align the translated ORF's of the following PheRS genes: *B. subtilis* (Swiss Protein Databank Accession No. P17921 (α subunit) and P17922 (β subunit)), *E. coli* (Swiss-Prot Accession No. P08312 (β subunit) and P07395 (β subunit)), *Hemophilus influenzae* (Swiss-Prot Accession No. P43819 (α subunit) and P43820 (β subunit)), *T. thermophilus* (Swiss-Prot Accession No. P27001 (α subunit) and P27002 (β subunit)), and *Mycoplasma genitalium* (Swiss-Prot Accession No. P47436 (α subunit) and P47437 (β subunit)).

For the Trp-5 (SEQ ID NO:29) and Trp-7 (SEQ ID NO:30) primers, translated ORF's of the following sequences were used in an alignment by the method of Jotun Hein (*Methods in Enzymology* 183:626–645, 1990): *B. stearothermophilus* (Swiss Protein Databank Accession No. P00953), *B. subtilis* (Swiss-Prot Accession No. P21656), and *E. coli* (Swiss-Prot Accession No. P00954).

For the T-Box primer (SEQ ID NO:24), the 5' untranslated regions of the following gene sequences were included in a DNA sequence alignment using the Lasergene System (Biocomputing Software for the Macintosh, from DNASTAR, Inc., Madison, Wis.): *Bacillus stearothermophilus* cysE-cysS (Gagnon, Y. et al., *J. Biol. Chem.* 269:7473–7482 (1994)), trps (GenBank Accession No. M14742), tyrS (GenBank Accession No. J01546), and valS (GenBank Accession No. M16318); *Bacillus subtilis* cysE-cysS (GenBank Accession No. L14580), ilv-leu (Graodoni, J. A. et al., *J. Bacteriol.* 174:3212–3219 (1992)), leuS (GenBank Accession No. M88581), phes (EMBL Accession No. X53057), serS (DBBJ Accession No. D26185), thrS (GenBank Accession No. M36594), thrZ (GenBank Accession No. M36593), trps (GenBank Accession No. M24068) tyrS (GenBank Accession No. M77668) and tyrZ (EMBL Accession No. X52480); Lactobacillus casei trp (Natori, Y. et al., *J. Biochem.* (Tokyo) 107:248–255 (1990)), and valS (GenBank Accession No. L08854); *Lactococcus lactis* his (Delorme, C. et al., *J. Bacteriol.* 174:6571–6579 (1997)), and trp (Bardowski, J. et al., *J. Bacteriol* 174:6563–6570 (1992)); and *Staphylococcus aureus* ileS (EMBL Accession No. X74219). See Henkin, T., *Molecular Microbiology* 13:381–387 (1994).

TABLE 1

| aRS | PRIMER NAME | SEQ ID NO: | PRIMER SEQUENCE (5'->3') |
|---|---|---|---|
| Ile/Leu | KIYO-16 | 14 | GCG AAT TCG GIT GGG AYA CIC AYG GIS TIC C |
| | KIYO-17 | 15 | GCG AAT TCG GIT GGG AYT GYC AYG GIC TIC C |
| | KIYO-18 | 16 | GCG AAT TCG ICA RCG ITA YTG GGG IRT ICC IAT |
| | KIYO-19 | 17 | GCG AAT TCG IAA YCG ITW YTG GGG IAC ICC IMT |
| | KIYO-20 | 18 | GCG AAT TCR AAC CAI CCI CGI GTY TGR TCI WWI CCY TC |
| | msi-1 | 19 | GGI CAY GCI YTI AAY AAR ATH YTI AAR GA |
| | msi-4 | 20 | CCR TGI CCI GGI GCI GTR TGI AC |
| Tyr | KIYO-154 | 21 | ACI GSI AAR ATY GGI GAY CCH ACH GG |
| | KIYO-156 | 22 | ATR TTI CCR TAY TGR TCI GWI CCI CCR ATY T |

TABLE 1-continued

| aRS | PRIMER NAME | SEQ ID NO: | PRIMER SEQUENCE (5'->3') |
|---|---|---|---|
| | Ser | KIYO-144 | CCR TCY TCI GTY TGR TAR TTY TC |
| | T-Box | 24 | AAN NNR GGT GGH ACC RCG |
| Phe | Phe-F1 | 25 | GTN IAR TAY YTI GGI AAR AAR GG |
| | Phe-R1 | 26 | SWI GGYTCI GTR AAI GGR AA |
| | Phe-F2 | 27 | TTY TTY CCI TTY ACI GAR CC |
| | Phe-R4 | 28 | GGR TGI ACY TGI CCI ATR AAI CCN A |
| Trp | Trp-5 | 29 | TTT TGT ATW GTW GAT CAA CAT GCW ATW ACW G |
| | Trp-7 | 30 | TCT AAA TGT TGT TTT TGA TCT TCW CCW ACW GG | a. IleRS and LeuRS gene fragments

The PCR amplifications were done in 50 µl volumes with 10 mM Tris-HCl (pH 8.3 at room temperature), 50 mM KCl, 2.5 mM MgCl$_2$, 200 µM each of dNTPs (pH 7.0), 10 ng of E. faecalis (ATCC Accession No. 33011) genomic DNA isolated as described in Example 1, 100 pmole of each of the primers and 2.5 units of Taq DNA polymerase (Boehringer Mannheim). The reactions were first incubated at 95° C. for 2 minutes, followed by 30 cycles of 95° C. (1 min), 50° C. (1 min), and 72° C. (2 min). An 8 minute extension period at 72° C. was added at the end of the 30 cycles. Table 2 lists the PCR primers and the DNA products of successful PCR amplifications.

The major products from the above PCR reactions were separated on a 1.2% agarose gel and purified from the gel by GeneClean (Bio 101). Four µl out of 15 µl of the purified DNA fragments were ligated to 50 ng of pT7Blue T-vector (Novagen). The ligated plasmids were transformed into E. coli DH5α cells (competent cells purchased from Gibco/BRL), and the transformants were plated on LB agar containing 100 µg/ml ampicillin, 30 µg/ml X-gal (5-bromo-4-chloro-3-indolyl-β-D-galactopyranoside), and 0.1 mM IPTG (isopropyl-β-D-thiogalactoside). Plasmid DNA was extracted from the white colonies. Plasmids containing inserts were identified by their reduced mobility, compared to that of the no-insert control plasmid, in agarose gel electrophoresis. The DNA sequences of the inserts were determined by the fmol DNA Sequencing System (Promega) with T7 and U19 primers that hybridize to the vector sequences flanking the cloning site (Novagen). By querying the sequences against the Non-redundant Protein Data Bases of the BLAST Network Service at the National Center for Biotechnology Information (NCBI), the following clones were identified as containing IleRS gene fragments (see Table 2): clone Ef1A-6 (containing a 1.4 kb IleRS gene fragment generated with primers KIYO-16 (SEQ ID NO:14), KIYO-17 (SEQ ID NO:15), and KIYO-20 (SEQ ID NO:18) and clones Ef6A-1 and Ef6A-3, (both containing a 0.7 kb IleRS gene fragment generated with primers msi-1 (SEQ ID NO:19) and msi-4 (SEQ ID NO:20).

Unexpectedly, clone Ef2-2, which contains a 1.4 kb DNA insert derived from a PCR fragment obtained with the KIYO-18 (SEQ ID NO:16), KIYO-19 (SEQ ID NO:17) and KIYO-20 (SEQ ID NO:18) primers (see Table 2), contained a fragment coding for the C-terminal half of LeuRS. This DNA fragment has the sequence of the KIYO-18 primer (SEQ ID NO:16) at both ends. The KIYO-18 primer (SEQ ID NO:16) was designed based on a small region of the IleRSs that has high amino acid sequence homology to the LeuRSs. The Ef2-2 fragment was amplified by specific binding of KIYO-18 (SEQ ID NO:16) to the LeuRS gene at the nucleotides encoding homologous regions in IleRS and LeuRS, and by nonspecific binding of the same primer to a region about 150 bp downstream of the stop codon of the LeuRS gene. Nonspecific priming is a common phenomenon in PCR reactions, and it has been utilized for cloning purposes (Parker, J. D., et al., Nucleic Acids Res. 19:3055–3060 (1991); Screaton, G. R., et al., Nucleic Acids Res. 21:2263–2264 (1993)).

TABLE 2

| aaRS | 5' Primer* | 3' Primer | Expected Size (kb) | PCR Products (kb) |
|---|---|---|---|---|
| Ile/Leu | KIYO-16 KIYO-17 | KIYO-20 | 1.4 | 1.1, 1.4 (major product), 1.7 |
| | msi-1 | msi-4 | 0.7 | 0.7 (major product), 1.0 |
| | KIYO-18, KIYO-19 | KIYO-20 | 0.3 | 1.4 |
| Tyr | KIYO-154 | KIYO-156 | 0.45 | 0.45 |
| Ser | T-Box | KIYO-144 | >1.2 | 1.4 |
| Trp | Trp-5 | Trp-7 | 0.35 | 0.35 |
| Phe | Phe-F1 | Phe-R1 | 0.7 | 0.7 |
| | Phe-F2 | Phe-R4 | 2.5 | 2.5 |

*KIYO-16 (SEQ ID NO: 14) and the alternative primer KIYO-17 (SEQ ID NO: 15) were designed to encode the same region of IleRS, each primer allowing for different amino acid sequence bias. KIYO-18 (SEQ ID NO: 16) and the alternative primer KIYO-19 (SEQ ID NO: 17) were also designed to encode the same region of IleRS (a different region from that for KIYO-16 and -17), each primer allowing for different amino acid sequence basis.

b. TyrRS gene fragment

To amplify the E. faecalis TyrRS gene, PCR amplifications were done in 50 µl volumes with 10 mM Tris-HCl (pH 8.3 at room temperature), 50 mM KCl, 1.5 mM MgCl$_2$, 50 µM each of dNTPs (pH 7.0), 40 ng of E. faecalis genomic DNA (Example 1), 100 pmole of each of the primers, and 1 unit of Taq DNA polymerase (Boehringer Mannheim). The reactions were 30 cycles of 95° C. (1.5 min), 55° C. (1.5 min), and 72° C. (2 min). Under these conditions, the combination of primers KIYO-154 (SEQ ID NO:21) and KIYO-156 (SEQ ID NO:22) (see Table 1) produced a DNA fragment of about 450 bp (see Table 2). This DNA fragment was purified by agarose gel and with GeneClean (Bio 101). Four µl out of 23 µl of purified DNA fragments were ligated to 50 ng pT7Blue T-vector (Novagen) and transformed into *E. coli* Novablue cells (Novagen). The transformants were plated on LB agar containing 100 µg/ml ampicillin, 30 µg/ml X-gal, and 0.1 mM IPTG. The white colonies were subjected to direct colony PCR screening with the T7 and U19 primers (Novagen). The plasmids containing inserts of the expected sizes were isolated, and the sequences of the inserts were determined by Sequenase (dideoxy) sequencing (USB) with the T7 and U19 primers (Novagen). By querying the sequences against the Non-redundant Protein Data Bases of the BLAST Network Service at the National Center for Biotechnology Information (NCBI), clones #8 and #10 were identified as containing DNA having sequences characteristic of a TyrRS gene.

c. SerRS gene fragment

A fragment of the *E. faecalis* SerRS gene was generated with PCR using T-Box (SEQ ID NO:24) and KIYO-144 (SEQ ID NO:23) as the primers (see Table 1). The PCR amplification was done in a 50 µl volume with 10 mM Tris-HCl (pH 8.3 at room temperature), 50 mM KCl, 1.5 mM $MgCl_2$, 50 µM each of dNTPs (pH 7.0), 10 ng of *E. faecalis* genomic DNA (Example 1), 100 pmole each of the primers, and 2.5 units of Taq DNA polymerase (Boehringer Mannheim). The reactions were carried out by 30 cycles of 94° C. (30 sec.), 55° C. (30 sec.), and 72° C. (70 sec.). A DNA fragment of 1.4 kb was generated in the reaction as identified by agarose gel electrophoresis (see Table 2).

The PCR products were purified by agarose gel electrophoresis and the GeneClean system (Bio 101). 7.5 µl out of 10 µl of the purified DNA fragment were ligated to 50 ng of pT7Blue(R) T-vector (Novagen). The ligated plasmids were transformed into *E. coli* DH5α cells (competent cells purchased from Gibco/BRL), and the transformants were plated on LB-agar plates containing 100 µg/ml ampicillin, 30 µg/ml X-gal, and 0.1 mM IPTG. The white colonies were subjected to direct colony PCR screening with the T7 and U19 primers (Novagen). Plasmids containing inserts of the expected size were isolated, and the sequences of the inserts were determined by dideoxy sequencing with Sequenase (USB), using the T7 and U19 primers. By querying the sequences against the Non-redundant Protein Data Base of the BLAST Network Service at the National Center for Biotechnology Information (NCBI), clone Tbox+K144 was identified as containing the coding sequence for the N-terminal end of the *E. faecalis* SerRS gene. The methionine initiation codon was identified by sequence comparison with the other SerRS genes available in the database and by its location as the first in-frame Met codon.

d. TrpRS gene fragments

The PCR reactions were done in 50 µl volumes containing 10 mM Tris-HCl (pH 8.3 at room temperature), 50 mM KCl, 1.5 mM $MgCl_2$, 200 µM each of dNTPs (pH 7.0), 100 ng of *E. faecalis* genomic DNA (Example 1), 100 pmole of each of the primers, and 2.5 units of Taq DNA polymerase (Boehringer Mannheim). The reactions were first incubated at 94° C. for 1 minute, followed by 35 cycles of 94° C. (30 sec.), 45° C. (1 min), and 72° C. (1.5 min). The thermocycle reactions were followed by an extension for 10 min at 72° C. Under these conditions, the combination of the Trp-5 (SEQ ID NO:29) and Trp-7 (SEQ ID NO:30) primers (see Table 1) generated a DNA fragment of 350 bp, in agreement with the expected size (see Table 2).

The amplified DNA fragment was purified by agarose gel and by the GeneClean method (Bio 101). Three µl out of 10 µl of purified DNA were ligated to 50 ng pT7Blue(R) T-vector (Novagen). The ligated plasmid DNA was transformed into *E. coli* DH5α cells (competent cells purchased from Gibco/BRL) and the transformants were plated on LB agar containing 100 µg/ml ampicillin, 30 µg/ml X-gal, and 0.1 mM IPTG. The resulting white colonies were subjected to direct colony PCR screening with the T7 and U19 primers (Novagen). Clones EfW1, EfW3, and EfW4 were identified as containing inserts of the expected size. The PCR products from the colony PCR screening were purified with the Wizard PCR Preparation Purification System (Promega) and directly sequenced with $^{33}$P-labelled T7 and U19 primers with the fmol DNA Sequencing System (Promega). By querying the sequences against the Non-redundant Protein Data Base of the BLAST Network Service at the National Center for Biotechnology Information (NCBI), these clones were identified as containing a portion of the *E. faecalis* TrpRS gene.

e. PheRS gene fragments

The PCR amplifications were done in 50 µl volumes containing 10 mM Tris-HCl (pH 8.3 at room temperature), 50 mM KCl, 2.5 mM $MgCl_2$, 200 µM each of dNTPs (pH 7.0), 10 ng of *E. faecalis* genomic DNA (Example 1), 100 pmole of each of the primers, and 2.5 units of Taq DNA polymerase (Boehringer Mannheim). The reactions were first incubated at 95° C. for 2 minutes, followed by 30 cycles of 95° C. (30 sec.), 50° C. (1 min), and 72° C. (2 min). An 8 minute extension at 72° C. followed the 30 cycles. Under these conditions, the combination of the Phe-F1 (SEQ ID NO:25) and Phe-R1 (SEQ ID NO:26) primers (see Table 1) generated a PCR fragment of about 700 bp (Table 2), and the combination of the Phe-F2 (SEQ ID NO:27) and Phe-R4 (SEQ ID NO:28) primers (see Table 1) generated a PCR fragment of about 2.5 kb (Table 2).

These amplified DNA fragments were purified with the Wizard PCR Preparation Purification System. Six µl out of 50 µl of the purified DNA were ligated to 50 ng of pT7Blue T-vector. The ligated plasmid DNA was transformed into *E. coli* DH5α cells (competent cells purchased from Gibco/BRL), and the transformants were plated on LB agar containing 100 µg/ml ampicillin, 30 µg/ml X-gal, and 0.1 mM IPTG. The resulting white colonies were subjected to direct colony PCR screening with the T7 and U19 primers (Novagen). Clones Ef2-1 and Ef5-1 were identified as containing inserts of the expected size.

The PCR products from the colony PCR screening were purified with the Wizard PCR Preparation Purification System (Promega) and directly sequenced using $^{33}$P-labelled T7 and U19 primers with the fmol DNA Sequencing System (Promega). By querying the sequences against the Non-redundant Protein Data Base of the BLAST Network Service at the National Center for Biotechnology Information (NCBI), clone Ef2-1, which contains a DNA fragment generated with the Phe-F1 (SEQ ID NO:25) and Phe-R1 (SEQ ID NO:26) primers, was identified as containing a partial coding region of the PheRS alpha subunit, and clone Ef5-1, which contains a DNA fragment generated with the Phe-F2 (SEQ ID NO:27) and Phe-R4 (SEQ ID NO:28) primers, was identified as containing partial coding regions of both the alpha and beta subunits. These results are consistent with the fact that primers Phe-F1 (SEQ ID NO:25), Phe-F2 SEQ ID NO:27), and Phe-R1 (SEQ ID NO:26) were based on conserved sequences in the alpha subunit, and primer Phe-R4 (SEQ ID NO:28) was designed based on conserved sequences in the beta subunit. These results also indicate that the gene encoding the PheRS alpha and beta subunits in *E. faecalis* displays a gene organization similar to that seen in the PheRS genes of some other organisms.

EXAMPLE 3

Obtaining Full-Length Genes Encoding E. faecalis IleRS, LeuRS, TyrRS, SerRS, TrpRS and PheRS a. IleRS, LeuRS, TrpRS and PheRS genes Semi-specific PCR was used to amplify the terminal regions of the E. faecalis IleRS, LeuRS, TrpRS, and PheRS genes. The method is based on the high frequency of nonspecific priming at relatively low annealing temperatures during PCR. In this method, as illustrated in FIG. 1, a specific primer (SP1), having a sequence completely identical to a region of the identified partial gene sequence, was paired with one of a set of oligonucleotides unrelated to the E. faecalis genome DNA sequence (nonspecific primers, a–h in FIG. 1) during PCR at relatively low annealing stringency. Some of the nonspecific primers anneal to some extent in the desired orientation to regions downstream of the specific primers and thus amplify the DNA sequences flanking the identified partial genes. The resulting PCR products were screened by fmol DNA Sequencing, (Promega) using $^{33}$P-labelled specific primer SP2, which is located downstream of SP1.

Semi-specific PCR amplifications were carried out in 50 µl volumes with 10 mM Tris-HCl (pH 8.3 at room temperature), 50 mM KCl, 1.5–2.5 mM MgCl$_2$, 200 µM each of dNTPs (pH 7.0), 10–20 ng of E. faecalis genomic DNA, 20 pmole of the specific primer as summarized in the list below (see also Table 3), 20 pmole of one of a series of nonspecific primers, and 2.5 units of Taq DNA polymerase (Boehringer Mannheim). The reactions were first incubated at 95° C. for 2 minutes, followed by 30 cycles of 95° C. (30 sec.), 50° C. (30 sec.), and 72° C. (2–3 min). An 8 minute extension period at 72° C. followed these 30 cycles.

For the PheRS gene, after the above thermal cycles, 0.25 pmole of EfP-2 (5'TCACGAATTTCATTTGCAAAGC) (SEQ ID NO:50) was added to the reaction for amplifying the N-terminal-encoding region. 0.25 pmole of EfP-5 (5'ATCCAGGCCGGACAGCATGG) (SEQ ID NO:51) was added to the reaction for amplifying the C-terminal-encoding region. Four cycles of 95° C. (30 sec.), 55° C. (30 sec.), and 72° C. (2 min.) were applied to these reactions after the addition of the primers. EfP-2 (SEQ ID NO:50) and EfP-5 (SEQ ID NO:51) are specific primers downstream of EfP-3 (SEQ ID NO:36) and EfP-6 (SEQ ID NO:37) that were used in the semi-specific PCR reactions.

For the TrpRS gene, the C-terminal sequence was obtained with two sequential semi-specific PCR reactions. In the first semi-specific PCR reaction, primers EFW-Probe 1 (SEQ ID NO:35) and MET-JT1A (SEQ ID NO:39) generated about 500 bp towards the C-terminal end of the TrpRS gene. In the second semi-specific PCR reaction combining EFTrp-3 (SEQ ID NO:34) and MET-JT3 (SEQ ID NO:40), a DNA fragment including the C-terminus of the gene was produced. The following list summarizes the combinations of specific and nonspecific primers that were successfully used to amplify the N- and C-terminal regions of the IleRS, TrpRS and PheRS genes, and the N-terminal region of the LeuRS gene.

| | |
|---|---|
| IleRS N-terminus: | Ef-Ile1A (specific) (SEQ ID NO: 31) |
| | Met-JT16 (nonspecific) (SEQ ID NO: 43) |
| IleRS C-terminus: | Ef-Ile4 (specific) (SEQ ID NO: 32) |
| | Met-JT1A (nonspecific) (SEQ ID NO: 39) |
| TrpRS N-terminus: | EFTrp-2 (specific) (SEQ ID NO: 33) |
| | MET-JT16 (nonspecific) (SEQ ID NO: 43) |
| TrpRS C-terminus: | EFW-Probe 1 (specific primer for the first step) (SEQ ID NO: 35) |
| | MET-JT1A (nonspecific primer for the first step) (SEQ ID NO: 39) |
| | EFTrp-3 (specific primer for the second step) (SEQ ID NO: 34) |
| | MET-JT3 (nonspecific primer for the second step) (SEQ ID NO: 40) |
| PheRS N-terminus: | EfP-3 (specific) (SEQ ID NO: 36) |
| | MET-JT4 (nonspecific) (SEQ ID NO: 41) |
| PheRS C-terminus: | EfP-6 (specific) (SEQ ID NO: 37) |
| | MET-JT14 (nonspecific) (SEQ ID NO: 42) |
| LeuRS N-terminus: | Ef-Leu6A (specific) (SEQ ID NO: 38) |
| | MET-JT3 (nonspecific) (SEQ ID NO: 40) |

TABLE 3

Primer Sequences in Semi-specific PCR Reactions

| Primer Name | SEQ ID NO: | Primer Sequence (5°->3') |
|---|---|---|
| Ef-Ile1A | 31 | CGA CTT GTG ATA AGG CAT ACT C |
| Ef-Ile4 | 32 | GGT TCT TCA CAT GAA GGA GTT TTA C |
| EFTrp-2 | 33 | TGT GTC ATT CGT TCT AAC TCA CC |
| EFTrp-3 | 34 | TGA TGA GCC AGC AGT GAT TCG C |
| EFW-Probe 1 | 35 | CCA AGA ACC GCA AAA GCT ACG CCA |
| EFP-3 | 36 | TTG CGC GCT TCA ATT GCT TCT G |
| EfP-6 | 37 | CTT AGT GGA AAG TAT TGT AGC |
| Ef-Leu6A | 38 | CAG GAT CAG TGG TAT TAA TTT C |
| MET-JT1A | 39 | GCT TTG AAT GGG GCA TTC CTT TGC C |
| MET-JT3 | 40 | GTA TGG GAT TGA AGA ATT ACG C |
| MET-JT4 | 41 | TAC ACC ACA TGT TTA GGA TCG TTC |
| MET-JT14 | 42 | TAT GCA ATT GCA TTT TAG GCA C |
| MET-JT16 | 43 | ACT CAT TTT CAC GCC CTC TAT C |

The amplified PCR products were purified with the Wizard PCR Preparation Purification System (Promega) and fully sequenced with the fmol DNA Sequencing System (Promega). The DNA sequences generated with each primer were processed with programs from Lasergene System (Biocomputing Software for the Macintosh; DNASTAR, Inc., Madison, Wis.). Similarity of each sequence to known aaRS genes in the database was determined by the BLAST analysis program. The individual sequences were assembled by the DNA Sequence Management Program (Lasergene System) to generate full-length genes. The initiation codon of each gene was identified by a comparison of homology with known corresponding aaRS sequences in the database using the Multiple Sequence Alignment program from Lasergene System (Biocomputing Software for the Macintosh; DNASTAR, Inc., Madison, Wis.), and by the existence of a ribosomal binding site upstream of the initiation codon. The in-frame stop codons were defined as the C-terminal ends of the genes and were confirmed by homology comparisons with the corresponding aaRS sequences available in GenBank.

The nucleotide sequence determined for the *E. faecalis* isoleucyl-tRNA synthetase gene is shown in SEQ ID NO:1. The ATG initiation codon at nucleotide position 213 in the *E. faecalis* IleRS gene was determined by sequence comparisons to the *S. aureus* IleRS gene (GenBank Accession No. X74219) and by the existence of an upstream GAGG ribosomal binding site separated by 9 basepairs from the ATG. It should be pointed out that there are 4 in-frame ATG codons in this region. The three ATG codons thought to not be initiation codons are at nucleotide positions 192, 207, and 219. The open reading frame is 2778 basepairs and encodes a polypeptide of 926 amino acids. The deduced amino acid sequence of the IleRS polypeptide contains a $^{64}$HLGH$^{67}$ motif, which resembles the HIGH consensus amino acid sequence motif, and a $^{593}$KMSKS$^{597}$ amino acid motif. These two sequence motifs are characteristic of all class I aaRSs. The *E. faecalis* IleRS amino acid sequence (SEQ ID NO:2) was compared with the amino acid sequences deduced from heterologous IleRS gene sequences available in the database, using the Multiple Sequence Alignment program from Lasergene System (Biocomputing Software for the Macintosh; DNASTAR, Inc., Madison, Wis.), which uses the Clustal method with the PAM250 residue weight table. By this analysis, the *E. faecalis* IleRS was most similar to *S. aureus* IleRS (74% amino acid sequence similarity), and is least similar to human cytoplasmic IleRS (22% amino acid sequence similarity). The ORF encoding B. faecalis IleRS is most similar to the ORF encoding Staphylococcus aureus IleRS, sharing 56% nucleotide sequence identity.

The nucleotide sequence determined for the *E. faecalis* leucyl-tRNA synthetase gene is shown in SEQ ID NO:3. The open reading frame is 2412 basepairs and encodes a polypeptide of 804 amino acids. The deduced amino acid sequence of LeuRS contains a $^{48}$HVGH$^{51}$ sequence, resembling the HIGH consensus motif, and a $^{576}$KMSKS$^{580}$ motif. The *E. faecalis* LeuRS amino acid sequence was compared with the amino acid sequences of other LeuRSs available in the database, using the Multiple Sequence Alignment program from Lasergene System (Biocomputing Software for the Macintosh; DNASTAR, Inc., Madison, Wis.), by the Clustal method with the PAM250 residue weight table. *E. faecalis* LeuRS is most similar to *B. subtilis* LeuRS (71% amino acid sequence similarity), and is least similar to cytoplasmic LeuRSs from eucaryotic organisms *S. cerevisiae*, *N. crassa*, and *Caenorhabditis elegans* (13% amino acid sequence similarity). The ORF encoding *E. faecalis* LeuRS is most similar to the ORF encoding Bacillus subtilis LeuRS, sharing 62% nucleotide sequence identity.

The nucleotide sequence determined for the *E. faecalis* tryptophanyl-tRNA synthetase gene is shown in SEQ ID NO:5. The open reading frame is 1008 basepairs and encodes a polypeptide of 336 amino acids (SEQ ID NO:6). The deduced amino acid sequence of TrpRS has a $^{15}$TIGN$^{18}$ sequence as the HIGH motif, and a $^{198}$KMSKS$^{202}$ motif. The *E. faecalis* TrpRS amino acid sequence was compared with the heterologous TrpRS sequences available in the database using the Multiple Sequence Alignment program (Lasergene System Biocomputing Software for the Macintosh; DNASTAR, Inc., Madison, Wis.), which uses the Clustal method with the PAM250 residue weight table. Of the polypeptide sequences in the database, *E. faecalis* TrpRS is most similar to *B. subtilis* TrpRS (66% amino acid sequence similarity), and is least similar to rabbit cytoplasmic TrpRS (10% amino acid sequence similarity). The ORF encoding *E. faecalis* TrpRS is most similar to the ORF encoding *Bacillus subtilis* TrpRS, sharing 59% nucleotide sequence identity.

The nucleotide sequence determined for the *E. faecalis* phenylalanyl-tRNA synthetase gene is shown in SEQ ID NO:7. Similar to its counterpart in other organisms, this gene has two open reading frames, coding for an alpha subunit (first open reading frame) and a beta subunit (second open reading frame). The open reading frame for the alpha subunit is 1044 basepairs and encodes a polypeptide of 348 amino acids (translation of first coding region in SEQ ID NO:7, which is (SEQ ID NO:8). The open reading frame for the beta subunit is 2421 basepairs, and encodes a polypeptide of 807 amino acid residues (translation of second ORF in FIGS. 5A–5B) (SEQ ID NO:9); translation starts from the ATG at nucleotide position 1139 in SEQ ID NO:7. The alpha subunit contains standard class II aminoacyl-tRNA synthetase defining motifs: amino acid positions 127–136 for motif 1, positions 200–216 for motif 2, and positions 312–323 for motif 3. The *E. faecalis* PheRS amino acid sequence was compared with the heterologous PheRS sequences available in the database using the Multiple Sequence Alignment program from Lasergene Systems. The alpha and beta subunits of *E. faecalis* PheRS are most similar to the respective subunits of *B. subtilis* PheRS (62% and 47% amino acid sequence similarity, respectively), and are least similar to *S. cerevisiae* and *C. elegans* PheRS (12% and 11% amino acid sequence similarity), respectively. The open reading frames encoding the PheRS a and P subunits of *E. faecalis* are most similar to those of *B. subtilis*, sharing 54% and 44% nucleotide sequence identity, respectively.

The DNA sequences of the ORF's of the *E. faecalis* isoleucyl-, leucyl-, phenylalanyl-, seryl-, tryptophanyl-, and tyrosyl-tRNA synthetase genes were compared to the sequences in the Non-Redundant DNA Sequence Database at NCBI (National Center for Biotechnology Information, National Library of Medicine) using the program BLAST (Altschul, S.F. et al., *J. Mol. Biol.* 215:403–410 (1990)). The Non-Redundant DNA Database includes all DNA sequences deposited in the GenBank, EMBL, DDBJ, and PDB databases. The BLAST version used was BLASTN 1.4.9MP. The complete coding sequences corresponding to the four best matches for each synthetase were aligned with the *E. faecalis* sequences using DNASTAR's Lasergene (Lasergene Version 1.58 DNASTAR, Inc.) implementation of the Clustal program (Higgins, D. G. and Sharp, P. M., *Gene* 73:237–244 (1988)) with the PAM250 residue weight table, using default parameters.

b. TyrRS gene

In order to obtain the full-length gene sequence for *E. faecalis* TyrRS, an *E. faecalis* genomic DNA library was constructed in phage lambda ZAP (Stratagene). To construct the library, 10 μg of *E. faecalis* genomic DNA (Example 1) was partially digested in 100 μl with 0.3 units of Sau3A (Boehringer Mannheim). After incubation at 37° C. for 30 minutes, the partially cleaved genomic DNA was fractionated by electrophoresis on a 0.8% agarose gel. The DNA fragments of 3–9 kb were purified using GeneClean (Bio 101). 2.7 μl out of 5 μl of purified DNA fragments were ligated overnight at 16° C. to 0.8 μg of dephosphorylated BamHI lambda ZAP Express vector arms (Stratagene) in 5 μl. The ligated phage DNA was packaged with Gigapack II Plus packaging extract (Stratagene) according to the user's manual. The resulting *E. faecalis* genomic DNA phage library contained about 200,000 independent clones. 45 μl out of 500 μl of the phage library were spread onto three 150 mm LB agar plates. For each plate, 15 μl of the phage library were mixed with 600 μl of XL1-Blue MRF' *E. coli* (Stratagene) cell culture that was freshly grown to an OD$_{600}$ of 0.5. The phage/*E. coli* cell mixture was then mixed with 8 ml of LB top agar and spread on an LB plate. After the top agar solidified at room temperature, the plates were incubated at 37° C. overnight. Duplicate lifts of the plaques on these plates were generated with GeneScreen nylon membranes (Dupont/NEN). These membranes were first soaked for 2 minutes in 0.2 N NaOH/1.5 M NaCl and then 5 minutes in 0.5 M Tris-HCl, pH 7.5/1.5 M NaCl. After rinsing with 2x SSC, the membranes were then dried in a vacuum oven at 80° C. for 30 minutes. The membranes were then incubated in prehybridization/hybridization solution (5x SSC/1x Denhardt's solution/0.1% SDS/0.1 mg/ml salmon sperm DNA/50% formamide) at 42° C. for 30 minutes before being probed with a $^{32}$P-labelled *E. faecalis* TyrRS gene fragment.

To make the *E. faecalis* TyrRS gene probe, the partial gene fragment was directly amplified from the genomic DNA with primers EFTYR-1 (5'-TTTGCAATTGAATATTATGTTTTT) (SEQ ID NO:52) and EFTYR-2 (5'-ACAAACGATGGAAGCTGTGCAACA) (SEQ ID NO:53). These two primers were designed based on the DNA sequence obtained from clone #8 (Example 2b). The amplification reaction was carried out in a 50 μl volume with 10 mM Tris-HCl (pH 8.3 at room temperature), 50 mM KCl, 1.5 mM MgCl$_2$, 200 μM each of dNTPs (pH 7.0), 400 ng of *E. faecalis* genomic DNA, 20 pmole of each of the primers, and 2.5 units of Taq DNA polymerase (Boehringer Mannheim). The reactions were first incubated at 95° C. for 2 minutes, followed by 30 cycles of 94° C. (70 sec.), 55° C. (1 min), and 72° C. (2 min). A final extension step (5 minutes at 72° C.) was added at the end of the 30 cycles. The amplified gene fragment was purified using GeneClean (Bio 101). 3.5 μl out of 10 μl of the purified PCR DNA were $^{32}$P-labelled to about 2×10$^7$ cpm with the Random Primed DNA Labeling kit (Boehringer Mannheim) using α-D[$^{32}$p] ATP.

The labelled probe was then purified by passage through a NAP-5 column (Pharmacia), denatured by the addition of 0.1 volume of 3 M NaOH, and added to the nylon membranes bearing the lifted plaques of the *E. faecalis* genomic DNA library, in 10 ml of prehybridization/hybridization solution. The hybridization was at 37° C. for 16 hours. The nylon membranes were then washed twice, each time in 250 ml 0.1x SSC /0.1% SDS at 23° C. for 15 minutes. Hybridizations were analyzed by autoradiography.

Six positive clones were identified. The corresponding plaques were isolated from the plate and eluted in 2 ml of SM solution for 16 hours. (SM solution is 100 mM NaCl, 8 mM MgSO$_4$, 50 mM Tris-HCl, pH 7.5, and 0.01% gelatin.) The eluted phages were plated as was done for the original library with 50-200 plaque-forming units on each plate. The phage clones were re-screened with the $^{32}$P-labelled *E. faecalis* TyrRS partial gene DNA fragment, using the procedure described above. Two of the six positive clones (#1 and #6) identified in the initial screen were positive in the re-screening. Three well-separated plaques for clone #1 (1-1, 1-2, 1-3) and 1 for clone #6 (6-1) were isolated, and the insert in clone 1-2 was fully sequenced.

The DNA sequences determined from the above isolated clones were used to determine the full-length DNA sequence of the *E. faecalis* tyrosyl-tRNA synthetase gene. Clone 1-2 (phagemid PBK-CMV EfTyrl-2) contained a 2.1 kb fragment which contains the full-length TyrRS gene. The nucleotide sequence is shown in SEQ ID NO:10. The open reading frame is 1254 basepairs and encodes a polypeptide of 418 amino acids SEQ ID NO:11. The deduced amino acid sequence of TyrRS has the class I aminoacyl-tRNA synthetase defining a $^{45}$HIGH$^{48}$ motif, and the $^{572}$KFGKT$^{576}$ sequence that resembles the KMSKS motif. The *E. faecalis* TyrRS amino acid sequence was compared with the heterologous TyrRS sequences available in the database using the Multiple Sequence Alignment program from the DNASTAR package using the Clustal method with the PAM250 residue weight table. The sequence of the ORF of the TyrRS gene was compared with the DNA sequence of known TyrRS genes, as in Example 3a above. *E. faecalis* TyrRS is most similar to *B. stearothermophilus* TyrRS (72% amino acid sequence similarity), and is least similar to *Podospora anserina* TyrRS (20% amino acid sequence similarity). The ORF encoding *E. faecalis* TyrRS is most similar to the ORF encoding *B. subtilis* TyRS, sharing 50% nucleotide sequence identity.

c. SerRS gene

PCR was used to obtain the sequence of the C-terminal end of the SerRS gene using the *E. faecalis* genomic DNA library described in Example 3b as the template. One μl of phage library was first heated to 95° C. for 5 minutes in 20 μl of 0.5% Tween-20/50 mM NaCl/10 mM EDTA/10 mM Tris-HCl, pH 7.4, and then diluted to 400 μl with H$_2$O. Ten μl of the treated phage were used as the template DNA in a 50 μl PCR reaction containing 10 mM Tris-HCl (pH 8.3 at room temperature), 50 mM KCl, 1.5 mM MgCl$_2$, 50 μM each of dNTPs (pH 7.0), 20 pmol of T3 primer (Stratagene) complementary to vector phage DNA, 20 pmole of PG-58 (5'GTCCAATATGCGCATACACTC) (SEQ ID NO:54) primer complementary to the *E. faecalis* SerRS gene, and 2.5 units of Taq DNA polymerase (Boehringer Mannheim). PG-58 (SEQ ID NO:54) was designed based on the sequence obtained from clone Tbox+K144. After 30 cycles of 94° C. (30 sec.), 55° C. (30 sec.), and 70° C. (70 sec.), a DNA fragment of 700 bp was detected by agarose gel electrophoresis.

This PCR reaction product was purified with the Wizard PCR Preparation Purification System (Promega) and sequenced with the fmol DNA Sequencing System (Promega) using a $^{33}$P-labelled primer PG-60 (5'CTCAATGGTTCTGGTTTAGC) (SEQ ID NO:71) proximal to PG-58 (SEQ ID NO:54). The 5'region of the PCR product is identical to the 3' region of the cloned partial *E. faecalis* SerRS gene, contains an open reading frame with an unambiguous stop codon, and encodes a polypeptide with an amino acid sequence homologous to the C-terminal amino acid sequences of known SerRS proteins in GenBank.

The N-terminal and C-terminal partial sequences were assembled using the DNA Sequence Management Program (Lasergene System; DNASTAR, Inc., Madison, Wis.) to generate the full-length SerRS gene sequence. The nucleotide sequence determined for the *E. faecalis* seryl-tRNA synthetase gene is shown in SEQ ID NO:12. The ORF is 1269 basepairs, encoding 423 amino acid residues. As a class II aminoacyl-tRNA synthetase, the deduced amino acid sequence of *E. faecalis* SerRS (SEQ ID NO:13) contains the three class defining motifs: amino acid positions 190–199 for motif 1, positions 261–285 for motif 2, and positions 380–395 for motif 3. The *E. faecalis* SerRS amino acid sequence was compared with the SerRS sequences available in the database by using the Multiple Sequence Alignment program from DNASTAR, Inc. The sequence of the ORF of the *E. faecalis* SerRS gene was compared with that of known SerRS genes, as in Example 3a above. *E. faecalis* SerRS is most similar to the *B. subtilis* SerRS (64% amino acid sequence similarity), and is least similar to the mouse cytoplasmic SerRS (14% amino acid sequence similarity). The ORF encoding *E. faecalis* SerRS is most similar to the ORF encoding *B. subtilis* SerRS, sharing 58% nucleotide sequence identity.

EXAMPLE 4

Cloning of the *E. faecalis* IleRS Full Length Gene by Genetic Complementation of an IleRS-Defective *E. coli* Strain The sequence of the full-length IleRS gene obtained with the semi-specific PCR method revealed a unique ClaI restriction endonuclease site 27 bp upstream of the ATG initiation codon, and a unique KpnI site 82 bp downstream of the TAA stop codon. The *E. faecalis* genomic DNA was digested with ClaI and KpnI and fractionated on a 1% agarose gel. DNA fragments of about 2.5–3.5 kb were purified from the gel with a GeneClean kit and ligated to a phagemid pTZ19R (USB) that had been digested with AccI (compatible with a ClaI site for DNA ligation), and with KpnI. The ligated DNA was then transformed into *E. coli* MI1 cells. The MI1 strain has an isoleucine auxotrophy due to an elevated K of the IleRS enzyme for isoleucine, and requires complex medium to supply isoleucine for growth (Iaccarino, M. and Berg, P., *J. Bacteriol.* 105:527–537 (1971); Schmidt, E. and Schimmel, P., *Science* 264:26514 267 (1994)). The transformation mixture was spread onto an M9 minimal medium plate to select for transformants capable of complementing a defective *E. coli* IleRS gene. After 3 days of incubation at 37° C., one colony about 2 mm in diameter appeared. Characterization of this clone by direct colony PCR screening and DNA sequencing indicated that it contained the ClaI/KpnI DNA fragment encompassing the full-length *E. faecalis* IleRS gene. This clone was called pTZEfIRS. Plasmid pTZEfIRS was transformed into *E. coli* strain DH5α.

EXAMPLE 5

Cloning of the *E. faecalis* Ile-, Leu-, Try-, Tyr-, Ser-, and Phe-tRNA Synthetase Genes into GST- and/or His-tag Fusion *E. coli* Expression Vectors a. GST-LeuRS and GST-SerRS expression constructs

*E. faecalis* leucyl- and seryl-tRNA synthetase genes were cloned into *E. coli* expression vector pGEX-4T-2 (Pharmacia) to express fusion proteins having glutathione S-transferase (GST) fused to the N-termini of the tRNA synthetases. The DNA fragments comprising the ORF's of the leucyl- and seryl-tRNA synthetases were generated by PCR amplification using the following PCR primers:

```
Leu 5' primer                         (SEQ ID NO:55)
5'cccggatccATGAGCTACAATCACAAAG
         BamHI Leu 3' primer                         (SEQ ID NO:56)
5'ccgcctcgagTTAATTTGCAACAATATTTAC
        XhoI Ser 5' primer                         (SEQ ID NO:57)
5'cgcggatccATGTTAGATGTAAAAATGATGCG
        BamHI Ser 3' primer                         (SEQ ID NO:58)
5'ccgctcgagCGGTTATTTAATAACTGTTAGGTTACC
       XhoI
```

The lowercase letters indicate nucleotides introduced for cloning purposes. The restriction sites flanking the ORF's are underlined and labelled.

PCR reactions were carried out in 50 μl with 20 mM Tris-HCl (pH 8.8 at 25° C.), 10 mM KCl, 10 mM $(NH_4)_2SO_4$, 0.1% Triton X-100, 10 ng of *E. faecalis* genomic DNA (Example 1), 20 pmole each of the appropriate 5' and 3' primers (above), 0.25 mM each of dNTPs, 2 mM $MgSO_4$, and 2 units of Vent DNA polymerase (New England Biolabs). The template genomic DNA was first denatured for 2 minutes at 95° C., followed by 30 cycles of 95° C. (30 sec.), 55° C. (30 sec.), and 72° C. (2 min.). An 8 minute extension period at 72° C. was added at the end of the 30 cycles. The predominant products in these PCR amplifications were a 2.4 kb fragment for the LeuRS gene, and a 1.3 kb fragment for the SerRS gene.

The amplified DNA fragments were purified using the Wizard PCR Preparation Purification System (Promega), and then digested with BamHI and XhoI restriction endonucleases (New England Biolabs), followed by gel purification using the GeneClean procedure. The purified DNA fragments were separately cloned into the BamHI and XhoI sites in the pGEX-4T-2 *E. coli* expression vector (Pharmacia), yielding plasmids $pC^3$582 for GST-LeuRS and pC3778 for GST-SerRS, both in *E. coli* strain DH5α. The gene sequences of the ORF's in both of these expression constructs were confirmed to be identical to the genomic gene sequences previously determined.

b. GST-TyrRS and GST-TrDRS expression constructs

The *E. faecalis* TyrRS and TrpRS genes were each cloned into pGEX4T-2NdeI, a modified pGEX-4T-2 plasmid, for expression as a GST-fusion protein in *E. coli*. To make pGEX4T-2NdeI, pGEX-4T-2 was linearized with BamEI and EcoRI, followed by purification by agarose gel and the GeneClean kit (Bio 101). The linearized pGEX-4T-2 DNA was then ligated with 5' phosphorylated oligonucleotides pGEX-A (GATCCCATATGGG) (SEQ ID NO:59) and pGEX-B (AATTCCCATATGG) (SEQ ID NO:60), which were annealed to each other by incubating for 2 min. at 85° C., and then for 15 min. each at 65° C., 37° C., 25° C., and 0° C., in order. The ligated DNA was transformed into *E. coli* DH5α cells (competent cells purchased from Gibco/BRL). The plasmids were isolated from the resulting transformants and characterized with restriction endonuclease mapping and DNA sequencing. The desired construct, pGEX4T-2NdeI, was identified and was characterized as identical to pGEX-4Tr-2 except that it contained the following DNA sequence between the BamHI site and EcoRI site, which introduces an NdeI site with its ATG codon in-frame with the glutathione S-transferase coding sequence: ggatccCATATGGgaattc (SEQ ID NO:61).

For cloning of the *E. faecalis* TyrRS and TrpRS genes into pGEX4T-2NdeI, the ORF's of the TyrRS and TrpRS genes were amplified by PCR using the following oligonucleotides as the primers:

```
EfTyr-5' (SEQ ID NO:62):
5'-gtttatcgtacacatATGAATATCATTGACGAGCTAGCATGGCGT
                 NdeI EfTyr-3' (SEQ ID NO:63):
5'-gttaccctactcgagCTAATCCATTACTTTTGCTAAAA
                 XhoI EfTrp-5' (SEQ ID NO:64):
5'-caattgttttcatATGAAAACAATTTTTTCTGGTATTCAGC
                NdeI EfTrp-3' (SEQ ID NO:65):
5'-tttccgctcgagCGGAAACTTCGCGGGTTTTTATTATG
             XhoI
```

The lowercase letters represent the nucleotides introduced for cloning purposes. The restriction sites flanking the ORF are underlined and labelled.

For the TyrRS gene, the PCR amplifications were carried out in 50 μl with 20 mM Tris-HCl (pH 8.8 at 25° C.), 10 mM KCl, 10 mM (NH4)2SO$_4$, 0.1% Triton X-100, 100 ng of *E. faecalis* genomic DNA (Example 1), 20 pmole each of the 5' and 3' primers, 0.2 mM each of dNTPs, 2 mM MgSO$_4$, and 2 units of Vent DNA polymerase (New England Biolabs). The reactions were first subjected to denaturing conditions for 2 minutes at 95° C., followed by 30 cycles of 95° C. (30 sec.), 55° C. (30 sec.), and 72° C. (2 min.). An 8 minute extension step at 72° C. followed the 30 cycles. The predominant product in the PCR reaction was a 1.2 kb DNA fragment.

For the TrpRS gene, the PCR reactions were carried out in 50 µl with 20 mM Tris-HCl (pH 8.8 at 25° C.), 10 mM KCl, 10 mM (NH4)2SO$_4$, 0.1% Triton X-100, 100 ng of *E. faecalis* genomic DNA (Example 1), 20 pmole each of the 5' and 3' primers, 0.1 mM each of dNTPs, 10 mM MgSO$_4$, and 2 units of Vent DNA polymerase (New England Biolabs). The reactions were first subjected to denaturing conditions for 1 minute at 94° C., followed by 30 cycles of 95° C. (30 sec.), 60° C. (30 sec.), and 74° C. (70 sec.). A 4 minute extension step at 74° C. followed the 30 cycles. The predominant product in the PCR reaction was a 1.1 kb DNA fragment.

The PCR products were purified with the Wizard PCR DNA Preparation and Purification System, then digested with NdeI and XhoI restriction endonucleases, followed by ligation with pGEX4T-2NdeI plasmid linearized with NdeI and XhoI. The ligated DNA was transformed into *E. coli* DH5α competent cells (purchased from Gibco/BRL), yielding clone EFTYRGST-VENT#6 for expression of the GST-TyrRS fusion, and clone pC$^3$689 for expression of the GST-TrpRS fusion. The gene sequences in both of these expression constructs were confirmed to be identical to the genomic gene sequences previously determined.

c. GST-IleRS expression construct

The *E. faecalis* IleRS gene was subcloned from pTZEfIRS (see Example 4) into pGEX4T-2NdeI (see Example 5b) for expression in *E. coli*. The ATG initiation codon of this gene forms part of an NdeI restriction endonuclease site, and there is an EcoRI site flanking the 3' end of IleRS gene in pTZEfIRS. Because there is also an EcoRI site within the IleRS gene, a combination of partial EcoRI and complete NdeI digestions was applied to produce a full-length gene DNA fragment. 3.5 αg of pTZEfIRS plasmid DNA were digested with NdeI restriction endonuclease in a 50 µl volume by incubation at 37° C. for 1 hour. After confirming complete digestion by examining 4 µl of the digested sample using agarose gel electrophoresis, 4 units of EcoRI were added to the remaining digestion reaction and incubated at 37° C. for 10 minutes. The digested DNA sample was then subjected to electrophoresis on a 1% agarose gel. The 2.9 kb DNA fragment was isolated and purified with the GeneClean kit (Bio 101) and ligated to pGEX4T-2NdeI plasmid linearized with NdeI and EcoRI. Direct PCR colony screening of the transformants revealed that clones 5-2 and 5-8 contained the *E. faecalis* IleRS gene. Sequencing of these two clones indicated that both of them contained a deletion mutation at nucleotide position 1270.

In order to obtain an *E. faecalis* IleRS expression construct with the wild type sequence, the 5-1510 bp IleRS gene fragment in plasmid pTZEfIRS was excised with the NdeI and NgoMI restriction endonucleases, and purified by agarose gel electrophoresis and GeneClean (Bio 101). The C-terminal part of the gene as well as the expression vector were obtained by digesting clone 5-2 plasmid DNA with the same restriction endonucleases (NdeI and NgoMI) and isolating the fragments by agarose gel electrophoresis and GeneClean. These two fragments of DNA were ligated together and transformed into DH5α, yielding pC$^3$642. Transformants were inoculated into 3 ml LB broth containing 50 µg/ml of ampicillin and incubated until the A$_{600}$ of the bacterial cultures reached 0.6 to 1. Protein expression was induced by the addition of IPTG to 1 mM. After 3 hours of IPTG-induced protein expression at 37° C., the bacterial cells were recovered by centrifugation, and resuspended in 200 µl SDS-PAGE sample buffer (50 mM Tris-HCl, pH 6.8, 100 mM dithiothreitol (DTT), 2% SDS, 0.1% bromophenol blue, 10% glycerol). After boiling for 5 minutes, the samples were loaded onto a 10% SDS-polyacrylamide gel. Staining the gel with Coomassie blue after electrophoresis revealed that clone pC$^3$642 expressed a 130 kDa protein, the expected size for the GST-fusion of *E. faecalis* IleRS. This clone was fully sequenced and found to contain the wild type *E. faecalis* IleRS sequence.

d. SerRS His-tag fusion construct

The *E. faecalis* SerRS gene was cloned into pET-15b and pET-20b(+) (Novagen) for expression as N- or C-terminal His-tag fusion proteins. To make the expression constructs, the following oligonucleotide primers were used in PCR reactions to amplify the region of the SerRS ORF:

```
EfHS-1                                    (SEQ ID NO:66)
5'gtgccaacatatgTTAGATGTAAAAATGATGC
         NdeI EfHS-2                                    (SEQ ID NO:67)
5'cagtcagtcgacTTTAATAACTGTTAGGTTACC
         SalI EfHS-3                                    (SEQ ID NO:68)
5'cagtcaggatccTTATTTAATAACTGTTAGGTTACC
         BamHI
```

The lowercase letters indicate nucleotides introduced for cloning purposes. The restriction sites flanking the ORF are underlined and labelled.

PCR reactions were carried out in 50 µl with 20 mM Tris-HCl (pH 8.8 at 25° C.), 10 mM KCl, 10 mM (NH$_4$)$_2$SO$_4$, 0.1% Triton X-100, 0.5 Ag pC$^3$778 plasmid DNA, 20 pmole each of the 5' and 3' primers (EfHS-1/EfHS-2 for C-terminal fusion and EfHS-l/EfHS-3 for N-terminal fusion), 0.5 mM each of dNTPs, 2-4 mM MgSO$_4$, and 1 unit of Vent DNA polymerase (New England Biolabs). The reactions were first denatured for 2 minutes at 95° C., followed by 20 cycles of 95° C. (30 sec.), 55° C. (30 sec.), and 72° C. (2 min.). An extension step of 72° C. for 10 minutes was added at the end of the 30 cycles. The predominant products in the PCR reactions were 1.3 kb fragments. The amplified DNA fragments were purified using the Wizard PCR Preparation Purification System (Promega) and then digested with NdeI and SalI restriction endonucleases (New England Biolabs) for the C-terminal fusion construct, or NdeI and BamHI for the N-terminal fusion. The digested DNA fragments were then purified by agarose gel electrophoresis and extraction of the DNA from agarose using the GeneClean method. The purified DNA fragments were separately cloned into the NdeI/XhoI sites of pET-20b (+) or the NdeI/BamHI sites of pET-15b *E. coli* expression vectors (Novagen) in DH5α cells, yielding pC$^3$731 for the N-terminal His-tag fusion, and pC$^3$734 for the C-terminal His-tag fusion. These plasmids were isolated and retransformed into BL21(DE3) cells for expression of the recombinant fusion proteins.

e. PheRS His-tag fusion construct

The *E. faecalis* PheRS gene was cloned into the pET-21 (+) expression vector (Novagen) to produce a polypeptide having the C-terminus of the beta subunit fused to a 6-His tag. To make the expression construct, the following oligonucleotide primers were used in the PCR reactions to amplify the PheRS ORF:

EfP-36                                    (SEQ ID NO:69)
5'-cgcggatccAGGGGAACGCATAATGACATTACAAGC
       BamHI EfP-37                                    (SEQ ID NO:70)
5'-acgtcagtcgacTCTTACTTCTACTTGATG
         SalI The lowercase letters indicate nucleotides introduced for cloning purposes. The restriction sites flanking the ORF are underlined and labelled.

PCR reactions were carried out in 50 µl with 20 mM Tris-HCl (pH 8.8 at 25° C.), 10 mM KCl, 10 mM (NH$_4$)$_2$SO$_4$, 0.1% Triton X-100, 100 ng of *E. faecalis* genomic DNA (Example 1), 20 pmole each of the EfP-36 and EfP-37 primers, 1.0 mM each of dNTPs, 6 mM MgSO$_4$, and 1 unit of Vent DNA polymerase (New England Biolabs). The components of the reaction were first subjected to denaturing conditions for 2 minutes at 95° C., followed by 30 cycles of 95° C. (30 sec.), 55° C. (30 sec.), and 72° C. (3.5 min.). An extension step of 72° C. for 10 minutes was added to the end of the 30 cycles. The predominant products in the PCR reactions were 3.6 kb fragments. The amplified DNA fragments were purified using Wizard PCR Preparation Purification System (Promega), and then digested with BamHI/SalI restriction endonucleases (New England Biolabs). The digested DNA fragments were then purified by electrophoresis on an agarose gel, and extracted from the agarose using the GeneClean method. The purified DNA fragments were cloned into the BamHI/SalI sites of the pET-21(+) *E. coli* expression vector (Novagen), yielding plasmid pC$^3$742 in *E. coli* strain DH5α.

Plasmid pC$^3$742 (in *E. coli* DH5α) was deposited in accordance with the provisions of the Budapest Treaty at the American Type Culture Collection (ATCC), 10801 University Boulevard, Manassas, Va. 20110-2209, U.S.A. on Jul. 21, 1999. The deposit has been assigned Patent Deposit Designation PTA-394.

EXAMPLE 6

Expression and Purification of Active Recombinant *E. faecalis* Aminoacyl-tRNA Synthetases a. GST-IleRS, GST-LeuRS, GST-SerRS, GST-TrDRS To express the recombinant GST fusion proteins, 20 ml of an overnight LB culture (with 100 µg/ml of ampicillin) of *E. coli* cells bearing one of the plasmids p03642 (IleRS), pC$^3$582 (LeuRS), pC$^3$689 (TrpRS), or pC$^3$778 (SerRS) were used to inoculate 2 liters of LB (with 100 µg/ml of ampicillin). The cells were grown at 37° C. for about 3.5 hours to reach OD$_{600}$ 0.6–1, before IPTG was added to a final concentration of 0.1 mM to induce expression of the recombinant proteins. After 1–3 days of IPTG-induced protein expression at 18° C., the bacterial cells were pelleted by centrifugation in a Beckman JA10 rotor for 20 minutes at 6000 rpm.

To purify the proteins, the cells were resuspended in 50 ml of 1x phosphate-buffered saline (1x PBS: 140 mM NaCl, 2.7 mM KCl, 10 mM Na$_2$HPO$_4$, 1.8 mM KH$_2$PO$_4$, pH 7.3), 1 mM DTT, 1x protease inhibitors (each at 5 µg/ml: leupeptin, pepstatin, chymostatin, and antipain), and 100 µg/ml lysozyme. The resuspended *E. coli* cells were lysed by French press. The cell lysates were centrifuged at 12,000g for 30 min at 4° C. Each supernatant was recovered and loaded onto a 10–20 ml glutathione-agarose affinity column equilibrated with 1x PBS/5 mM DTT at 4° C.

After the samples were loaded, the columns were washed with 500 ml of 1x PBS with 5 mM DTT at 4° C. The GST-aaRS fusion proteins that bound specifically to the glutathione-agarose columns were eluted with 30 ml of 10 mM glutathione, 50 mM Tris-HCl (pH 8.0), in three 10 ml aliquots at 25° C. The eluted fusion proteins were concentrated to a volume of about 3 ml, using Centriprep-30 centrifuge concentrators (Amicon). In order to store the protein in the desired HEPES buffer solution, the 3 ml of concentrated protein were diluted to 15 ml with 100 mM HEPES (pH 7.5) and 5 mM DTT, and then concentrated back to about 3 ml in the same Centriprep concentrator. The concentrated proteins were again diluted to 15 ml with 100 mM HEPES (pH 7.5) and 5 mM DTT, and then concentrated to a final volume of 0.1 ml for GST-IleRS, 3 ml for GST-LeuRS, 2.5 ml for GST-SerRS, and 2.5 ml for GST-TrpRS. The concentrated protein solutions were mixed with 1 M DTT to a final concentration of 10 mM and then with an equal volume of glycerol. The proteins were stored at −20° C. 2.5 mg to 38 mg of protein were purified, according to Bradford assays (Pierce).

The purified proteins were analyzed on an 8% SDS-polyacrylamide gel stained with Coomassie blue. They all appeared to be more than 75% pure and to possess the predicted apparent molecular weights.

Figure 2:
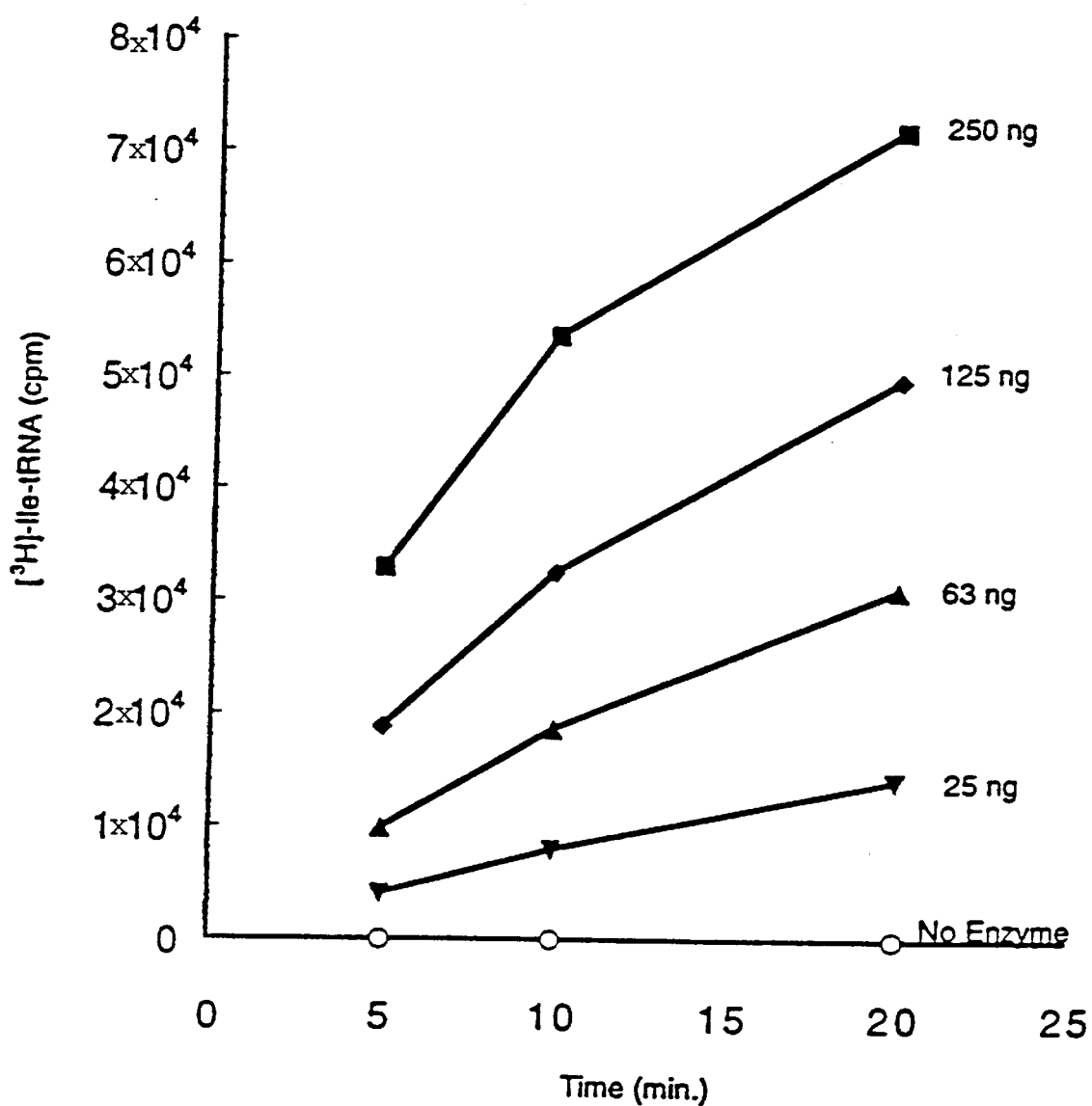
FIG. 2 is a graph illustrating the aminoacylation activity (cpm, counts per minute of [$^3$H]isoleucyl-tRNA) over time (minutes) of purified N-terminal GST-IleRS expressed from plasmid pC$^3$642 as described in Example 6a, using crude total tRNA from *E. coli*. The aminoacylation activities were assayed with 250 ng (filled squares), 125 ng (filled diamonds), 63 ng (filled triangles), or 25 ng (filled inverted triangles) of GST-IleRS in each of the reactions. The line with open circles shows a control reaction containing no enzyme.

For testing the recombinant *E. faecalis* IleRS charging activity, the purified GST-IleRS was diluted to between 2.5 µg/ml and 25 µg/ml in 50 mM HEPES, pH 7.5/0.05 mg/ml BSA (bovine serum albumin)/10 mM DTT/1% dimethyl sulfoxide (DMSO). The diluted enzyme was incubated at 25° C. for 20 minutes. Ten µl of the diluted enzyme were then mixed with 40 µl of reaction cocktail that contained the following: 2.5 µmole HEPES, pH 7.5, 0.5 µmole MgCl$_{21}$ 1 µmole KCl, 0.4 µmole DTT, 1% of DMSO (v/v), 0.2 µmole ATP, 10 nmole *E. coli* total tRNA (Sigma), 0.238 nmole unlabelled isoleucine, and 0.0125 nmole [$^3$H]-labelled isoleucine (Amersham; specific activity 94 Ci/mmol). The reactions were carried out at 25° C., and 15 µl aliquots were removed at each time point and applied to filter paper discs (3 MM, Whatman) which were then immediately soaked in 5% (wt/vol) trichloroacetic acid (TCA). Filters were washed for three 10-minute periods in 5% TCA, rinsed in 95% ethanol and 100% ether, and the incorporation of [$^3$H]-amino acid into tRNA (formation of [$^3$H]-isoleucine-tRNA) was measured in Betafluor by liquid scintillation counting. Results are shown in FIG. 2.

Figure 3:
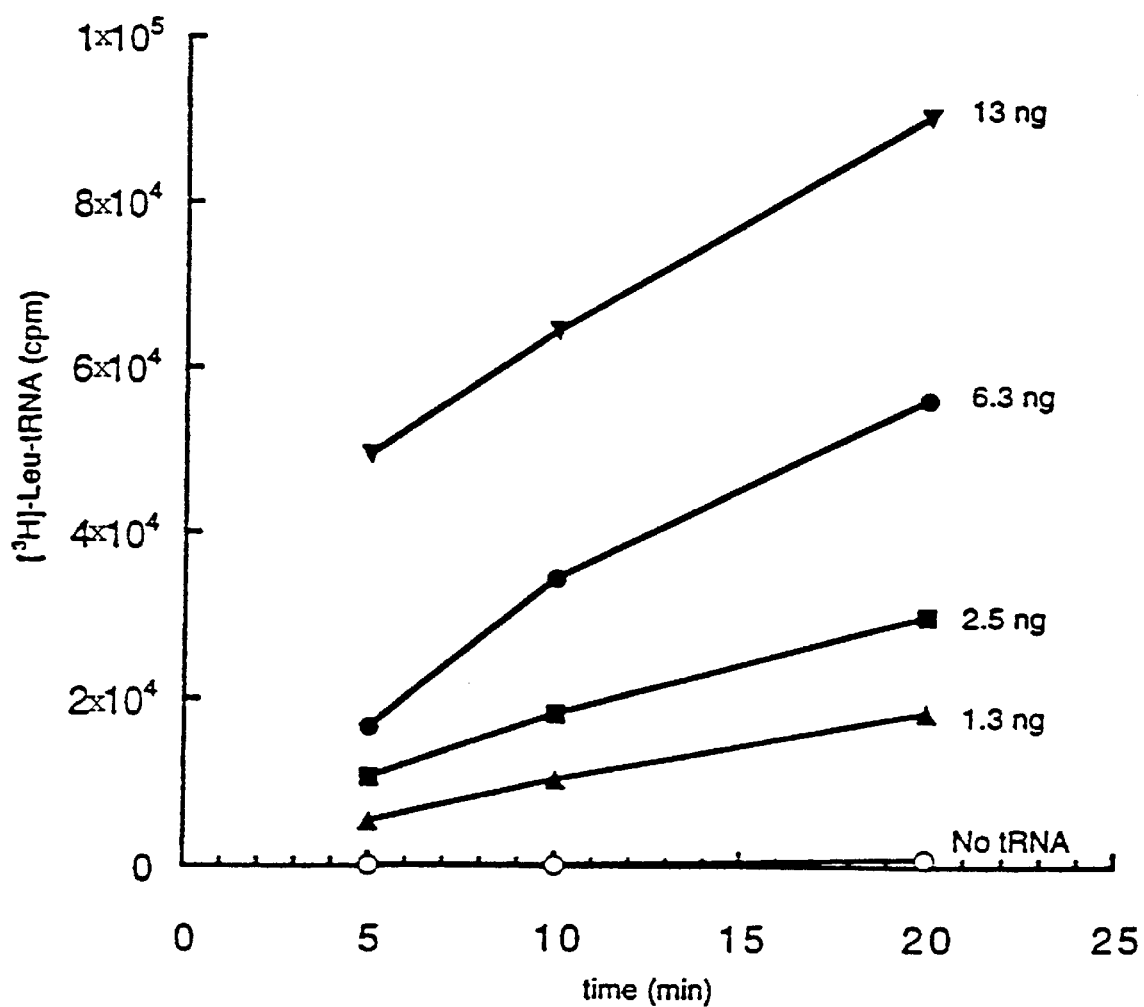
FIG. 3 is a graph illustrating the aminoacylation activity (cpm, counts per minute of [³H]leucyl-tRNA) over time (minutes) of purified N-terminal GST-LeuRS expressed from plasmid pC³582 as described in Example 6a, using crude total tRNA from *E. coli*. The aminoacylation activities were assayed with 13 ng (filled inverted triangles), 6.3 ng (filled circles), 2.5 ng (filled squares), or 1.3 ng (filled triangles) of GST-LeuRS in each of the reactions. The line with open circles shows a control reaction containing 13 ng of GST-LeuRS but no tRNA. The line with open circles shows a control reaction containing 13 ng of GST-LeuRS but no tRNA.

For testing the charging activity of the recombinant *E. faecalis* LeuRS, purified GST-LeuRS was diluted to between between 0.13 µg/ml and 1.3 µg/ml in 50 mM HEPES, pH 7.5/0.05 mg/ml BSA/10 mM DTT/1% DMSO. The diluted enzyme was incubated at 25° C. for 20 minutes. Ten µl of the diluted enzyme were then mixed with 40 µl of reaction cocktail that contained the following reagents: 2.5 µmole HEPES, pH 7.5, 0.5 µmole MgCl$_2$, 1 pmole KCl, 0.4 µmole DTT, 19 DMSO, 0.2 µmole ATP, 4.5 nmole *E. coli* total tRNA (Sigma), 0.9 nmole unlabelled leucine, and 0.1 nmole [$^3$H]- labelled leucine (Amersham; specific activity 53 Ci/mmol). The reactions were carried out at 25° C., and 15 µl aliquots were removed at each time point and applied to filter paper discs (3 MM, Whatman) which were then immediately soaked in 5% (wt/vol) TCA. Filters were washed for three 10-minute periods in 5% TCA, rinsed in 95% ethanol and 100% ether, and the incorporation of [$^3$H]-leucine into tRNA (formation of [$^3$H]-leucine-tRNA) was measured in Betafluor by liquid scintillation counting. Results are shown in FIG. 3.

Figure 4:
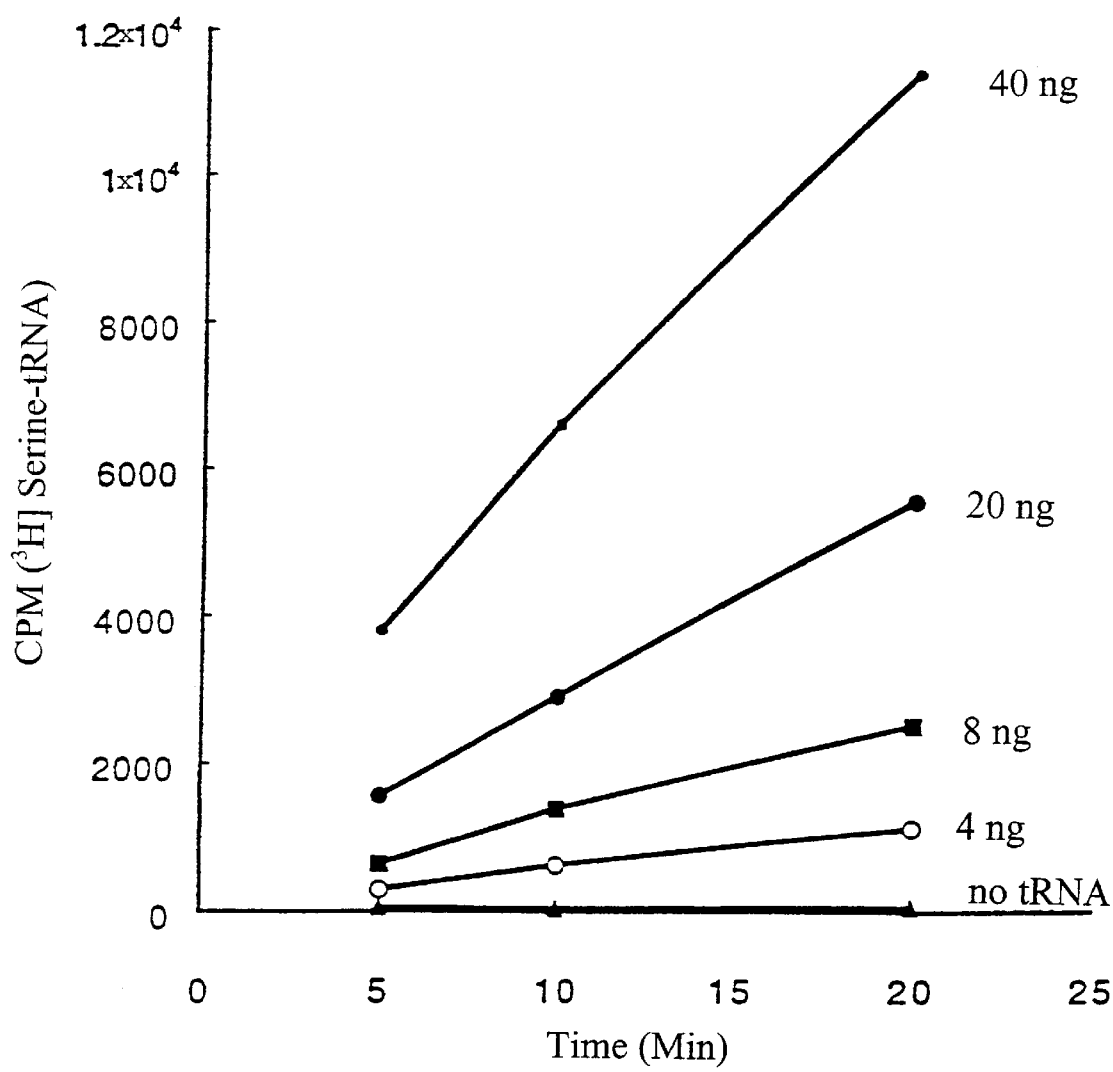
FIG. 4 is a graph illustrating the aminoacylation activity (cpm, counts per minute of [³H]seryl-tRNA) over time (minutes) of purified N-terminal GST-SerRS expressed from plasmid pC³778 as described in Example 6a, using crude total tRNA from *E. coli*. The aminoacylation activities were assayed with 40 ng (small filled circles), 20 ng (large filled circles), 8 ng (filled squares), or 4 ng (open circles) of GST-SerRS in each of the reactions. The line with filled triangles shows a control reaction containing 40 ng of purified GST-SerRS but no tRNA.

For testing the recombinant *E. faecalis* SerRS charging activity, the purified GST-SerRS was diluted to between 0.4 μg/ml and 4 μg/ml in 50 mM HEPES, pH 7.5/0.05 mg/ml bovine serum albumin/10 mM DTT/1% DMSO. The diluted enzyme was incubated at 25° C. for 20 minutes. Ten μl of the diluted enzyme were then mixed with 40 μl of reaction cocktail containing the following: 2.5 μmole HEPES, pH 7.5, 0.5 μmole $MgCl_{21}$ 1 μmole KCl, 0.4 μmole DTT, 1% DMSO, 0.2 μmole ATP, 4.5 nmole *E. coli* total tRNA (Sigma), 0.9 nmole unlabelled serine and 0.1 nmole [$^3$H]-labelled serine (Amersham; specific activity 21.7 Ci/mmol). The reactions were carried out at 25° C., and 15 μl aliquots were removed at each time point and applied to filter paper discs (3 MM, Whatman) which were then immediately soaked in 5% (wt/vol) trichloroacetic acid. Filters were washed for three 10-minute periods in 5% TCA, rinsed in 95% ethanol and 100% ether, and the incorporation of [$^3$H]-serine into tRNA (formation of [$^3$H]-serine-tRNA) was measured in Betafluor by liquid scintillation counting. Results are shown in FIG. 4.

Figure 5:
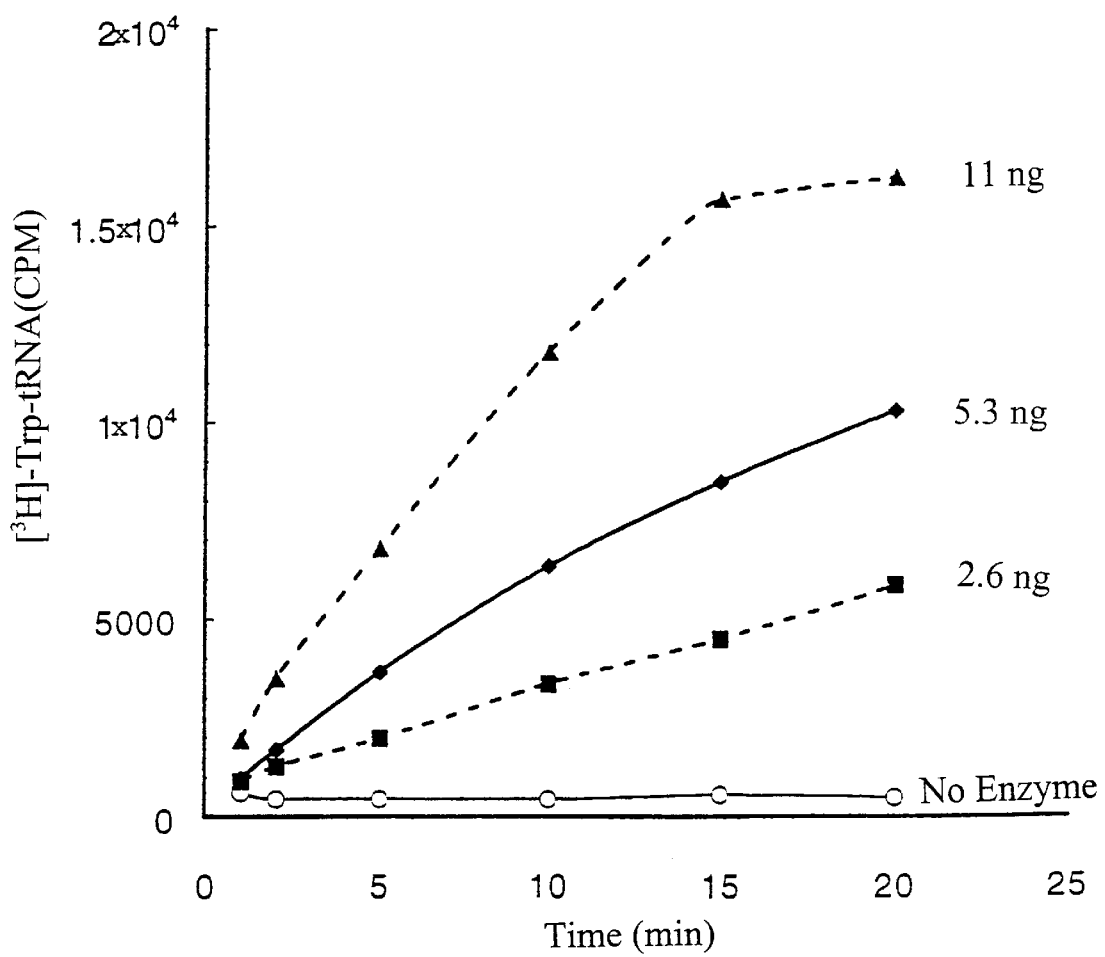
FIG. 5 is a graph illustrating the aminoacylation activity (cpm, counts per minute of [³H]tryptophanyl-tRNA) over time (minutes) of purified N-terminal GST-TrpRS expressed from plasmid pC³689 as described in Example 6a, using crude total tRNA from *E. coli*. The aminoacylation activities were assayed with 11 ng (filled triangles), 5.3 ng (filled diamonds), or 2.6 ng (filled squares) of GST-TrpRS in each of the reactions. The line with open circles shows a control reaction containing no enzyme.

For testing the recombinant *E. faecalis* TrpRS charging activity, the purified GST-TrpRS was diluted to 0.18 μg/ml to 0.7 μg/ml in 50 mM HEPES, pH 7.5/0.05 mg/ml bovine serum albumin/10 mM DTT/1% DMSO. The diluted enzyme was incubated at 25° C. for 20 minutes. Fifteen μl of the diluted enzyme were then mixed with 60 μl of reaction cocktail that contained the following: 3.75 μmole HEPES, pH 7.5, 0.75 μmole $MgCl_2$, 15 μmole KCl, 0.6 μmole DTT, 1% DMSO, 0.075 μmole ATP, 27 nmole *E. coli* total tRNA (Sigma), 0.2 nmole unlabelled tryptophan, and 0.05 nmole [3H]-labelled tryptophan (Dupont/NEN; specific activity 20 Ci/mmol). The reactions were carried out at 25° C., and 10 μl aliquots were removed at each time point and applied to filter paper discs (3 MM, Whatman) which were then immediately soaked in 5% (wt/vol) trichloroacetic acid. Filters were washed for three 60-minute periods in 5% TCA, rinsed in 95% ethanol and 100% ether, and the incorporation of [3H]-tryptophan into tRNA (formation of [$^3$H]-tryptophan-tRNA) was measured in Betafluor by liquid scintillation counting. Results are shown in FIG. 5.

b. GST-TyrRS

To express the recombinant *E. faecalis* GST fusion TyrRS, 400 ml of overnight LB culture (with 100 μg/ml of ampicillin) of *E. coli* cells bearing plasmid EFTYRGST-VENT#6 were added to 1.6 liter of fresh LB broth containing 100 μg/ml ampicillin. The cells were grown at 37° C. for 1 hour and expression of GST-TyrRS was induced by the addition of IPTG to 0.4 mM. After 5 hours of growth with induced protein expression, the cells were pelleted by centrifugation in a Beckman JA10 rotor for 10 minutes at 6000 rpm.

To purify the protein, the cells were resuspended in 40 ml of 1x PBS, 5 mM DTT, lx protease inhibitors (see Example 6a), and 100 μg/ml lysozyme. The resuspended *E. coli* cells were lysed by French press. The cell lysate was centrifuged at 12,000g for 30 min at 4° C. and the supernatant was recovered, mixed with Triton X-100 to 1% final concentration and loaded onto a 10 ml glutathione-agarose affinity column equilibrated with lx PBS/5 mM DTT at 40° C.

After the sample was loaded, the column was washed with 250 ml 1x PBS containing 5 mM DTT and 150 mM NaCl at 40C. The *E. faecalis* GST-TyrRS protein that bound specifically to glutathione-agarose was then eluted with 40 ml of 10 mM glutathione, 50 mM Tris-HCl (pH 8.0), added in four 10 ml aliquots at 25° C. The eluted fusion protein was concentrated in Centriprep-10 (Amicon), and the buffer was exchanged to 100 mM HEPES (pH 7.5) as described in Example 6a. The protein was concentrated to 6 ml before it was mixed with an equal volume of glycerol, and DTT was added to 10 mM. The purified *E. faecalis* GST-TyrRS was stored at −20° C. The yield of purified protein was about 38 mg, according to a Bradford assay (Pierce).

The purified *E. faecalis* GST-TyrRS was analyzed on a 10% SDS-polyacrylamide gel. It appeared to be greater than 850 pure by Coomassie blue staining, with an apparent molecular weight of around 70 kDa.

Figure 6:
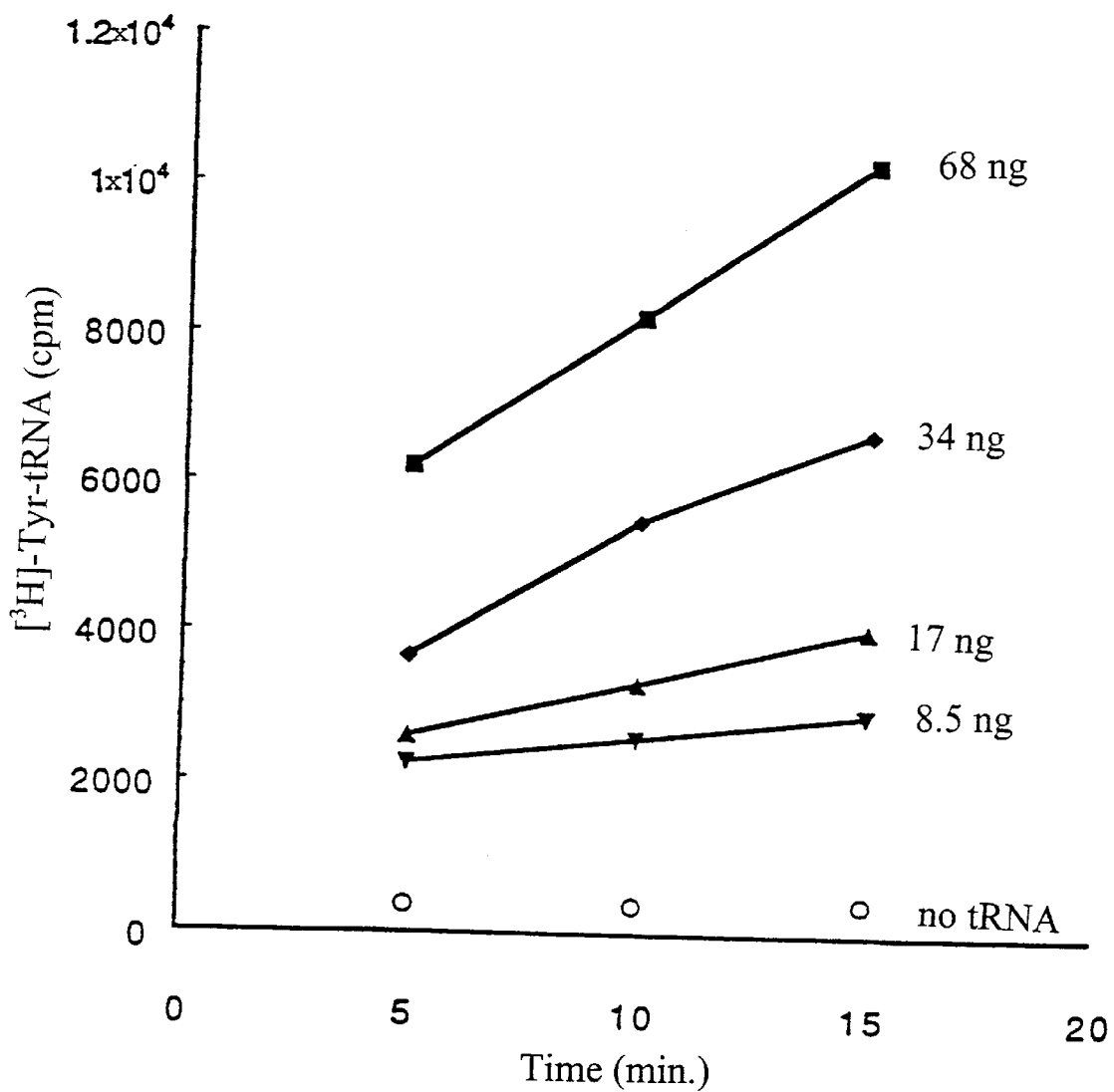
FIG. 6 is a graph illustrating the aminoacylation activity (cpm, counts per minute of [³H]tyrosyl-tRNA) over time (minutes) of purified N-terminal GST-TyrRS expressed from plasmid EFTYRGST-VENT#6 as described in Example 6b, using crude total tRNA from *E. coli*. The aminoacylation activities were assayed with 68 ng (filled squares), 34 ng (filled diamonds), 17 ng (filled triangles), or 8.5 ng (filled inverted triangles) of the purified GST-TyrRS in each of the reactions. The open circles show a control reaction containing 68 ng GST-TyrRS but no tRNA.

For testing the recombinant *E. faecalis* TyrRS charging activity, the purified GST-TyrRS was diluted, 0.85 μg/ml to 6.8 μg/ml, in 50 mM HEPES, pH 7.5,/0.05 mg/ml bovine serum albumin /10 mM DTT/1% DMSO. The diluted enzyme was incubated at 25° C. for 20 minutes. Ten μl of the diluted enzyme were then mixed with 40 μl of reaction cocktail that contained the following reagents: 2.5 μmole HEPES, pH 7.5, 0.5 μmole $MgCl_{21}$ 1 μmole KCl, 0.4 μmole DTT, 1% DMSO (v/v), 0.2 μmole ATP, 4.5 nmole *E. coli* total tRNA (Sigma or Boehringer Mannheim), 0.9 nmole unlabelled amino acid and 0.1 nmole [$^3$H]-labelled amino acid (Amersham; specific activity 57 Ci/mmol). The reactions were carried out at 25° C., and 15 μl aliquots were removed at each time point and applied to filter paper discs (3 MM, Whatman) which were then immediately soaked in 5% (wt/vol) trichloroacetic acid. Filters were washed for three 60-minute periods in 5% TCA, rinsed in 95% ethanol and 100% ether, and the incorporation of [$^3$H]-tyrosine into tRNA (formation of [$^3$H]-tyrosine-tRNA) was measured in Betafluor by liquid scintillation counting. Results are shown in FIG. 6.

c. SerRS His-tag fusion protein

To express the His-tag fusion of *E. faecalis* SerRS, 10 ml of overnight culture of *E. coli* BL21(DE3) cells, containing either plasmid p$C^3$731 or p$C^3$734, were used to inoculate 1 liter of fresh LB broth containing 60 μg/ml ampicillin. The cells were grown at 37° C. to an $OD_{600}$ of about 0.4, and then induced by the addition of 0.4 mM IPTG to clone 4-2 (an isolate of BL21(DE3)/p$C^3$734) and 1 mM IPTG to clone 2-12 (an isolate of BL21(DE3)/p$C^3$731) to induce expression of the recombinant proteins. Three hours after the induction of expression at 37° C., the cells were pelleted by centrifugation. The cells were lysed and the His-tag fusion proteins were bound to His-Bind resin (Novagen) according to the pET System Manual (Novagen). After three 16.7 ml washes with lx bind buffer (Novagen) and three 15 ml washes with 20 mM imidazole/500 mM NaCl/20 mM Tris-HCl, pH 7.9, the His-fusion proteins were eluted with two 15 ml aliquots of 200 mM imidazole/500 mM NaCl/20 mM Tris-HCl, pH 7.9. The samples were concentrated in Centriprep-10, and exchanged to 100 mM HEPES (pH 7.5) as described in Example 6a. Yields of 4.8 mg and 2.3 mg were obtained for the N-terminal fusion protein and the C-terminal fusion protein, respectively.

The purified His-tag fusion of *E. faecalis* SerRS was analyzed on a 10% SDS-polyacrylamide gel. The protein appeared to be greater than 80% pure by Coomassie blue staining, with an apparent molecular weight of around 48 kDa.

Figure 7A:
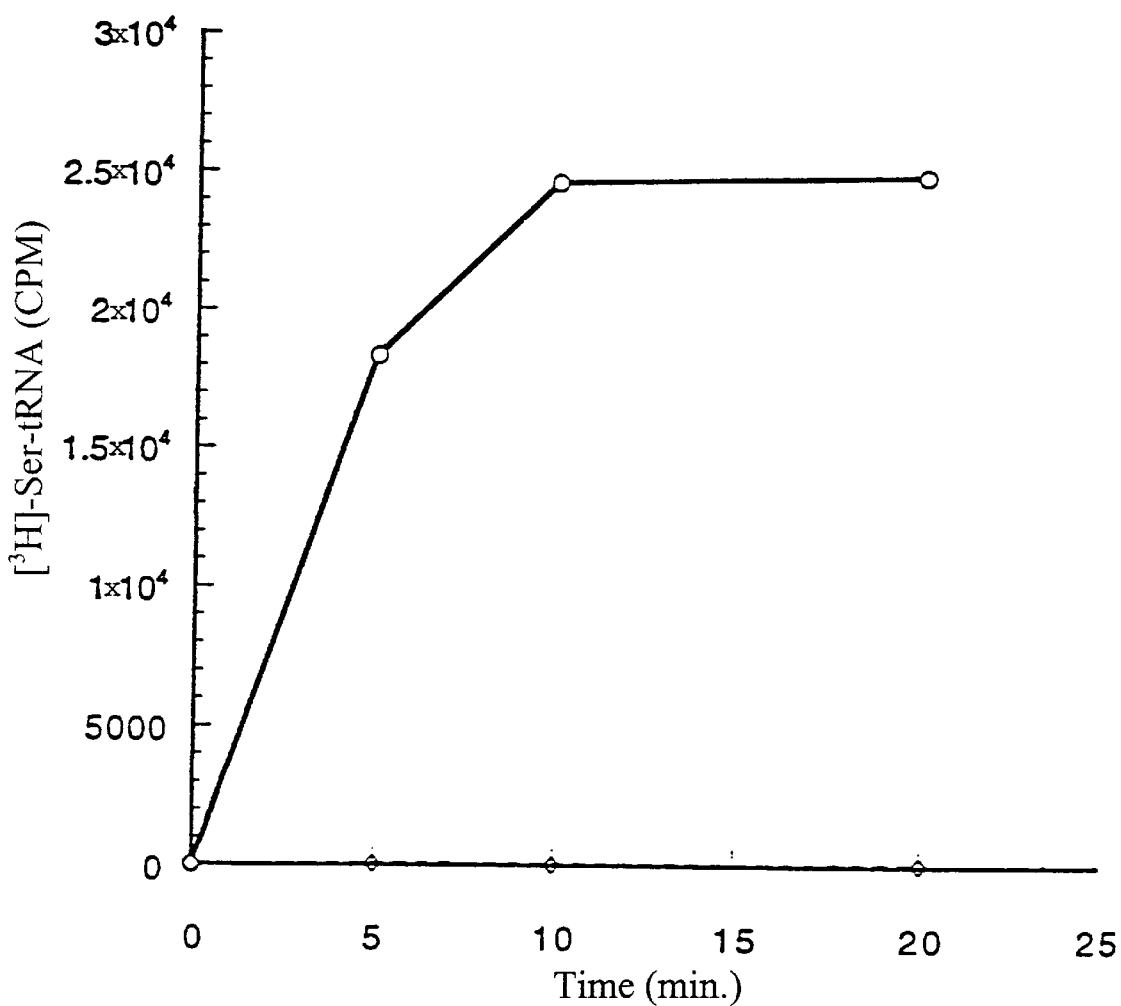
FIG. 7A is a graph illustrating the aminoacylation activity (cpm, counts per minute of [³H]seryl-tRNA) over time (minutes) of the purified N-terminal His-tag fusion SerRS (240 ng, open circles) expressed from plasmid pC³731 as described in Example 6c, using crude total tRNA from *E. coli*. The dashed line with open diamonds shows a no enzyme control reaction.
Figure 7B:
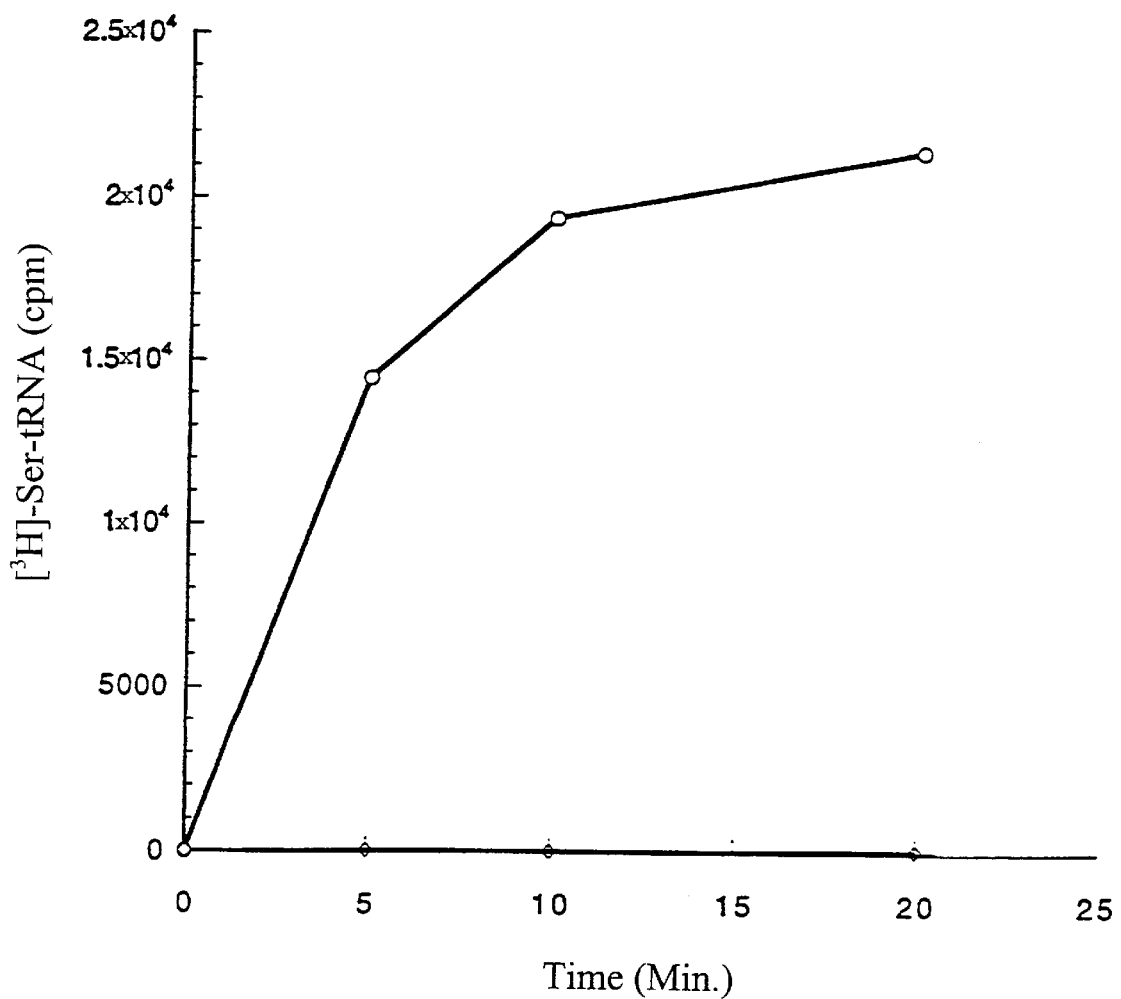
FIG. 7B is a graph illustrating the aminoacylation activity (cpm, counts per minute of [³H]seryl-tRNA) over time (minutes) of the purified C-terminal His-tag fusion SerRS (46 ng, open circles) expressed from plasmid pC³734 as described in Example 6c, using crude total tRNA from *E. coli*. The dashed line with open diamonds shows a control reaction containing no enzyme.

For testing the charging activities of the N-terminal His-tag and C-terminal His-tag fusion of *E. faecalis* SerRS, the purified proteins were diluted to 24 μg/ml (N-terminal His tag) or 4.6 μg/ml (C-terminal His-tag) in 50 mM HEPES, pH 7.5/0.05 mg/ml BSA/10 mM DTT/1% DMSO. The diluted enzyme was incubated at 25° C. for 20 minutes. Ten μl of the diluted enzyme were then mixed with 40 μl of reaction cocktail that contained the following: 2.5 pmole HEPES, pH 7.5, 0.5 μmole MgCl$_2$, 1 μmole KCl, 0.4 μmole DTT, 1 DMSO, 0.2 μmole ATP, 4.5 nmole *E. coli* total tRNA (Sigma or Boehringer Mannheim), 0.9 nmole unlabelled amino acid, and 0.1 nmole [$^3$H]-labelled amino acid (Amersham; specific activity 21.7 Ci/mmol). The reactions were carried out at 25° C., and equal volume (10 or 15 μl) aliquots were removed at each time point and applied to filter paper discs (3 MM, Whatman) which were then immediately soaked in 5% (wt/vol) trichloroacetic acid. Filters were washed for three 10-minute periods in 5% TCA, rinsed in 95% ethanol and 100% ether, and the incorporation of [$^3$H]-serine into tRNA (formation of [$^3$H]-serine-tRNA) was measured in Betafluor by liquid scintillation counting. Results are shown in FIG. 7A and FIG. 7B.

d. PheRS His-tag fusion protein

To express the His-tag fusion of *E. faecalis* PheRS, two 10 ml overnight cultures of *E. coli* BL21(DE3) cells containing plasmid pC$^3$742 were used to inoculate two 1-liter cultures of fresh LB broth containing 60 μg/ml ampicillin. The cells were grown at 37° C. to an OD$_{600}$ of 0.6 to 0.75, and IPTG was added to 1 mM to induce the expression of the recombinant proteins. After 3 days of growth at 18° C. following induction, the cells were pelleted by centrifugation. The cells were lysed, and the His-tag fusion proteins were bound to a 20 ml His-Bind column (Novagen) according to the pET System Manual (Novagen). After 3 washes with 83 ml of 1x bind buffer (Novagen), one 100 ml wash with 10 mM imidazole/500 mM NaCl/20 mM Tris-HCl, pH 7.9, and one 100 ml wash with 20 mM imidazole/500 mM NaCl/20 mM Tris-HCl, pH 7.9, the His-fusion protein was eluted with two applications of 60 ml 200 mM imidazole/500 mM NaCl/20 mM Tris-HCl, pH 7.9. The samples were concentrated in a Centriprep-10 centrifuge concentrator, and the buffer was exchanged to 100 mM HEPES (pH 7.5) with Sephadex G-25 columns. The purified sample was mixed with an equal volume of glycerol and stored at -20° C. 106 mg of protein were obtained as quantified by a Bradford assay (Pierce).

The purified His-tag fusion of *E. faecalis* PheRS was analyzed on a 10% SDS-polyacrylamide gel. As expected, the sample contained a predominant species of about 90 kDa, corresponding to the size of the beta subunit, and a species about 39 kDa, corresponding to the size of the alpha subunit. The molar ratio between the beta and alpha subunits was about 2.3 to 1, as determined by densitometer scanning. The purified *E. faecalis* PheRS was tested for aminoacylation activity.

Figure 8:
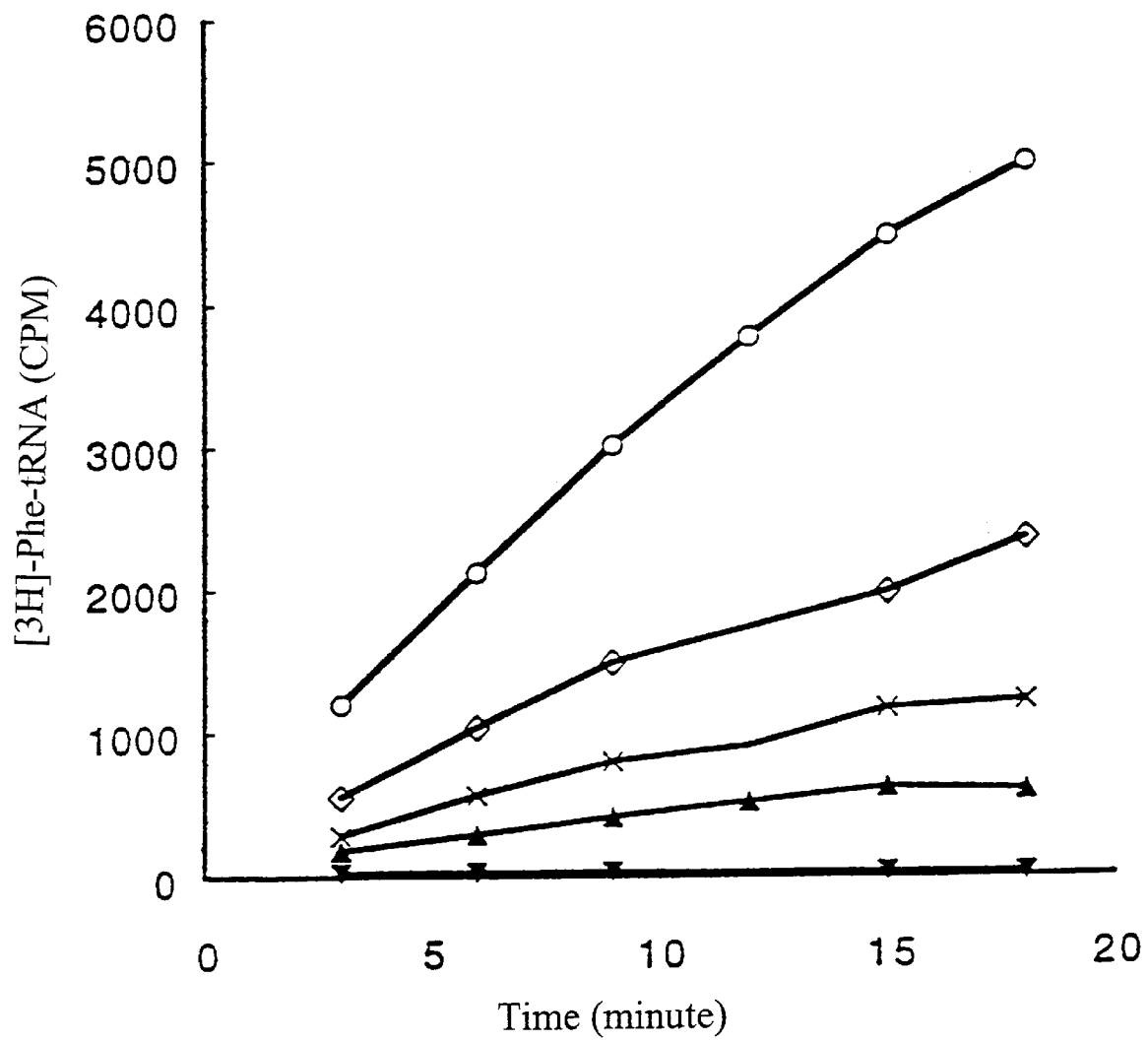
FIG. 8 is a graph illustrating the aminoacylation activity (cpm, counts per minute of [³H]phenylalanyl-tRNA) over time (minutes) of purified PheRS fusion protein (with His-tag fused to the C-terminus of the beta subunit) that was expressed from plasmid pC³742 as described in Example 6d, using crude total tRNA from *E. coli*. The aminoacylation activities were assayed with 200 ng (open circles), 100 ng (open diamonds), 50 ng (x), or 25 ng (filled triangles) of purified His-tag PheRS in each of the reactions. The line with the filled inverted triangles shows a no enzyme control.

For testing the recombinant *E. faecalis* PheRS charging activity, the purified His-tag fusion of *E. faecalis* PheRS was diluted to between 1.66 and 13.3 μg/ml in 50 mM HEPES, pH 7.5/50 mM KCl/10 mM MgCl$_2$/0.05 mg/ml BSA/10 mM DTT/15 DMSO. The diluted enzyme was incubated at 25° C. for 20 minutes. Fifteen μl of the diluted enzyme were then mixed with 60 μl of reaction cocktail containing the following quantities of reagents: 3.75 μmole HEPES, pH 8.0, 0.56 μmole MgCl$_2$, 3.75 μmole KCl, 0.6 μmole DTT, 1% DMSO, 3 nmole ATP, 4.5 nmole *E. coli* total tRNA (Boehringer Mannheim), 56 pmole unlabelled phenylalanine and 19 μmole [$^3$H]-labelled phenylalanine (Amersham; specific activity 132 Ci/mmol). The reactions were carried out at 25° C., 15 μl aliquots were removed at each time point and quenched in a 96-well filter plate (Millipore, catalog no. MAFBNOB50) prefilled with 100 μl of cold 5% TCA. The liquid in the filter plate was drained by applying vacuum suction on the manifold. The plate was subsequently washed 2 times with 200 μl 5% TCA, 2 times with 100 μl deionized H$_2$O with continuous vacuum suction, and 2 times with 100 μl ethanol. The plate was heat-dried under vacuum, 100 μl Microscint was added to each well, and the incorporation of [$^3$H]-phenylalanine into tRNA (formation of [$^3$H]-phenylalanine-tRNA) was measured by liquid scintillation counting in a TopCount counter (Packard). Results are shown in FIG. 8.

EXAMPLE 7

Southern Analysis of *E. faecalis* aaRS Genes

Southern analyses of genomic *E. faecalis* DNA with *E. faecalis* IleRS, LeuRS, SerRS, PheRS, and TrpRS gene fragments as probes were performed using essentially the methods described in Sambrook, J. et al. (*Molecular Cloning: A Laboratory Manual*, 2nd edition, Cold Spring Harbor Laboratory Press, 1989). 2.5 μg of restriction enzyme-digested *E. faecalis* genomic DNA (Example 1) separated by electrophoresis on an agarose gel were transferred by capillary action to a GeneScreen (Dupont) or Hybond-N (Amersham) nylon membrane. (See last column of Table 4 for restriction enzymes used.) The membranes were prehybridized in 10 ml prehybridization/hybridization solution (6x SSC, 5X Denhardt's solution, 0.5% SDS, 100 μg/ml sheared salmon sperm DNA) at 65° C. for 2–5 hr.

On the blot probed with *E. faecalis* PheRS-specific DNA, equal amounts of genomic DNAs from *E. coli, S. aureus,* and *H. influenzae* digested with restriction enzymes were also included as negative controls. On the blot probed with *E. faecalis* SerRS-specific DNA, equal amounts of genomic DNAs from *H. pylori, M. catarrhalis,* and *H. influenzae* were also included as negative controls.

PCR amplifications were used to generate the probes for hybridization. The radioactive labelling of the probes for the IleRS, LeuRS, and PheRS genes was carried out in 50 μl (100 μl for PheRS) containing 10 mM Tris-HCl (pH 8.3 at room temperature), 50 mM KCl, 2.5 mM MgCl$_2$, 0.4 μM each of the upstream and downstream primers, 200 μM dCTP, dGTP, dTTP, 3 μM dATP, 1 μCi/μl α-[$^{32}$P]dATP (3000 Ci/mmole, Dupont/NEN), and 0.05 unit/μl of Taq DNA polymerase (Boehringer Mannheim) and the corresponding template as indicated in Table 4. The reactions were first incubated at 95° C. for 2 minutes followed by 30 cycles of 95° C. (30 sec.), 55° C. (30 sec.), 72° C. (2 min.). An additional extension step was carried out for 8 minutes at 72° C. at the end of the 30 cycles. The labelling reaction for the TrpRS probe was carried out in 50 μl containing 10 mM Tris-HCl (pH 8.3 at room temperature), 50 mM KCl, 2.5 MM MgCl$_{21}$ 0.4 μM each of upstream and downstream primers, 200 μM DATP, dGTP, dTTP, 2 μM dCTP, 1 μCi/μl α-[$^{32}$P]dCTP (3000 Ci/mmole, Dupont/NEN), and 0.05 unit/ μl of Taq DNA polymerase (Boehringer Mannheim), and the corresponding template as indicated in Table 4. The reactions were first incubated at 94° C. for 2 minutes followed by 30 cycles of 94° C. (30 sec.), 60GC (30 sec.), 72° C. (1 min.), with extension for an additional 4 minutes at 72° C. after the thermocycles. The labelling reaction for the SerRS probe was carried out in 50 μl containing 10 mM Tris-HCl (pH 8.3 at room temperature), 50 mM KCl, 2.5 mM MgCl$_2$, 1 μM each of upstream and downstream primers, 25 μM DATP, dCTP, dGTP, dTTP, 2 μCi/μl α-[$^{32}$P]DATP (3000 Ci/mmole, Dupont/NEN), 0.05 unit/μl of Taq DNA polymerase (Boehringer Mannheim), and the corresponding template as indicated in Table 4. The reaction was carried out using 30 cycles of 94° C. (30 sec.), 55° C. (30 sec.), 72° C. (70 sec.).

The $^{32}$P-labelled probes were purified by Sephadex G25 or G50 spin columns (Boehringer Mannheim), denatured by heating to 95° C. for 5 min., and added to the nylon hybridization membranes in 10 ml of hybridization solution (6x SSC/10 mM EDTA/0.5% SDS/5x Denhardt's solution/ 100 μg/ml sheared and denatured salmon sperm DNA). The hybridizations were at 64–65° C. for 16 hours. The hybridized blots were then washed as follows: IleRS, LeuRS: two times with 2x SSC/0.5% SDS solution at room temperature for 15 minutes each, two times with 0.2x SSC/0.5% SDS at 65° C. for one hour each; TrpRS: two times with 2x SSC at room temperature for 5 minutes each, 2 times with 2x SSC/1% SDS for 30 minutes each, and two times with 0.1x SSC at room temperature for 30 minutes each; PheRS: two times with 2x SSC/0.1% SDS at room temperature for 5 minutes each, two times with 0.2x SSC/0.11 SDS at room temperature for 5 minutes each, two times with 0.2x SSC/ 0.1% SDS at 42° C. for 5 minutes each; SerRS: 3 times with 2x SSC/0.1% SDS at 65° C. for 30 minutes each. The washed blots were then analyzed by autoradiography. Table 4 summarizes the results of these high stringency Southern hybridizations. No cross-hybridization was seen to any of the negative control DNAs.

TABLE 4

| aaRS Gene | DNA Template | Primers for Probe Synthesis | Size of Restriction Fragments Detected on Southern |
|---|---|---|---|
| Ile | Ef1A-6 (plasmid) | T7 & U19 (Novagen) | ~4 kb (HindIII) |
| Leu | Ef2-2 (plasmid) | T7 & U19 (Novagen) | ~3.2 kb (HindIII) |
| Ser | PCR fragment amplified with primer PG77, PG78 | PG77, PG78 | ~2.5 kb (EcoRI) |
| Trp | pC$^3$689 (plasmid) | EfW-D, Efw-11 | 6.8 kb (HindIII) |
| Phe | pC$^3$742 (plasmid) | EfP-9, EfP-11 | 450 bp and 1.4 kb (HindIII/XhoI) |

Primer Sequences

PG77 (SEQ ID NO:44): 5'CGCGGATCCATGTTAGAT-GTAAAAATGATGCG

PG78 (SEQ ID NO:45): 5'CCGCTCGAGCGGTTATT-TAATAACTGTTAGGTTACC

EfW-D (SEQ ID NO:46): 5'AATGGTTGGTGATATCGT-GTTGTA

EfW-11 (SEQ ID NO:47): 5'GCTAAATCT-GCTTTGAAGCTTCC

EfP-9 (SEQ ID NO:48): 5'GGAACGCATAATGACAT-TACAAGC

EfP-11 (SEQ ID NO:49): 5'TCCACTAATGTCGCT-TCTGC

EXAMPLE 8

Assays for Inhibitors of Enzymatic Activity

Biochemical Assays

The extent of aminoacylation of tRNA catalyzed by enterococcal aminoacyl-tRNA synthetase was measured by monitoring the incorporation of [$^3$H]-labelled amino acid into tRNA. Aminoacylation reactions in the absence of test compounds were measured as control activity, reactions with known inhibitors were employed to assess the sensitivity of the system, and reactions containing combinations of test compounds were used to identify novel inhibitors. Where a mixture of test compounds was found to inhibit activity, subsequent assays using individual test compounds were run.

The fusion protein GST-LeuRS produced from the pC$^3$582 plasmid and purified as in Example 6a was used at a 1:42,000 dilution (1.4 nM) pre-incubated at 25° C. with 50 mM HEPES (pH 7.5), 0.05 mg/ml bovine serum albumin, 10 mM dithiothreitol, and 2.5% DMSO with or without a test mixture or a control compound, in 20 μl volumes in the wells of a microtiter plate (Falcon tissue culture plate, catalog no. 3077). After 30 minutes, the pre-incubation mixture was supplemented to a final concentration in the assay of 10 mM magnesium chloride, 20 mM potassium chloride, 0.5 mM ATP, 5 μM [$^3$H]leucine (6 Ci/mmol), 90 μM crude E. coli tRNA and 1.4% DMSO, to a final volume of 35 microliters, and incubated at 25° C. A 15 microliter aliquot was removed at 10 minutes and added to an individual well of a Millipore filtration plate (MultiScreen-FB, MAFB NOB 10) containing 100 microliters of cold 5%(wt/vol) trichloroacetic acid. Trichloroacetic acid precipitable [$^3$H]leucine-tRNA was collected on a Millipore MultiScreen filtration station. Filtration plates were washed two times with 5% trichloroacetic acid, twice with water, and dried overnight. One hundred microliters of Microscint-20 were added to each well. Radioactivity was counted in a TopCount microplate scintillation counter (Packard). Radioactivity was reported as a percentage of the control aminoacylation activity, as shown in Table 5 below. CB211 is a known inhibitor used as a positive control.

TABLE 5

| Compound ID | Concentration in Assay (μM) | cpm | % Activity |
|---|---|---|---|
| none | 0 | 10,510 | 100 |
| CB211 | 0.01 | 99 | 1 |
| CB211 | 0.001 | 855 | 8 |
| CB211 | 0.0001 | 6709 | 64 |
| CB7521 | 100 | 831 | 8 |
| CB7521 | 100 | 575 | 5 |
| CB7521 | 50 | 1362 | 13 |
| CB7521 | 10 | 6516 | 62 |
| CB7521 | 2 | 9287 | 88 |

The fusion protein His-tag PheRS produced from the pC$^3$742 plasmid and purified as in Example 6d was used at a 1:6,000 dilution (2.2 nM) pre-incubated at 25° C. with 50 mM HEPES (pH 7.5), 0.05 mg/ml bovine serum albumin, 50 nM potassium chloride, 10 mM magnesium chloride, 10 mM dithiothreitol, and 2.5% DMSO with or without a test mixture or a control compound, in 20 μl volumes in the wells of a microtiter plate (Falcon tissue culture plate, catalog no. 3077). After 30 minutes, the pre-incubation mixture was supplemented to a final concentration in the assay of 7.5 mM magnesium chloride, 50 mM potassium chloride, 0.04 mM ATP, 1 μM [$^3$H]phenylalanine (15 Ci/mmol), 60 μM crude E. coli tRNA and 1.4% DMSO to a final volume of 35 microliters and incubated at 25° C. A 15 microliter aliquot was removed at 10 minutes and added to an individual well of a Millipore filtration plate (MultiScreen-FB, MAFB NOB 10) containing 100 microliters of cold 5% (wt/vol) trichloroacetic acid. Trichloroacetic acid precipitable [$^3$H]phenylalanine-tRNA was collected on a Millipore MultiScreen filtration station. Filtration plates were washed two times with 5% trichloroacetic acid, twice with water and dried overnight. One hundred microliters of Microscint-20 were added to each well. Radioactivity was counted in a TopCount microplate scintillation counter (Packard). Radioactivity was reported as a percentage of the control aminoacylation activity, as shown in Table 6 below. CB16913 is a known inhibitor used as a positive control.

TABLE 6

| Compound ID | Concentration in Assay ($\mu$M) | cpm | % Activity |
| --- | --- | --- | --- |
| none | 0 | 8037 | 100 |
| CB16913 | 0.1 | 171 | 2 |
| CB16913 | 0.01 | 991 | 12 |
| CB16913 | 0.001 | 4799 | 59 |
| CB16913 | 0.0001 | 7318 | 91 |
| CB6535 | 10 | 1951 | 24 |
| CB6535 | 5 | 2804 | 35 |
| CB6535 | 2.5 | 4139 | 51 |
| CB6535 | 1.25 | 4661 | 58 |
| CB6535 | 0.625 | 7647 | 95 |

Seryl-tRNA synthetase produced from partially purified extracts prepared as in Example 9 was pre-incubated at 25° C. with 50 mM HEPES (pH 7.5), 0.05 mg/ml bovine serum albumin, 10 mM dithiothreitol, and 2.5% DMSO with or without a test mixture or a control compound, in 20 $\mu$l volumes in the wells of a microtiter plate (Falcon tissue culture plate, catalog no. 3077). After 30 minutes, the pre-incubation mixture was supplemented to a final concentration in the assay of 15 mM magnesium chloride, 50 mM potassium chloride, 0.3 mM ATP, 5 $\mu$M [$^3$H]serine (2 Ci/mmol), 90 $\mu$M crude E. coli tRNA and 1.4% DMSO, to a final volume of 35 microliters, and incubated at 25OC. A 15 microliter aliquot was removed at 10 minutes and added to an individual well of a Millipore filtration plate (MultiScreen-FB, MAFB NOB 10) containing 100 microliters of cold 5% (wt/vol) trichloroacetic acid. Trichloroacetic acid precipitable [$^3$H]serine-tRNA was collected on a Millipore MultiScreen filtration station. Filtration plates were washed two times with 5% trichloroacetic acid, twice with water and dried overnight. One hundred microliters of Microscint-20 was added to each well. Radioactivity was counted in a TopCount microplate scintillation counter (Packard). Radioactivity was reported as a percentage of the control aminoacylation activity, as shown in Table 7 below. CB492 is a known inhibitor used as a positive control.

TABLE 7

| Compound ID | Concentration in Assay ($\mu$M) | cpm | % Activity |
| --- | --- | --- | --- |
| none | 0 | 5443 | 100 |
| CB492 | 10 | 82 | 2 |
| CB492 | 1 | 287 | 5 |
| CB492 | 0.1 | 1732 | 32 |
| CB492 | 0.01 | 4729 | 87 |

Whole Cell Antimicrobial Screening Assays for Inhibitors

Compounds were tested for antimicrobial activity against a panel of enterococci according to standard procedures described by the National Committee for Clinical Laboratory Standards (NCCLS document M7-A3, Vol. 13, No. 25, 1993/NCCLS document M27-P, Vol. 12, No. 25, 1992). Compounds were dissolved in 100% dimethyl sulfoxide and were diluted to 100 $\mu$g/ml in Mueller-Hinton broth. The final concentration of dimethyl sulfoxide incubated with cells is less than or equal to 1%. For minimum inhibitory concentration (MIC) determinations, 2-fold dilutions of compounds were added to wells of a Nunc microwell plate containing 5x10$^4$ bacterial cells (ATCC No. 6569, ATCC No. 33011, ATCC No. 14506, and ATCC No. 29212) in a final volume of 100 $\mu$l of Mueller-Hinton broth. Plates were incubated overnight at 37° C., and optical densities (measure of cell growth) were measured using a Molecular Devices SpectraMax 250 plate reader. The MIC value is defined as the lowest compound concentration inhibiting growth of the test organism. The MIC (in $\mu$g/ml) values for CB7521 on the enterococci tested are presented in Table 8 below.

TABLE 8

| ATCC # | Species | Compound Number | MIC ($\mu$g/ml) |
| --- | --- | --- | --- |
| 6569 | E. faecium | CB7521 | 6.3 |
| 33011 | E. faecalis | CB7521 | 3.1 |
| 14506 | E. faecalis | CB7521 | 3.1 |
| 29212 | E. faecalis | CB7521 | 3.1 |

EXAMPLE 9

Preparation of Partially-Purified E. faecalis ktRNA-Synthetase

Glycerol cultures of Enterococcus faecalis (ATCC No. 6538P) were streaked onto Mueller-Hinton broth plates and incubated overnight at 37° C. The colonies were scraped off the plates and used to inoculate a 20 ml starter culture in Luria broth. The culture was then incubated with shaking at 37° C. for 24 h. Ten milliliters of the culture were subsequently used to inoculate 1 L of Luria broth in a 4 L flask. The 1 L culture was incubated overnight at 37° C. with shaking. Cells at an OD$_{600}$ of approximately 3 were harvested the next morning by centrifuging at 4400 x g for 15 minutes.

The cell pellet (10–12 g) was suspended in 2 ml of lysis buffer [20 mM K$_2$HPO$_4$, pH 7.4, 10% glycerol, 5 mM DTT, 1 tablet protease inhibitor cocktail (Complete, Boehringer Mannheim) per 50 ml lysis buffer] per gram of cell pellet, then stirred for 60 min at 4° C. Cells were lysed by 4 cycles of freezing and thawing (dry ice/ethanol bath alternated with water at 25° C.) followed by 2 cycles through a French press at 1200 psi. The lysate was then subjected to a low speed (20,000 x g for 30 min.) and a high speed (100,000 x g, 60 min.) centrifugation to remove cell debris and organelles. The pH of the lysate was adjusted to 7.4 with 1 M KHPO$_4$. The lysate was loaded onto a DEAE column (Pharmacia) pre-equilibrated in buffer A (20 mM K$_2$HPO$_4$, pH 7.4, 10% glycerol, 5 mM DTT) and eluted with an ascending phosphate gradient from 20 to 500 mM K$_2$HPO$_4$ under the same glycerol and DTT concentrations. Fractions containing tRNA synthetase activity were collected, pooled and concentrated, and stored at –20° C. in 40% glycerol.

Activity in the partially-purified extract was screened for and standardized using a tRNA charging assay under the following conditions. The assay buffer contained 30 mM HEPES, pH 7.5, 30 mM KCl, 10 mM MgCl$_2$ and 90 mM crude E. coli tRNA (Boehringer-Mannheim, Indianapolis, Ind.). Concentrations of amino acid and ATP in the reaction are given in Table 9. The extract preparation was diluted in an enzyme dilution buffer containing 100 mM HEPES, 0.1 mg/ml BSA and 20 mM DTT, before use. Reactions were carried out at 25° C. and initiated by addition of 10 $\mu$l of enzyme. The total assay volume was 50 $\mu$l. At 3 or 4 time intervals (usually 5, 10, and 15 minutes) a 10 μl aliquot of the reaction was removed and added to 200 μl of ice cold 5% trichloroacetic acid in the well of a 96 well filter plate (Millipore, Bedford, Mass.).

After the assay was complete, the filter plates were placed on a vacuum manifold and the liquid removed. The wells were then washed 3 times with 200 μl of 5% TCA, 1 time with 200 μl of water and 1 time with 200 μl 95% ethanol. The wash solutions were all at 4° C. The plates were dried for several minutes under a heat lamp followed by drying for 30 minutes in a vacuum oven at 50° C. Subsequently, the TCA precipitable counts were measured by addition of 100 μl of Microscint 20 (Packard, Meriden, Conn.) to the wells and counting the plates using a Packard Topcount scintillation counter.

Each of the individual synthetases was assayed at an ATP concentration similar to the enzyme's $K_m$ for ATP and at an amino acid concentration similar to the enzyme's $K_m$ for the amino acid, to a maximum concentration of 20 μM. The tritiated amino acids used in the assay were isotopically diluted to a final specific activity of 4 Ci/mmol. The synthetase-containing extract was diluted to give an optimal amount of signal at a 10 minute time period (2000 CPM or higher) and the amount of enzyme activity was quantitated as the dilution of the extract stock required to obtain the desired signal at 10 min. Amino acid and ATP concentration, final extract dilutions in the assay and the observed signal at 10 minutes reaction time (in CPM) are listed in Table 9. In all cases the accumulation of product with time was found to be linear. Thus, the observed counts at 10 minutes can be assumed to be a gross estimate of the rate of reaction per 10 minutes. No detectable activity was found for AspRS or for HisRS under these assay conditions (<200 CPM at 10 minutes reaction time).

TABLE 9

Conditions for Screening for Aminoacyl-tRNA Synthetase Activity in *E. faecalis* Extracts

| Synthetase | Amino Acid (μm) | ATP (μM) | Extract Dilution | CPM at 10 min |
|---|---|---|---|---|
| Alanine | 20 | 35 | 1/60 | 4800 |
| Arginine | 2 | 15 | 1/60 | 4500 |
| Aspartate | 20 | 25 | 1/100 | 4000 |
| Glutamate | 20 | 1000 | 1/50 | 3000 |
| Glycine | 20 | 140 | 1/1500 | 6500 |
| Isoleucine | 15 | 95 | 1/300 | 4600 |
| Leucine | 16 | 100 | 1/900 | 5000 |
| Lysine | 15 | 30 | 1/100 | 2500 |
| Methionine | 20 | 50 | 1/50 | 3000 |
| Phenylalanine | 7 | 35 | 1/50 | 3000 |
| Proline | 20 | 150 | 1/100 | 2200 |
| Serine | 20 | 15 | 1/300 | 3000 |
| Threonine | 20 | 250 | 1/60 | 3000 |
| Tryptophan | 16 | 90 | 1/60 | 1500 |
| Tyrosine | 7 | 85 | 1/900 | 4000 |
| Valine | 20 | 45 | 1/200 | 3000 |

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. An isolated nucleic acid which encodes at least a portion of an enterococcal aminoacyl-tRNA synthetase having catalytic activity or binding function, said nucleic acid sharing at least about 90% DNA sequence identity with a DNA having a sequence selected from the group consisting of:

a) the coding region in SEQ ID NO:1;
b) the coding region in SEQ ID NO:3;
c) the coding region in SEQ ID NO:5;
d) nucleotides 85–1128 in SEQ ID NO:7;
e) nucleotides 1139–3559 in SEQ ID NO:7;
f) the coding region in SEQ ID NO:10; and
g) the coding region in SEQ ID NO:12.

2. An isolated nucleic acid which encodes at least a portion of an *Enterococcus faecalis* aminoacyl-tRNA synthetase having catalytic activity or binding function, wherein the aminoacyl-tRNA synthetase has an amino acid sequence selected from the group consisting of:

a) SEQ ID NO:2;
b) SEQ ID NO:4;
c) SEQ ID NO:6;
d) SEQ ID NO:8;
e) SEQ ID NO:9;
f) SEQ ID NO:11; and
g) SEQ ID NO:13.

3. An isolated nucleic acid which encodes at least a functional portion of an *Enterococcus faecalis* aminoacyl-tRNA synthetase, said portion having catalytic or binding function, wherein the aminoacyl-tRNA synthetase is selected from the group: leucyl-tRNA synthetase, tyrosyl-tRNA synthetase, isoleucyl-tRNA synthetase, seryl-tRNA synthetase, phenylalanyl-tRNA synthetase and tryptophanyl-tRNA synthetase.

4. An isolated nucleic acid which encodes at least a functional portion of a phenylalanyl-tRNA synthetase of *Enterococcus faecalis*, said portion having catalytic activity or binding function.

5. An isolated nucleic acid which encodes at least a functional portion of an aminoacyl-tRNA synthetase of *Enterococcus faecalis*, said portion having catalytic activity or binding function, said nucleic acid comprising a nucleic acid which encodes a polypeptide having an amino acid sequence selected from the group consisting of:

a) the amino acid sequence shown in SEQ ID NO:2;
b) the amino acid sequence shown in SEQ ID NO:4,
c) the amino acid sequence shown in SEQ ID NO:6;
d) the amino acid sequence of the α subunit shown in SEQ ID NO:8;
e) the amino acid sequence of the β subunit shown in SEQ ID NO:9;
f) the amino acid sequence shown in SEQ ID NO:11; and
g) the amino acid sequence shown in SEQ ID NO:13.

6. An isolated nucleic acid which encodes a protein comprising an enterococcal aminoacyl-tRNA synthetase or portion thereof having catalytic activity or binding function, and which hybridizes under high stringency conditions, using wash buffers of increasing stringency, including 0.2x SSC/0.1% SDS wash buffer at a temperature of 60° C. to 65° C., to a DNA molecule selected from the group consisting of:

a) the DNA molecule shown in SEQ ID NO:1;
b) the DNA molecule shown in SEQ ID NO:3;
c) the DNA molecule shown in SEQ ID NO:5;
d) the DNA molecule shown in SEQ ID NO:7;
e) the DNA molecule shown in SEQ ID NO:10; and
f) the DNA molecule shown in SEQ ID NO:12.

7. The isolated nucleic acid of claim 6 wherein the enterococcal aminoacyl-tRNA synthetase or portion thereof has catalytic activity.

8. An isolated nucleic acid encoding an enterococcal aminoacyl-tRNA synthetase, comprising a first open reading frame encoding an α subunit and a second open reading frame encoding a β subunit, wherein the first open reading frame shares at least about 90% nucleotide sequence identity with nucleotides 85–1128 in SEQ ID NO:7 and the second open reading frame shares at least about 90% nucleotide sequence identity with nucleotides 1139–3559 in SEQ ID NO:7.

9. An isolated nucleic acid which encodes an a subunit and a β subunit of an enterococcal aminoacyl-tRNA synthetase, wherein the α subunit is the protein encoded by the first coding region in SEQ ID NO:7 and the β subunit is the protein encoded by the second coding region in SEQ ID NO:7.

10. A vector comprising nucleic acid which encodes a polypeptide comprising at least a functional portion of an *Enterococcus faecalis* phenylalanyl-tRNA synthetase, said portion having catalytic activity or binding function.

11. A vector comprising nucleic acid which encodes a polypeptide comprising at least a functional portion of an enterococcal aminoacyl-tRNA synthetase, said portion having catalytic activity or binding function, wherein the nucleic acid hybridizes under high stringency conditions, using wash buffers of increasing stringency, including 0.2x SSC/0.1% SDS was buffer at a temperature of 60° C. to 65° C., to a DNA molecule selected from the group consisting of:

a) the DNA molecule shown in SEQ ID NO:1;
b) the DNA molecule shown in SEQ ID NO;3;
c) the DNA molecule shown in SEQ ID NO:5;
d) the DNA molecule shown in SEQ ID NO:7;
e) the DNA molecule shown in SEQ ID NO:10; and
f) the DNA molecule shown in SEQ ID NO:12.

12. A vector comprising nucleic acid which encodes a polypeptide comprising at least a functional portion of an aminoacyl-tRNA synthetase, said portion having catalytic activity or binding function, wherein the aminoacyl-tRNA synthetase is an *Enterococcus faecalis* aminoacyl-tRNA synthetase selected from the group: leucyl-tRNA synthetase, tyrosyl-tRNA synthetase, isoleucyl-tRNA synthetase, seryltRNA synthetase, tryptophanyl-tRNA synthetase and phenylalanyl-tRNA synthetase.

13. An expression vector comprising nucleic acid encoding a fusion protein comprising *Enterococcus faecalis* aminoacyl-tRNA synthetase or functional portion thereof, said portion having catalytic activity or binding function, wherein said nucleic acid comprises all or part of a coding, sequence for an *Enterococcus faecalis* phenylalanyl-tRNA synthetase, and wherein the coding sequence is operably linked to one or more expression control regions.

14. A host cell comprising recombinant nucleic acid encoding one or more polypeptides comprising an *Enterococcus faecalis* phenylalanyl-tRNA synthetase or a functional portion thereof, said portion having catalytic activity or binding function.

15. A host cell comprising recombinant nucleic acid encoding one or more polypeptides comprising an *Enterococcus faecalis* aminoacyl-tRNA synthetase, wherein the *Enterococcus faecalis* aminoacyl-tRNA synthetase is selected from the group: leucyl-tRNA synthetase, tyrosyl-tRNA synthetase, isoleucyl-tRNA synthetase, tryptophanyl-tRNA synthetase, seryl-tRNA synthetase, and phenylalanyl-tRNA synthetase.

16. A host cell comprising a recombinant nucleic acid encoding a protein comprising an enterococcal aminoacyl-tRNA synthetase or portion thereof having catalytic activity or binding function, said portion having catalytic activity or binding function, wherein the recombinant nucleic acid hybridizes under high stringency conditions using wash buffers of increasing stringency, including 0.2x SSC/0.1% SDS wash buffer at a temperature of 60° C. to 65° C. to a DNA molecule selected from the group consisting of,
 a) the DNA molecule shown in SEQ ID NO:1;
 b) the DNA molecule shown in SEQ ID NO:3;
 c) the DNA molecule shown in SEQ ID NO:5;
 d) the DNA molecule shown in SEQ ID NO:7;
 e) the DNA molecule shown in SEQ ID NO:10; and
 f) the DNA molecule shown in SEQ ID NO:12.

17. A host cell comprising a recombinant nucleic acid encoding a fusion protein comprising an *Enterococcus faecalis* phenylalanyl-tRNA synthetase or a subunit thereof.

18. A method for producing an *Enterococcus faecalis* phenylalanyl-tRNA synthetase or a functional portion thereof, said portion having catalytic activity or binding function, comprising the following steps:
 a) constructing one or more recombinant nucleic acid vector(s) comprising all or part of a coding sequence for an *Enterococcus faecalis* phenylalanyl-tRNA synthetase;
 b) introducing the vector(s) into suitable host cells whereby the coding sequence(s) are under control of transcription signals and are linked to appropriate translation signals; and
 c) maintaining the host cells under conditions in which an *Enterococcus faecalis* phenylalanyl-tRNA synthetase or a functional portion thereof is produced.

19. The method of claim 18 further comprising isolating the *Enterococcus faecalis* phenylalanyl-tRNA synthetase or functional portion thereof.

20. A method for producing active *Enterococcus faecalis* phenylalanyl-tRNA synthetase comprising introducing one or more recombinant nucleic acid vector(s) comprising one or more coding sequence(s) for all or a functional part of an *Enterococcus faecalis* phenylalanyl-tRNA synthetase into suitable host cells, said part having catalytic activity or binding function, and maintaining the host cells under conditions in which the gene is expressed.

21. The method of claim 20 further comprising the step of isolating said phenylalanyl-tRNA synthetase.

22. A method for producing a polypeptide comprising an *Enterococcus faecalis* phenylalanyl-tRNA synthetase or a functional portion thereof, said portion having catalytic activity or binding function, comprising maintaining a host cell comprising a recombinant nucleic acid encoding said polypeptide under conditions suitable for expression of the nucleic acid, whereby the encoded polypeptide is produced.

23. The method of claim 22 further comprising the step of isolating the polypeptide.

24. A method for producing a polypeptide comprising an *Enterococcus faecalis* phenylalanyl-tRNA synthetase or a functional portion thereof, said portion having catalytic activity or binding function, comprising maintaining a host cell comprising a recombinant nucleic acid encoding said polypeptide under conditions suitable for expression of the nucleic acid and production of said polypeptide, and recovering said polypeptide.

25. An isolated nucleic acid which encodes a protein comprising a enterococcal phenylalanyl-tRNA synthetase or porn on thereof having catalytic activity or binding function which hybridizes under high stringency conditions, using wash buffers of increased stringency, including 0.2x SSC/0.1% SDS wash buffer at a temperature of 60° C. to 65° C., to a DNA molecule having the sequence of nucleotides 85–3559 in SEQ ID NO:7 or to the complement thereof.

26. A host cell comprising a recombinant nucleic acid encoding a protein comprising an *Enterococcus faecalis* phenylalanyl-tRNA synthetase or portion thereof having catalytic activity or binding function.

27. A method for producing a protein comprising an *Enterococcus faecalis* phenylalanyl-tRNA synthetase or a portion thereof having catalytic activity or binding function, comprising maintaining the host cell of claim 26 under conditions suitable for expression of said recombinant nucleic acid, whereby said protein is produced.

28. Isolated nucleic acid which hybridizes under high stringency conditions, using wash buffers of increasing stringency including 0.2x SSC/0.1% SDS wash buffer a temperature of 60° C. to 66° C., to a strand of DNA having a sequence selected from the group consisting of the sequences shown in SEQ ID NO: 1, SEQ ID NO:3, SEQ. ID NO:5, SEQ ID NO:7, SEQ ID NO: 10 and SEQ ID NO 12.

29. An isolated nucleic acid which encodes at least a functional portion of a leucyl-tRNA synthetase of *Enterococcus faecalis*, said portion having catalytic activity or binding function.

30. An isolated nucleic acid which encodes at least a functional portion of a tyrosyl-tRNA synthetase of *Enterococcus faecalis*, said portion having catalytic activity or binding function.

31. An isolated nucleic acid which encodes at least a functional portion of a isoleucyl-tRNA synthetase of *Enterococcus faecalis*, said portion having catalytic activity or binding function.

32. An isolated nucleic acid which encodes at least a functional portion of a seryl-tRNA synthetase of *Enterococcus faecalis*, said portion having catalytic activity or binding function.

33. An isolated nucleic acid which encodes at least a functional portion of a tryptophanyl-tRNA synthetase of *Enterococcus faecalis*, said portion having catalytic activity or binding function.

34. A vector comprising nucleic acid which encodes a polypeptide comprising at least a functional portion of an *Enterococcus faecalis* leucyl-tRNA synthetase, said portion having catalytic activity or binding function.

35. A vector comprising nucleic acid which encodes a polypeptide comprising at least a functional portion of an *Enterococcus faecalis* tyrosyl-tRNA synthetase, said portion having catalytic activity or binding function.

36. A vector comprising nucleic acid which encodes a polypeptide comprising at least a functional portion of an *Enterococcus faecalis* isoleucyl-tRNA synthetase, said portion having catalytic activity or binding function.

37. A vector comprising nucleic acid which encodes a polypeptide comprising at least a functional portion of an *Enterococcus faecalis* seryl-tRNA synthetase, said portion having catalytic activity or binding function.

38. A vector comprising nucleic acid which encodes a polypeptide comprising at least a functional portion of an *Enterococcus faecalis* tryptophanyl-tRNA synthetase, said portion having catalytic activity or binding function.

39. An expression vector comprising nucleic acid encoding a fusion protein comprising an*Enterococcus faecalis* aminoacyl-tRNA synthetase or functional portion thereof, said portion having catalytic activity or binding function, wherein said nucleic acid comprises all or part of a coding sequence for an *Enterococcus faecalis* leucyl-tRNA synthetase, and wherein the coding sequence is operably linked to one or more expression control regions.

40. An expression vector comprising nucleic acid encoding a fusion protein comprising an *Enterococcus faecalis* aminoacyl-tRNA synthetase or functional portion thereof, said portion having catalytic activity or binding function, wherein said nucleic acid comprises all or part of a coding sequence for an *Enterococcus faecalis* tyrosyl-tRNA synthetase, and wherein the coding sequence is operably linked to one or more expression control regions.

41. An expression vector comprising nucleic acid encoding a fusion protein comprising an *Enterococcus faecalis* aminoacyl-tRNA synthetase or functional portion thereof, said portion having catalytic activity or binding function, wherein said nucleic acid comprises all or part of a coding sequence for an *Enterococcus faecalis* isoleucyl-tRNA synthetase, and wherein the coding sequence is operably linked to one or more expression control regions.

42. An expression vector comprising nucleic acid encoding a fusion protein comprising an *Enterococcus faecalis* aminoacyl-tRNA synthetase or functional portion thereof, said portion having catalytic activity or binding function, wherein said nucleic acid comprises all or part of a coding sequence for an *Enterococcus faecalis* seryl-tRNA synthetase, and wherein the coding sequence is operably linked to one or more expression control regions.

43. An expression vector comprising nucleic acid encoding a fusion protein comprising an *Enterococcus faecalis* aminoacyl-tRNA synthetase or functional portion thereof, said portion having catalytic activity or binding function, wherein said nucleic acid comprises all or part of a coding sequence for an *Enterococcus faecalis* tryptophanyl-tRNA synthetase, and wherein the coding sequence is operably linked to one or more expression control regions.

44. A host cell comprising recombinant nucleic acid encoding one or more polypeptides comprising an *Enterococcus faecalis* leucyl-tRNA synthetase or a functional portion thereof, said portion having catalytic activity or binding function.

45. A host cell comprising recombinant nucleic acid encoding one or more polypeptides comprising an *Enterococcus faecalis* tyrosyl-tRNA synthetase or a functional portion thereof, said portion having catalytic activity or binding function.

46. A host cell comprising recombinant nucleic acid encoding one or more polypeptides comprising an *Enterococcus faecalis* isoleucyl-tRNA synthetase or a functional portion thereof, said portion having catalytic activity or binding function.

47. A host cell comprising recombinant nucleic acid encoding one or more polypeptides comprising an *Enterococcus faecalis* seryl-tRNA synthetase or a functional portion thereof, said portion having catalytic activity or binding function.

48. A host cell comprising recombinant nucleic acid encoding one or more polypeptides comprising an *Enterococcus faecalis* tryptophanyl-tRNA synthetase or a functional portion thereof, said portion having catalytic activity or binding function.

49. A host cell comprising a recombinant nucleic acid encoding a fusion protein comprising an *Enterococcus faecalis* leucyl-tRNA synthetase or a subunit thereof.

50. A host cell comprising a recombinant nucleic acid encoding a fusion protein comprising an *Enterococcus faecalis* tyrosyl-tRNA synthetase or a subunit thereof.

51. A host cell comprising a recombinant nucleic acid encoding a fusion protein comprising an *Enterococcus faecalis* isoleucyl-tRNA synthetase or a subunit thereof.

52. A host cell comprising a recombinant nucleic acid encoding a fusion protein comprising an *Enterococcus faecalis* seryl-tRNA synthetase or a subunit thereof.

53. A host cell comprising a recombinant nucleic acid encoding a fusion protein comprising an *Enterococcus faecalis* tryptophanyl-tRNA synthetase or a subunit thereof.

54. A method for producing an *Enterococcus faecalis* leucyl-tRNA synthetase or a functional portion thereof, said portion having catalytic activity or binding function, comprising the following steps:

a) constructing one or more recombinant nucleic acid vector(s) comprising all or part of a coding sequence for an *Enterococcus faecalis* leucyl-tRNA synthetase;

b) introducing the vector(s) into suitable host cells whereby the coding sequence(s) are under control of transcription signals and are linked to appropriate translation signals; and c) maintaining the host cells under conditions in which an *Enterococcus faecalis* leucyl-tRNA synthetase or a functional portion thereof is produced.

55. The method of claim 54 further comprising isolating the *Enterococcus faecalis* leucyl-tRNA synthetase or functional portion thereof.

56. A method for producing an *Enterococcus faecalis* tyrosyl-tRNA synthetase or a functional portion thereof, said portion having catalytic activity or binding function, comprising the following steps:

a) constructing one or more recombinant nucleic acid vector(s) comprising all or part of a coding sequence for an *Enterococcus faecalis* tyrosyl-tRNA synthetase;

b) introducing the vector(s) into suitable host cells whereby the coding sequence(s) are under control of transcription signals and are linked to appropriate translation signals; and c) maintaining the host cells under conditions in which an *Enterococcus faecalis* tyrosyl-tRNA synthetase or a functional portion thereof is produced.

57. The method of claim 56 further comprising isolating the *Enterococcus faecalis* tyrosyl-tRNA synthetase or functional portion thereof.

58. A method for producing an *Enterococcus faecalis* isoleucyl-tRNA synthetase or a functional portion thereof, said portion having catalytic activity or binding function, comprising the following steps:

a) constructing one or more recombinant nucleic acid vector(s) comprising all or part of a coding sequence for an *Enterococcus faecalis* isoleucyl-tRNA synthetase;

b) introducing the vector(s) into suitable host cells whereby the coding sequence(s) are under control of transcription signals and are linked to appropriate translation signals; and c) maintaining the host cells under conditions in which an *Enterococcus faecalis* isoleucyl-tRNA synthetase or a functional portion thereof is produced.

59. The method of claim 58 further comprising isolating the *Enterococcus faecalis* isoleucyl-tRNA synthetase or functional portion thereof.

60. A method for producing an *Enterococcus faecalis* seryl-tRNA synthetase or a functional portion thereof, said portion having catalytic activity or binding function, comprising the following steps:

a) constructing one or more recombinant nucleic acid vector(s) comprising all or part of a coding sequence for an *Enterococcus faecalis* seryl-tRNA synthetase;

b) introducing the vector(s) into suitable host cells whereby the coding sequence(s) are under control of transcription signals and are linked to appropriate translation signals; and c) maintaining the host cells under conditions in which an *Enterococcus faecalis* seryl-tRNA synthetase or a functional portion thereof is produced.

61. The method of claim 60 further comprising isolating the *Enterococcus faecalis* seryl-tRNA synthetase or functional portion thereof.

62. A method for producing an *Enterococcus faecalis* tryptophanyl-tRNA synthetase or a functional portion thereof, said portion having catalytic activity or binding function, comprising the following steps:

a) constructing one or more recombinant nucleic acid vector(s) comprising all or part of a coding sequence for an *Enterococcus faecalis* tryptophanyl-tRNA synthetase;

b) introducing the vector(s) into suitable host cells whereby the coding sequence(s) are under control of transcription signals and are linked to appropriate translation signals; and c) maintaining the host cells under conditions in which an *Enterococcus faecalis* tryptophanyl-tRNA synthetase or a functional portion thereof is produced.

63. The method of claim 62 further comprising isolating the *Enterococcus faecalis* tryptophanyl-tRNA synthetase or functional portion thereof.

64. A method for producing active *Enterococcus faecalis* leucyl-tRNA synthetase comprising introducing one or more nucleic acid vector(s) comprising one or more coding sequence(s) for all or a functional part of an *Enterococcus faecalis* leucyl-tRNA synthetase into suitable host cells, said part having catalytic activity or binding function, and maintaining the host cells under conditions in which the coding sequence(s) are expressed.

65. The method of claim 64 further comprising the step of isolating said leucyl-tRNA synthetase.

66. A method for producing active *Enterococcus faecalis* tyrosyl-tRNA synthetase comprising introducing one or more nucleic acid vector(s) comprising one or more coding sequence(s) for all or a functional part of an *Enterococcus faecalis* tyrosyl-tRNA synthetase into suitable host cells, said part having catalytic activity or binding function, and maintaining the host cells under conditions in which the coding sequence(s) are expressed.

67. The method of claim 66 further comprising the step of isolating said tyrosyl-tRNA synthetase.

68. A method for producing active *Enterococcus faecalis* isoleucyl-tRNA synthetase comprising introducing one or more nucleic acid vector(s) comprising one or more coding sequence(s) for all or a functional part of an *Enterococcus faecalis* isoleucyl-tRNA synthetase into suitable host cells, said part having catalytic activity or binding function, and maintaining the host cells under conditions in which the coding sequence(s) are expressed.

69. The method of claim 68 further comprising the step of isolating said isoleucyl-tRNA synthetase.

70. A method for producing active *Enterococcus faecalis* seryl-tRNA synthetase comprising introducing one or more nucleic acid vector(s) comprising one or more coding sequence(s) for all or a functional part of an *Enterococcus faecalis* seryl-tRNA synthetase into suitable host cells, said part having catalytic activity or binding function, and maintaining the host cells under conditions in which the coding sequence(s) are expressed.

71. The method of claim 70 further comprising the step of isolating said seryl-tRNA synthetase.

72. A method for producing active *Enterococcus faecalis* tryptophanyl-tRNA synthetase comprising introducing one or more nucleic acid vector(s) comprising one or more coding sequence(s) for all or a functional part of an *Enterococcus faecalis* tryptophanyl-tRNA synthetase into suitable host cells, said part having catalytic activity or binding function, and maintaining the host cells under conditions in which the coding sequence(s) are expressed.

73. The method of claim 72 further comprising the step of isolating said tryptophanyl-tRNA synthetase.

74. A method for producing a polypeptide comprising an *Enterococcus faecalis* leucyl-tRNA synthetase or a functional portion thereof, said portion having catalytic activity or binding function, comprising maintaining a host cell comprising a recombinant nucleic acid encoding said polypeptide under conditions suitable for expression of the nucleic acid, whereby the encoded polypeptide is produced.

75. The method of claim 74 further comprising the step of isolating the polypeptide.

76. A method for producing a polypeptide comprising an *Enterococcus faecalis* tyrosyl-tRNA synthetase or a functional portion thereof, said portion having catalytic activity or binding function, comprising maintaining a host cell comprising a recombinant nucleic acid encoding said polypeptide under conditions suitable for expression of the nucleic acid, whereby the encoded polypeptide is produced.

77. The method of claim 76 further comprising the step of isolating the polypeptide.

78. A method for producing a polypeptide comprising an *Enterococcus faecalis* isoleucyl-tRNA synthetase or a functional portion thereof, said portion having catalytic activity or binding function, comprising maintaining a host cell comprising a recombinant nucleic acid encoding said polypeptide under conditions suitable for expression of the nucleic acid, whereby the encoded polypeptide is produced.

79. The method of claim 78 further comprising the step of isolating the polypeptide.

80. A method for producing a polypeptide comprising an *Enterococcus faecalis* seryl-tRNA synthetase or a functional portion thereof, said portion having catalytic activity or binding function, comprising maintaining a host cell comprising a recombinant nucleic acid encoding said polypeptide under conditions suitable for expression of the nucleic acid, whereby the encoded polypeptide is produced.

81. The method of claim 80 further comprising the step of isolating the polypeptide.

82. A method for producing a polypeptide comprising an *Enterococcus faecalis* tryptophanyl-tRNA synthetase or a functional portion thereof, said portion having catalytic activity or binding function, comprising maintaining a host cell comprising a recombinant nucleic acid encoding said polypeptide under conditions suitable for expression of the nucleic acid, whereby the encoded polypeptide is produced.

83. The method of claim 82 further comprising the step of isolating the polypeptide.

84. A method for producing a polypeptide comprising an *Enterococcus faecalis* leucyl-tRNA synthetase or a functional portion thereof, said portion having catalytic activity or binding function, comprising maintaining a host cell comprising a recombinant nucleic acid encoding said polypeptide under conditions suitable for expression of the nucleic acid and production of said polypeptide, and recovering said polypeptide.

85. A method for producing a polypeptide comprising an *Enterococcus faecalis* tyrosyl-tRNA synthetase or a functional portion thereof, said portion having catalytic activity or binding function, comprising maintaining a host cell comprising a recombinant nucleic acid encoding said polypeptide under conditions suitable for expression of the nucleic acid and production of said polypeptide, and recovering said polypeptide.

86. A method for producing a polypeptide comprising an *Enterococcus faecalis* isoleucyl-tRNA synthetase or a functional portion thereof, said portion having catalytic activity or binding function, comprising maintaining a host cell comprising a recombinant nucleic acid encoding said polypeptide under conditions suitable for expression of the nucleic acid and production of said polypeptide, and recovering said polypeptide.

87. A method for producing a polypeptide comprising an *Enterococcus faecalis* seryl-tRNA synthetase or a functional portion thereof, said portion having catalytic activity or binding function, comprising maintaining a host cell comprising a recombinant nucleic acid encoding said polypeptide under conditions suitable for expression of the nucleic acid and production of said polypeptide, and recovering said polypeptide.

88. A method for producing a polypeptide comprising an *Enterococcus faecalis* tryptophanyl-tRNA synthetase or a functional portion thereof, said portion having catalytic activity or binding function, comprising maintaining a host cell comprising a recombinant nucleic acid encoding said polypeptide under conditions suitable for expression of the nucleic acid and production of said polypeptide, and recovering said polypeptide.

89. An isolated nucleic acid which encodes a protein comprising an enterococcal isoleucyl-tRNA synthetase or portion thereof having catalytic activity or binding function, and which hybridizes under high stringency conditions, using wash buffers of increasing stringency, including 0.2x SSC/0.1% SDS wash buffer at a temperature of 60° C. to 65° C., to a DNA molecule having the sequence of nucleotides 213–2990 in SEQ ID NO: 1 or to the complement thereof.

90. A host cell comprising a recombinant nucleic acid encoding a protein comprising an *Enterococcus faecalis* isoleucyl-tRNA synthetase or portion thereof having catalytic activity or binding function.

91. A method for producing a protein comprising an *Enterococcus faecalis* isoleucyl-tRNA synthetase or a portion thereof having catalytic activity or binding function, comprising maintaining the host cell of claim 90 under conditions suitable for expression of said recombinant nucleic acid, whereby said protein is produced.

92. An isolated nucleic acid which encodes a protein comprising an enterococcal leucyl-tRNA synthetase or portion thereof having catalytic activity or binding function, and which hybridizes under high stringency conditions, using wash buffers of increasing stringency, including 0.2x SSC/0.1% SDS wash buffer at a temperature of 60° C. to 65° C., to a DNA molecule having the sequence of nucleotides 74–2485 in SEQ ID NO:3 or to the complement thereof.

93. A host cell comprising a recombinant nucleic acid encoding a protein comprising an *Enterococcus faecalis* leucyl-tRNA synthetase or portion thereof having catalytic activity or binding function.

94. A method for producing a protein comprising an *Enterococcus faecalis* leucyl-tRNA synthetase or a portion thereof having catalytic activity or binding function, comprising maintaining the host cell of claim 93 under conditions suitable for expression of said recombinant nucleic acid, whereby said protein is produced.

95. An isolated nucleic acid which encodes a protein comprising an enterococcal tryptophanyl-tRNA synthetase or portion thereof having catalytic activity or binding function, and which hybridizes under high stringency conditions, using wash buffers of increasing stringency, including 0.2x SSC/0.1% SDS wash buffer at a temperature of 60° C. to 65° C., to a DNA molecule having the sequence of nucleotides 187–1194 in SEQ ID NO:5 or to the complement thereof.

96. A host cell comprising a recombinant nucleic acid encoding a protein comprising an *Enterococcus faecalis* tryptophanyl-tRNA synthetase or portion thereof having catalytic activity or binding function.

97. A method for producing a protein comprising an *Enterococcus faecalis* tryptophanyl-tRNA synthetase or a portion thereof having catalytic activity or binding function, comprising maintaining the host cell of claim 96 under conditions suitable for expression of said recombinant nucleic acid, whereby said protein is produced.

98. An isolated nucleic acid which encodes a protein comprising an enterococcal tyrosyl-tRNA synthetase or portion thereof having catalytic activity or binding function, and which hybridizes under high stringency conditions, using wash buffers of increasing stringency, including 0.2x SSC/0. 1% SDS wash buffer at a temperature of 60° C. to 65° C., to a DNA molecule having the sequence of nucleotides 132–1385 in SEQ ID NO:10 or to the complement thereof.

99. A host cell comprising a recombinant nucleic acid encoding a protein comprising an *Enterococcus faecalis* tyrosyl-tRNA synthetase or portion thereof having catalytic activity or binding function.

100. A method for producing a protein comprising an *Enterococcus faecalis* tyrosyl-tRNA synthetase or a portion thereof having catalytic activity or binding function, comprising maintaining the host cell of claim 99 under conditions suitable for expression of said recombinant nucleic acid, whereby said protein is produced.

101. An isolated nucleic acid which encodes a protein comprising an enterococcal seryl-tRNA synthetase or portion thereof having catalytic activity or binding function, and which hybridizes under high stringency conditions, using wash buffers of increasing stringency, including 0.2x SSC/0.1 % SDS wash buffer at a temperature of 60° C. to 65° C., to a DNA molecule having the sequence of nucleotides 132–1400 in SEQ ID NO:12 or to the complement thereof.

102. A host cell comprising a recombinant nucleic acid encoding a protein comprising an enterococcal seryl-tRNA synthetase or portion thereof having catalytic activity or binding function.

103. A method for producing a protein comprising an enterococcal seryl-tRNA synthetase or a portion thereof having catalytic activity or binding function, comprising maintaining the host cell of claim 102 under conditions suitable for expression of said recombinant nucleic acid, whereby said protein is produced.

104. An isolated nucleic acid molecule, wherein said nucleic acid molecule encodes a protein comprising a phenylalanyl-tRNA synthetase or functional portion thereof encoded by an *Enterococcus faecalis*-derived portion of pC$^3$742, pC$^3$742 having been assigned Patent Deposit Designation PTA-394, wherein said phenylalanyl-tRNA synthetase or functional portion thereof has catalytic activity or binding function.

105. A host cell comprising a recombinant nucleic acid molecule, wherein said nucleic acid molecule encodes a protein comprising a phenylalanyl-tRNA synthetase or portion thereof encoded by an *Enterococcus faecalis*-derived portion of pC$^3$742, pC$^3$742 having been assigned Patent Deposit Designation PTA-394, wherein said phenylalanyl-tRNA synthetase or portion thereof has catalytic activity or binding function.

106. A method for producing a polypeptide comprising phenylalanyl-tRNA synthetase or a portion thereof encoded by an *Enterococcus faecalis*-derived portion of pC$^3$742, pC$^3$742 having been assigned Patent Deposit Designation PTA-394, wherein said phenylalanyl-tRNA synthetase or portion thereof has catalytic activity or binding function, comprising maintaining a host cell of claim 105 under conditions suitable for expression of said protein, whereby said polypeptide is produced.

107. The method of claim 106 further comprising isolating the polypeptide.

108. An isolated nucleic acid molecule, wherein said nucleic acid encodes a protein comprising an active phenylalanyl-tRNA synthetase encoded by pC$^3$742, pC$^3$742 having been assigned Patent Deposit Designation PTA-394.

109. A host cell comprising a recombinant nucleic acid molecule, wherein said nucleic acid molecule encodes a protein comprising an active phenylalanyl-tRNA synthetase encoded by pC$^3$742, pC$^3$742 having been assigned Patent Deposit Designation PTA-394.

110. Plasmid pC$^3$742, which has been assigned Patent Deposit Designation PTA-394.

\* \* \* \* \*

SEQUENCE LISTING (1) GENERAL INFORMATION:

(iii) NUMBER OF SEQUENCES: 71

(2) INFORMATION FOR SEQ ID NO:1:

(i) SEQUENCE CHARACTERISTICS:
        (A) LENGTH: 3212 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 213..2990

(xi) SEQUENCE DESCRIPTION: SEQ ID NO:1:

```
TTCTGAACAC TTGAGTAGGA ACTGCCGGAT AATTACCCGT TATCAATTTC AGAGAAAGTA         60

GGGGCAACTC TACTTTGAAT TTGGGTGGTA ACACGAGTAC TTCGTCCCTT GGGATGGAGT        120

ACTCTTTTTT TATCTACTTT TATCAGCTAT CGTTCATCTT TAGTATGAAC TAACACAATT        180

AAATCGATAA AATGAAAGCG AGGCAAATGC AT ATG AAA ATG AAA GAA ACA TTG         233
                                   Met Lys Met Lys Glu Thr Leu
                                    1               5

CAA TTA GGA AAA ACA GCT TTT CCA ATG CGT GGG AAC TTG CCA AAC CGT          281
Gln Leu Gly Lys Thr Ala Phe Pro Met Arg Gly Asn Leu Pro Asn Arg
         10                  15                  20

GAA GCA GAA TGG CAA AAA GAT TGG GAA GAA AAA GGC TTA TAT GAA CAA          329
```

-continued

| | | | | | | | | | | | | | | | |
|---|---|---|---|---|---|---|---|---|---|---|---|---|---|---|---|
| | Glu | Ala | Glu | Trp | Gln | Lys | Asp | Trp | Glu | Glu | Lys | Gly | Leu | Tyr | Glu | Gln |
| | | 25 | | | | 30 | | | | 35 | | | | | | |
| CGT | CAA | AAA | TTA | AAC | GAA | GGA | AAA | CCA | ACC | TTT | GTT | TTA | CAT | GAT | GGC | 377 |
| Arg | Gln | Lys | Leu | Asn | Glu | Gly | Lys | Pro | Thr | Phe | Val | Leu | His | Asp | Gly | |
| 40 | | | | | 45 | | | | 50 | | | | | 55 | | |
| CCT | CCC | TAT | GCA | AAC | GGA | AAT | ATT | CAT | TTA | GGA | CAT | TCT | TTG | AAT | AAA | 425 |
| Pro | Pro | Tyr | Ala | Asn | Gly | Asn | Ile | His | Leu | Gly | His | Ser | Leu | Asn | Lys | |
| | | | | 60 | | | | | 65 | | | | | 70 | | |
| ATC | AGT | AAA | GAT | ATT | ATT | ATT | CGT | TCA | AAA | TCA | ATG | TCT | GGT | TTC | CGT | 473 |
| Ile | Ser | Lys | Asp | Ile | Ile | Ile | Arg | Ser | Lys | Ser | Met | Ser | Gly | Phe | Arg | |
| | | | 75 | | | | | 80 | | | | | 85 | | | |
| TCT | CCT | TAT | GTG | CCT | GGT | TGG | GAT | ACT | CAT | GGT | TTA | CCA | ATT | GAG | CAA | 521 |
| Ser | Pro | Tyr | Val | Pro | Gly | Trp | Asp | Thr | His | Gly | Leu | Pro | Ile | Glu | Gln | |
| | | | 90 | | | | | 95 | | | | | 100 | | | |
| GTG | TTA | ACC | AAT | AAA | GGG | GTT | AAA | CGT | AAA | GAA | ATG | ACT | GTC | GCT | GAG | 569 |
| Val | Leu | Thr | Asn | Lys | Gly | Val | Lys | Arg | Lys | Glu | Met | Thr | Val | Ala | Glu | |
| | | 105 | | | | | 110 | | | | | 115 | | | | |
| TAT | CGC | GAA | AAA | TGT | AAA | GAG | TAT | GCC | TTA | TCA | CAA | GTC | GAT | AAA | CAA | 617 |
| Tyr | Arg | Glu | Lys | Cys | Lys | Glu | Tyr | Ala | Leu | Ser | Gln | Val | Asp | Lys | Gln | |
| 120 | | | | | 125 | | | | | 130 | | | | | 135 | |
| CGT | AAC | GAT | TTT | AAA | CGT | TTA | GGT | GTG | TCA | GGT | GAT | TGG | GAA | CAT | CCA | 665 |
| Arg | Asn | Asp | Phe | Lys | Arg | Leu | Gly | Val | Ser | Gly | Asp | Trp | Glu | His | Pro | |
| | | | | 140 | | | | | 145 | | | | | 150 | | |
| TAC | ATT | ACG | TTA | GAT | CCA | GAG | TAT | GAA | GCA | GCA | GAA | ATT | CGT | GTT | TTT | 713 |
| Tyr | Ile | Thr | Leu | Asp | Pro | Glu | Tyr | Glu | Ala | Ala | Glu | Ile | Arg | Val | Phe | |
| | | | 155 | | | | | 160 | | | | | 165 | | | |
| GGT | AAG | ATG | GCA | GAA | AAA | GGC | TAT | ATT | TAT | AAA | GGC | TTA | AAA | CCA | ATT | 761 |
| Gly | Lys | Met | Ala | Glu | Lys | Gly | Tyr | Ile | Tyr | Lys | Gly | Leu | Lys | Pro | Ile | |
| | | 170 | | | | | 175 | | | | | 180 | | | | |
| TAT | TGG | TCT | CCT | TCA | AGT | GAA | TCT | TCT | TTA | GCA | GAA | GCA | GAA | ATT | GAA | 809 |
| Tyr | Trp | Ser | Pro | Ser | Ser | Glu | Ser | Ser | Leu | Ala | Glu | Ala | Glu | Ile | Glu | |
| | 185 | | | | | 190 | | | | | 195 | | | | | |
| TAC | AAA | GAT | GTA | AAA | TCA | CCT | TCT | ATT | TAC | GTA | GCT | TTT | AAT | GTG | GCC | 857 |
| Tyr | Lys | Asp | Val | Lys | Ser | Pro | Ser | Ile | Tyr | Val | Ala | Phe | Asn | Val | Ala | |
| 200 | | | | | 205 | | | | | 210 | | | | | 215 | |
| GAT | GGT | AAA | GGT | CTT | TTA | GAT | AAC | GAG | ACA | GCC | TTC | GTC | ATC | TGG | ACG | 905 |
| Asp | Gly | Lys | Gly | Leu | Leu | Asp | Asn | Glu | Thr | Ala | Phe | Val | Ile | Trp | Thr | |
| | | | | 220 | | | | | 225 | | | | | 230 | | |
| ACA | ACT | CCT | TGG | ACA | TTA | CCA | GCC | AAC | TTA | GGT | ATT | TCA | GTT | AAT | CCT | 953 |
| Thr | Thr | Pro | Trp | Thr | Leu | Pro | Ala | Asn | Leu | Gly | Ile | Ser | Val | Asn | Pro | |
| | | | 235 | | | | | 240 | | | | | 245 | | | |
| GAT | TTT | ACG | TAT | GTT | GAA | GTG | AAG | GCA | GAC | GGT | CGT | AAA | TTT | GTA | ATT | 1001 |
| Asp | Phe | Thr | Tyr | Val | Glu | Val | Lys | Ala | Asp | Gly | Arg | Lys | Phe | Val | Ile | |
| | | 250 | | | | | 255 | | | | | 260 | | | | |
| GCT | AAA | GAT | TTA | TTA | ACA | ACA | GTT | AAA | GAA | GCG | ATT | GGT | TGG | GAA | GAA | 1049 |
| Ala | Lys | Asp | Leu | Leu | Thr | Thr | Val | Lys | Glu | Ala | Ile | Gly | Trp | Glu | Glu | |
| 265 | | | | | 270 | | | | | 275 | | | | | | |
| GTA | GAA | GTC | TTG | CGA | GAA | TTT | TCT | GGT | GAA | AAA | TTA | GAT | CGT | ATG | ACA | 1097 |
| Val | Glu | Val | Leu | Arg | Glu | Phe | Ser | Gly | Glu | Lys | Leu | Asp | Arg | Met | Thr | |
| 280 | | | | | 285 | | | | | 290 | | | | | 295 | |
| GCT | CAA | CAT | CCA | TTC | TAT | GAT | CGA | ACA | TCA | CTT | GTT | ATG | CTA | GGC | GAC | 1145 |
| Ala | Gln | His | Pro | Phe | Tyr | Asp | Arg | Thr | Ser | Leu | Val | Met | Leu | Gly | Asp | |
| | | | | 300 | | | | | 305 | | | | | 310 | | |
| CAC | GTG | ACG | CTA | GAT | GCC | GGG | ACT | GGC | TTA | GTT | CAT | ACC | GCA | CCA | GGA | 1193 |
| His | Val | Thr | Leu | Asp | Ala | Gly | Thr | Gly | Leu | Val | His | Thr | Ala | Pro | Gly | |
| | | | 315 | | | | | 320 | | | | | 325 | | | |
| CAT | GGT | GAA | GAT | GAC | TAT | ATC | GTT | AGC | CGT | AAA | TAT | GAT | TTA | CCT | GTT | 1241 |
| His | Gly | Glu | Asp | Asp | Tyr | Ile | Val | Ser | Arg | Lys | Tyr | Asp | Leu | Pro | Val | |
| | | 330 | | | | | 335 | | | | | 340 | | | | |

```
ATT TCT CCT GTT GAC AGT CGA GGG GTC TTT ACA GAT GAA GCA CCT GGT    1289
Ile Ser Pro Val Asp Ser Arg Gly Val Phe Thr Asp Glu Ala Pro Gly
345                 350                 355

TTT GAA GGA ATT TTC TAT GAC AAA GCG AAT CCA ATG ATT ACT GAG TTA    1337
Phe Glu Gly Ile Phe Tyr Asp Lys Ala Asn Pro Met Ile Thr Glu Leu
360                 365                 370                 375

TTA GAA GAA AAA GGC GCG TTA TTA AAA TTA GAT TTC TTT ACG CAT AGT    1385
Leu Glu Glu Lys Gly Ala Leu Leu Lys Leu Asp Phe Phe Thr His Ser
            380                 385                 390

TAT CCA CAT GAC TGG CGT ACC AAA AAA CCA GTT ATC TAC CGT GCA ACG    1433
Tyr Pro His Asp Trp Arg Thr Lys Lys Pro Val Ile Tyr Arg Ala Thr
                395                 400                 405

CCA CAA TGG TTT GCT TCA ATC TCT AAA TTC CGT CAA GAT ATT TTA GAT    1481
Pro Gln Trp Phe Ala Ser Ile Ser Lys Phe Arg Gln Asp Ile Leu Asp
            410                 415                 420

GAA GTT GAG AAA GTT GAC TGG CTA ATT CCT TGG GGA AAA ACA CGT TTG    1529
Glu Val Glu Lys Val Asp Trp Leu Ile Pro Trp Gly Lys Thr Arg Leu
                425                 430                 435

TAT AAT ATG ATT CGT GAC CGT GGT GAT TGG GTA ATC TCT CGT CAA AGA    1577
Tyr Asn Met Ile Arg Asp Arg Gly Asp Trp Val Ile Ser Arg Gln Arg
440                 445                 450                 455

GCG TGG GGT GTA CCA TTA CCG ATC TTC TAT GCT GAA AAT GGG GAA GCC    1625
Ala Trp Gly Val Pro Leu Pro Ile Phe Tyr Ala Glu Asn Gly Glu Ala
                460                 465                 470

ATC ATT ACG CCA GAA ACA ATT GAA CAT GTA GCG AAT TTA TTT GCA GAA    1673
Ile Ile Thr Pro Glu Thr Ile Glu His Val Ala Asn Leu Phe Ala Glu
            475                 480                 485

CAT GGA TCA AAT ATC TGG TTT ATG CGT GAA GCA AAA GAG TTA CTA CCA    1721
His Gly Ser Asn Ile Trp Phe Met Arg Glu Ala Lys Glu Leu Leu Pro
                490                 495                 500

GCC GGC TTT ACA CAT CCA GGT TCA CCA AAT GGC GAG TTT ACC AAA GAA    1769
Ala Gly Phe Thr His Pro Gly Ser Pro Asn Gly Glu Phe Thr Lys Glu
505                 510                 515

ACA GAT ATC ATG GAC GTT TGG TTT GAC TCA GGT TCT TCA CAT GAA GGA    1817
Thr Asp Ile Met Asp Val Trp Phe Asp Ser Gly Ser Ser His Glu Gly
520                 525                 530                 535

GTT TTA CGA GAA AGA GAA GAG TTA ACT TTC CCA GCA GAT ATG TAT TTA    1865
Val Leu Arg Glu Arg Glu Glu Leu Thr Phe Pro Ala Asp Met Tyr Leu
                540                 545                 550

GAA GGT TCT GAC CAA TAT CGT GGT TGG TTT AAC TCA AGT ATT ACA ACA    1913
Glu Gly Ser Asp Gln Tyr Arg Gly Trp Phe Asn Ser Ser Ile Thr Thr
            555                 560                 565

AGT GTT GCT ATC AAT GGG GTA GCG CCT TAT AAA TCA ATC ATT TCT CAA    1961
Ser Val Ala Ile Asn Gly Val Ala Pro Tyr Lys Ser Ile Ile Ser Gln
                570                 575                 580

GGG ATG GTT CTC GAT GGC GAA GGC CGT AAG ATG AGT AAA TCG TTA GGC    2009
Gly Met Val Leu Asp Gly Glu Gly Arg Lys Met Ser Lys Ser Leu Gly
            585                 590                 595

AAT ACT ATC TTA CCT GAA AAA GTT ATC AAC CAA ATG GGT GCA GAT ATC    2057
Asn Thr Ile Leu Pro Glu Lys Val Ile Asn Gln Met Gly Ala Asp Ile
600                 605                 610                 615

TTA CGC TTG TGG GTA AGT AGT GTT GAC GCG GAA GCC GAT GTG CGT GTC    2105
Leu Arg Leu Trp Val Ser Ser Val Asp Ala Glu Ala Asp Val Arg Val
                620                 625                 630

TCA ATG GAT ATC TTA AAC CAA GTA TCT GAA GTG TAC CGG AAA ATC CGT    2153
Ser Met Asp Ile Leu Asn Gln Val Ser Glu Val Tyr Arg Lys Ile Arg
            635                 640                 645

AAT ACT ATG CGT TTC TTG TTA GCG AAT ACG AGT GAT TTT AAT CCA GCT    2201
Asn Thr Met Arg Phe Leu Leu Ala Asn Thr Ser Asp Phe Asn Pro Ala
                650                 655                 660
```

```
GAG CAT ACT GTA GCT TAT GCT GAT TTA CGT TCT GTA GAT AAA TAC ATG    2249
Glu His Thr Val Ala Tyr Ala Asp Leu Arg Ser Val Asp Lys Tyr Met
    665                 670                 675

ACG GTT CGT TTA AAT CAA GTC ATT CAA GAA ATC CGT GAA AAT GGT TAT    2297
Thr Val Arg Leu Asn Gln Val Ile Gln Glu Ile Arg Glu Asn Gly Tyr
680                 685                 690                 695

GAA AAA TAT AAT TTC ATG CAT ATT TAT CGG ACA GTT ATG AAC TTC TTA    2345
Glu Lys Tyr Asn Phe Met His Ile Tyr Arg Thr Val Met Asn Phe Leu
                700                 705                 710

ACT GTG GAT CTA TCT TCT TTC TAT TTA GAC TTT GCG AAA GAT GTC GTT    2393
Thr Val Asp Leu Ser Ser Phe Tyr Leu Asp Phe Ala Lys Asp Val Val
            715                 720                 725

TAT ATT GAA GCT GAA AAC GAT TAT CAA CGT CGT TGT ATG CAG ACT GTT    2441
Tyr Ile Glu Ala Glu Asn Asp Tyr Gln Arg Arg Cys Met Gln Thr Val
        730                 735                 740

TTC TAC CAA ACA TTG GTT TCA TTA ACA AAA CTA TTG ACA CCA ATT ATT    2489
Phe Tyr Gln Thr Leu Val Ser Leu Thr Lys Leu Leu Thr Pro Ile Ile
    745                 750                 755

CCA CAT ACA GCG GAA GAA ATT TGG AGT TTC TTA CAA GAA GAA GAA GAG    2537
Pro His Thr Ala Glu Glu Ile Trp Ser Phe Leu Gln Glu Glu Glu Glu
760                 765                 770                 775

TAT GTG CAA TTA GCT GAA TTC CCA GGT TAC GAA ACG TTT ACT AAT GAA    2585
Tyr Val Gln Leu Ala Glu Phe Pro Gly Tyr Glu Thr Phe Thr Asn Glu
                780                 785                 790

GAA GAA TTG ATG GAT ACA TGG GCA GCC TTT ATG GAT TTC CGT GAC AAT    2633
Glu Glu Leu Met Asp Thr Trp Ala Ala Phe Met Asp Phe Arg Asp Asn
            795                 800                 805

GTC TTA AAA GCG TTG GAA GAA GCT CGT CAT TCT AAA TTA ATC GGT AAA    2681
Val Leu Lys Ala Leu Glu Glu Ala Arg His Ser Lys Leu Ile Gly Lys
        810                 815                 820

TCG TTA GAA GCT AAA GTG ACC GTT TAT CCA AAT GAA CAA ATT CGT CAA    2729
Ser Leu Glu Ala Lys Val Thr Val Tyr Pro Asn Glu Gln Ile Arg Gln
    825                 830                 835

TTA ATG ACA GCT GTT GAT GCA GAT ATT GCT CAA TTA CTA ATT GTT TCC    2777
Leu Met Thr Ala Val Asp Ala Asp Ile Ala Gln Leu Leu Ile Val Ser
840                 845                 850                 855

GAC TTT GAA GTA TCA AAA GAA GTA GCA CCT AGT GAA GCT GTT CAA TTT    2825
Asp Phe Glu Val Ser Lys Glu Val Ala Pro Ser Glu Ala Val Gln Phe
                860                 865                 870

GAA GAC ATG GCT ATT TTA GTT GAA AAA GCA GAA GGC GAA ACG TGT GAC    2873
Glu Asp Met Ala Ile Leu Val Glu Lys Ala Glu Gly Glu Thr Cys Asp
            875                 880                 885

CGT TGT CGT TCC GTT CGT CAA GAT GTC GGC TCA GAT GAA AAA TTA CCA    2921
Arg Cys Arg Ser Val Arg Gln Asp Val Gly Ser Asp Glu Lys Leu Pro
        890                 895                 900

ACA CTT TGT GGC CGT TGT GCA CAC ATT GTT GAA GAA AAT TAT CCA GAA    2969
Thr Leu Cys Gly Arg Cys Ala His Ile Val Glu Glu Asn Tyr Pro Glu
    905                 910                 915

GCG GTT GCT GAA GGA TTC GAA TAAACAAGAA AAAAGATCCG CTAGTCGTTA       3020
Ala Val Ala Glu Gly Phe Glu
920                 925

ACTAGCGGAT CTTTTTTGGC TTATTTATTG ATCAAGTTGA CCGCGGTCAC GGTACCAATT  3080

ATCTGGTTGC CATTCCCAAG TAAAGCCATC TTTTTCTAAT AAGTCGAAGG CAGCTTGCGG  3140

CGCCCATTGT GCCAGCGGCA TAATTAGGGA AGAAACGTC TGTTTATCC CAAGCATGTC    3200

GAATAATGTC AA                                                     3212

(2) INFORMATION FOR SEQ ID NO:2:
```

(i) SEQUENCE CHARACTERISTICS:
          (A) LENGTH: 926 amino acids
          (B) TYPE: amino acid
          (D) TOPOLOGY: linear (ii) MOLECULE TYPE: protein (xi) SEQUENCE DESCRIPTION: SEQ ID NO:2:

Met Lys Met Lys Glu Thr Leu Gln Leu Gly Lys Thr Ala Phe Pro Met
 1               5                  10                  15

Arg Gly Asn Leu Pro Asn Arg Glu Ala Glu Trp Gln Lys Asp Trp Glu
            20                  25                  30

Glu Lys Gly Leu Tyr Glu Gln Arg Gln Lys Leu Asn Glu Gly Lys Pro
        35                  40                  45

Thr Phe Val Leu His Asp Gly Pro Tyr Ala Asn Gly Asn Ile His
    50                  55                  60

Leu Gly His Ser Leu Asn Lys Ile Ser Lys Asp Ile Ile Ile Arg Ser
65                  70                  75                  80

Lys Ser Met Ser Gly Phe Arg Ser Pro Tyr Val Pro Gly Trp Asp Thr
                85                  90                  95

His Gly Leu Pro Ile Glu Gln Val Leu Thr Asn Lys Gly Val Lys Arg
            100                 105                 110

Lys Glu Met Thr Val Ala Glu Tyr Arg Glu Lys Cys Lys Glu Tyr Ala
        115                 120                 125

Leu Ser Gln Val Asp Lys Gln Arg Asn Asp Phe Lys Arg Leu Gly Val
    130                 135                 140

Ser Gly Asp Trp Glu His Pro Tyr Ile Thr Leu Asp Pro Glu Tyr Glu
145                 150                 155                 160

Ala Ala Glu Ile Arg Val Phe Gly Lys Met Ala Glu Lys Gly Tyr Ile
                165                 170                 175

Tyr Lys Gly Leu Lys Pro Ile Tyr Trp Ser Pro Ser Ser Glu Ser Ser
            180                 185                 190

Leu Ala Glu Ala Glu Ile Glu Tyr Lys Asp Val Lys Ser Pro Ser Ile
        195                 200                 205

Tyr Val Ala Phe Asn Val Ala Asp Gly Lys Gly Leu Leu Asp Asn Glu
    210                 215                 220

Thr Ala Phe Val Ile Trp Thr Thr Thr Pro Trp Thr Leu Pro Ala Asn
225                 230                 235                 240

Leu Gly Ile Ser Val Asn Pro Asp Phe Thr Tyr Val Glu Val Lys Ala
                245                 250                 255

Asp Gly Arg Lys Phe Val Ile Ala Lys Asp Leu Leu Thr Thr Val Lys
            260                 265                 270

Glu Ala Ile Gly Trp Glu Glu Val Glu Val Leu Arg Glu Phe Ser Gly
        275                 280                 285

Glu Lys Leu Asp Arg Met Thr Ala Gln His Pro Phe Tyr Asp Arg Thr
    290                 295                 300

Ser Leu Val Met Leu Gly Asp His Val Thr Leu Asp Ala Gly Thr Gly
305                 310                 315                 320

Leu Val His Thr Ala Pro Gly His Gly Glu Asp Tyr Ile Val Ser
                325                 330                 335

Arg Lys Tyr Asp Leu Pro Val Ile Ser Pro Val Asp Ser Arg Gly Val
            340                 345                 350

Phe Thr Asp Glu Ala Pro Gly Phe Glu Gly Ile Phe Tyr Asp Lys Ala
        355                 360                 365

-continued

```
Asn Pro Met Ile Thr Glu Leu Leu Glu Glu Lys Gly Ala Leu Leu Lys
    370                 375                 380

Leu Asp Phe Phe Thr His Ser Tyr Pro His Asp Trp Arg Thr Lys Lys
385                 390                 395                 400

Pro Val Ile Tyr Arg Ala Thr Pro Gln Trp Phe Ala Ser Ile Ser Lys
                405                 410                 415

Phe Arg Gln Asp Ile Leu Asp Glu Val Glu Lys Val Asp Trp Leu Ile
            420                 425                 430

Pro Trp Gly Lys Thr Arg Leu Tyr Asn Met Ile Arg Asp Arg Gly Asp
            435                 440                 445

Trp Val Ile Ser Arg Gln Arg Ala Trp Gly Val Pro Leu Pro Ile Phe
    450                 455                 460

Tyr Ala Glu Asn Gly Glu Ala Ile Ile Thr Pro Glu Thr Ile Glu His
465                 470                 475                 480

Val Ala Asn Leu Phe Ala Glu His Gly Ser Asn Ile Trp Phe Met Arg
                485                 490                 495

Glu Ala Lys Glu Leu Leu Pro Ala Gly Phe Thr His Pro Gly Ser Pro
            500                 505                 510

Asn Gly Glu Phe Thr Lys Glu Thr Asp Ile Met Asp Val Trp Phe Asp
    515                 520                 525

Ser Gly Ser Ser His Glu Gly Val Leu Arg Glu Arg Glu Glu Leu Thr
530                 535                 540

Phe Pro Ala Asp Met Tyr Leu Glu Gly Ser Asp Gln Tyr Arg Gly Trp
545                 550                 555                 560

Phe Asn Ser Ser Ile Thr Thr Ser Val Ala Ile Asn Gly Val Ala Pro
                565                 570                 575

Tyr Lys Ser Ile Ile Ser Gln Gly Met Val Leu Asp Gly Glu Gly Arg
            580                 585                 590

Lys Met Ser Lys Ser Leu Gly Asn Thr Ile Leu Pro Glu Lys Val Ile
            595                 600                 605

Asn Gln Met Gly Ala Asp Ile Leu Arg Leu Trp Val Ser Ser Val Asp
    610                 615                 620

Ala Glu Ala Asp Val Arg Val Ser Met Asp Ile Leu Asn Gln Val Ser
625                 630                 635                 640

Glu Val Tyr Arg Lys Ile Arg Asn Thr Met Arg Phe Leu Leu Ala Asn
                645                 650                 655

Thr Ser Asp Phe Asn Pro Ala Glu His Thr Val Ala Tyr Ala Asp Leu
            660                 665                 670

Arg Ser Val Asp Lys Tyr Met Thr Val Arg Leu Asn Gln Val Ile Gln
            675                 680                 685

Glu Ile Arg Glu Asn Gly Tyr Glu Lys Tyr Asn Phe Met His Ile Tyr
    690                 695                 700

Arg Thr Val Met Asn Phe Leu Thr Val Asp Leu Ser Ser Phe Tyr Leu
705                 710                 715                 720

Asp Phe Ala Lys Asp Val Val Tyr Ile Glu Ala Glu Asn Asp Tyr Gln
                725                 730                 735

Arg Arg Cys Met Gln Thr Val Phe Tyr Gln Thr Leu Val Ser Leu Thr
            740                 745                 750

Lys Leu Leu Thr Pro Ile Ile Pro His Thr Ala Glu Glu Ile Trp Ser
            755                 760                 765

Phe Leu Gln Glu Glu Glu Glu Tyr Val Gln Leu Ala Glu Phe Pro Gly
    770                 775                 780

Tyr Glu Thr Phe Thr Asn Glu Glu Glu Leu Met Asp Thr Trp Ala Ala
```

-continued

```
                    785                 790                 795                 800
Phe Met Asp Phe Arg Asp Asn Val Leu Lys Ala Leu Glu Glu Ala Arg
                805                 810                 815

His Ser Lys Leu Ile Gly Lys Ser Leu Glu Ala Lys Val Thr Val Tyr
                820                 825                 830

Pro Asn Glu Gln Ile Arg Gln Leu Met Thr Ala Val Asp Ala Asp Ile
                835                 840                 845

Ala Gln Leu Leu Ile Val Ser Asp Phe Glu Val Ser Lys Glu Val Ala
                850                 855                 860

Pro Ser Glu Ala Val Gln Phe Glu Asp Met Ala Ile Leu Val Glu Lys
865                 870                 875                 880

Ala Glu Gly Glu Thr Cys Asp Arg Cys Arg Ser Val Arg Gln Asp Val
                885                 890                 895

Gly Ser Asp Glu Lys Leu Pro Thr Leu Cys Gly Arg Cys Ala His Ile
                900                 905                 910

Val Glu Glu Asn Tyr Pro Glu Ala Val Ala Glu Gly Phe Glu
                915                 920                 925
```

(2) INFORMATION FOR SEQ ID NO:3:

(i) SEQUENCE CHARACTERISTICS:
        (A) LENGTH: 2641 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 74..2485

(xi) SEQUENCE DESCRIPTION: SEQ ID NO:3:

```
GTCAGAATAG TGACAATGGC TGCAGGTGGC AAATTTTAAG AATGAAAAAT TTTATATTAC      60

TAGGAGGAAT AAC ATG AGC TAC AAT CAC AAA GAG ATT GAG AAA AAA TGG      109
            Met Ser Tyr Asn His Lys Glu Ile Glu Lys Lys Trp
              1               5                  10

CAA AAA TAT TGG GCT AAG AAC AAT TGT TTC AAT ACA TTG GAC GAC CCA      157
Gln Lys Tyr Trp Ala Lys Asn Asn Cys Phe Asn Thr Leu Asp Asp Pro
         15                  20                  25

AAT AAA GAA AAA TTT TAT GCA CTA GAT ATG TTT CCC TAT CCA TCT GGA      205
Asn Lys Glu Lys Phe Tyr Ala Leu Asp Met Phe Pro Tyr Pro Ser Gly
 30                  35                  40

CAA GGC TTA CAC GTA GGT CAC CCG GAA GGC TAT ACA GCA ACC GAT ATT      253
Gln Gly Leu His Val Gly His Pro Glu Gly Tyr Thr Ala Thr Asp Ile
 45                  50                  55                  60

CTT TCA CGT ATG AAA CGT GCG CAA GGC TAT AAT GTG TTG CAT CCA ATG      301
Leu Ser Arg Met Lys Arg Ala Gln Gly Tyr Asn Val Leu His Pro Met
                 65                  70                  75

GGC TGG GAT GCG TTT GGT TTG CCA GCA GAG CAA TAT GCG TTA GAT ACA      349
Gly Trp Asp Ala Phe Gly Leu Pro Ala Glu Gln Tyr Ala Leu Asp Thr
             80                  85                  90

GGA AAT GAC CCA GCT GAA TTT ACT AAG AAA AAT ATC GAA ACA TTC CGT      397
Gly Asn Asp Pro Ala Glu Phe Thr Lys Lys Asn Ile Glu Thr Phe Arg
         95                  100                 105

CGC CAA ATT AAT TCA CTA GGA TTC AGC TAT GAT TGG AAT CGT GAA ATT      445
Arg Gln Ile Asn Ser Leu Gly Phe Ser Tyr Asp Trp Asn Arg Glu Ile
    110                 115                 120

AAT ACC ACT GAT CCT GAG TAT TAC AAA TGG ACA CAA TGG ATA TTT ACA      493
Asn Thr Thr Asp Pro Glu Tyr Tyr Lys Trp Thr Gln Trp Ile Phe Thr
125                 130                 135                 140
```

```
AAA TTA TAT GAA AAA GGG TTA GCT TAT GAA GCA GAA GTT GCG GTT AAC        541
Lys Leu Tyr Glu Lys Gly Leu Ala Tyr Glu Ala Glu Val Ala Val Asn
                145                 150                 155

TGG GTC CCT GAA TTA GGA ACT GTT ATT TCA AAT GAA GAA GTC ATT GAT        589
Trp Val Pro Glu Leu Gly Thr Val Ile Ser Asn Glu Glu Val Ile Asp
            160                 165                 170

GGA AAA AGT GAA CGT GGC GGT TAT GAT GTG GTT CGC CGA CCA ATG CGT        637
Gly Lys Ser Glu Arg Gly Gly Tyr Asp Val Val Arg Arg Pro Met Arg
        175                 180                 185

CAA TGG ATG CTG AAA ATT ACT GCT TAT GCA GAT CGC TTA TTA GAA GAT        685
Gln Trp Met Leu Lys Ile Thr Ala Tyr Ala Asp Arg Leu Leu Glu Asp
    190                 195                 200

TTA GAG CTT GTT GAT TGG CCA GAG AGT ATT AAA GAT ATG CAA CGA AAT        733
Leu Glu Leu Val Asp Trp Pro Glu Ser Ile Lys Asp Met Gln Arg Asn
205                 210                 215                 220

TGG ATT GGA CGT TCT GAA GGA GCC AAT GTG ACC TTT AAA GTC GCT GGC        781
Trp Ile Gly Arg Ser Glu Gly Ala Asn Val Thr Phe Lys Val Ala Gly
                225                 230                 235

ACA GAA GAA AGT TTC ACG GTG TTT ACA ACC CGT CCT GAT ACC TTG TTT        829
Thr Glu Glu Ser Phe Thr Val Phe Thr Thr Arg Pro Asp Thr Leu Phe
            240                 245                 250

GGT GCA ACC TAT ACT GTT CTA GCT CCT GAA CTA GAA CTA GTG AAA AAA        877
Gly Ala Thr Tyr Thr Val Leu Ala Pro Glu Leu Glu Leu Val Lys Lys
        255                 260                 265

ATT ACG ACA CCT GAA CAA ACA GCA GCT GTA GAA GCA TAT ATT GAA GAA        925
Ile Thr Thr Pro Glu Gln Thr Ala Ala Val Glu Ala Tyr Ile Glu Glu
    270                 275                 280

ACC TCA AAA AAA TCT GAT TTA AAT AGA ACG GAT TTA GCA AAA GAA AAA        973
Thr Ser Lys Lys Ser Asp Leu Asn Arg Thr Asp Leu Ala Lys Glu Lys
285                 290                 295                 300

ACA GGT GTT TTC ACA GGT GCG TAT GCT ATA AAT CCA GTC AAT GGC CAA       1021
Thr Gly Val Phe Thr Gly Ala Tyr Ala Ile Asn Pro Val Asn Gly Gln
                305                 310                 315

GAA ATT CCA ATT TGG ATT GGC GAT TAT GTT TTA GCA AGC TAT GGC ACA       1069
Glu Ile Pro Ile Trp Ile Gly Asp Tyr Val Leu Ala Ser Tyr Gly Thr
            320                 325                 330

GGC GCA ATC ATG GCG GTC CCA GCA CAT GAT GAA CGG GAT TAC GAA TTT       1117
Gly Ala Ile Met Ala Val Pro Ala His Asp Glu Arg Asp Tyr Glu Phe
        335                 340                 345

GCG AAA ACA TTT GGC ATT GAT ATC CTA CCA GTA ATC GCA GGT GGC GAC       1165
Ala Lys Thr Phe Gly Ile Asp Ile Leu Pro Val Ile Ala Gly Gly Asp
    350                 355                 360

ATT ACA ACA GAA GCC TAT ACA GGG GAT GGA CCG CAT ATC AAT TCT GAT       1213
Ile Thr Thr Glu Ala Tyr Thr Gly Asp Gly Pro His Ile Asn Ser Asp
365                 370                 375                 380

TTC TTA AAT GGA TTA AAC AAA GCA GAA GCC ATC GCT AAA ATG AAT GAG       1261
Phe Leu Asn Gly Leu Asn Lys Ala Glu Ala Ile Ala Lys Met Asn Glu
                385                 390                 395

TGG CTA GAA GAA AAT CAC GTA GGG AAA AAA GAA GTA TCT TAT CGT TTA       1309
Trp Leu Glu Glu Asn His Val Gly Lys Lys Glu Val Ser Tyr Arg Leu
            400                 405                 410

CGT GAC TGG TTA TTC TCT CGT CAA CGC TAC TGG GGT GAA CCA ATT CCT       1357
Arg Asp Trp Leu Phe Ser Arg Gln Arg Tyr Trp Gly Glu Pro Ile Pro
        415                 420                 425

GTG ATC CAT TGG GAA GAT GGA ACA ACC ACG GTT CCT GAA TCT GAG            1405
Val Ile His Trp Glu Asp Gly Thr Thr Thr Val Pro Glu Ser Glu
    430                 435                 440

TTA CCT CTA CGT TTA CCA GTA ACA TCG GAT ATT CGC CCA AGT GGA ACT       1453
Leu Pro Leu Arg Leu Pro Val Thr Ser Asp Ile Arg Pro Ser Gly Thr
445                 450                 455                 460
```

```
GGG GAA TCG CCA TTA GCA AAC ATT GAT GAA TGG GTC AAT GTC GTC GAC      1501
Gly Glu Ser Pro Leu Ala Asn Ile Asp Glu Trp Val Asn Val Val Asp
                465                 470                 475

CCT GAA ACT GGC ATG AAG GGA AAA CGT GAA ACG AAT ACT ATG CCA CAA      1549
Pro Glu Thr Gly Met Lys Gly Lys Arg Glu Thr Asn Thr Met Pro Gln
                480                 485                 490

TGG GCT GGA AGC TCT TGG TAT TAC TTA CGA TTC ATT GAT CCT CAT AAT      1597
Trp Ala Gly Ser Ser Trp Tyr Tyr Leu Arg Phe Ile Asp Pro His Asn
                495                 500                 505

AAA AAT GAA ATT GCT GAT TTT GAA AAA TTA AAA CGT TGG TTA CCA GTT      1645
Lys Asn Glu Ile Ala Asp Phe Glu Lys Leu Lys Arg Trp Leu Pro Val
510                 515                 520

GAT ATC TAT ATT GGT GGT GCC GAA CAT GCG GTG CTG CAT TTA CTT TAT      1693
Asp Ile Tyr Ile Gly Gly Ala Glu His Ala Val Leu His Leu Leu Tyr
525                 530                 535                 540

GCT CGT TTT TGG CAT AAA TTC TTA TAT GAT ATT GGT GTG GTT CCT ACC      1741
Ala Arg Phe Trp His Lys Phe Leu Tyr Asp Ile Gly Val Val Pro Thr
                545                 550                 555

AAA GAA CCT TTC CAA AAA TTA TAC AAC CAA GGT ATG ATT TTA GGA GAA      1789
Lys Glu Pro Phe Gln Lys Leu Tyr Asn Gln Gly Met Ile Leu Gly Glu
                560                 565                 570

AAC AAC GAA AAA ATG TCT AAA TCA CGT GGC AAT GTT GTA AAT CCC GAT      1837
Asn Asn Glu Lys Met Ser Lys Ser Arg Gly Asn Val Val Asn Pro Asp
                575                 580                 585

GAT GTG GTG GCT AAA TAT GGT GCG GAT ACG TTA CGT CTT TAT GAA ATG      1885
Asp Val Val Ala Lys Tyr Gly Ala Asp Thr Leu Arg Leu Tyr Glu Met
                590                 595                 600

TTC ATG GGC CCA TTA GAT GCT TCC ATT GCT TGG AAT GAA AAT GGC TTA      1933
Phe Met Gly Pro Leu Asp Ala Ser Ile Ala Trp Asn Glu Asn Gly Leu
605                 610                 615                 620

GAA GGA AGT CGT AAA TTC TTA GAT CGC GTT TGG CGT CTG ATT GTT GAT      1981
Glu Gly Ser Arg Lys Phe Leu Asp Arg Val Trp Arg Leu Ile Val Asp
                625                 630                 635

GAA GAA GGC AAA ATG CGT GAC CGA ATT ACC ACA ATT AAT GAT GGC CGT      2029
Glu Glu Gly Lys Met Arg Asp Arg Ile Thr Thr Ile Asn Asp Gly Arg
                640                 645                 650

TTA ACG AAA GTT TAT CAC CAA ACG GTT AAA AAA GTG ACA GAA GAT ATG      2077
Leu Thr Lys Val Tyr His Gln Thr Val Lys Lys Val Thr Glu Asp Met
                655                 660                 665

GCA AAC TTG CAC TTT AAT ACA GCG ATT TCT CAA TTA ATG GTT TTT GTG      2125
Ala Asn Leu His Phe Asn Thr Ala Ile Ser Gln Leu Met Val Phe Val
670                 675                 680

AAT GAA GCC AAT AAA GTG GAT GCC TTA CCT TAT GAA TAT GTG GAA GGA      2173
Asn Glu Ala Asn Lys Val Asp Ala Leu Pro Tyr Glu Tyr Val Glu Gly
685                 690                 695                 700

TTT GTC CAA TTA CTT GCG CCA ATC GCG CCA CAT ATT GGT GAA GAA CTA      2221
Phe Val Gln Leu Leu Ala Pro Ile Ala Pro His Ile Gly Glu Glu Leu
                705                 710                 715

TGG CAA ATT TTA GGT AAC GAG GAA AGT TTA ACT TAT GTC CCT TGG CCA      2269
Trp Gln Ile Leu Gly Asn Glu Glu Ser Leu Thr Tyr Val Pro Trp Pro
                720                 725                 730

ACC TAT GAT GAA GCA GCC TTA GTA GAA GAT GAA GTG GAA GTA GTT TTC      2317
Thr Tyr Asp Glu Ala Ala Leu Val Glu Asp Glu Val Glu Val Val Phe
                735                 740                 745

CAA GTG AAC GGA AAA TTA CGT GGC AAA CAA AAT GTC GCT CGT GGG TTA      2365
Gln Val Asn Gly Lys Leu Arg Gly Lys Gln Asn Val Ala Arg Gly Leu
                750                 755                 760

AGC AAA GAA GAA TTA GAA CAA ATT GCA ATG AAC CAT GAA GCT GTT AAA      2413
Ser Lys Glu Glu Leu Glu Gln Ile Ala Met Asn His Glu Ala Val Lys
```

-continued

```
765                770                775                780
GAA TTT ATT GAA GGA AAA ACA GTG CGC AAA GTG ATT GCT GTT CCA GAT           2461
Glu Phe Ile Glu Gly Lys Thr Val Arg Lys Val Ile Ala Val Pro Asp
                    785                 790                 795

AAA TTA GTA AAT ATT GTT GCA AAT TAAGTTATAT GTTTTTATTA AAAAAAGAGC         2515
Lys Leu Val Asn Ile Val Ala Asn
                800

CGGACGTATC AAAAGCGTCA GGCTCTTTTT AAGGTTGTTT TGTTTTACCT TTTTGATTCA        2575

TATGTTCTTT ACATGTGATT GTTATAACCG AAAGCAAGGC GATGAAGAGA AAAAAGTAAC        2635

CGATCG                                                                    2641
```

(2) INFORMATION FOR SEQ ID NO:4:

(i) SEQUENCE CHARACTERISTICS:
        (A) LENGTH: 804 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Tyr Asn His Lys Glu Ile Glu Lys Lys Trp Gln Lys Tyr Trp
 1               5                  10                  15

Ala Lys Asn Asn Cys Phe Asn Thr Leu Asp Asp Pro Asn Lys Glu Lys
                20                  25                  30

Phe Tyr Ala Leu Asp Met Phe Pro Tyr Pro Ser Gly Gln Gly Leu His
            35                  40                  45

Val Gly His Pro Glu Gly Tyr Thr Ala Thr Asp Ile Leu Ser Arg Met
        50                  55                  60

Lys Arg Ala Gln Gly Tyr Asn Val Leu His Pro Met Gly Trp Asp Ala
65                  70                  75                  80

Phe Gly Leu Pro Ala Glu Gln Tyr Ala Leu Asp Thr Gly Asn Asp Pro
                85                  90                  95

Ala Glu Phe Thr Lys Lys Asn Ile Glu Thr Phe Arg Arg Gln Ile Asn
            100                 105                 110

Ser Leu Gly Phe Ser Tyr Asp Trp Asn Arg Glu Ile Asn Thr Thr Asp
        115                 120                 125

Pro Glu Tyr Tyr Lys Trp Thr Gln Trp Ile Phe Thr Lys Leu Tyr Glu
    130                 135                 140

Lys Gly Leu Ala Tyr Glu Ala Glu Val Ala Val Asn Trp Val Pro Glu
145                 150                 155                 160

Leu Gly Thr Val Ile Ser Asn Glu Glu Val Ile Asp Gly Lys Ser Glu
                165                 170                 175

Arg Gly Gly Tyr Asp Val Val Arg Arg Pro Met Arg Gln Trp Met Leu
            180                 185                 190

Lys Ile Thr Ala Tyr Ala Asp Arg Leu Leu Glu Asp Leu Glu Leu Val
        195                 200                 205

Asp Trp Pro Glu Ser Ile Lys Asp Met Gln Arg Asn Trp Ile Gly Arg
    210                 215                 220

Ser Glu Gly Ala Asn Val Thr Phe Lys Val Ala Gly Thr Glu Glu Ser
225                 230                 235                 240

Phe Thr Val Phe Thr Thr Arg Pro Asp Thr Leu Phe Gly Ala Thr Tyr
                245                 250                 255

Thr Val Leu Ala Pro Glu Leu Glu Leu Val Lys Lys Ile Thr Thr Pro
            260                 265                 270
```

-continued

```
Glu Gln Thr Ala Ala Val Glu Ala Tyr Ile Glu Glu Thr Ser Lys Lys
        275                 280                 285

Ser Asp Leu Asn Arg Thr Asp Leu Ala Lys Glu Lys Thr Gly Val Phe
    290                 295                 300

Thr Gly Ala Tyr Ala Ile Asn Pro Val Asn Gly Gln Glu Ile Pro Ile
305                 310                 315                 320

Trp Ile Gly Asp Tyr Val Leu Ala Ser Tyr Gly Thr Gly Ala Ile Met
            325                 330                 335

Ala Val Pro Ala His Asp Glu Arg Asp Tyr Glu Phe Ala Lys Thr Phe
            340                 345                 350

Gly Ile Asp Ile Leu Pro Val Ile Ala Gly Gly Asp Ile Thr Thr Glu
            355                 360                 365

Ala Tyr Thr Gly Asp Gly Pro His Ile Asn Ser Asp Phe Leu Asn Gly
            370                 375                 380

Leu Asn Lys Ala Glu Ala Ile Ala Lys Met Asn Glu Trp Leu Glu Glu
385                 390                 395                 400

Asn His Val Gly Lys Lys Glu Val Ser Tyr Arg Leu Arg Asp Trp Leu
            405                 410                 415

Phe Ser Arg Gln Arg Tyr Trp Gly Glu Pro Ile Pro Val Ile His Trp
            420                 425                 430

Glu Asp Gly Thr Thr Thr Val Pro Glu Ser Glu Leu Pro Leu Arg
            435                 440                 445

Leu Pro Val Thr Ser Asp Ile Arg Pro Ser Gly Thr Gly Glu Ser Pro
450                 455                 460

Leu Ala Asn Ile Asp Glu Trp Val Asn Val Val Asp Pro Glu Thr Gly
465                 470                 475                 480

Met Lys Gly Lys Arg Glu Thr Asn Thr Met Pro Gln Trp Ala Gly Ser
            485                 490                 495

Ser Trp Tyr Tyr Leu Arg Phe Ile Asp Pro His Asn Lys Asn Glu Ile
            500                 505                 510

Ala Asp Phe Glu Lys Leu Lys Arg Trp Leu Pro Val Asp Ile Tyr Ile
            515                 520                 525

Gly Gly Ala Glu His Ala Val Leu His Leu Leu Tyr Ala Arg Phe Trp
            530                 535                 540

His Lys Phe Leu Tyr Asp Ile Gly Val Val Pro Thr Lys Glu Pro Phe
545                 550                 555                 560

Gln Lys Leu Tyr Asn Gln Gly Met Ile Leu Gly Glu Asn Asn Glu Lys
            565                 570                 575

Met Ser Lys Ser Arg Gly Asn Val Val Asn Pro Asp Asp Val Val Ala
            580                 585                 590

Lys Tyr Gly Ala Asp Thr Leu Arg Leu Tyr Glu Met Phe Met Gly Pro
            595                 600                 605

Leu Asp Ala Ser Ile Ala Trp Asn Glu Asn Gly Leu Glu Gly Ser Arg
            610                 615                 620

Lys Phe Leu Asp Arg Val Trp Arg Leu Ile Val Asp Glu Glu Gly Lys
625                 630                 635                 640

Met Arg Asp Arg Ile Thr Thr Ile Asn Asp Gly Arg Leu Thr Lys Val
            645                 650                 655

Tyr His Gln Thr Val Lys Lys Val Thr Glu Asp Met Ala Asn Leu His
            660                 665                 670

Phe Asn Thr Ala Ile Ser Gln Leu Met Val Phe Val Asn Glu Ala Asn
            675                 680                 685

Lys Val Asp Ala Leu Pro Tyr Glu Tyr Val Glu Gly Phe Val Gln Leu
```

-continued

```
                690                  695                  700
Leu Ala Pro Ile Ala Pro His Ile Gly Glu Glu Leu Trp Gln Ile Leu
705                 710                  715                  720

Gly Asn Glu Glu Ser Leu Thr Tyr Val Pro Trp Pro Thr Tyr Asp Glu
                725                  730                  735

Ala Ala Leu Val Glu Asp Glu Val Glu Val Val Phe Gln Val Asn Gly
                740                  745                  750

Lys Leu Arg Gly Lys Gln Asn Val Ala Arg Gly Leu Ser Lys Glu Glu
                755                  760                  765

Leu Glu Gln Ile Ala Met Asn His Glu Ala Val Lys Glu Phe Ile Glu
770                 775                  780

Gly Lys Thr Val Arg Lys Val Ile Ala Val Pro Asp Lys Leu Val Asn
785                 790                  795                  800

Ile Val Ala Asn
```

(2) INFORMATION FOR SEQ ID NO:5:

(i) SEQUENCE CHARACTERISTICS:
        (A) LENGTH: 1338 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 187..1194

(xi) SEQUENCE DESCRIPTION: SEQ ID NO:5:

```
TTTTATGAAA TTTTATGGAT ATTCGTTATG ATTCTGTAAA AAAGTAATAC AGTTTTCTAT      60

TTTTATGGTT GCTGTTATAA TTTACTTCTC TTGGTGATTT TTCAAGAAGT TCCCATGTAT     120

TTTTTTCTAA TAAAATGTAT AATAGAACTA TTCACTATCT TAAGTCTAAA GTCAGGTGGT     180

TATTTA ATG AAA ACA ATT TTT TCT GGT ATT CAG CCC AGT GGT ACT CCG        228
       Met Lys Thr Ile Phe Ser Gly Ile Gln Pro Ser Gly Thr Pro
         1               5                  10

ACA ATC GGA AAT TAC ATT GGT GCA ATG AAA CAA TTT ATC GAA TTA CAA       276
Thr Ile Gly Asn Tyr Ile Gly Ala Met Lys Gln Phe Ile Glu Leu Gln
 15                  20                  25                  30

AAT GAA TAC AAT TGT TAT TTT TGT ATT GTG GAT GAA CAT GCC ATT ACC       324
Asn Glu Tyr Asn Cys Tyr Phe Cys Ile Val Asp Glu His Ala Ile Thr
                35                  40                  45

GTT CCC CAA GAA CCG CAA AAG CTA CGC CAA CAA ATT CGT AGC TTA GCA       372
Val Pro Gln Glu Pro Gln Lys Leu Arg Gln Gln Ile Arg Ser Leu Ala
             50                  55                  60

GCT CTT TAC CTA GCG GTT GGT TTA GAC CCA CAA AAA GCA ACA ATT TTC       420
Ala Leu Tyr Leu Ala Val Gly Leu Asp Pro Gln Lys Ala Thr Ile Phe
         65                  70                  75

ATA CAG TCT GAA GTG AGT GCC CAT GCA GAA GCT GGT TGG ATC ATT CAG       468
Ile Gln Ser Glu Val Ser Ala His Ala Glu Ala Gly Trp Ile Ile Gln
 80                  85                  90

TGC AAT ACT TCT ATT GGT GAG TTA GAA CGA ATG ACA CAA TTT AAA GAT       516
Cys Asn Thr Ser Ile Gly Glu Leu Glu Arg Met Thr Gln Phe Lys Asp
 95                 100                 105                 110

AAA TCG CAA AAA AAT GGT CGT GCT GGC GTA AGC GCT GGT CTT TTA ACA       564
Lys Ser Gln Lys Asn Gly Arg Ala Gly Val Ser Ala Gly Leu Leu Thr
                115                 120                 125

TAC CCT CCA TTA ATG GTT GGT GAT ATC GTG TTG TAC AAT GCT GAC TTA       612
Tyr Pro Pro Leu Met Val Gly Asp Ile Val Leu Tyr Asn Ala Asp Leu
            130                 135                 140
```

```
GTG CCA GTC GGA GAT GAT CAA AAA CAA CAT TTA GAA TTA ACA CGT GAT        660
Val Pro Val Gly Asp Asp Gln Lys Gln His Leu Glu Leu Thr Arg Asp
        145                 150                 155

TTT GTG GAA CGC TTC AAT AAA CGT TAT GCC CAA AAA AAT CAA GAA ATT        708
Phe Val Glu Arg Phe Asn Lys Arg Tyr Ala Gln Lys Asn Gln Glu Ile
160                 165                 170

TTA ACG ATG CCT GAA GTA AAA ATC GCT GAG CAA GGT AGT CGA ATT ATG        756
Leu Thr Met Pro Glu Val Lys Ile Ala Glu Gln Gly Ser Arg Ile Met
175                 180                 185                 190

AGC TTA CAA GAA CCA ACG AAA AAG ATG AGT AAG TCC GAT ACA AAT GTG        804
Ser Leu Gln Glu Pro Thr Lys Lys Met Ser Lys Ser Asp Thr Asn Val
        195                 200                 205

AAG GGC TTT ATT TCA ATG CTT GAT GAG CCA GCA GTG ATT CGC AAA AAA        852
Lys Gly Phe Ile Ser Met Leu Asp Glu Pro Ala Val Ile Arg Lys Lys
        210                 215                 220

ATC CGC TCT GCT GTA ACT GAT TCA ACT GGT GTA ATT GAA TAT AAT AAA        900
Ile Arg Ser Ala Val Thr Asp Ser Thr Gly Val Ile Glu Tyr Asn Lys
        225                 230                 235

GAA GAA AAG CCT GGC ATT ACT AAC TTA CTA AAT ATT TAT TCT GCT GCG        948
Glu Glu Lys Pro Gly Ile Thr Asn Leu Leu Asn Ile Tyr Ser Ala Ala
240                 245                 250

ACA GGT CAA ACT GTT GAG GAA CTT GTT CAA GCA TAC GAA GGC AAA GGC        996
Thr Gly Gln Thr Val Glu Glu Leu Val Gln Ala Tyr Glu Gly Lys Gly
255                 260                 265                 270

TAT GGA GAC TTC AAA GCA GAT TTA GCA GAA GCA GTA GTT GCC TTA TTA       1044
Tyr Gly Asp Phe Lys Ala Asp Leu Ala Glu Ala Val Val Ala Leu Leu
                275                 280                 285

GAA CCT ATT CAA GTG CGC TAC CAA GAG CTT CTA GCT TCA GAA GAA TTA       1092
Glu Pro Ile Gln Val Arg Tyr Gln Glu Leu Leu Ala Ser Glu Glu Leu
                290                 295                 300

GAT ATG ATT TTA GAT GAG GGC GCA GAA AAC GCT CGC CAG GTA GCC AAC       1140
Asp Met Ile Leu Asp Glu Gly Ala Glu Asn Ala Arg Gln Val Ala Asn
        305                 310                 315

AAA ACA CTT CAA CGA ATG AAA AAT GCT GTT GGT TTG GGA AGA AAA GTT       1188
Lys Thr Leu Gln Arg Met Lys Asn Ala Val Gly Leu Gly Arg Lys Val
        320                 325                 330

CGG CGC TAACTAAACA TAATAAAAAC CGCGAAGTT TTATTCGCGG GTTTTTTTAT         1244
Arg Arg
335

GTTCTGAATT CAGCATCGTA CAGCCGACGA TAGTCACCTG TATACGCGTA CAAAGTTTCA     1304

GTGTTCCATC TTCTAAAATT TCTTTGGTCA CTCA                                 1338

(2) INFORMATION FOR SEQ ID NO:6:

(i) SEQUENCE CHARACTERISTICS:
        (A) LENGTH: 336 amino acids
        (B) TYPE: amino acid
        (D) TOPOLOGY: linear (ii) MOLECULE TYPE: protein (xi) SEQUENCE DESCRIPTION: SEQ ID NO:6:

Met Lys Thr Ile Phe Ser Gly Ile Gln Pro Ser Gly Thr Pro Thr Ile
1               5                   10                  15

Gly Asn Tyr Ile Gly Ala Met Lys Gln Phe Ile Glu Leu Gln Asn Glu
                20                  25                  30

Tyr Asn Cys Tyr Phe Cys Ile Val Asp Glu His Ala Ile Thr Val Pro
            35                  40                  45

Gln Glu Pro Gln Lys Leu Arg Gln Gln Ile Arg Ser Leu Ala Ala Leu
        50                  55                  60
```

```
Tyr Leu Ala Val Gly Leu Asp Pro Gln Lys Ala Thr Ile Phe Ile Gln
 65                  70                  75                  80

Ser Glu Val Ser Ala His Ala Glu Ala Gly Trp Ile Ile Gln Cys Asn
             85                  90                  95

Thr Ser Ile Gly Glu Leu Glu Arg Met Thr Gln Phe Lys Asp Lys Ser
            100                 105                 110

Gln Lys Asn Gly Arg Ala Gly Val Ser Ala Gly Leu Leu Thr Tyr Pro
        115                 120                 125

Pro Leu Met Val Gly Asp Ile Val Leu Tyr Asn Ala Asp Leu Val Pro
        130                 135                 140

Val Gly Asp Asp Gln Lys Gln His Leu Glu Leu Thr Arg Asp Phe Val
145                 150                 155                 160

Glu Arg Phe Asn Lys Arg Tyr Ala Gln Lys Asn Gln Glu Ile Leu Thr
                165                 170                 175

Met Pro Glu Val Lys Ile Ala Glu Gln Gly Ser Arg Ile Met Ser Leu
            180                 185                 190

Gln Glu Pro Thr Lys Lys Met Ser Lys Ser Asp Thr Asn Val Lys Gly
        195                 200                 205

Phe Ile Ser Met Leu Asp Glu Pro Ala Val Ile Arg Lys Lys Ile Arg
    210                 215                 220

Ser Ala Val Thr Asp Ser Thr Gly Val Ile Glu Tyr Asn Lys Glu Glu
225                 230                 235                 240

Lys Pro Gly Ile Thr Asn Leu Leu Asn Ile Tyr Ser Ala Ala Thr Gly
                245                 250                 255

Gln Thr Val Glu Glu Leu Val Gln Ala Tyr Glu Gly Lys Gly Tyr Gly
            260                 265                 270

Asp Phe Lys Ala Asp Leu Ala Glu Ala Val Val Ala Leu Leu Glu Pro
        275                 280                 285

Ile Gln Val Arg Tyr Gln Glu Leu Leu Ala Ser Glu Glu Leu Asp Met
    290                 295                 300

Ile Leu Asp Glu Gly Ala Glu Asn Ala Arg Gln Val Ala Asn Lys Thr
305                 310                 315                 320

Leu Gln Arg Met Lys Asn Ala Val Gly Leu Gly Arg Lys Val Arg Arg
                325                 330                 335

(2) INFORMATION FOR SEQ ID NO:7:

(i) SEQUENCE CHARACTERISTICS:
        (A) LENGTH: 3600 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 85..1128

(ix) FEATURE:
        (A) NAME/KEY: CDS
        (B) LOCATION: 1139..3559

(xi) SEQUENCE DESCRIPTION: SEQ ID NO:7:

CCGACGATGT TTTAGGATCG TTCCTTTGAA AGGAATGGGT TATCGTTTTT TTTAGTTTAA      60

ATAAAAGATA GAGGGAACG CATA ATG ACA TTA CAA GCG CAA TTA GAA GCT         111
                         Met Thr Leu Gln Ala Gln Leu Glu Ala
                          1               5

CTT AGA GAC AAT ACG CTC AAA GAA ATC GCA CAA GTT GCT ACT TTA AAA      159
Leu Arg Asp Asn Thr Leu Lys Glu Ile Ala Gln Val Ala Thr Leu Lys
```

-continued

```
          10                  15                  20                  25
GAA TTA AAC CAA ATT CGC GTA GAA ACA TTA GGG AAA AAA GGG CCA ATC         207
Glu Leu Asn Gln Ile Arg Val Glu Thr Leu Gly Lys Lys Gly Pro Ile
                    30                  35                  40

ACC GAA GTA TTA AGA GGC ATG AAA AAC CTT TCA CCA GAA GAA CGA CCA         255
Thr Glu Val Leu Arg Gly Met Lys Asn Leu Ser Pro Glu Glu Arg Pro
                45                  50                  55

GTG GTG GGG GGC TTT GCA AAT GAA ATT CGT GAT TTA TTA ACA GAA GCA         303
Val Val Gly Gly Phe Ala Asn Glu Ile Arg Asp Leu Leu Thr Glu Ala
                60                  65                  70

ATT GAA GCG CGC AAA GTT GTT TTA GAA AAC GAA GCA TTA AAT GCG GCA         351
Ile Glu Ala Arg Lys Val Val Leu Glu Asn Glu Ala Leu Asn Ala Ala
        75                  80                  85

CTA AAA GAA GAA AGT TTA GAT GTA ACT TTA CCT GGA AAA CAA ATG CCT         399
Leu Lys Glu Glu Ser Leu Asp Val Thr Leu Pro Gly Lys Gln Met Pro
90                  95                  100                 105

CAA GGC ACA CGT CAT ATT TTG ACA CAA GTT ATG GAA GAG ATT GAA GAT         447
Gln Gly Thr Arg His Ile Leu Thr Gln Val Met Glu Glu Ile Glu Asp
                    110                 115                 120

ATT TTC TTA GGC ATG GGT TAT CAA GTA GTG GAA GGA TAC GAA GTA GAA         495
Ile Phe Leu Gly Met Gly Tyr Gln Val Val Glu Gly Tyr Glu Val Glu
                125                 130                 135

TCC GAT CAT TAT AAT TTC GAA CGC ATG AAT CTA CCA AAA GAT CAT CCG         543
Ser Asp His Tyr Asn Phe Glu Arg Met Asn Leu Pro Lys Asp His Pro
            140                 145                 150

GCA CGC GAC ATG CAA GAT ACG TTT TAT ATT TCA GAT GAG ATG TTA ATT         591
Ala Arg Asp Met Gln Asp Thr Phe Tyr Ile Ser Asp Glu Met Leu Ile
        155                 160                 165

CGT ACG CAT ACT TCA CCA GTT CAA GCT CGA ACA ATG GAA AAA CAC GAT         639
Arg Thr His Thr Ser Pro Val Gln Ala Arg Thr Met Glu Lys His Asp
170                 175                 180                 185

TTT TCA AAA GGT GCA TTA CGA ATG ATT TCT CCT GGG AAA GTA TTC CGT         687
Phe Ser Lys Gly Ala Leu Arg Met Ile Ser Pro Gly Lys Val Phe Arg
                    190                 195                 200

CGT GAT ACA GAT GAT GCG ACA CAT AGT CAC CAA TTC CAT CAG ATT GAA         735
Arg Asp Thr Asp Asp Ala Thr His Ser His Gln Phe His Gln Ile Glu
                205                 210                 215

GGC CTT GTT GTC GAT AAA AAT GTC ACA ATG GGT GAT TTA AAA GGG ACG         783
Gly Leu Val Val Asp Lys Asn Val Thr Met Gly Asp Leu Lys Gly Thr
            220                 225                 230

TTA GAA GTC ATG ATG AAA AAA ATG TTT GGT GAA GAT CGT AAA ATT CGT         831
Leu Glu Val Met Met Lys Lys Met Phe Gly Glu Asp Arg Lys Ile Arg
        235                 240                 245

TTA CGT CCT AGC TAT TTC CCT TTT ACA GAA CCT TCA GTC GAA GTA GAT         879
Leu Arg Pro Ser Tyr Phe Pro Phe Thr Glu Pro Ser Val Glu Val Asp
250                 255                 260                 265

GTT AGC TGT TTT AAA TGT GGC GGC GCA GGT TGT AAC GTC TGC AAA CAT         927
Val Ser Cys Phe Lys Cys Gly Gly Ala Gly Cys Asn Val Cys Lys His
                    270                 275                 280

ACA GGT TGG ATT GAA ATT TTA GGT GCG GGG ATG GTT CAT CCA GAT GTG         975
Thr Gly Trp Ile Glu Ile Leu Gly Ala Gly Met Val His Pro Asp Val
                285                 290                 295

TTA CAA ATG TCA GGG ATT GAT CCA ACA GAG TAC TCA GGC TTT GCC TTT        1023
Leu Gln Met Ser Gly Ile Asp Pro Thr Glu Tyr Ser Gly Phe Ala Phe
            300                 305                 310

GGC TTA GGA CCA GAT CGC GTT GCT ATG TTA CGT TAT GGT GTA AAT GAT        1071
Gly Leu Gly Pro Asp Arg Val Ala Met Leu Arg Tyr Gly Val Asn Asp
        315                 320                 325

ATC CGT AAT TTT TAT CAA AAT GAT TTA CGT TTC TTA AAT CAA TTC AAG        1119
```

```
Ile Arg Asn Phe Tyr Gln Asn Asp Leu Arg Phe Leu Asn Gln Phe Lys
330                 335                 340                 345

GTA AAG GAG TAGTTGAAAA ATG TTA GTT TCT TAT AAA TGG TTA AAT GAA         1168
Val Lys Glu            Met Leu Val Ser Tyr Lys Trp Leu Asn Glu
                        1               5                   10

TAT GTT AAT CTT TCA AAC GTT ACT CCG CAA GAA TTA GCG GAC AAA ATG        1216
Tyr Val Asn Leu Ser Asn Val Thr Pro Gln Glu Leu Ala Asp Lys Met
                15              20                  25

TCT GTG ACA GGT ATC GAA GTT GAG GGC GTT GCT GTA CCT GAA GAA GGA        1264
Ser Val Thr Gly Ile Glu Val Glu Gly Val Ala Val Pro Glu Glu Gly
            30              35                  40

TTA AAG AAA ATT GTT GTC GGT GAA GTA AAA GAA TGT GTT CCT CAT CCA        1312
Leu Lys Lys Ile Val Val Gly Glu Val Lys Glu Cys Val Pro His Pro
        45              50                  55

AAC TCT GAC CAC TTA TCA ATT TGC CAA GTA GAC ATC GGT GAA GAA GAG        1360
Asn Ser Asp His Leu Ser Ile Cys Gln Val Asp Ile Gly Glu Glu Glu
    60              65                  70

TTG TCA CAA ATT GTT TGT GGA GCA CCA AAT GTG AAA GCC GGA ATT AAA        1408
Leu Ser Gln Ile Val Cys Gly Ala Pro Asn Val Lys Ala Gly Ile Lys
75              80                  85                      90

GTC ATC GTG GCG TTA CCT GGT TCA AGA ATT GCA GGA AAT CAA AAA ATT        1456
Val Ile Val Ala Leu Pro Gly Ser Arg Ile Ala Gly Asn Gln Lys Ile
                95                  100                 105

AAA AAA GGT AAA ATG CGT GGC GAA GTC TCT AAC GGA ATG ATT TGT TCG        1504
Lys Lys Gly Lys Met Arg Gly Glu Val Ser Asn Gly Met Ile Cys Ser
            110                 115                 120

TTA GAA GAG CTA GGA TAT TCA GAT AAT GTC GTA CCA AAA GCC TAC GCT        1552
Leu Glu Glu Leu Gly Tyr Ser Asp Asn Val Val Pro Lys Ala Tyr Ala
        125                 130                 135

GAA GGG ATT TAT TAT TTA CCT CAA GAA GCA GTG AAT GGG ACA CCT GTT        1600
Glu Gly Ile Tyr Tyr Leu Pro Gln Glu Ala Val Asn Gly Thr Pro Val
    140                 145                 150

TTC CCT TAT TTA GAC ATG GAT GAT GCG ATT ATT GAA TTA TCA ATT ACA        1648
Phe Pro Tyr Leu Asp Met Asp Asp Ala Ile Ile Glu Leu Ser Ile Thr
155                 160                 165                 170

CCA AAC CGT GCA GAT GCA TTA AGT ATG AGA GGG GTA GCC TAT GAA GTT        1696
Pro Asn Arg Ala Asp Ala Leu Ser Met Arg Gly Val Ala Tyr Glu Val
                175                 180                 185

GGC GCA ATT TAT CGT CAA ACG CCT CAG TTT AAT GAT CCC AAA CTC AAA        1744
Gly Ala Ile Tyr Arg Gln Thr Pro Gln Phe Asn Asp Pro Lys Leu Lys
            190                 195                 200

GAA GAT GCT TCA GAT AAC GTG GAA AAT TAC GTA ACA GTG ACT GTT GAA        1792
Glu Asp Ala Ser Asp Asn Val Glu Asn Tyr Val Thr Val Thr Val Glu
        205                 210                 215

GAT TCA CAA GAT GCA CCA GCG TAT CAA ATT CGT GTC ATT AAA GAT GTG        1840
Asp Ser Gln Asp Ala Pro Ala Tyr Gln Ile Arg Val Ile Lys Asp Val
    220                 225                 230

ACG ATT GCA GAA AGT CCT CAG TGG TTG CAA AAC CGA TTG ATG AAT GAA        1888
Thr Ile Ala Glu Ser Pro Gln Trp Leu Gln Asn Arg Leu Met Asn Glu
235                 240                 245                 250

GGA ATC CGT CCG ATT AAC AAT GTG GTG GAC GTG ACA AAT TAT ATT TTA        1936
Gly Ile Arg Pro Ile Asn Asn Val Val Asp Val Thr Asn Tyr Ile Leu
                255                 260                 265

TTA TTA TTT GGT CAA CCA TTG CAT GCA TTT GAT TAT CAA AAA TTA GAT        1984
Leu Leu Phe Gly Gln Pro Leu His Ala Phe Asp Tyr Gln Lys Leu Asp
            270                 275                 280

AGT AAA GAA ATC TTG GTT CGT CGA GCA ACA GCA GCA GAA GAA CTA ATT        2032
Ser Lys Glu Ile Leu Val Arg Arg Ala Thr Ala Ala Glu Glu Leu Ile
        285                 290                 295
```

```
ACA TTA GAT GGT GAA ACA CGT CAA TTA ACA GAA GAA AAT ATC GTC ATT     2080
Thr Leu Asp Gly Glu Thr Arg Gln Leu Thr Glu Glu Asn Ile Val Ile
    300                 305                 310

ACG AAT GGA AAA ACG CCT GTC GGC TTA GCC GGT GTA ATG GGT GGA GCT     2128
Thr Asn Gly Lys Thr Pro Val Gly Leu Ala Gly Val Met Gly Gly Ala
315                 320                 325                 330

AAT TCT GAA ATC AGT CAA GAA ACA ACA ACT GTG GCT TTA GAA GCG GCA     2176
Asn Ser Glu Ile Ser Gln Glu Thr Thr Thr Val Ala Leu Glu Ala Ala
                335                 340                 345

TTG TTC AAT CCA TTG TCT ATT CGC AAA ACG TCT AAA CAA TTC AAT TTA     2224
Leu Phe Asn Pro Leu Ser Ile Arg Lys Thr Ser Lys Gln Phe Asn Leu
            350                 355                 360

CGG AGT GAA TCT TCA AGT AGA TTT GAA AAA GGC ATC AAC CAA GCG ACA     2272
Arg Ser Glu Ser Ser Ser Arg Phe Glu Lys Gly Ile Asn Gln Ala Thr
        365                 370                 375

GTT GGG CTA GCT TGT GAT GTG GCA GCC GCG ATG ATT GCA GAG TTA GCC     2320
Val Gly Leu Ala Cys Asp Val Ala Ala Ala Met Ile Ala Glu Leu Ala
    380                 385                 390

GAC GGA ACA GTA GTC TCA GGC ACT GCA ATT GGT TCT GAA GTG GCC GTT     2368
Asp Gly Thr Val Val Ser Gly Thr Ala Ile Gly Ser Glu Val Ala Val
395                 400                 405                 410

AAA GAA GCG CAG GTA GCT GTG ACT TTA GAA CGA ATC AAC CAA TAT TTA     2416
Lys Glu Ala Gln Val Ala Val Thr Leu Glu Arg Ile Asn Gln Tyr Leu
                415                 420                 425

GGC ACT GCA TTA GAT GAA GCA ACG GTG AAT GAA ATT TTT GAA GCA CTC     2464
Gly Thr Ala Leu Asp Glu Ala Thr Val Asn Glu Ile Phe Glu Ala Leu
            430                 435                 440

GGT TTT GCT TAT GAA GTA AAT CAA GGC GCA TAT GAA ATT ACG ATT CCA     2512
Gly Phe Ala Tyr Glu Val Asn Gln Gly Ala Tyr Glu Ile Thr Ile Pro
        445                 450                 455

CCA AGA CGT TGG GAT ATT GCG ATT GAA GCA GAT ATT ATT GAA GAA GTG     2560
Pro Arg Arg Trp Asp Ile Ala Ile Glu Ala Asp Ile Ile Glu Glu Val
    460                 465                 470

GCG CGC ATT TAT GGA TAT GAT CAT TTA CCT TCA ACA TTG CCA AGT GGA     2608
Ala Arg Ile Tyr Gly Tyr Asp His Leu Pro Ser Thr Leu Pro Ser Gly
475                 480                 485                 490

GAA ACA GTT GCT GGA AGT CTA ACC AAA GCA CAA CAT GTT ACG CGC CAA     2656
Glu Thr Val Ala Gly Ser Leu Thr Lys Ala Gln His Val Thr Arg Gln
                495                 500                 505

TTA AAG AGC TTA CTG GAA GGT CAT GGT ACG AGT GAA GCC ATC AGC TAT     2704
Leu Lys Ser Leu Leu Glu Gly His Gly Thr Ser Glu Ala Ile Ser Tyr
            510                 515                 520

GCG TTG ACA ACA GAA GAA AAA TCC CGT CAA TTT ATG ATG AAA GAA AGT     2752
Ala Leu Thr Thr Glu Glu Lys Ser Arg Gln Phe Met Met Lys Glu Ser
        525                 530                 535

CAA ACA ACA CGG TTG CAA TGG CCA ATG AGT GAA GAG CGT TCT GTG TTA     2800
Gln Thr Thr Arg Leu Gln Trp Pro Met Ser Glu Glu Arg Ser Val Leu
    540                 545                 550

CGT ATG AAC TTA ATT TCT GGT TTA TTA GAT GAT GTC GCA TAC AAT GTG     2848
Arg Met Asn Leu Ile Ser Gly Leu Leu Asp Asp Val Ala Tyr Asn Val
555                 560                 565                 570

GCA CGT AAA AAT AAT AAT ATC GCC TTC TAC GAA GTA GGA CGC GTT TTC     2896
Ala Arg Lys Asn Asn Asn Ile Ala Phe Tyr Glu Val Gly Arg Val Phe
                575                 580                 585

TAC CAA ACA GAA GAT CCA ACA AAA AAT TTA CCT ACA GAA GAA AAT CAC     2944
Tyr Gln Thr Glu Asp Pro Thr Lys Asn Leu Pro Thr Glu Glu Asn His
            590                 595                 600

TTA GCA CTT GCT TTA ACT GGT AAT ACA ATG GTT AAA GAT TGG CAA ACA     2992
Leu Ala Leu Ala Leu Thr Gly Asn Thr Met Val Lys Asp Trp Gln Thr
        605                 610                 615
```

```
AAA GCA ACA GCC GTT GAT TTT TAT ACA GTA AAA GGC TTA GTG GAA AGT     3040
Lys Ala Thr Ala Val Asp Phe Tyr Thr Val Lys Gly Leu Val Glu Ser
    620                 625                 630

ATT GTA GCT GTT TTA GGA TTA ACA GAA AAA ATC AGT TAT CAA GCG ACA     3088
Ile Val Ala Val Leu Gly Leu Thr Glu Lys Ile Ser Tyr Gln Ala Thr
635                 640                 645                 650

ACG GCG ATT CCA GAA ATG CAT CCA GGC CGG ACA GCA TGG ATT TAT TTA     3136
Thr Ala Ile Pro Glu Met His Pro Gly Arg Thr Ala Trp Ile Tyr Leu
                655                 660                 665

AAA GAT GAA GTG GTT GGT TTT GTC GGA CAA GTT CAC CCA ACG ACA GCA     3184
Lys Asp Glu Val Val Gly Phe Val Gly Gln Val His Pro Thr Thr Ala
            670                 675                 680

AAA GCG TAC GAT ATT CCT GAA ACA TAT GTT GCT GAA TTA AAC TTG CAA     3232
Lys Ala Tyr Asp Ile Pro Glu Thr Tyr Val Ala Glu Leu Asn Leu Gln
                685                 690                 695

CAA TTA GTA GCC ACA GAA GCA GGC GGG GTT ACT TAT GAA GCA GTT TCT     3280
Gln Leu Val Ala Thr Glu Ala Gly Gly Val Thr Tyr Glu Ala Val Ser
700                 705                 710

AAA TTC CCA GCA GTT TCT CGA GAT ATT GCT TTA TTA GTC GAT GAA ACA     3328
Lys Phe Pro Ala Val Ser Arg Asp Ile Ala Leu Leu Val Asp Glu Thr
715                 720                 725                 730

GTT ACC AAT CAA GAA CTA GTT AAA ACT ATT TCA GAT AAC GCA GGT AAA     3376
Val Thr Asn Gln Glu Leu Val Lys Thr Ile Ser Asp Asn Ala Gly Lys
                735                 740                 745

TAT TTG AAA GAG ATT CAT TTA TTT GAT GTA TAT CAA GGT GAA AAA CTA     3424
Tyr Leu Lys Glu Ile His Leu Phe Asp Val Tyr Gln Gly Glu Lys Leu
            750                 755                 760

GGC GCT GGC AAA AAA TCA ATG GCG TAT AGT TTA ACT TTC GTT AAT GCA     3472
Gly Ala Gly Lys Lys Ser Met Ala Tyr Ser Leu Thr Phe Val Asn Ala
            765                 770                 775

GAA GCG ACA TTA GTG GAT GAA GAA ATT AAC CGT TCA ATG GAA AAA GTT     3520
Glu Ala Thr Leu Val Asp Glu Glu Ile Asn Arg Ser Met Glu Lys Val
            780                 785                 790

GAA AAA GCG CTA ATT GAA AAA CAT CAA GTA GAA GTA AGA TAAAATAAAA      3569
Glu Lys Ala Leu Ile Glu Lys His Gln Val Glu Val Arg
795                 800                 805

ACGGGAAAGT GGGGCATAAG TCGAAATGAC T                                  3600

(2) INFORMATION FOR SEQ ID NO:8:

(i) SEQUENCE CHARACTERISTICS:
        (A) LENGTH: 348 amino acids
        (B) TYPE: amino acid
        (D) TOPOLOGY: linear (ii) MOLECULE TYPE: protein (xi) SEQUENCE DESCRIPTION: SEQ ID NO:8:

Met Thr Leu Gln Ala Gln Leu Glu Ala Leu Arg Asp Asn Thr Leu Lys
1               5                   10                  15

Glu Ile Ala Gln Val Ala Thr Leu Lys Glu Leu Asn Gln Ile Arg Val
            20                  25                  30

Glu Thr Leu Gly Lys Lys Gly Pro Ile Thr Glu Val Leu Arg Gly Met
        35                  40                  45

Lys Asn Leu Ser Pro Glu Glu Arg Pro Val Val Gly Gly Phe Ala Asn
    50                  55                  60

Glu Ile Arg Asp Leu Leu Thr Glu Ala Ile Glu Ala Arg Lys Val Val
65                  70                  75                  80

Leu Glu Asn Glu Ala Leu Asn Ala Ala Leu Lys Glu Glu Ser Leu Asp
```

```
                     85                 90                  95
Val Thr Leu Pro Gly Lys Gln Met Pro Gln Gly Thr Arg His Ile Leu
                100                 105                110

Thr Gln Val Met Glu Glu Ile Glu Asp Ile Phe Leu Gly Met Gly Tyr
            115                 120                 125

Gln Val Val Glu Gly Tyr Glu Val Ser Asp His Tyr Asn Phe Glu
        130                 135                 140

Arg Met Asn Leu Pro Lys Asp His Pro Ala Arg Asp Met Gln Asp Thr
145                 150                 155                 160

Phe Tyr Ile Ser Asp Glu Met Leu Ile Arg Thr His Thr Ser Pro Val
                165                 170                 175

Gln Ala Arg Thr Met Glu Lys His Asp Phe Ser Lys Gly Ala Leu Arg
            180                 185                 190

Met Ile Ser Pro Gly Lys Val Phe Arg Arg Asp Thr Asp Asp Ala Thr
                195                 200                 205

His Ser His Gln Phe His Gln Ile Glu Gly Leu Val Val Asp Lys Asn
        210                 215                 220

Val Thr Met Gly Asp Leu Lys Gly Thr Leu Glu Val Met Met Lys Lys
225                 230                 235                 240

Met Phe Gly Glu Asp Arg Lys Ile Arg Leu Arg Pro Ser Tyr Phe Pro
                245                 250                 255

Phe Thr Glu Pro Ser Val Glu Val Asp Val Ser Cys Phe Lys Cys Gly
                260                 265                 270

Gly Ala Gly Cys Asn Val Cys Lys His Thr Gly Trp Ile Glu Ile Leu
            275                 280                 285

Gly Ala Gly Met Val His Pro Asp Val Leu Gln Met Ser Gly Ile Asp
        290                 295                 300

Pro Thr Glu Tyr Ser Gly Phe Ala Phe Gly Leu Gly Pro Asp Arg Val
305                 310                 315                 320

Ala Met Leu Arg Tyr Gly Val Asn Asp Ile Arg Asn Phe Tyr Gln Asn
                325                 330                 335

Asp Leu Arg Phe Leu Asn Gln Phe Lys Val Lys Glu
                340                 345

(2) INFORMATION FOR SEQ ID NO:9:

(i) SEQUENCE CHARACTERISTICS:
        (A) LENGTH: 807 amino acids
        (B) TYPE: amino acid
        (D) TOPOLOGY: linear (ii) MOLECULE TYPE: protein (xi) SEQUENCE DESCRIPTION: SEQ ID NO:9:

Met Leu Val Ser Tyr Lys Trp Leu Asn Glu Tyr Val Asn Leu Ser Asn
  1                 5                  10                  15

Val Thr Pro Gln Glu Leu Ala Asp Lys Met Ser Val Thr Gly Ile Glu
                 20                  25                  30

Val Glu Gly Val Ala Val Pro Glu Gly Leu Lys Lys Ile Val Val
             35                  40                  45

Gly Glu Val Lys Glu Cys Val Pro His Pro Asn Ser Asp His Leu Ser
     50                  55                  60

Ile Cys Gln Val Asp Ile Gly Glu Glu Leu Ser Gln Ile Val Cys
 65                  70                  75                  80

Gly Ala Pro Asn Val Lys Ala Gly Ile Lys Val Ile Val Ala Leu Pro
                 85                  90                  95
```

```
Gly Ser Arg Ile Ala Gly Asn Gln Lys Ile Lys Lys Gly Lys Met Arg
                100                 105                 110
Gly Glu Val Ser Asn Gly Met Ile Cys Ser Leu Glu Glu Leu Gly Tyr
            115                 120                 125
Ser Asp Asn Val Val Pro Lys Ala Tyr Ala Glu Gly Ile Tyr Tyr Leu
        130                 135                 140
Pro Gln Glu Ala Val Asn Gly Thr Pro Val Phe Pro Tyr Leu Asp Met
145                 150                 155                 160
Asp Asp Ala Ile Ile Glu Leu Ser Ile Thr Pro Asn Arg Ala Asp Ala
                165                 170                 175
Leu Ser Met Arg Gly Val Ala Tyr Glu Val Gly Ala Ile Tyr Arg Gln
            180                 185                 190
Thr Pro Gln Phe Asn Asp Pro Lys Leu Lys Glu Asp Ala Ser Asp Asn
        195                 200                 205
Val Glu Asn Tyr Val Thr Val Thr Val Glu Asp Ser Gln Asp Ala Pro
        210                 215                 220
Ala Tyr Gln Ile Arg Val Ile Lys Asp Val Thr Ile Ala Glu Ser Pro
225                 230                 235                 240
Gln Trp Leu Gln Asn Arg Leu Met Asn Glu Gly Ile Arg Pro Ile Asn
            245                 250                 255
Asn Val Val Asp Val Thr Asn Tyr Ile Leu Leu Phe Gly Gln Pro
            260                 265                 270
Leu His Ala Phe Asp Tyr Gln Lys Leu Asp Ser Lys Glu Ile Leu Val
        275                 280                 285
Arg Arg Ala Thr Ala Ala Glu Glu Leu Ile Thr Leu Asp Gly Glu Thr
290                 295                 300
Arg Gln Leu Thr Glu Glu Asn Ile Val Ile Thr Asn Gly Lys Thr Pro
305                 310                 315                 320
Val Gly Leu Ala Gly Val Met Gly Gly Ala Asn Ser Glu Ile Ser Gln
                325                 330                 335
Glu Thr Thr Thr Val Ala Leu Glu Ala Ala Leu Phe Asn Pro Leu Ser
            340                 345                 350
Ile Arg Lys Thr Ser Lys Gln Phe Asn Leu Arg Ser Glu Ser Ser Ser
        355                 360                 365
Arg Phe Glu Lys Gly Ile Asn Gln Ala Thr Val Gly Leu Ala Cys Asp
        370                 375                 380
Val Ala Ala Ala Met Ile Ala Glu Leu Ala Asp Gly Thr Val Val Ser
385                 390                 395                 400
Gly Thr Ala Ile Gly Ser Glu Val Ala Val Lys Glu Ala Gln Val Ala
            405                 410                 415
Val Thr Leu Glu Arg Ile Asn Gln Tyr Leu Gly Thr Ala Leu Asp Glu
            420                 425                 430
Ala Thr Val Asn Glu Ile Phe Glu Ala Leu Gly Phe Ala Tyr Glu Val
        435                 440                 445
Asn Gln Gly Ala Tyr Glu Ile Thr Ile Pro Pro Arg Arg Trp Asp Ile
    450                 455                 460
Ala Ile Glu Ala Asp Ile Ile Glu Glu Val Ala Arg Ile Tyr Gly Tyr
465                 470                 475                 480
Asp His Leu Pro Ser Thr Leu Pro Ser Gly Glu Thr Val Ala Gly Ser
            485                 490                 495
Leu Thr Lys Ala Gln His Val Thr Arg Gln Leu Lys Ser Leu Leu Glu
            500                 505                 510
```

```
Gly His Gly Thr Ser Glu Ala Ile Ser Tyr Ala Leu Thr Thr Glu Glu
        515                 520                 525

Lys Ser Arg Gln Phe Met Met Lys Glu Ser Gln Thr Thr Arg Leu Gln
530                 535                 540

Trp Pro Met Ser Glu Glu Arg Ser Val Leu Arg Met Asn Leu Ile Ser
545                 550                 555                 560

Gly Leu Leu Asp Asp Val Ala Tyr Asn Val Ala Arg Lys Asn Asn Asn
                565                 570                 575

Ile Ala Phe Tyr Glu Val Gly Arg Val Phe Tyr Gln Thr Glu Asp Pro
            580                 585                 590

Thr Lys Asn Leu Pro Thr Glu Glu Asn His Leu Ala Leu Ala Leu Thr
        595                 600                 605

Gly Asn Thr Met Val Lys Asp Trp Gln Thr Lys Ala Thr Ala Val Asp
    610                 615                 620

Phe Tyr Thr Val Lys Gly Leu Val Glu Ser Ile Val Ala Val Leu Gly
625                 630                 635                 640

Leu Thr Glu Lys Ile Ser Tyr Gln Ala Thr Thr Ala Ile Pro Glu Met
                645                 650                 655

His Pro Gly Arg Thr Ala Trp Ile Tyr Leu Lys Asp Glu Val Val Gly
            660                 665                 670

Phe Val Gly Gln Val His Pro Thr Thr Ala Lys Ala Tyr Asp Ile Pro
        675                 680                 685

Glu Thr Tyr Val Ala Glu Leu Asn Leu Gln Gln Leu Val Ala Thr Glu
690                 695                 700

Ala Gly Gly Val Thr Tyr Glu Ala Val Ser Lys Phe Pro Ala Val Ser
705                 710                 715                 720

Arg Asp Ile Ala Leu Leu Val Asp Glu Thr Val Thr Asn Gln Glu Leu
                725                 730                 735

Val Lys Thr Ile Ser Asp Asn Ala Gly Lys Tyr Leu Lys Glu Ile His
            740                 745                 750

Leu Phe Asp Val Tyr Gln Gly Glu Lys Leu Gly Ala Gly Lys Lys Ser
        755                 760                 765

Met Ala Tyr Ser Leu Thr Phe Val Asn Ala Glu Ala Thr Leu Val Asp
770                 775                 780

Glu Glu Ile Asn Arg Ser Met Glu Lys Val Glu Lys Ala Leu Ile Glu
785                 790                 795                 800

Lys His Gln Val Glu Val Arg
                805

(2) INFORMATION FOR SEQ ID NO:10:

(i) SEQUENCE CHARACTERISTICS:
        (A) LENGTH: 1430 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 132..1385

(xi) SEQUENCE DESCRIPTION: SEQ ID NO:10:

AAATTTCGTG AACCCGTGTA TACATAGAAA TAAACACGGG ATATCGTGTA AAACAAGTG      60

TGTTAATCGT TGTTTCGTT AAATGAACGA TTTCCTATAA AGAGATAATT ATAAATATGG     120

AGGGTGATAA C ATG AAT ATC ATT GAC GAG CTA GCA TGG CGT GAT GCA ATC    170
            Met Asn Ile Ile Asp Glu Leu Ala Trp Arg Asp Ala Ile
              1               5                  10
```

```
AAT CAA CAA ACA AAC GAA GAA GGA CTA AGA GAA CTT ACA GAA AAT ACG     218
Asn Gln Gln Thr Asn Glu Glu Gly Leu Arg Glu Leu Thr Glu Asn Thr
         15                  20                  25

AGC ATT TCG CTA TAT TGC GGT GTC GAT CCA ACT GGA GAT AGC ATG CAT     266
Ser Ile Ser Leu Tyr Cys Gly Val Asp Pro Thr Gly Asp Ser Met His
 30                  35                  40                  45

ATT GGA CAT TTA ATT CCT TTT ATG ATG ATG AAA CGA TTC CAA TTA GCA     314
Ile Gly His Leu Ile Pro Phe Met Met Met Lys Arg Phe Gln Leu Ala
                 50                  55                  60

GGT CAT CAC CCA TAC ATT TTA ATT GGT GGC GGA ACT GGA ACA ATT GGT     362
Gly His His Pro Tyr Ile Leu Ile Gly Gly Gly Thr Gly Thr Ile Gly
             65                  70                  75

GAT CCA AGT GGA CGA ACA ACC GAA CGT GTC TTA CAA ACG ATG GAA GCT     410
Asp Pro Ser Gly Arg Thr Thr Glu Arg Val Leu Gln Thr Met Glu Ala
         80                  85                  90

GTG CAA CAT AAT GTG GAC AGT CTT TCA AAT CAA ATG AAA AAA TTA TTT     458
Val Gln His Asn Val Asp Ser Leu Ser Asn Gln Met Lys Lys Leu Phe
 95                 100                 105

GGT AAA GAT GCT GAG GTA ACA ATG GTG AAC AAC TAC GAT TGG TTA TCA     506
Gly Lys Asp Ala Glu Val Thr Met Val Asn Asn Tyr Asp Trp Leu Ser
110                 115                 120                 125

GAA CTA TCT TTA TTA GAT TTT TTA AGA GAT TAC GGG AAA AAC TTT AAT     554
Glu Leu Ser Leu Leu Asp Phe Leu Arg Asp Tyr Gly Lys Asn Phe Asn
                130                 135                 140

GTC AAC ACG ATG TTG GCA AAA GAC ATT GTC GCT AGT CGT TTA GAA AGT     602
Val Asn Thr Met Leu Ala Lys Asp Ile Val Ala Ser Arg Leu Glu Ser
            145                 150                 155

GGC ATT TCC TTT ACA GAA TTC ACA TAC CAA ATT CTT CAA TCA ATT GAC     650
Gly Ile Ser Phe Thr Glu Phe Thr Tyr Gln Ile Leu Gln Ser Ile Asp
        160                 165                 170

TTT TAC ACA TTG CAT AAA AAA CAT AAT ATT CAA TTG CAA ATT GGT GGC     698
Phe Tyr Thr Leu His Lys Lys His Asn Ile Gln Leu Gln Ile Gly Gly
    175                 180                 185

GCT GAT CAA TGG GGC AAT ATC ACT GCA GGA TTA GAT TTG ATT CGT AAA     746
Ala Asp Gln Trp Gly Asn Ile Thr Ala Gly Leu Asp Leu Ile Arg Lys
190                 195                 200                 205

AAA GAA GGA CCA GAA GCC AAA GTA TTC GGG TTA ACC ATT CCT TTA ATG     794
Lys Glu Gly Pro Glu Ala Lys Val Phe Gly Leu Thr Ile Pro Leu Met
                210                 215                 220

CTA AAA GCA GAT GGT ACA AAA TTT GGG AAA ACA GCG GGT GGC GCT ATC     842
Leu Lys Ala Asp Gly Thr Lys Phe Gly Lys Thr Ala Gly Gly Ala Ile
            225                 230                 235

TGG TTA GAT CCT AAG AAA ACC TCA CCA TTT GAA TTC TAC CAA TTC TGG     890
Trp Leu Asp Pro Lys Lys Thr Ser Pro Phe Glu Phe Tyr Gln Phe Trp
        240                 245                 250

TTA AAC CAA GAT GAT CGT GAT GTC ATC AAA TAC TTG AAA TTC TTT ACT     938
Leu Asn Gln Asp Asp Arg Asp Val Ile Lys Tyr Leu Lys Phe Phe Thr
    255                 260                 265

TTC TTA GAT AAA GAA GAA ATC GAT GCG TTA GCT GAA AAA GTT GAA AAA     986
Phe Leu Asp Lys Glu Glu Ile Asp Ala Leu Ala Glu Lys Val Glu Lys
270                 275                 280                 285

GAA CCA GGT AAA CGT GAA GCA CAA AGA CGC TTA GCT GAA GAA GTG ACA    1034
Glu Pro Gly Lys Arg Glu Ala Gln Arg Arg Leu Ala Glu Glu Val Thr
                290                 295                 300

CGA TTT GTT CAC GAT GAT GCA GCA TTA GAA GAA GCG CAA AAA ATT TCA    1082
Arg Phe Val His Asp Asp Ala Ala Leu Glu Glu Ala Gln Lys Ile Ser
            305                 310                 315

GAA GCT CTT TTC TCA GGC AAC ATT AAA GAC TTA ACG ATT GAG GAA ATC    1130
Glu Ala Leu Phe Ser Gly Asn Ile Lys Asp Leu Thr Ile Glu Glu Ile
```

```
              320                 325                 330
GAG CAA GGG TTA GAA CAT GTG CCA ACT GTT GAA ATT ACC AAA GAT GCT    1178
Glu Gln Gly Leu Glu His Val Pro Thr Val Glu Ile Thr Lys Asp Ala
            335                 340                 345

AAA AAC ATC GTA GAT TGG TTA GTT GAC ACA GAA ATC GAA CCA TCA AAA    1226
Lys Asn Ile Val Asp Trp Leu Val Asp Thr Glu Ile Glu Pro Ser Lys
350                 355                 360                 365

CGT CAA GCT CGC GAA GAT GTG AGC GGA GGA GCT ATA AGT ATT AAC GGT    1274
Arg Gln Ala Arg Glu Asp Val Ser Gly Gly Ala Ile Ser Ile Asn Gly
                370                 375                 380

GAC CGA GTT ACC GAT TTA GAT TTT GCA GTC GAT CCA ACA CAA CAT TTC    1322
Asp Arg Val Thr Asp Leu Asp Phe Ala Val Asp Pro Thr Gln His Phe
            385                 390                 395

GAT GGA AAA TTC GTT GTT GTA CGG GAA GGG AAG AAA AAT TAC TTT TTA    1370
Asp Gly Lys Phe Val Val Val Arg Glu Gly Lys Lys Asn Tyr Phe Leu
            400                 405                 410

GCA AAA GTA ATG GAT TAGAAATTGA TAATAATTTC TCGAAGAGAA GACGTGTGAT    1425
Ala Lys Val Met Asp
415

TATTT                                                              1430

(2) INFORMATION FOR SEQ ID NO:11:

(i) SEQUENCE CHARACTERISTICS:
        (A) LENGTH: 418 amino acids
        (B) TYPE: amino acid
        (D) TOPOLOGY: linear (ii) MOLECULE TYPE: protein (xi) SEQUENCE DESCRIPTION: SEQ ID NO:11:

Met Asn Ile Ile Asp Glu Leu Ala Trp Arg Asp Ala Ile Asn Gln Gln
 1               5                  10                  15

Thr Asn Glu Glu Gly Leu Arg Glu Leu Thr Glu Asn Thr Ser Ile Ser
                20                  25                  30

Leu Tyr Cys Gly Val Asp Pro Thr Gly Asp Ser Met His Ile Gly His
            35                  40                  45

Leu Ile Pro Phe Met Met Met Lys Arg Phe Gln Leu Ala Gly His His
        50                  55                  60

Pro Tyr Ile Leu Ile Gly Gly Thr Gly Thr Ile Gly Asp Pro Ser
65              70                  75                  80

Gly Arg Thr Thr Glu Arg Val Leu Gln Thr Met Glu Ala Val Gln His
                85                  90                  95

Asn Val Asp Ser Leu Ser Asn Gln Met Lys Lys Leu Phe Gly Lys Asp
                100                 105                 110

Ala Glu Val Thr Met Val Asn Asn Tyr Asp Trp Leu Ser Glu Leu Ser
            115                 120                 125

Leu Leu Asp Phe Leu Arg Asp Tyr Gly Lys Asn Phe Asn Val Asn Thr
        130                 135                 140

Met Leu Ala Lys Asp Ile Val Ala Ser Arg Leu Glu Ser Gly Ile Ser
145                 150                 155                 160

Phe Thr Glu Phe Thr Tyr Gln Ile Leu Gln Ser Ile Asp Phe Tyr Thr
                165                 170                 175

Leu His Lys Lys His Asn Ile Gln Leu Gln Ile Gly Gly Ala Asp Gln
            180                 185                 190

Trp Gly Asn Ile Thr Ala Gly Leu Asp Leu Ile Arg Lys Lys Glu Gly
        195                 200                 205
```

```
Pro Glu Ala Lys Val Phe Gly Leu Thr Ile Pro Leu Met Leu Lys Ala
    210                 215                 220

Asp Gly Thr Lys Phe Gly Lys Thr Ala Gly Gly Ala Ile Trp Leu Asp
225                 230                 235                 240

Pro Lys Lys Thr Ser Pro Phe Glu Phe Tyr Gln Phe Trp Leu Asn Gln
                245                 250                 255

Asp Asp Arg Asp Val Ile Lys Tyr Leu Lys Phe Phe Thr Phe Leu Asp
            260                 265                 270

Lys Glu Glu Ile Asp Ala Leu Ala Glu Lys Val Glu Lys Glu Pro Gly
        275                 280                 285

Lys Arg Glu Ala Gln Arg Arg Leu Ala Glu Val Thr Arg Phe Val
    290                 295                 300

His Asp Asp Ala Ala Leu Glu Glu Ala Gln Lys Ile Ser Glu Ala Leu
305                 310                 315                 320

Phe Ser Gly Asn Ile Lys Asp Leu Thr Ile Glu Glu Ile Glu Gln Gly
                325                 330                 335

Leu Glu His Val Pro Thr Val Glu Ile Thr Lys Asp Ala Lys Asn Ile
            340                 345                 350

Val Asp Trp Leu Val Asp Thr Glu Ile Glu Pro Ser Lys Arg Gln Ala
        355                 360                 365

Arg Glu Asp Val Ser Gly Gly Ala Ile Ser Ile Asn Gly Asp Arg Val
    370                 375                 380

Thr Asp Leu Asp Phe Ala Val Asp Pro Thr Gln His Phe Asp Gly Lys
385                 390                 395                 400

Phe Val Val Val Arg Glu Gly Lys Lys Asn Tyr Phe Leu Ala Lys Val
                405                 410                 415

Met Asp (2) INFORMATION FOR SEQ ID NO:12:

(i) SEQUENCE CHARACTERISTICS:
        (A) LENGTH: 1409 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 132..1400

(xi) SEQUENCE DESCRIPTION: SEQ ID NO:12:

AACTTGGGTG GTACCGCGAG ATTTCCAGTC ATTTCGTCCC AAGAATATTT ATTTTTGGGG    60

TGAGATGGCT TTTTTGTTGT TTCTACAAC AGTTATTATT GATTATGTAC TAATTTTAAG   120

GAGGAAAAAA T ATG TTA GAT GTA AAA ATG ATG CGT CAA AAT TTT GAC GAA    170
            Met Leu Asp Val Lys Met Met Arg Gln Asn Phe Asp Glu
             1               5                   10

GTA AAA GCA AAG CTA CAA ACC CGT GGT GTG AAA GAA GAA ATC TTA GTG    218
Val Lys Ala Lys Leu Gln Thr Arg Gly Val Lys Glu Glu Ile Leu Val
 15                  20                  25

GAA TTT CTG CGT TTA GAT GAA AGT CGC CGT GAT TTA TTA GTC AAA GTC    266
Glu Phe Leu Arg Leu Asp Glu Ser Arg Arg Asp Leu Leu Val Lys Val
 30                  35                  40                  45

GAA GAA ATG AAA AAA TAC CGG AAC GAT GTG TCT GCT GAA ATT GCT CAA    314
Glu Glu Met Lys Lys Tyr Arg Asn Asp Val Ser Ala Glu Ile Ala Gln
             50                  55                  60

TTA AAA CGG AAC AAA GAA GAT GCA ACG GCC AAA ATC GCG GAA ATG AAA    362
Leu Lys Arg Asn Lys Glu Asp Ala Thr Ala Lys Ile Ala Glu Met Lys
         65                  70                  75
```

```
GAA GTC GGC GGT AAT ATT AAA GCG TTA GAT GCA GAA ATT AAT GCT ATT          410
Glu Val Gly Gly Asn Ile Lys Ala Leu Asp Ala Glu Ile Asn Ala Ile
             80                  85                  90

GAC GAA GAG CTA CGT GGG ATC ACA ACT ACT TTA CCG AAC TTG CCA GAT          458
Asp Glu Glu Leu Arg Gly Ile Thr Thr Thr Leu Pro Asn Leu Pro Asp
         95                 100                 105

GAT TCT GTG CCT GTT GGT GCT GGT GAA GAA GAA AAT GTA GAA GTA CGT          506
Asp Ser Val Pro Val Gly Ala Gly Glu Glu Glu Asn Val Glu Val Arg
110                 115                 120                 125

CGT TGG AGT GAA CCA AGA ACT TTT GCT TTT GAA CCA AAA CCA CAC TGG          554
Arg Trp Ser Glu Pro Arg Thr Phe Ala Phe Glu Pro Lys Pro His Trp
                130                 135                 140

GAA GTC GCT GAA AAC TTA GGC ATT CTA GAT TTT GAA CGT GGT GCC AAA          602
Glu Val Ala Glu Asn Leu Gly Ile Leu Asp Phe Glu Arg Gly Ala Lys
            145                 150                 155

GTA GCT GGT AGC CGT TTT GTT TAT TAC AAA GGC TTA GGT GCA CGC TTA          650
Val Ala Gly Ser Arg Phe Val Tyr Tyr Lys Gly Leu Gly Ala Arg Leu
            160                 165                 170

GAA CGT GCG TTA TAC AAC TTC ATG TTA GAT TTA CAT GTT TAT GAA CAT          698
Glu Arg Ala Leu Tyr Asn Phe Met Leu Asp Leu His Val Tyr Glu His
        175                 180                 185

GGC TAT ACA GAA ATG ATT ACG CCT TAT ATC GTT AAT GAC ACC GCC ATG          746
Gly Tyr Thr Glu Met Ile Thr Pro Tyr Ile Val Asn Asp Thr Ala Met
190                 195                 200                 205

TTC GGG ACT GGC CAA TTT CCT AAA TTT AAA GAA GAT GTC TTC CAA TTA          794
Phe Gly Thr Gly Gln Phe Pro Lys Phe Lys Glu Asp Val Phe Gln Leu
                210                 215                 220

CAA GAT ACG GAT TTA ACG TTA ATT CCA ACT GCG GAA GTC CCT TTA ACC          842
Gln Asp Thr Asp Leu Thr Leu Ile Pro Thr Ala Glu Val Pro Leu Thr
                225                 230                 235

AAT TAC TAC AAC AAT GAA ATT TTA GAT GGC AAG GAT TTA CCG ATT TAC          890
Asn Tyr Tyr Asn Asn Glu Ile Leu Asp Gly Lys Asp Leu Pro Ile Tyr
            240                 245                 250

TTT ACG GCC TTG AGC CCT TCT TTC CGT TCT GAA GCT GGT AGC GCT GGT          938
Phe Thr Ala Leu Ser Pro Ser Phe Arg Ser Glu Ala Gly Ser Ala Gly
            255                 260                 265

CGT GAC ACA CGA GGA TTA ATT CGT TTA CAC CAA TTT AAT AAA GTC GAA          986
Arg Asp Thr Arg Gly Leu Ile Arg Leu His Gln Phe Asn Lys Val Glu
270                 275                 280                 285

ATG GTT AAA TTT AGT GAT GCA GAG CAT TCT TAT GAG GAA TTA GAA AAA         1034
Met Val Lys Phe Ser Asp Ala Glu His Ser Tyr Glu Glu Leu Glu Lys
                290                 295                 300

ATG ACG AAT AAT GCC GAA GAA ATT CTG CAA AAA CTG GGA TTA CCT TAC         1082
Met Thr Asn Asn Ala Glu Glu Ile Leu Gln Lys Leu Gly Leu Pro Tyr
                305                 310                 315

CGT GTC ATG GCT CTT TCA ACA GGT GAC ATG GGC TTC TCA GCT GCG AAA         1130
Arg Val Met Ala Leu Ser Thr Gly Asp Met Gly Phe Ser Ala Ala Lys
                320                 325                 330

ACT TAT GAC TTG GAA GTT TGG ATT CCC GCT CAA GAG ACA TAC CGT GAA         1178
Thr Tyr Asp Leu Glu Val Trp Ile Pro Ala Gln Glu Thr Tyr Arg Glu
            335                 340                 345

ATT AGT TCA TGC TCA AAC TGT GAA GAT TTC CAA GCG CGC CGT GCG ATG         1226
Ile Ser Ser Cys Ser Asn Cys Glu Asp Phe Gln Ala Arg Arg Ala Met
350                 355                 360                 365

ATT CGT TAC CGT GAT GAA AAT GAT AAA GTC CAA TAT GCG CAT ACA CTC         1274
Ile Arg Tyr Arg Asp Glu Asn Asp Lys Val Gln Tyr Ala His Thr Leu
                370                 375                 380

AAT GGT TCT GGT TTA GCC GTG GGA CGG ACA GTC GCT GCT ATT TTA GAA         1322
Asn Gly Ser Gly Leu Ala Val Gly Arg Thr Val Ala Ala Ile Leu Glu
```

```
                385                 390                 395
AAC TAC CAA AAC GAA GAT GGC TCT GTA ACT GTA CCA GAA GTC CTA GTT       1370
Asn Tyr Gln Asn Glu Asp Gly Ser Val Thr Val Pro Glu Val Leu Val
            400                 405                 410

CCT TAC ATG GGT AAC CTA ACA GTT ATT AAA TAAAGGGAA                     1409
Pro Tyr Met Gly Asn Leu Thr Val Ile Lys
415                 420
```

(2) INFORMATION FOR SEQ ID NO:13:

(i) SEQUENCE CHARACTERISTICS:
        (A) LENGTH: 423 amino acids
        (B) TYPE: amino acid
        (D) TOPOLOGY: linear (ii) MOLECULE TYPE: protein (xi) SEQUENCE DESCRIPTION: SEQ ID NO:13:

```
Met Leu Asp Val Lys Met Met Arg Gln Asn Phe Asp Glu Val Lys Ala
 1               5                  10                  15

Lys Leu Gln Thr Arg Gly Val Lys Glu Glu Ile Leu Val Glu Phe Leu
                20                  25                  30

Arg Leu Asp Glu Ser Arg Arg Asp Leu Leu Val Lys Val Glu Glu Met
            35                  40                  45

Lys Lys Tyr Arg Asn Asp Val Ser Ala Glu Ile Ala Gln Leu Lys Arg
50                  55                  60

Asn Lys Glu Asp Ala Thr Ala Lys Ile Ala Glu Met Lys Glu Val Gly
65                  70                  75                  80

Gly Asn Ile Lys Ala Leu Asp Ala Glu Ile Asn Ala Ile Asp Glu Glu
                85                  90                  95

Leu Arg Gly Ile Thr Thr Thr Leu Pro Asn Leu Pro Asp Asp Ser Val
                100                 105                 110

Pro Val Gly Ala Gly Glu Glu Glu Asn Val Glu Val Arg Arg Trp Ser
            115                 120                 125

Glu Pro Arg Thr Phe Ala Phe Glu Pro Lys Pro His Trp Glu Val Ala
130                 135                 140

Glu Asn Leu Gly Ile Leu Asp Phe Glu Arg Gly Ala Lys Val Ala Gly
145                 150                 155                 160

Ser Arg Phe Val Tyr Tyr Lys Gly Leu Gly Ala Arg Leu Glu Arg Ala
                165                 170                 175

Leu Tyr Asn Phe Met Leu Asp Leu His Val Tyr Glu His Gly Tyr Thr
            180                 185                 190

Glu Met Ile Thr Pro Tyr Ile Val Asn Asp Thr Ala Met Phe Gly Thr
                195                 200                 205

Gly Gln Phe Pro Lys Phe Lys Glu Asp Val Phe Gln Leu Gln Asp Thr
210                 215                 220

Asp Leu Thr Leu Ile Pro Thr Ala Glu Val Pro Leu Thr Asn Tyr Tyr
225                 230                 235                 240

Asn Asn Glu Ile Leu Asp Gly Lys Asp Leu Pro Ile Tyr Phe Thr Ala
                245                 250                 255

Leu Ser Pro Ser Phe Arg Ser Glu Ala Gly Ser Ala Gly Arg Asp Thr
            260                 265                 270

Arg Gly Leu Ile Arg Leu His Gln Phe Asn Lys Val Glu Met Val Lys
            275                 280                 285

Phe Ser Asp Ala Glu His Ser Tyr Glu Glu Leu Glu Lys Met Thr Asn
290                 295                 300
```

```
Asn Ala Glu Glu Ile Leu Gln Lys Leu Gly Leu Pro Tyr Arg Val Met
305                 310                 315                 320

Ala Leu Ser Thr Gly Asp Met Gly Phe Ser Ala Ala Lys Thr Tyr Asp
                325                 330                 335

Leu Glu Val Trp Ile Pro Ala Gln Glu Thr Tyr Arg Glu Ile Ser Ser
                340                 345                 350

Cys Ser Asn Cys Glu Asp Phe Gln Ala Arg Arg Ala Met Ile Arg Tyr
                355                 360                 365

Arg Asp Glu Asn Asp Lys Val Gln Tyr Ala His Thr Leu Asn Gly Ser
370                 375                 380

Gly Leu Ala Val Gly Arg Thr Val Ala Ala Ile Leu Glu Asn Tyr Gln
385                 390                 395                 400

Asn Glu Asp Gly Ser Val Thr Val Pro Glu Val Leu Val Pro Tyr Met
                405                 410                 415

Gly Asn Leu Thr Val Ile Lys
                420
```

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 11
        (D) OTHER INFORMATION: /mod_base= i (ix) FEATURE:
        (A) NAME/KEY: modified_base
        (B) LOCATION: 20
        (D) OTHER INFORMATION: /mod_base= i (ix) FEATURE:
        (A) NAME/KEY: modified_base
        (B) LOCATION: 26
        (D) OTHER INFORMATION: /mod_base= i (ix) FEATURE:
        (A) NAME/KEY: modified_base
        (B) LOCATION: 29
        (D) OTHER INFORMATION: /mod_base= i (xi) SEQUENCE DESCRIPTION: SEQ ID NO:14:

GCGAATTCGG NTGGGAYACN CAYGGNSTNC C                         31

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 11
        (D) OTHER INFORMATION: /mod_base= i (ix) FEATURE:
        (A) NAME/KEY: modified_base
        (B) LOCATION: 26
        (D) OTHER INFORMATION: /mod_base= i (ix) FEATURE:
        (A) NAME/KEY: modified_base
        (B) LOCATION: 29

(D) OTHER INFORMATION: /mod_base= i (xi) SEQUENCE DESCRIPTION: SEQ ID NO:15:

GCGAATTCGG NTGGGAYTGY CAYGGNCTNC C                              31

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 10
        (D) OTHER INFORMATION: /mod_base= i (ix) FEATURE:
        (A) NAME/KEY: modified_base
        (B) LOCATION: 16
        (D) OTHER INFORMATION: /mod_base= i (ix) FEATURE:
        (A) NAME/KEY: modified_base
        (B) LOCATION: 25
        (D) OTHER INFORMATION: /mod_base= i (ix) FEATURE:
        (A) NAME/KEY: modified_base
        (B) LOCATION: 28
        (D) OTHER INFORMATION: /mod_base= i (ix) FEATURE:
        (A) NAME/KEY: modified_base
        (B) LOCATION: 31
        (D) OTHER INFORMATION: /mod_base= i (xi) SEQUENCE DESCRIPTION: SEQ ID NO:16:

GCGAATTCGN CARCGNTAYT GGGGNRTNCC NAT                            33

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 10
        (D) OTHER INFORMATION: /mod_base= i (ix) FEATURE:
        (A) NAME/KEY: modified_base
        (B) LOCATION: 16
        (D) OTHER INFORMATION: /mod_base= i (ix) FEATURE:
        (A) NAME/KEY: modified_base
        (B) LOCATION: 25
        (D) OTHER INFORMATION: /mod_base= i (ix) FEATURE:
        (A) NAME/KEY: modified_base
        (B) LOCATION: 28
        (D) OTHER INFORMATION: /mod_base= i (ix) FEATURE:
        (A) NAME/KEY: modified_base
        (B) LOCATION: 31
        (D) OTHER INFORMATION: /mod_base= i (xi) SEQUENCE DESCRIPTION: SEQ ID NO:17:

```
GCGAATTCGN AAYCGNTWYT GGGGNACNCC NMT                                    33
```

(2) INFORMATION FOR SEQ ID NO:18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 18
        (D) OTHER INFORMATION: /mod_base= i (ix) FEATURE:
        (A) NAME/KEY: modified_base
        (B) LOCATION: 21
        (D) OTHER INFORMATION: /mod_base= i (ix) FEATURE:
        (A) NAME/KEY: modified_base
        (B) LOCATION: 30
        (D) OTHER INFORMATION: /mod_base= i (ix) FEATURE:
        (A) NAME/KEY: modified_base
        (B) LOCATION: 33
        (D) OTHER INFORMATION: /mod_base= i (xi) SEQUENCE DESCRIPTION: SEQ ID NO:18:

```
GCGAATTCRA ACCANCCNCG NGTYTGRTCN WWNCCYTC                               38
```

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 24
        (D) OTHER INFORMATION: /mod_base= i (xi) SEQUENCE DESCRIPTION: SEQ ID NO:19:

```
GGNCAYGCNY TNAAYAARAT HYTNAARGA                                         29
```

(2) INFORMATION FOR SEQ ID NO:20:

(i) SEQUENCE CHARACTERISTICS:
        (A) LENGTH: 23 base pairs

```
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:20:

CCRTGNCCNG GNGCNGTRTG NAC                                         23

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:21:

ACNGSNAARA TYGGNGAYCC HACHGG                                      26

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 18
        (D) OTHER INFORMATION: /mod_base= i
```

```
    (ix) FEATURE:
         (A) NAME/KEY: modified_base
         (B) LOCATION: 21
         (D) OTHER INFORMATION: /mod_base= i (ix) FEATURE:
         (A) NAME/KEY: modified_base
         (B) LOCATION: 24
         (D) OTHER INFORMATION: /mod_base= i (xi) SEQUENCE DESCRIPTION: SEQ ID NO:22:

ATRTTNCCRT AYTGRTCNGW NCCNCCRATY T                                    31

(2) INFORMATION FOR SEQ ID NO:23:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ix) FEATURE:
         (A) NAME/KEY: modified_base
         (B) LOCATION: 9
         (D) OTHER INFORMATION: /mod_base= i (xi) SEQUENCE DESCRIPTION: SEQ ID NO:23:

CCRTCYTCNG TYTGRTARTT YTC                                             23

(2) INFORMATION FOR SEQ ID NO:24:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO:24:

AANNNRGGTG GHACCRCG                                                   18

(2) INFORMATION FOR SEQ ID NO:25:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ix) FEATURE:
         (A) NAME/KEY: modified_base
         (B) LOCATION: 4
         (D) OTHER INFORMATION: /mod_base= i (ix) FEATURE:
         (A) NAME/KEY: modified_base
         (B) LOCATION: 12
         (D) OTHER INFORMATION: /mod_base= i (ix) FEATURE:
         (A) NAME/KEY: modified_base
         (B) LOCATION: 15
         (D) OTHER INFORMATION: /mod_base= i (xi) SEQUENCE DESCRIPTION: SEQ ID NO:25:

GTNNARTAYY TNGGNAARAA RGG                                             23

(2) INFORMATION FOR SEQ ID NO:26:

(i) SEQUENCE CHARACTERISTICS:
         (A) LENGTH: 20 base pairs
```

(B) TYPE: nucleic acid
        (C) STRANDEDNESS: single
        (D) TOPOLOGY: linear (ix) FEATURE:
        (A) NAME/KEY: modified_base
        (B) LOCATION: 3
        (D) OTHER INFORMATION: /mod_base= i (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:26:

SWNGGYTCNG TRAANGGRAA                                                     20

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 9
        (D) OTHER INFORMATION: /mod_base= i (ix) FEATURE:
        (A) NAME/KEY: modified_base
        (B) LOCATION: 15
        (D) OTHER INFORMATION: /mod_base= i (xi) SEQUENCE DESCRIPTION: SEQ ID NO:27:

TTYTTYCCNT TYACNGARCC                                                     20

(2) INFORMATION FOR SEQ ID NO:28:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ix) FEATURE:
        (A) NAME/KEY: modified_base
        (B) LOCATION: 6
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 15
        (D) OTHER INFORMATION: /mod_base= i (ix) FEATURE:
        (A) NAME/KEY: modified_base
        (B) LOCATION: 21
        (D) OTHER INFORMATION: /mod_base= i (xi) SEQUENCE DESCRIPTION: SEQ ID NO:28:

GGRTGNACYT GNCCNATRAA NCCNA                                               25

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:29:

TTTTGTATWG TWGATCAACA TGCWATWACW G                             31

(2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:30:

TCTAAATGTT GTTTTTGATC TTCWCCWACW GG                            32

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:31:

CGACTTGTGA TAAGGCATAC TC                                       22

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:32:

GGTTCTTCAC ATGAAGGAGT TTTAC                                25

(2) INFORMATION FOR SEQ ID NO:33:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:33:

TGTGTCATTC GTTCTAACTC ACC                                    23

(2) INFORMATION FOR SEQ ID NO:34:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:34:

TGATGAGCCA GCAGTGATTC GC                                       22

(2) INFORMATION FOR SEQ ID NO:35:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:35:

CCAAGAACCG CAAAAGCTAC GCCA                                    24

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:36:

TTGCGCGCTT CAATTGCTTC TG                                      22

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:37:

CTTAGTGGAA AGTATTGTAG C                                       21

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:38:

CAGGATCAGT GGTATTAATT TC                                      22

(2) INFORMATION FOR SEQ ID NO:39:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:39:

GCTTTGAATG GGGCATTCCT TTGCC                                  25

(2) INFORMATION FOR SEQ ID NO:40:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:40:

GTATGGGATT GAAGAATTAC GC                                      22

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:41:

TACACCACAT GTTTAGGATC GTTC                                              24

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:42:

TATGCAATTG CATTTTAGGC AC                                                22

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:43:

ACTCATTTTC ACGCCCTCTA TC                                                22

(2) INFORMATION FOR SEQ ID NO:44:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:44:

CGCGGATCCA TGTTAGATGT AAAAATGATG CG                                     32

(2) INFORMATION FOR SEQ ID NO:45:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:45:

CCGCTCGAGC GGTTATTTAA TAACTGTTAG GTTACC                                 36

(2) INFORMATION FOR SEQ ID NO:46:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:46:

AATGGTTGGT GATATCGTGT TGTA                                              24

(2) INFORMATION FOR SEQ ID NO:47:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:47:

GCTAAATCTG CTTTGAAGCT TCC                                            23

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:48:

GGAACGCATA ATGACATTAC AAGC                                           24

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:49:

TCCACTAATG TCGCTTCTGC                                                20

(2) INFORMATION FOR SEQ ID NO:50:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:50:

TCACGAATTT CATTTGCAAA GC                                             22

(2) INFORMATION FOR SEQ ID NO:51:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:51:

ATCCAGGCCG GACAGCATGG                                                20

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:52:

TTTGCAATTG AATATTATGT TTTT                                           24

(2) INFORMATION FOR SEQ ID NO:53:

(i) SEQUENCE CHARACTERISTICS:

```
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:53:

ACAAACGATG GAAGCTGTGC AACA                                           24

(2) INFORMATION FOR SEQ ID NO:54:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:54:

GTCCAATATG CGCATACACT C                                              21

(2) INFORMATION FOR SEQ ID NO:55:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (xi) SEQUENCE DESCRIPTION: SEQ ID NO:55:

CCCGGATCCA TGAGCTACAA TCACAAAG                                       28

(2) INFORMATION FOR SEQ ID NO:56:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO:56:

CCGCCTCGAG TTAATTTGCA ACAATATTTA C                                   31

(2) INFORMATION FOR SEQ ID NO:57:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO:57:

CGCGGATCCA TGTTAGATGT AAAAATGATG CG                                  32

(2) INFORMATION FOR SEQ ID NO:58:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (xi) SEQUENCE DESCRIPTION: SEQ ID NO:58:

CCGCTCGAGC GGTTATTTAA TAACTGTTAG GTTACC                              36

(2) INFORMATION FOR SEQ ID NO:59:

(i) SEQUENCE CHARACTERISTICS:
            (A) LENGTH: 13 base pairs
```

(B) TYPE: nucleic acid
        (C) STRANDEDNESS: single
        (D) TOPOLOGY: linear (xi) SEQUENCE DESCRIPTION: SEQ ID NO:59:

GATCCCATAT GGG                                                          13

(2) INFORMATION FOR SEQ ID NO:60:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:60:

AATTCCCATA TGG                                                          13

(2) INFORMATION FOR SEQ ID NO:61:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:61:

GGATCCCATA TGGGAATTC                                                    19

(2) INFORMATION FOR SEQ ID NO:62:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:62:

GTTTATCGTA CACATATGAA TATCATTGAC GAGCTAGCAT GGCGT                        45

(2) INFORMATION FOR SEQ ID NO:63:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:63:

GTTACCCTAC TCGAGCTAAT CCATTACTTT TGCTAAAA                                38

(2) INFORMATION FOR SEQ ID NO:64:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:64:

CAATTGTTTT CATATGAAAA CAATTTTTTC TGGTATTCAG C                            41

(2) INFORMATION FOR SEQ ID NO:65:

(i) SEQUENCE CHARACTERISTICS:
        (A) LENGTH: 38 base pairs
        (B) TYPE: nucleic acid (C) STRANDEDNESS: single
        (D) TOPOLOGY: linear (xi) SEQUENCE DESCRIPTION: SEQ ID NO:65:

TTTCCGCTCG AGCGGAAACT TCGCGGGTTT TTATTATG                                    38

(2) INFORMATION FOR SEQ ID NO:66:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:66:

GTGCCAACAT ATGTTAGATG TAAAAATGAT GC                                         32

(2) INFORMATION FOR SEQ ID NO:67:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:67:

CAGTCAGTCG ACTTTAATAA CTGTTAGGTT ACC                                        33

(2) INFORMATION FOR SEQ ID NO:68:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:68:

CAGTCAGGAT CCTTATTTAA TAACTGTTAG GTTACC                                     36

(2) INFORMATION FOR SEQ ID NO:69:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:69:

CGCGGATCCA GGGGAACGCA TAATGACATT ACAAGC                                     36

(2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:70:

ACGTCAGTCG ACTCTTACTT CTACTTGATG                                            30

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single -continued (D) TOPOLOGY: linear (xi) SEQUENCE DESCRIPTION: SEQ ID NO:71:

CTCAATGGTT CTGGTTTAGC                                          20